(12) United States Patent
Parnaby et al.

(10) Patent No.: US 12,412,387 B2
(45) Date of Patent: Sep. 9, 2025

(54) STATE-BASED BASE CALLING

(71) Applicant: Illumina, Inc., San Diego, CA (US)

(72) Inventors: Gavin Derek Parnaby, Laguna Niguel, CA (US); Eric Jon Ojard, San Francisco, CA (US); Dorna Kashefhaghighi, Menlo Park, CA (US)

(73) Assignee: Illumina, Inc., San Diego, CA (US)

( * ) Notice: Subject to any disclaimer, the term of this patent is extended or adjusted under 35 U.S.C. 154(b) by 392 days.

(21) Appl. No.: 17/944,809

(22) Filed: Sep. 14, 2022

(65) Prior Publication Data

US 2023/0298339 A1    Sep. 21, 2023

Related U.S. Application Data

(60) Provisional application No. 63/247,296, filed on Sep. 22, 2021, provisional application No. 63/247,301, filed on Sep. 22, 2021.

(51) Int. Cl.
*G06V 10/94* (2022.01)
*G06N 3/0464* (2023.01)
(Continued)

(52) U.S. Cl.
CPC ......... *G06V 10/955* (2022.01); *G06N 3/0464* (2023.01); *G06N 3/084* (2013.01);
(Continued)

(58) Field of Classification Search
CPC .... G06V 10/955; G06V 20/698; G06V 10/82; G16B 40/20; G16B 30/00; G06N 3/0464; G06N 3/084
See application file for complete search history.

(56) References Cited

U.S. PATENT DOCUMENTS

2015/0169824 A1\* 6/2015 Kermani ............... G16B 30/10
702/19
2019/0212295 A1\* 7/2019 Dehlinger ............ C12Q 1/6874
(Continued)

FOREIGN PATENT DOCUMENTS

WO    2015/084985 A2    6/2015
WO    2020/191387 A1    6/2020
(Continued)

OTHER PUBLICATIONS

Boža, Vladimír, Broňa Brejová, and Tomáš Vinař. "DeepNano: deep recurrent neural networks for base calling in MinION nanopore reads." PloS one 12.6 (2017): e0178751. (Year: 2017).\*
(Continued)

*Primary Examiner* — Utpal D Shah
(74) *Attorney, Agent, or Firm* — Keller Preece PLLC

(57) ABSTRACT

The technology disclosed relates to state-based base calling. In particular, the technology disclosed relates to incorporating state information about data from previous sequencing cycles into the analysis of data from a current sequencing cycle when generating a base call for the current sequencing cycle. For example, when generating a base call for an Nth sequencing cycle, the technology disclosed can incorporate into the base calling logic state information about data from sequencing cycles 1 to N-1.

30 Claims, 60 Drawing Sheets
(19 of 60 Drawing Sheet(s) Filed in Color)

(51) Int. Cl.
  *G06N 3/084* (2023.01)
  *G06V 10/82* (2022.01)
  *G06V 20/69* (2022.01)
  *G16B 30/00* (2019.01)
  *G16B 40/20* (2019.01)

(52) U.S. Cl.
  CPC ............ *G06V 10/82* (2022.01); *G06V 20/698* (2022.01); *G16B 30/00* (2019.02); *G16B 40/20* (2019.02)

(56) References Cited

U.S. PATENT DOCUMENTS

| | | | |
|---|---|---|---|
| 2020/0251183 A1* | 8/2020 | Kashefhaghighi | G16B 40/00 |
| 2020/0302297 A1 | 9/2020 | Jaganathan et al. | |
| 2021/0265016 A1* | 8/2021 | Vessere | G06V 10/7715 |
| 2021/0265017 A1* | 8/2021 | Dutta | G16B 40/10 |

FOREIGN PATENT DOCUMENTS

| | | |
|---|---|---|
| WO | 2020-191390 A2 | 9/2020 |
| WO | 2020-232410 A1 | 11/2020 |
| WO | 2021/167911 A1 | 8/2021 |
| WO | 2021-168353 A2 | 8/2021 |

OTHER PUBLICATIONS

Wigoda Noa: "Illumina Primary Analysis Pipeline & Quality Control", 1-28, Nov. 19, 2019 (Nov. 19, 2019), XP055870543, Retrieved from the Internet: URL:https://dors.weizmann.ac.il/course/course2019-20/Noa_IlluminaPrimaryAnalysisPipeline.pdf [retrieved on Dec. 8, 2021]; the whole document.

Kircher Martin et al: "Improved base calling for the Illumina Genome Analyzer using machine learning strategies", Genome Biology, Biomed Central Ltd, vol. 10, No. 8, Aug. 14, 2009 (Aug. 14, 2009), p. R83, XP021061445, ISSN: 1465-6906, DOI: 10.1186/GB-2009-10-8-R83.

* cited by examiner

Pixel P

| | Channel 1 | Channel 2 |
|---|---|---|
| Cycle 1 | $v_1^1$ 512 | $v_1^2$ 522 |
| Cycle 2 | $v_2^1$ 513 | $v_2^2$ 523 |
| Cycle 3 | $v_3^1$ 514 | $v_3^2$ 524 |
| Cycle 4 | $v_4^1$ 515 | $v_4^2$ 525 |
| Cycle 5 | $v_5^1$ 516 | $v_5^2$ 526 |
| Cycle 5 State | $f\{v_1^1, v_2^1, v_3^1, v_4^1, v_5^1\}$ 532 | $f\{v_1^2, v_2^2, v_3^2, v_4^2, v_5^2\}$ 536 |

Per-Channel States 500

$f = AVG, MAX, MIN, EXPWEGAVG, MOVAVG, EXPMOVAVG, STDEV$

Figure 5

Current Sequencing Cycle N

Per-Channel AVG States 1000

| Pixels 601 | Channel 1 Intensity Values 602 | Channel 2 Intensity Values 603 | Channel 1 AVG State Values 1004 | Channel 2 AVG State Values 1005 |
|---|---|---|---|---|
| (1, 1) | $x_N^1$ | $y_N^1$ | $\text{AVG}\{x_N^1 \ldots x_1^1\}$ | $\text{AVG}\{y_N^1 \ldots y_1^1\}$ |
| (1, 2) | $x_N^2$ | $y_N^2$ | $\text{AVG}\{x_N^2 \ldots x_1^2\}$ | $\text{AVG}\{y_N^2 \ldots y_1^2\}$ |
| (1, 3) | $x_N^3$ | $y_N^3$ | $\text{AVG}\{x_N^3 \ldots x_1^3\}$ | $\text{AVG}\{y_N^3 \ldots y_1^3\}$ |
| (1, 4) | $x_N^4$ | $y_N^4$ | $\text{AVG}\{x_N^4 \ldots x_1^4\}$ | $\text{AVG}\{y_N^4 \ldots y_1^4\}$ |
| (1, 5) | $x_N^5$ | $y_N^5$ | $\text{AVG}\{x_N^5 \ldots x_1^5\}$ | $\text{AVG}\{y_N^5 \ldots y_1^5\}$ |
| ... | ... | ... | ... | ... |
| $(i, j)$ | $x_N^k$ | $y_N^k$ | $\text{AVG}\{x_N^k \ldots x_1^k\}$ | $\text{AVG}\{y_N^k \ldots y_1^k\}$ |

Figure 10

Current Sequencing Cycle N

Pan-Channel AVG AVG States 1100

| Pixels 601 | Channel 1 Intensity Values 602 | Channel 2 Intensity Values 603 | Pan-Channel AVG AVG State Values 1108 |
|---|---|---|---|
| (1, 1) | $x_N^1$ | $y_N^1$ | |
| (1, 2) | $x_N^2$ | $y_N^2$ | |
| (1, 3) | $x_N^3$ | $y_N^3$ | Pixel-Wise Averages of Columns 1004 and 1005 in Figure 10 |
| (1, 4) | $x_N^4$ | $y_N^4$ | |
| (1, 5) | $x_N^5$ | $y_N^5$ | |
| ... | ... | ... | ... |
| (i, j) | $x_N^k$ | $y_N^k$ | ... |

Base Call-Directed ON and OFF State Generation 1700

| Pixel P | | Channel 1 (1754) | Channel 2 (1756) |
|---|---|---|---|
| Cycle 1 | Base Call G | OFF $x_1^P$ | OFF $y_1^P$ |
| Cycle 2 | Base Call C | OFF $x_2^P$ | ON $y_2^P$ |
| Cycle 3 | Base Call T | ON $x_3^P$ | ON $y_3^P$ |
| Cycle 4 | Base Call A | ON $x_4^P$ | OFF $y_4^P$ |
| Cycle 5 | Base Call C | OFF $x_5^P$ | ON $y_5^P$ |
| Cycle 6 | Base Call G | OFF $x_6^P$ | OFF $y_6^P$ |
| Cycle 7 | Base Call T | ON $x_7^P$ | ON $y_7^P$ |
| Cycle 8 | Base Call A | ON $x_8^P$ | OFF $y_8^P$ |
| Cycle 9 | Base Call C | OFF $x_9^P$ | ON $y_9^P$ |
| Cycle 10 | Base Call T | ON $x_{10}^P$ | ON $y_{10}^P$ |

Figure 17A

| Per-Channel State Calculation for Cycle 11 | | $f = AVG, MAX, MIN, EXPWEGAVG, MOVAVG, EXPMOVAVG, STDEV$ |
|---|---|---|
| Channel 1 INACTIVE (OFF) State | 1702 | $f\{ x_1^P, x_2^P, x_5^P, x_6^P, x_9^P \}$ |
| Channel 1 ACTIVE (ON) State | 1712 | $f\{ x_3^P, x_4^P, x_7^P, x_8^P, x_{10}^P \}$ |
| Channel 2 INACTIVE (OFF) State | 1722 | $f\{ y_1^P, y_4^P, y_6^P, y_8^P \}$ |
| Channel 2 ACTIVE (ON) State | 1732 | $f\{ y_2^P, y_3^P, y_5^P, y_7^P, y_9^P, y_{10}^P \}$ |

Figure 17B

| Cycle 11 | Channel 1 (1764) | Channel 2 (1766) | 1702 | 1712 | 1722 | 1732 |
|---|---|---|---|---|---|---|
| | $x_{11}^P$ | $y_{11}^P$ | | | | |

Figure 17C

OFF State Update 1800

| Pixel *P* | | Channel 1 (1854) | Channel 2 (1856) |
|---|---|---|---|
| Cycle 11 | Base Call G | OFF $x_{11}^{P}$ | OFF $y_{11}^{P}$ |

Figure 18A

| Per-Channel State Calculation for Cycle 12 | *f* = AVG, MAX, MIN, EXPWEGAVG, MOVAVG, EXPMOVAVG, STDEV | |
|---|---|---|
| Channel 1 INACTIVE (OFF) State | 1802 | $f\{\underline{1702}, x_{11}^{P}\}$ |
| Channel 1 ACTIVE (ON) State | 1812 | 1712 (no change) |
| Channel 2 INACTIVE (OFF) State | 1822 | $f\{\underline{1722}, y_{11}^{P}\}$ |
| Channel 2 ACTIVE (ON) State | 1832 | 1732 (no change) |

Figure 18B

| Cycle 12 | Channel 1 (1864) | Channel 2 (1866) | | | | |
|---|---|---|---|---|---|---|
|  | $x_{12}^{P}$ | $y_{12}^{P}$ | 1802 | 1812 | 1822 | 1832 |

Figure 18C

ON and OFF State Update 2000

| Pixel P | | Channel 1 (2054) | Channel 2 (2056) |
|---|---|---|---|
| Cycle 13 | Base Call A | ON $x_{13}^P$ | OFF $y_{13}^P$ |

Figure 20A

| Per-Channel State Calculation for Cycle 14 | | $f$ = AVG, MAX, MIN, EXPWEGAVG, MOVAVG, EXPMOVAVG, STDEV |
|---|---|---|
| Channel 1 INACTIVE (OFF) State | 2002 | 1902 (no change) |
| Channel 1 ACTIVE (ON) State | 2012 | $f\{\ 1912,\ x_{13}^P\ \}$ |
| Channel 2 INACTIVE (OFF) State | 2022 | $f\{\ 1922,\ y_{13}^P\ \}$ |
| Channel 2 ACTIVE (ON) State | 2032 | 1932 (no change) |

Figure 20B

| Cycle 14 | Channel 1 (2064) | Channel 2 (2066) | | | | |
|---|---|---|---|---|---|---|
| | $x_{14}^P$ | $y_{14}^P$ | 2002 | 2014 | 2022 | 2032 |

Figure 20C

Per-Channel ON and OFF State Determination using Global MAX and MIN and Exponential Weighted Averages 2300

Pixel *P*

| | Channel 1 | Channel 2 |
|---|---|---|
| Cycle 1 | 171.4 | 619.2 |
| Cycle 2 | -150.2 | 5.9 |
| Cycle 3 | 1345.5 — 2374 | 821.3 |
| Cycle 4 | 933.3 | 540.1 |
| Cycle 5 | -63.8 — 2314 | -16.0 — 2318 |
| Cycle 6 | Global Max = 1345.5 — 2312<br>2322 — 1768 (attribution to active state)<br>Active State | Global Min = -16.0 — 2316<br>2326 — -90.1 (attribution to inactive state)<br>Inactive State |
| 2332 — | Exponential Weighted Average<br>2334 — [1345.5 * 0.12] + [1768 * 0.88] | Exponential Weighted Average — 2338<br>2336 — [-16.0 * 0.12] + [-90.1 * 0.88] |
| 2342 — | EWA 6 = 1717.3 — 2344 | EWA 6 = -81.208 — 2348 |
| Cycle 7 | 2352 — 5.9 (attribution to inactive state)<br>Inactive State<br>Global Min = -150.2 — 2314<br>2344 — (no change) | 2356 — 151.5 (attribution to active state)<br>Active State<br>Global Max = 821.3 — 2316<br>2346 — (no change) |
| 2342 — | Exponential Weighted Average<br>2364 — [-150.2 * 0.12] + [5.9 * 0.88]<br>EWA 6 = 1717.3<br>(no change) | Exponential Weighted Average — 2348<br>2366 — [821.3 * 0.12] + [151.5 * 0.88]<br>EWA 6 = -81.208<br>(no change) |
| 2372 — | EWA 7 = 1717.3 — 2374 | EWA 7 = 231.876 — 2378<br>2376 |

Figure 23

Base Call-Directed Per-Channel ON and OFF State Determination using Exponential Weighted Averages 2500

| Pixel P | Channel 1 | Channel 2 |
|---|---|---|
| Cycle 1 | 171.4 | 619.2 |
| Cycle 2 | -150.2 | 5.9 |
| Cycle 3 | 1345.5 — 2374 | 821.3 |
| Cycle 4 | 933.3 | 540.1 |
| Cycle 5 — 2312 | -63.8 | -16.0 |
| Cycle 6 | 2322 — 1788 (attribution to active state) | 2326 — -90.1 (attribution to inactive state) |
| Base Call A | 2504 — ON | 2506 — OFF |
| | Active State | Inactive State |
| 2332 | Exponential Weighted Average 2314 Global Min = (no change) 2344 | Exponential Weighted Average 2316 Global Max = 821.3 (no change) 2346 |
| 2342 | EWA 6 = 1717.3 [1345.5 * 0.12] + [1788 * 0.88] | EWA 6 = [ * 0.12] + [-90.1 * 0.88] = -81.208 — 2338 |
| Cycle 7 | 2372 — 5.9 | 2376 — 151.5 |
| Base Call C | 2514 — OFF | 2516 — ON |
| | Active State | Inactive State |
| 2512 | EWA 6 = 1717.3 (no change) 2342 | Exponential Weighted Average 2366 [821.3 * 0.12] + [151.5 * 0.88] = 231.876 |
| 2372 | EWA 7 = -12832 EWA 7 = 1717.3 2374 | EWA 7 = 231.876 — 2376 EWA 6 = -81.208 (no change) EWA 7 = -81.208 — 2378 |

Figure 25

Reduction in error rates of 30% have been demonstrated, compared to DeepRTA system without state
- 'compute' cost is negligible
- Hardware compatible

Inference Results on 25X Human Build

| | Number of reads | Error rate (R1, R2, avg) | SNP Recall | SNP Precision | SNP F1 | Indel Recall | Indel Precision | Indel F1 |
|---|---|---|---|---|---|---|---|---|
| RTA+Eq | 605,717,554 | 0.41,0.72,0.56 | 0.990142 | 0.998558 | 0.994332 | 0.971573 | 0.978162 | 0.974856 |
| DeepRTA (k14_1m) | 602,022,776 | 0.36,0.63,0.50 | 0.990882 | 0.998508 | 0.994680 | 0.976982 | 0.977608 | 0.977295 |
| DeepRTA_extrachannels (k14_1m_onoff_expavg) | 609,209,246 | 0.31,0.54,0.42 | 0.990985 | 0.99849 | 0.994724 | 0.977727 | 0.977748 | 0.977737 |

Figure 57

STATE-BASED BASE CALLING

PRIORITY APPLICATIONS

This application claims benefit of U.S. Provisional patent application Ser. No. 63/247,296, titled "State-Based Base Calling Per-Well State-Based Base Calling," filed on Sep. 22, 2021; and U.S. Provisional Patent Application No. 63/247,301, titled "Compressed State-Based Base Calling Sample Space-to-Pixel Space State Transformation for Base Calling," filed on Sep. 22, 2021. The priority applications are incorporated by reference for all purposes as if fully set forth herein.

FIELD OF THE TECHNOLOGY DISCLOSED

The technology disclosed relates to artificial intelligence type computers and digital data processing systems and corresponding data processing methods and products for emulation of intelligence (i.e., knowledge based systems, reasoning systems, and knowledge acquisition systems); and including systems for reasoning with uncertainty (e.g., fuzzy logic systems), adaptive systems, machine learning systems, and artificial neural networks. In particular, the technology disclosed relates to using deep neural networks such as deep convolution neural networks for analyzing data.

INCORPORATIONS

The following are incorporated by reference for all purposes as if fully set forth herein:

U.S. Nonprovisional Patent Application Ser. No. 17/944,948, titled "COMPRESSED STATE-BASED BASE CALLING," filed contemporaneously;

U.S. Nonprovisional patent application Ser. No. 17/308,035, titled "EQUALIZATION-BASED IMAGE PROCESSING AND SPATIAL CROSSTALK ATTENUATOR," filed 4 May 2021;

U.S. Provisional Patent Application No. 63/106,256, titled "SYSTEMS AND METHODS FOR PER-CLUSTER INTENSITY CORRECTION AND BASE CALLING," filed 27 Oct. 2020;

U.S. Nonprovisional patent application Ser. No. 15/909,437, titled "OPTICAL DISTORTION CORRECTION FOR IMAGED SAMPLES," filed on 1 Mar. 2018;

U.S. Nonprovisional patent application Ser. No. 16/825,987, titled "TRAINING DATA GENERATION FOR ARTIFICIAL INTELLIGENCE-BASED SEQUENCING," filed 20 Mar. 2020;

U.S. Nonprovisional patent application Ser. No. 16/825,991 titled "ARTIFICIAL INTELLIGENCE-BASED GENERATION OF SEQUENCING METADATA," filed 20 Mar. 2020;

U.S. Nonprovisional patent application Ser. No. 16/826,126, titled "ARTIFICIAL INTELLIGENCE-BASED BASE CALLING," filed 20 Mar. 2020;

U.S. Nonprovisional patent application Ser. No. 16/826,134, titled "ARTIFICIAL INTELLIGENCE-BASED QUALITY SCORING," filed 20 Mar. 2020;

U.S. Nonprovisional patent application Ser. No. 16/826,168, titled "ARTIFICIAL INTELLIGENCE-BASED SEQUENCING," filed 21 Mar. 2020;

U.S. Nonprovisional patent application Ser. No. 17/175,546, titled "ARTIFICIAL INTELLIGENCE-BASED BASE CALLING OF INDEX SEQUENCES," filed 12 Feb. 2021;

U.S. Nonprovisional patent application Ser. No. 17/180,542, titled "ARTIFICIAL INTELLIGENCE-BASED MANY-TO-MANY BASE CALLING," filed 19 Feb. 2021;

U.S. Nonprovisional patent application Ser. No. 17/176,151, titled "KNOWLEDGE DISTILLATION-BASED COMPRESSION OF ARTIFICIAL INTELLIGENCE-BASED BASE CALLER," filed 15 Feb. 2021;

U.S. Provisional Patent Application No. 63/072,032, titled "DETECTING AND FILTERING CLUSTERS BASED ON ARTIFICIAL INTELLIGENCE-PREDICTED BASE CALLS," filed 28 Aug. 2020;

U.S. Provisional Patent Application No. 63/161,880, titled "TILE LOCATION AND/OR CYCLE BASED WEIGHT SET SELECTION FOR BASE CALLING," filed 16 Mar. 2021;

U.S. Provisional Patent Application No. 63/161,896, titled "NEURAL NETWORK PARAMETER QUANTIZATION FOR BASE CALLING," filed 16 Mar. 2021;

U.S. Nonprovisional patent application Ser. No. 17/176,147, titled "HARDWARE EXECUTION AND ACCELERATION OF ARTIFICIAL INTELLIGENCE-BASED BASE CALLER," filed 15 Feb. 2021;

U.S. Provisional Patent Application No. 63/228,954, titled "BASE CALLING USING MULTIPLE BASE CALLER MODELS," filed 3 Aug. 2021;

U.S. Nonprovisional patent application Ser. No. 17/179,395, titled "DATA COMPRESSION FOR ARTIFICIAL INTELLIGENCE-BASED BASE CALLING," filed 18 Feb. 2021;

U.S. Nonprovisional patent application Ser. No. 17/180,480, titled "SPLIT ARCHITECTURE FOR ARTIFICIAL INTELLIGENCE-BASED BASE CALLER," filed 19 Feb. 2021;

U.S. Nonprovisional patent application Ser. No. 17/180,513, titled "BUS NETWORK FOR ARTIFICIAL INTELLIGENCE-BASED BASE CALLER," filed 19 Feb. 2021;

U.S. Provisional Patent Application No. 63/169,163, titled "ARTIFICIAL INTELLIGENCE-BASED BASE CALLER WITH CONTEXTUAL AWARENESS," filed 31 Mar. 2021;

U.S. Provisional Patent Application No. 63/216,419, titled "SELF-LEARNED BASE CALLER, TRAINED USING OLIGO SEQUENCES," filed 29 Jun. 2021;

U.S. Provisional Patent Application No. 63/216,404, titled "SELF-LEARNED BASE CALLER, TRAINED USING ORGANISM SEQUENCES," filed 29 Jun. 2021;

U.S. Provisional Patent Application No. 63/223,408, titled "SPECIALIST SIGNAL PROFILERS FOR BASE CALLING," filed 19 Jul. 2021;

U.S. Provisional Patent Application No. 63/226,707, titled "QUALITY SCORE CALIBRATION OF BASECALLING SYSTEMS," filed 28 Jul. 2021;

U.S. Provisional Patent Application No. 63/217,644, titled "EFFICIENT ARTIFICIAL INTELLIGENCE-BASED BASE CALLING OF INDEX SEQUENCES," filed 1 Jul. 2021;

U.S. Nonprovisional patent application Ser. No. 14/530,299, titled "IMAGE ANALYSIS USEFUL FOR PATTERNED OBJECTS," filed on 31 Oct. 2014;

U.S. Nonprovisional patent application Ser. No. 15/153,953, titled "METHODS AND SYSTEMS FOR ANALYZING IMAGE DATA," filed on 3 Dec. 2014;

U.S. Nonprovisional patent application Ser. No. 15/863,241, titled "PHASING CORRECTION," filed on 5 Jan. 2018;

U.S. Nonprovisional patent application Ser. No. 14/020,570, titled "CENTROID MARKERS FOR IMAGE ANALY- SIS OF HIGH DENSITY CLUSTERS IN COMPLEX POLYNUCLEOTIDE SEQUENCING," filed on 6 Sep. 2013;

U.S. Nonprovisional patent application Ser. No. 12/565,341, titled "METHOD AND SYSTEM FOR DETERMINING THE ACCURACY OF DNA BASE IDENTIFICATIONS," filed on 23 Sep. 2009;

U.S. Nonprovisional patent application Ser. No. 12/295,337, titled "SYSTEMS AND DEVICES FOR SEQUENCE BY SYNTHESIS ANALYSIS," filed on 30 Mar. 2007;

U.S. Nonprovisional patent application Ser. No. 12/020,739, titled "IMAGE DATA EFFICIENT GENETIC SEQUENCING METHOD AND SYSTEM," filed on 28 Jan. 2008;

U.S. Nonprovisional patent application Ser. No. 13/833,619, titled "BIOSENSORS FOR BIOLOGICAL OR CHEMICAL ANALYSIS AND SYSTEMS AND METHODS FOR SAME," filed on 15 Mar. 2013;

U.S. Nonprovisional patent application Ser. No. 15/175,489, titled "BIOSENSORS FOR BIOLOGICAL OR CHEMICAL ANALYSIS AND METHODS OF MANUFACTURING THE SAME," filed on 7 Jun. 2016;

U.S. Nonprovisional patent application Ser. No. 13/882,088, titled "MICRODEVICES AND BIOSENSOR CARTRIDGES FOR BIOLOGICAL OR CHEMICAL ANALYSIS AND SYSTEMS AND METHODS FOR THE SAME," filed on 26 Apr. 2013;

U.S. Nonprovisional patent application Ser. No. 13/624,200, titled "METHODS AND COMPOSITIONS FOR NUCLEIC ACID SEQUENCING," filed on 21 Sep. 2012;

U.S. Nonprovisional patent application Ser. No. 13/006,206, titled "DATA PROCESSING SYSTEM AND METHODS," filed on 13 Jan. 2011;

U.S. Nonprovisional patent application Ser. No. 15/936,365, titled "DETECTION APPARATUS HAVING A MICROFLUOROMETER, A FLUIDIC SYSTEM, AND A FLOW CELL LATCH CLAMP MODULE," filed on 26 Mar. 2018;

U.S. Nonprovisional patent application Ser. No. 16/567,224, titled "FLOW CELLS AND METHODS RELATED TO SAME," filed on 11 Sep. 2019;

U.S. Nonprovisional patent application Ser. No. 16/439,635, titled "DEVICE FOR LUMINESCENT IMAGING," filed on 12 Jun. 2019;

U.S. Nonprovisional patent application Ser. No. 15/594,413, titled "INTEGRATED OPTOELECTRONIC READ HEAD AND FLUIDIC CARTRIDGE USEFUL FOR NUCLEIC ACID SEQUENCING," filed on 12 May 2017;

U.S. Nonprovisional patent application Ser. No. 16/351,193, titled "ILLUMINATION FOR FLUORESCENCE IMAGING USING OBJECTIVE LENS," filed on 12 Mar. 2019;

U.S. Nonprovisional patent application Ser. No. 12/638,770, titled "DYNAMIC AUTOFOCUS METHOD AND SYSTEM FOR ASSAY IMAGER," filed on 15 Dec. 2009; and U.S. Nonprovisional patent application Ser. No. 13/783,043, titled "KINETIC EXCLUSION AMPLIFICATION OF NUCLEIC ACID LIBRARIES," filed on 1 Mar. 2013.

BACKGROUND

The subject matter discussed in this section should not be assumed to be prior art merely as a result of its mention in this section. Similarly, a problem mentioned in this section or associated with the subject matter provided as background should not be assumed to have been previously recognized in the prior art. The subject matter in this section merely represents different approaches, which in and of themselves can also correspond to implementations of the claimed technology.

The rapid improvement in computation capability has made deep convolution neural networks (CNNs) a great success in recent years on many computer vision tasks with significantly improved accuracy. During the inference phase, many applications demand low latency processing of one image with strict power consumption requirement, which reduces the efficiency of graphics processing unit (GPU) and other general-purpose platform, bringing opportunities for specific acceleration hardware, e.g., field programmable gate array (FPGA), by customizing the digital circuit specific for the deep learning algorithm inference. However, deploying CNNs on portable and embedded systems is still challenging due to large data volume, intensive computation, varying algorithm structures, and frequent memory accesses.

As convolution contributes most operations in CNNs, the convolution acceleration scheme significantly affects the efficiency and performance of a hardware CNN accelerator. Convolution involves multiply and accumulate (MAC) operations with four levels of loops that slide along kernel and feature maps. The first loop level computes the MAC of pixels within a kernel window. The second loop level accumulates the sum of products of the MAC across different input feature maps. After finishing the first and second loop levels, a final output pixel is obtained by adding the bias. The third loop level slides the kernel window within an input feature map. The fourth loop level generates different output feature maps.

FPGAs have gained increasing interests and popularity in particular to accelerate the inference tasks, due to their (1) high degree of reconfigurability, (2) faster development time compared to application specific integrated circuits (ASICs) to catch up with the rapid evolving of CNNs, (3) good performance, and (4) superior energy efficiency compared to GPUs. The high performance and efficiency of an FPGA can be realized by synthesizing a circuit that is customized for a specific computation to directly process billions of operations with the customized memory systems. For instance, hundreds to thousands of digital signal processing (DSP) blocks on modern FPGAs support the core convolution operation, e.g., multiplication and addition, with high parallelism. Dedicated data buffers between external on-chip memory and on-chip processing engines (PEs) can be designed to realize the preferred dataflow by configuring tens of Mbyte on-chip block random access memories (BRAM) on the FPGA chip.

Efficient dataflow and hardware architecture of CNN acceleration are desired to minimize data communication while maximizing resource utilization to achieve high performance. An opportunity arises to design methodology and framework to accelerate the inference process of various CNN algorithms on acceleration hardware with high performance, efficiency, and flexibility.

The key feature of next generation sequencing (NGS) technologies is parallelization and the main mechanism underlying several sequencing platforms is sequencing-by-synthesis (SBS). Briefly, tens to hundreds of millions of random DNA fragments get sequenced simultaneously by sequentially building up complementary bases of single-stranded DNA templates and by capturing the synthesis information in a series of raw images of fluorescence.

Extracting the actual sequence information (i.e., strings in {A, C, G, T}) from image data involves two computational tasks, namely image analysis and base calling. The primary function of image analysis is to translate image data into fluorescence intensity data for each DNA fragment, while the goal of base calling is to infer sequence information from the obtained intensity data.

There are a number of stochastic and contextual sources of variation that can reduce base calling accuracy. For example, k-mer biases in base calling are affected by GC content of the sequenced genome. Base callers can exhibit bias when applied to GC-rich regions of DNA, primarily due to reduced sequence complexity but also as a result of polymerase chain reaction (PCR) bias during amplification steps.

The accuracy of base calling is of essential importance for various downstream applications including sequence assembly, SNP calling, and genotype calling. Improving base calling accuracy can enable achieving desired performance of downstream applications with smaller sequencing coverage, which translates to a reduction in the sequencing cost.

Training neural networks for base calling requires large amounts of computer memory, which increases exponentially with increasing image size and numerosity. Computer memory becomes a limiting factor because the backpropagation algorithm for optimizing deep neural networks requires the storage of intermediate activations. Since the size and numerosity of these intermediate activations increases proportionate to the input size and numerosity, memory quickly fills up with larger and more images.

Base callers that use neural networks, for example, the ones disclosed in commonly owned patent application Ser. Nos. 16/826,126; 16/826,134; 16/826,168; 17/175,546; 17/180,542; 17/176,151; 63/072,032; 63/161,880; 63/161,896; 17/176,147; 63/228,954; 17/179,395; 17/180,480; 17/180,513; 63/169,163; and 63/217,644, make a base call prediction using image data for a sliding window of sequencing cycles, according to one implementation. Increasing the size of the sliding window to include image data from more sequencing cycles would increase complexity of the neural networks and also add additional burden on available compute and memory.

An opportunity arises to configure base calling operations to incorporate contextual information from a multitude of past sequencing cycles. More accurate base calling with reduced error rates, particularly towards attenuating k-mer bias, may result.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

The color drawings also may be available in PAIR via the Supplemental Content tab. In the drawings, like reference characters generally refer to like parts throughout the different views. Also, the drawings are not necessarily to scale, with an emphasis instead generally being placed upon illustrating the principles of the technology disclosed. In the following description, various implementations of the technology disclosed are described with reference to the following drawings, in which:

FIG. 5 illustrates one implementation of generating per-channel states for pixels in sequencing images processed as input for base calling.

FIG. 10 illustrates one implementation of generating per-channel AVG (average) states for pixels in sequencing images processed as input for base calling.

FIGS. 17A, 17B, and 17C illustrate base call-directed ON and OFF state generation for a current sequencing cycle eleven (Cycle 11).

FIGS. 18A, 18B, and 18C expand on FIGS. 17A, 17B, and 17C and illustrate how the OFF state is updated at a next sequencing cycle twelve (Cycle 12).

FIGS. 20A, 20B, and 20C further expand on FIGS. 19A, 19B, and 19C and illustrate how both the ON and OFF states are updated at a yet next sequencing cycle fourteen (Cycle 14).

FIG. 23 depicts an example of generating per-channel state information for base calling using exponential weighted averaging.

FIG. 25 depicts an example of generating per-channel state information for base calling using exponential weighted averaging that is directed by previously called bases.

FIG. 57 compares base calling performance of RTA with the Equalizer implementation (RTA+Eq), the DeepRTA without state information (DeepRTA (k14_1m)), and the disclosed DeepRTA with State (DeepRTA_extrachannels (k14_1,_onoff_expavg)) from the perspective of secondary analysis tasks and metrics like number of called reads, read mismatch error rate for Read 1 and Read 1 and their average, single nucleotide polymorphism (SNP) recall, SNO precision, SNP calling accuracy (F1 score), insertion/deletion (Indel) recall, Indel precision, and Indel calling accuracy (F1 score).

DETAILED DESCRIPTION

Figure 1:
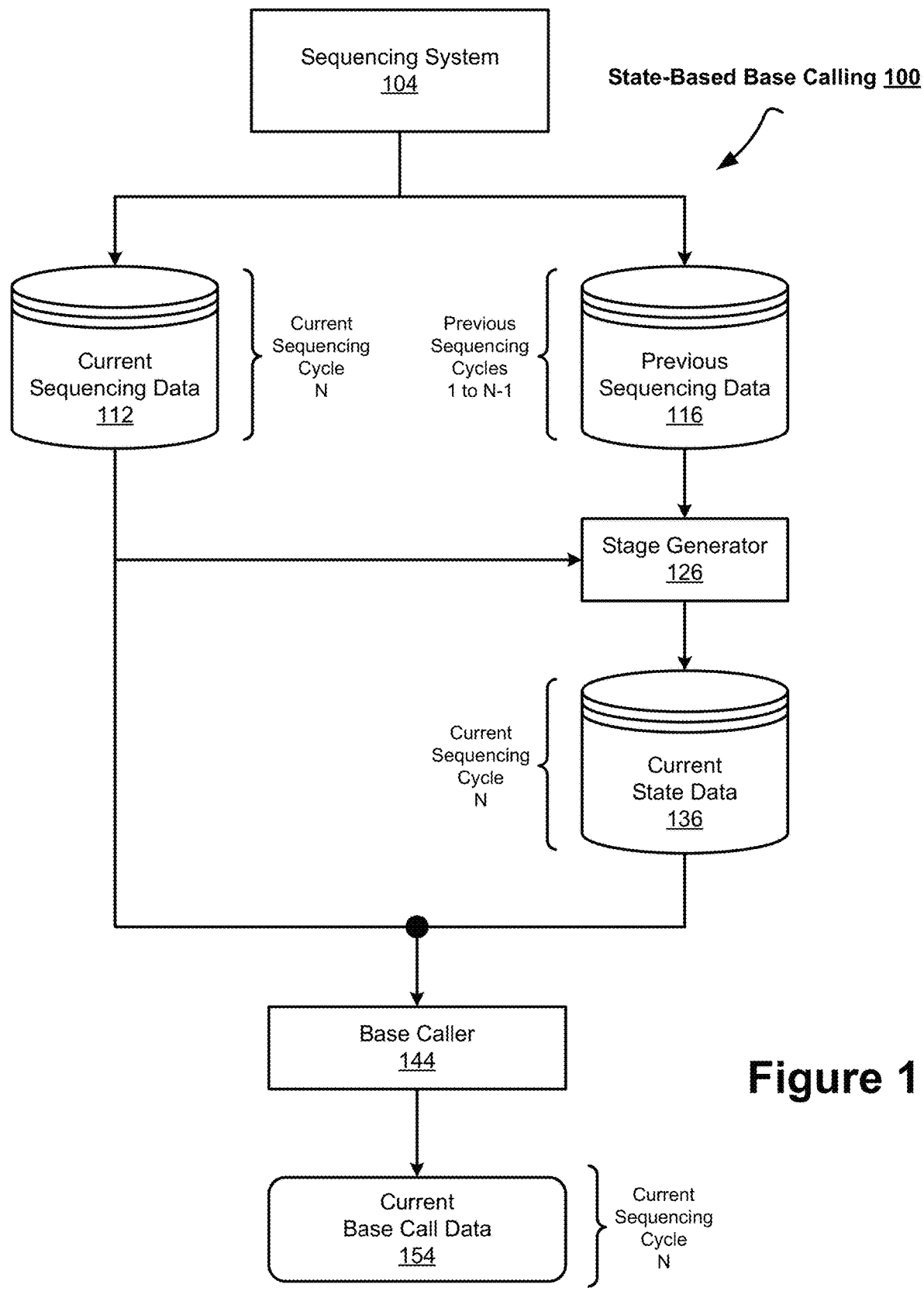
FIG. 1 is a high-level diagram of the disclosed state-based base calling.

The following discussion is presented to enable any person skilled in the art to make and use the technology disclosed and is provided in the context of a particular application and its requirements. Various modifications to the disclosed implementations will be readily apparent to those skilled in the art, and the general principles defined herein can be applied to other implementations and applications without departing from the spirit and scope of the technology disclosed. Thus, the technology disclosed is not intended to be limited to the implementations shown but is to be accorded the widest scope consistent with the principles and features disclosed herein.

The detailed description of various implementations will be better understood when read in conjunction with the appended drawings. To the extent that the figures illustrate diagrams of the functional blocks of the various implementations, the functional blocks are not necessarily indicative of the division between hardware circuitry. Thus, for example, one or more of the functional blocks (e.g., modules, processors, or memories) may be implemented in a single piece of hardware (e.g., a general purpose signal processor or a block of random access memory, hard disk, or the like) or multiple pieces of hardware. Similarly, the programs may be stand-alone programs, may be incorporated as subroutines in an operating system, may be functions in an installed software package, and the like. It should be understood that the various implementations are not limited to the arrangements and instrumentality shown in the drawings.

The processing engines and databases of the figures, designated as modules, can be implemented in hardware or software, and need not be divided up in precisely the same blocks as shown in the figures. Some of the modules can also be implemented on different processors, computers, or servers, or spread among a number of different processors, computers, or servers. In addition, it will be appreciated that some of the modules can be combined, operated in parallel or in a different sequence than that shown in the figures without affecting the functions achieved. The modules in the figures can also be thought of as flowchart steps in a method. A module also need not necessarily have all its code disposed contiguously in memory; some parts of the code can be separated from other parts of the code with code from other modules or other functions disposed in between.

Introduction

The technology disclosed relates to state-based base calling. In particular, the technology disclosed relates to incorporating state information about data from previous sequencing cycles into the analysis of data from a current sequencing cycle when generating a base call for the current sequencing cycle. For example, when generating a base call for an Nth sequencing cycle, the technology disclosed can incorporate into the base calling logic state information about data from sequencing cycles 1 to N–1.

The following discussion describes various implementations of the disclosed state-based base calling. The implementations vary by virtue of different data and processing aspects. For example, different "methods" or "logics" of generating state information yield different types of states. Also, "the thing" whose historic values are tracked for state generation can vary from implementation to implementation. Furthermore, once generated, "when," "where," and "how" the state information is processed for base calling give rise to varied implementations of the technology disclosed.

State-Based Base Calling

FIG. 1 is a high-level diagram of the disclosed state-based base calling 100. Base calling is the process of determining the nucleotide composition of a sequence. In one implementation, base calling involves analyzing image data, i.e., sequencing images, produced during a sequencing run (or sequencing reaction) carried out by a sequencing system such as Illumina's iSeq, HiSeqX, HiSeq 3000, HiSeq 4000, HiSeq 2500, NovaSeq 6000, NextSeq 550, NextSeq 1000, NextSeq 2000, NextSeqDx, MiSeq, and MiSeqDx. In other implementations, base calling can involve inferring sequence reads from non-image sequencing data.

Sequencing system 104 can be used for the sequencing of nucleic acids. Applicable techniques include those where nucleic acids are attached at fixed locations in an array (e.g., the wells of a flow cell) and the array is imaged repeatedly. In such implementations, the sequencing system 104 can obtain images in two different color channels, which can be used to distinguish a particular nucleotide base type from another. More particularly, the sequencing system 104 can implement a process referred to as "base calling," which generally refers to a process of a determining a base call (e.g., adenine (A), cytosine (C), guanine (G), or thymine (T)) for a given spot location of an image at an imaging cycle. During two-channel base calling, for example, image data extracted from two images can be used to determine the presence of one of four base types by encoding base identity as a combination of the intensities of the two images. For a given spot or location in each of the two images, base identity can be determined based on whether the combination of signal identities is [on, on], [on, off], [off, on], or [off, off].

Output data from the sequencing system 104 can be communicated to a real time analysis module (not shown). Real time analysis module, in various implementations, executes computer readable instructions for analyzing the image data (e.g., image quality scoring, base calling, etc.), reporting or displaying the characteristics of the beam (e.g., focus, shape, intensity, power, brightness, position) to a graphical user interface (GUI), etc. These operations can be performed in real-time during imaging cycles to minimize downstream analysis time and provide real time feedback and troubleshooting during an imaging run. In implementations, real time analysis module can be a computing device that is communicatively coupled to and controls an imaging sub-system of the sequencing system 104.

The following discussion outlines how the sequencing images are generated and what they depict, in accordance with one implementation.

In some implementations, base calling decodes the intensity data encoded in the sequencing images into nucleotide sequences. In one implementation, the Illumina sequencing platforms employ cyclic reversible termination (CRT) chemistry for base calling. The process relies on growing nascent strands complementary to template strands with fluorescently-labeled nucleotides, while tracking the emitted signal of each newly added nucleotide. The fluorescently-labeled nucleotides have a 3' removable block that anchors a fluorophore signal of the nucleotide type.

Sequencing occurs in repetitive cycles, each comprising three steps: (a) extension of a nascent strand by adding the fluorescently-labeled nucleotide; (b) excitation of the fluorophore using one or more lasers of an optical sub-system of the sequencing system 104 and imaging through different filters of the optical sub-system, yielding the sequencing images; and (c) cleavage of the fluorophore and removal of the 3' block in preparation for the next sequencing cycle. Incorporation and imaging cycles are repeated up to a designated number of sequencing cycles, defining the read length. Using this approach, each cycle interrogates a new position along the template strands.

The tremendous power of the Illumina sequencers stems from their ability to simultaneously execute and sense millions or even billions of clusters (also called "clusters") undergoing CRT reactions. A cluster comprises approximately one thousand identical copies of a template strand, though clusters vary in size and shape. The clusters are grown from the template strand, prior to the sequencing run, by bridge amplification or exclusion amplification of the input library. The purpose of the amplification and cluster growth is to increase the intensity of the emitted signal since the imaging device cannot reliably sense fluorophore signal of a single strand. However, the physical distance of the strands within a cluster is small, so the imaging device perceives the cluster of strands as a single spot.

Sequencing occurs in a flow cell (or biosensor)—a small glass slide that holds the input strands. The flow cell is connected to the optical system, which comprises microscopic imaging, excitation lasers, and fluorescence filters. The flow cell comprises multiple chambers called lanes. The lanes are physically separated from each other and may contain different tagged sequencing libraries, distinguishable without sample cross contamination. In some implementations, the flow cell comprises a patterned surface. A "patterned surface" refers to an arrangement of different regions in or on an exposed layer of a solid support.

The imaging device of the sequencing system 104 (e.g., a solid-state imager such as a charge-coupled device (CCD) or a complementary metal-oxide-semiconductor (CMOS) sensor) takes snapshots at multiple locations along the lanes in a series of non-overlapping regions called tiles. For example, there can be sixty four or ninety six tiles per lane. A tile holds hundreds of thousands to millions of clusters.

The output of the sequencing run is the sequencing images. Sequencing images depict intensity emissions of the clusters and their surrounding background using a grid (or array) of pixelated units (e.g., pixels, superpixels, subpixels). The intensity emissions are stored as intensity values of the pixelated units. The sequencing images have dimensions w x h of the grid of pixelated units, where w (width) and h (height) are any numbers ranging from 1 and 100,000 (e.g., 115×115, 200×200, 1800×2000, 2200×25000, 2800×3600, 4000×400). In some implementations, w and h are the same. In other implementations, w and h are different. The sequencing images depict intensity emissions generated as a result of nucleotide incorporation in the nucleotide sequences during the sequencing run. The intensity emissions are from associated clusters and their surrounding background.

A data flow logic (not shown) provides the sequencing images to a base caller 144 for base calling, in accordance with one implementation. The base caller 144 accesses the sequencing images on a patch-by-patch basis (or a tile-by-tile basis), in accordance with one implementation. Each of the patches is a sub-grid (or sub-array) of pixelated units in the grid of pixelated units that forms the sequencing images. The patches have dimensions q×r of the sub-grid of pixelated units, where q (width) and r (height) are any numbers ranging from 1 and 10000 (e.g., 3×3, 5×5, 7×7, 10×10, 15×15, 25×25, 64×64, 78×78, 115 x 115). In some implementations, q and r are the same. In other implementations, q and r are different. In some implementations, the patches extracted from a sequencing image are of the same size. In other implementations, the patches are of different sizes. In some implementations, the patches can have overlapping pixelated units (e.g., on the edges).

Sequencing produces m sequencing images per sequencing cycle for corresponding m image channels, in accordance with some implementations. That is, each of the sequencing images has one or more image (or intensity) channels (analogous to the red, green, blue (RGB) channels of a color image). In one implementation, each image channel corresponds to one of a plurality of filter wavelength bands. In another implementation, each image channel corresponds to one of a plurality of imaging events at a sequencing cycle. In yet another implementation, each image channel corresponds to a combination of illumination with a specific laser and imaging through a specific optical filter. The image patches are tiled (or accessed) from each of the m image channels for a particular sequencing cycle. In different implementations such as 4-, 2-, and 1-channel chemistries, m is 4 or 2. In other implementations, m is 1, 3, or greater than 4. In other implementations, the images can be in blue and violet color channels instead of or in addition to the red and green color channels.

Consider, for example, that a sequencing run is implemented using two different image channels: a blue channel and a green channel. Then, at each sequencing cycle, the sequencing run produces a blue image and a green image.

This way, for a series of k sequencing cycles of the sequencing run, a sequence of k pairs of blue and green images is produced as output and stored as the sequencing images. Accordingly, a sequence of k pairs of blue and green image patches is generated for the patch-level processing by the base caller 144.

The sequencing system 104 can also generate non-image sequencing data, in accordance with other implementations. In one implementation, the sequencing data can be based on pH changes induced by the release of hydrogen ions during molecule extension. The pH changes can be detected and converted to a voltage change that is proportional to the number of bases incorporated. In yet another implementation, the sequencing data can be constructed, for example, from nanopore sensing that uses biosensors to measure the disruption in current as a cluster passes through a nanopore or near its aperture while determining the identity of the base. In one implementation, the nanopore-based sequencing can be based on the following concept: pass a single strand of DNA (or RNA) through a membrane via a nanopore and apply a voltage difference across the membrane. The nucleotides present in the pore can affect the pore's electrical resistance, so current measurements over time can indicate the sequence of DNA bases passing through the pore. This electrical current signal (the 'squiggle' due to its appearance when plotted) is the raw data gathered by a sequencer. These measurements can be stored as 16-bit integer data acquisition (DAC) values, taken at 4 kHz frequency (for example). With a DNA strand velocity of ~450 base pairs per second, this can give approximately nine raw observations per base on average. This signal can then be processed to identify breaks in the open pore signal corresponding to individual reads. These stretches of raw signal can be base called—the process of converting DAC values into a sequence of DNA bases. In some implementations, the sequencing data can comprise normalized or scaled DAC values.

Current sequencing data 112 includes sequencing data generated by the sequencing data 104 for a current sequencing cycle of a sequencing run. In FIG. 1, the current sequencing cycle is identified as the "N" sequencing cycle.

Previous sequencing data 116 includes sequencing data generated by the sequencing data 104 for one or more previous sequencing cycles of the sequencing run. The previous sequencing cycles precede the current sequencing cycle. In FIG. 1, the previous sequencing cycles are identified as the "i to N−1" sequencing cycles. In other implementations, the previous sequencing data 116 includes sequencing data for a subset of the 1 to N−1 sequencing cycles.

State generator 126 uses the current sequencing data 112 and the previous sequencing data 116 to generate current state data 136 for the current sequencing cycle. The state generator 126 can be a value or function that is applied to the sequencing data to generate a desired result. The state generator 126 can be applied to the sequencing data by any of a variety of mathematical manipulations including, but not limited to addition, subtraction, division, multiplication, or a combination thereof. The state generator 126 can be a mathematical formula, logic function, computer implemented algorithm, or the like. The sequencing data can be image data, electrical data, or a combination thereof.

In one implementation, the state generator 126 generates the current state data 136 by accumulating summary statistics of the current sequencing data 112 and the previous sequencing data 116. Examples of the summary statistics include maximum value, minimum value, average (mean), exponential weighted average, moving (running) average, exponential moving average, mode, standard deviation, variance, skewness, kurtosis, percentiles, and entropy. In other implementations, the state generator 126 determines secondary statistics based on the summary statistics. Examples of the secondary statistics include deltas, sums, series of maximum values, series of minimum values, minimum of the maximum values in the series, and maximum of minimum values in the series.

The base caller 144 generates current base call data 154 for the current sequencing cycle in response to processing the current sequencing data 112 and the current state data 136. The current base call data 154 can include base calls for one or more clusters. In some implementations, the current sequencing data 112 and the current state data 136 are combined prior to processing by the base caller 144. The combination can be brought about by, for example, summing operations, element-wise multiplication operations, element-wise multiplication and summation (convolution) operations, and concatenation operations.

Examples of the base caller 144 include different base calling procedures available for the Illumina platform, such as Real-Time Analysis (RTA), BlindCall, freelbis, Softy, AYB, OnlineCall, BM-BC, ParticleCall, TotalReCaller, naiveBayesCall, Srfim, BayesCall, Ibis, Rolexa, Alta-Cyclic, and Bustard. Examples of the base caller 144 also include Illumina's neural network-based offerings, such as the ones disclosed in commonly owned patent application Ser. Nos. 16/825,987; 16/825,991; 16/826,126; 16/826,134; 16/826,134; 16/826,168; 17/175,546; 17/180,542; 17/176,151; 63/072,032; 63/161,880; 63/161,896; 17/176,147; 63/228,954; 17/179,395; 17/180,480; 17/180,513; 63/169,163; and 63/217,644, collectively referred to herein as "DeepRTA" or "Deep Learning Primary Analysis." Yet other examples of the base caller 144 include different base calling procedures available for the Oxford Nanopore Technologies (ONT), such as Metrichor, Nanocall, DeepNano, Nanonet, Scrappie, Albacore, Guppy, Basecrawller, Chiron, Halcyon, MinCall, SACall, Causalcall, and WaveNano.

Pixelated State Data

Figure 2:
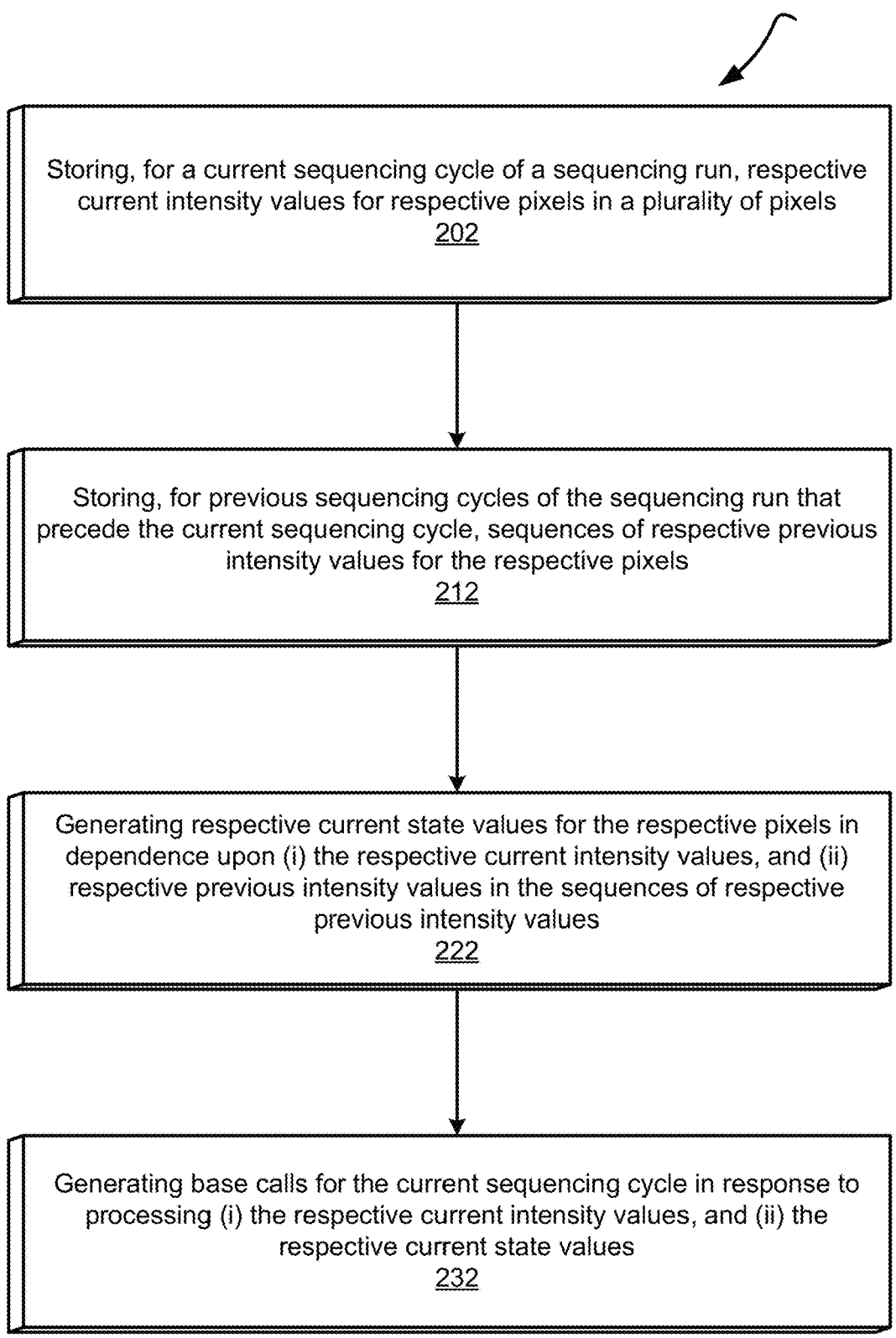
FIG. 2 illustrates one implementation of executing a base calling operation using state information generated based on historic intensity values of pixels in the sequencing images.

FIG. 2 illustrates one implementation of executing a base calling operation using state information 200 generated based on historic intensity values of pixels in the sequencing images.

At action 202, a memory stores (e.g., in the datastore 112), for a current sequencing cycle of a sequencing run, respective current intensity values for respective pixels in a plurality of pixels. At action 212, the memory stores (e.g., in the datastore 116), for one or more previous sequencing cycles of the sequencing run that precede the current sequencing cycle, sequences of respective previous intensity values for the respective pixels. In one implementation, respective intensity values for the respective pixels are each characterized by channel-specific intensity values for a plurality of channels. In one implementation, wherein the channels correspond to a combination of illumination with a specific laser and imaging through a specific optical filter. In another implementation, the channels correspond to filter wavelength bands. In yet another implementation, the channels correspond to imaging events at a sequencing cycle.

At action 222, the state generator 126, having access to the memory, generates respective current state values for the respective pixels in dependence upon (i) the respective current intensity values, and (ii) respective previous intensity values in the sequences of respective previous intensity values. Also, the state generator 126 stores the respective current state values in the memory. In some implementations, respective state values for the respective pixels are each characterized by channel-specific state values for the plurality of channels. In one implementation, the respective current state values are pixel-wise encoded with the respective current intensity values. In some implementations, channel-specific state values for a subset of channels in the plurality of channels are pixel-wise encoded with the respective current intensity values. In some implementations, the channel-specific state values are averaged across channels in the plurality of channels to generate respective pan-channel current state values. In one implementation, the respective pan-channel current state values are pixel-wise encoded with the respective current intensity value.

In some implementations, the pixel-wise encoding includes pixel-wise concatenation. In other implementations, the pixel-wise encoding includes pixel-wise summing. In yet other implementations, the pixel-wise encoding includes element-wise multiplication. In yet other implementations, the pixel-wise encoding includes element-wise multiplication and summation (convolution).

In one implementation, the respective state values are configured to characterize historic intensity patterns of the respective pixels. In another implementation, the historic intensity patterns are configured to compensate for losses in base calling accuracy of the base caller 144. In yet another implementation, the historic intensity patterns are configured to compensate for losses in base calling accuracy of the base caller 144 when base calling bases for k-mers. In yet another implementation, the respective state values are configured to discern respective signal profiles of the clusters.

In one implementation, the respective current state values are respective current average intensities determined for the respective pixels at the current sequencing cycle from (i) the respective previous intensity values, and (ii) the respective current intensity values. In some implementations, the respective current average intensities are each characterized by channel-specific current average intensities.

In another implementation, the respective current state values are respective current maximum intensities determined for the respective pixels at the current sequencing cycle from (i) the respective previous intensity values, and (ii) the respective current intensity values. In some implementations, the respective current maximum intensities are each characterized by channel-specific current maximum intensities.

In yet another implementation, the respective current state values are respective current maximum intensities determined for the respective pixels at the current sequencing cycle from (i) the respective previous intensity values, and (ii) the respective current intensity values. In some implementations, the respective current maximum intensities are each characterized by channel-specific current maximum intensities.

In yet another implementation, the respective current state values are respective current minimum intensities determined for the respective pixels at the current sequencing cycle from (i) the respective previous intensity values, and (ii) the respective current intensity values. In some implementations, the respective current minimum intensities are each characterized by channel-specific current minimum intensities.

In yet another implementation, the respective current state values are respective current exponentially weighted average intensities determined for the respective pixels at the current sequencing cycle from (i) the respective previous intensity values, and (ii) the respective current intensity values. In some implementations, the respective current exponentially weighted average intensities are determined based on weighting recent sequencing cycles more than earlier sequencing cycles. In other implementations, the respective current exponentially weighted average intensities are each characterized by channel-specific current exponentially weighted average intensities.

In yet another implementation, the respective current state values are respective current moving average intensities determined for the respective pixels at the current sequencing cycle from (i) the respective current intensity values, and (ii) a rolling subset of the respective previous intensity values. In some implementations, the respective current moving average intensities are each characterized by channel-specific current moving average intensities.

In some implementations, each of the respective current intensity values is attributed to an active state bucket or an inactive state bucket based on comparison of the respective current intensity values to respective current active state intensities and respective current inactive state intensities. In one implementation, the respective current active state intensities are respective current global maximum intensities determined for the respective pixels at the current sequencing cycle from (i) the respective previous intensity values. In some implementations, the respective current global maximum intensities are each characterized by channel-specific current global maximum intensities.

In one implementation, the respective current inactive state intensities are respective current global minimum intensities determined for the respective pixels at the current sequencing cycle from (i) the respective previous intensity values. In some implementations, the respective current global minimum intensities are each characterized by channel-specific current global minimum intensities.

In one implementation, the respective current state values further include respective current active state values and respective current inactive state values generated for the respective pixels at the current sequencing cycle. In some implementations, the respective current active state values are each characterized by channel-specific current active state values. In other implementations, the respective current inactive state values are each characterized by channel-specific current inactive state values.

In one implementation, a current active state value for a pixel in a subject channel is determined at the current sequencing cycle from (i) a current intensity value for the pixel in the subject channel that is detected and attributed to the active state bucket at the current sequencing cycle, and (ii) previous intensity values for the pixel in the subject channel that are detected at the previous sequencing cycles.

In some implementations, the current intensity value is attributed to the active state bucket based on comparison of the current intensity value to a global maximum value and a global minimum value determined from the previous intensity values in the subject channel. In other implementations, the current intensity value is attributed to the active state bucket based on comparison of the current intensity value to a previous active state value and a previous inactive state value determined at a preceding sequencing cycle in the subject channel. In one implementation, the current active state value is an exponentially weighted average determined from the current intensity value and the previous intensity values. In another implementation, the current active state value is an average determined from the current intensity value and the previous intensity values. In yet another implementation, the current active state value is a moving average determined from the current intensity value and a rolling subset of the previous intensity values. In yet another implementation, the current active state value is a minimum value determined from the current intensity value and the previous intensity values. In yet another implementation, the current active state value is a maximum value determined from the current intensity value and the previous intensity values.

In one implementation, the current active state value is carried from the preceding sequencing cycle and not redetermined at the current sequencing cycle when the current intensity value is attributed to the inactive state bucket at the current sequencing cycle.

In one implementation, a current inactive state value for the pixel in the subject channel is determined at the current sequencing cycle from (i) a current intensity value for the pixel in the subject channel that is detected and attributed to the inactive state bucket at the current sequencing cycle, and (ii) previous intensity values for the pixel in the subject channel that are detected at the previous sequencing cycles.

In some implementations, the current intensity value is attributed to the inactive state bucket based on comparison of the current intensity value to a global maximum value and a global minimum value determined from the previous intensity values in the subject channel. In other implementations, the current intensity value is attributed to the inactive state bucket based on comparison of the current intensity value to a previous inactive state value and a previous inactive state value determined at a preceding sequencing cycle in the subject channel.

In some implementations, the current intensity value is attributed to the inactive state bucket when the current intensity value is closer to the global minimum value than to the global maximum value. In some implementations, the current intensity value is attributed to the active state bucket when the current intensity value is closer to the global maximum value than to the global minimum value.

In one implementation, the current inactive state value is an exponentially weighted average determined from the current intensity value and the previous intensity values. In another implementation, the current inactive state value is an average determined from the current intensity value and the previous intensity values. In yet another implementation, the current inactive state value is a moving average determined from the current intensity value and a rolling subset of the previous intensity values. In yet another implementation, the current inactive state value is a minimum value determined from the current intensity value and the previous intensity values. In yet another implementation, the current inactive state value is a maximum value determined from the current intensity value and the previous intensity values.

In some implementations, the current inactive state value is carried from the preceding sequencing cycle and not redetermined at the current sequencing cycle when the current intensity value is attributed to the active state bucket at the current sequencing cycle.

At action 232, the base caller 144, having access to the memory, generates base calls for the current sequencing cycle in response to processing (i) the respective current intensity values, and (ii) the respective current state values. In some implementations, the base calls for the current sequencing cycle include base calls for one or more clusters for which the respective current signal values and the respective previous signal values are detected.

In one implementation, the base caller 144 is a neural network. In some implementations, the neural network is a convolutional neural network. In one implementation, the convolutional neural network includes a plurality of spatial convolution layers and a plurality of temporal convolution layers.

In some implementations, the base caller 144 is trained using sequencing images generated offline for an already-executed sequencing run. In one implementation, the respective state values for the respective pixels are calculated offline for each sequencing cycle of the already-executed sequencing run in advance of base calling by the base caller 144. In one implementation, the base caller 144 is trained to use the respective state values to compensate for losses in base calling accuracy.

In some implementations, the respective current state values are iteratively generated at each sequencing cycle of the sequencing run. In some implementations, the memory is further configured to store, for next sequencing cycles of the sequencing run, sequences of respective next intensity values for the respective pixels. In some implementations, the base caller 144 is further configured to generate the base calls for the current sequencing cycle in response to processing (i) the respective current intensity values, (ii) respective previous intensity values in the sequences of respective previous intensity values for one or more of the previous sequencing cycles, (iii) respective next intensity values in the sequences of respective next intensity values for one or more of the next sequencing cycles, and (iv) the respective state values. In some implementations, the respective state values are pixel-wise encoded with respective previous intensity values and the respective next intensity values.

Per-Pixel States

Figure 3:
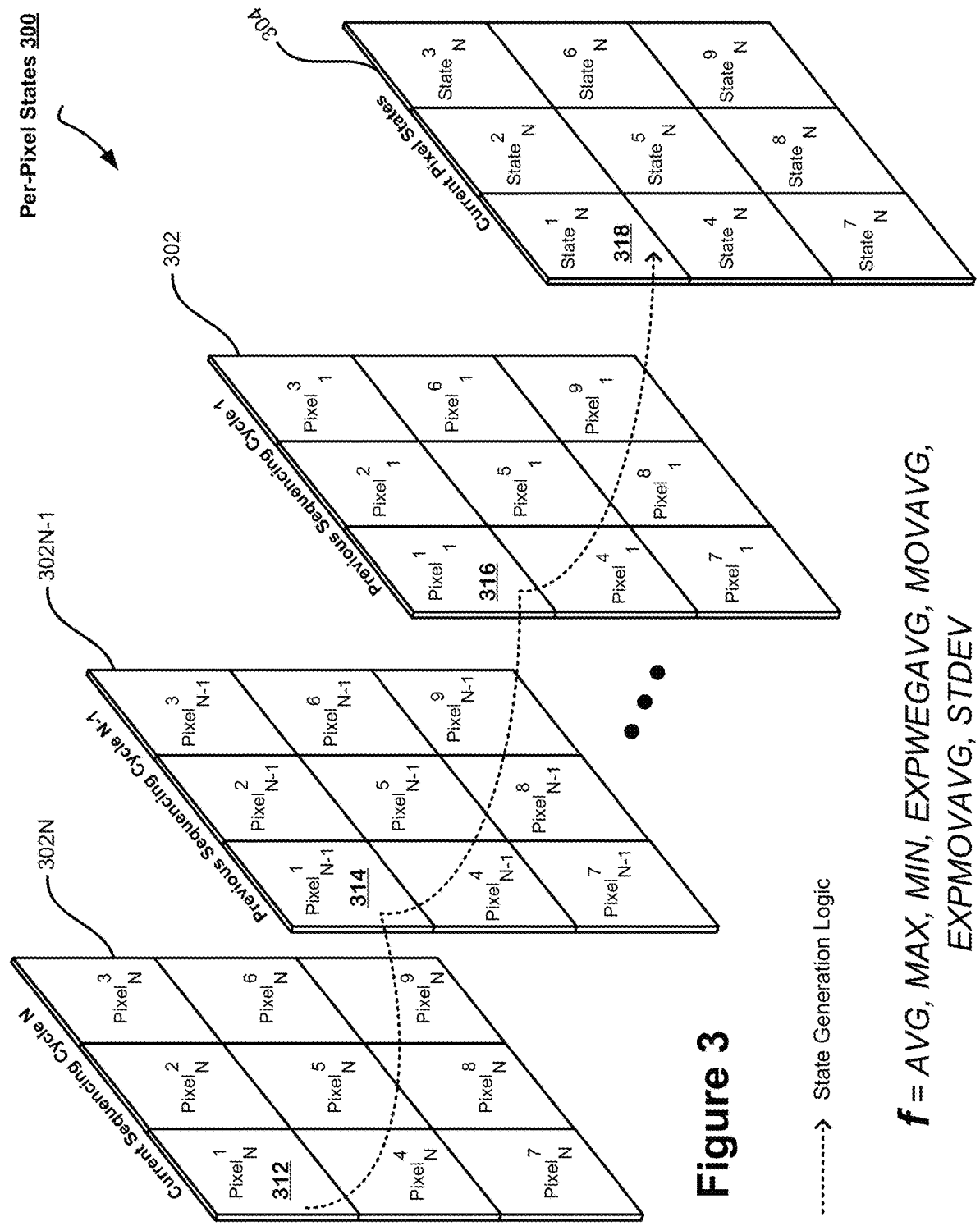
FIG. 3 illustrates one implementation of generating per-pixel states for pixels in sequencing images processed as input for base calling.

FIG. 3 illustrates one implementation of generating per-pixel states 300 for pixels in sequencing images processed as input for base calling. FIG. 3 depicts example pixel grids 302N, 302N−1, . . . , 302 of sizes 3×3. FIG. 3 also shows a per-pixel state grid 304. The pixel grids 302N, 302N−1, . . . , 302 represent sequencing images that are provided as input to the base caller 144 for base calling. Pixels in the pixel grids 302N, 302N−1, . . . , 302 can have intensity values for a plurality of image channels, for example, a red channel and a blue channel. Pixel grid 302N is generated for a current sequencing cycle N of a sequencing run and depicts intensity emissions generated as a result of nucleotide incorporation in a set of clusters at the current sequencing cycle N. Similarly, pixel grid 302N−1 is generated for a previous sequencing cycle N−1 of the sequencing run and depicts intensity emissions generated as a result of nucleotide incorporation in the set of clusters at the previous sequencing cycle N−1. Likewise, pixel grid 302 is generated for a first sequencing cycle 1 of the sequencing run and depicts intensity emissions generated as a result of nucleotide incorporation in the set of clusters at the first sequencing cycle 1.

From a spatial perspective, the pixel grids 302N, 302N−1, . . . , 302 can be considered to share nine pixels 1-9. In FIG. 3, the nine pixels 1-9 are indexed by same per-pixel superscripts across the pixel grids 302N, 302N−1, . . . , 302. From a temporal perspective, the nine pixels 1-9 can be considered to depict a first set of intensity values at a current timestep N, a second set of intensity values at a previous timestep N−1, and a third set of intensity values at a first timestep 1. Intensity values in the first, second, and third sets of intensity values can be considered to be arranged in a temporal sequence. In FIG. 3, the time-varying intensity values are indexed by different per-pixel superscripts across the pixel grids 302N, 302N−1, . . . , 302.

A current pixel state 318 for a given pixel can be calculated at the current sequencing N based on a current intensity value 312 of the given pixel at the current sequencing N and previous intensity values 314, ..., 316 of the given pixel at the respective previous sequencing cycles N−1 to 1. The previous intensity values 314, ..., 316 of the given pixel can be considered to be arranged in a previous intensity sequence starting at a previous intensity position N−1 and terminating at a previous intensity position 1.

In one implementation, the current pixel state 318 is the output of a state generation logic (or function) that takes as input the current intensity value 312 and the previous intensity values 314, ..., 316. In one implementation, the state generation logic can select a maximum value from among the current intensity value 312 and the previous intensity values 314, ..., 316, and use the maximum value as the current pixel state 318. In another implementation, the state generation logic can select a minimum value from among the current intensity value 312 and the previous intensity values 314, ..., 316, and use the minimum value as the current pixel state 318. In yet another implementation, the state generation logic can determine an average (mean) of the current intensity value 312 and the previous intensity values 314, ..., 316, and use the average as the current pixel state 318. In yet another implementation, the state generation logic can determine an exponential weighted average of the current intensity value 312 and the previous intensity values 314, ..., 316, and use the exponential weighted average as the current pixel state 318. In yet another implementation, the state generation logic can determine a moving (running) average of the current intensity value 312 and the previous intensity values 314, ..., 316, and use the moving average as the current pixel state 318. In yet another implementation, the state generation logic can determine an exponential moving average of the current intensity value 312 and the previous intensity values 314, ..., 316, and use the exponential moving average as the current pixel state 318. In yet another implementation, the state generation logic can determine a standard deviation of the current intensity value 312 and the previous intensity values 314, ..., 316, and use the standard deviation as the current pixel state 318. This process is implemented for each of the nine pixels 1-9 such that a respective current pixel state is determined for each of the nine pixels 1-9. Current pixel states generated by the state generation logic for the nine pixels 1-9 form the per-pixel state grid 304, according to the example illustrated in FIG. 3. In one implementation, the state generation logic is implemented by the state generator 126.

Pixel-Wise State Encoding

Figure 4:
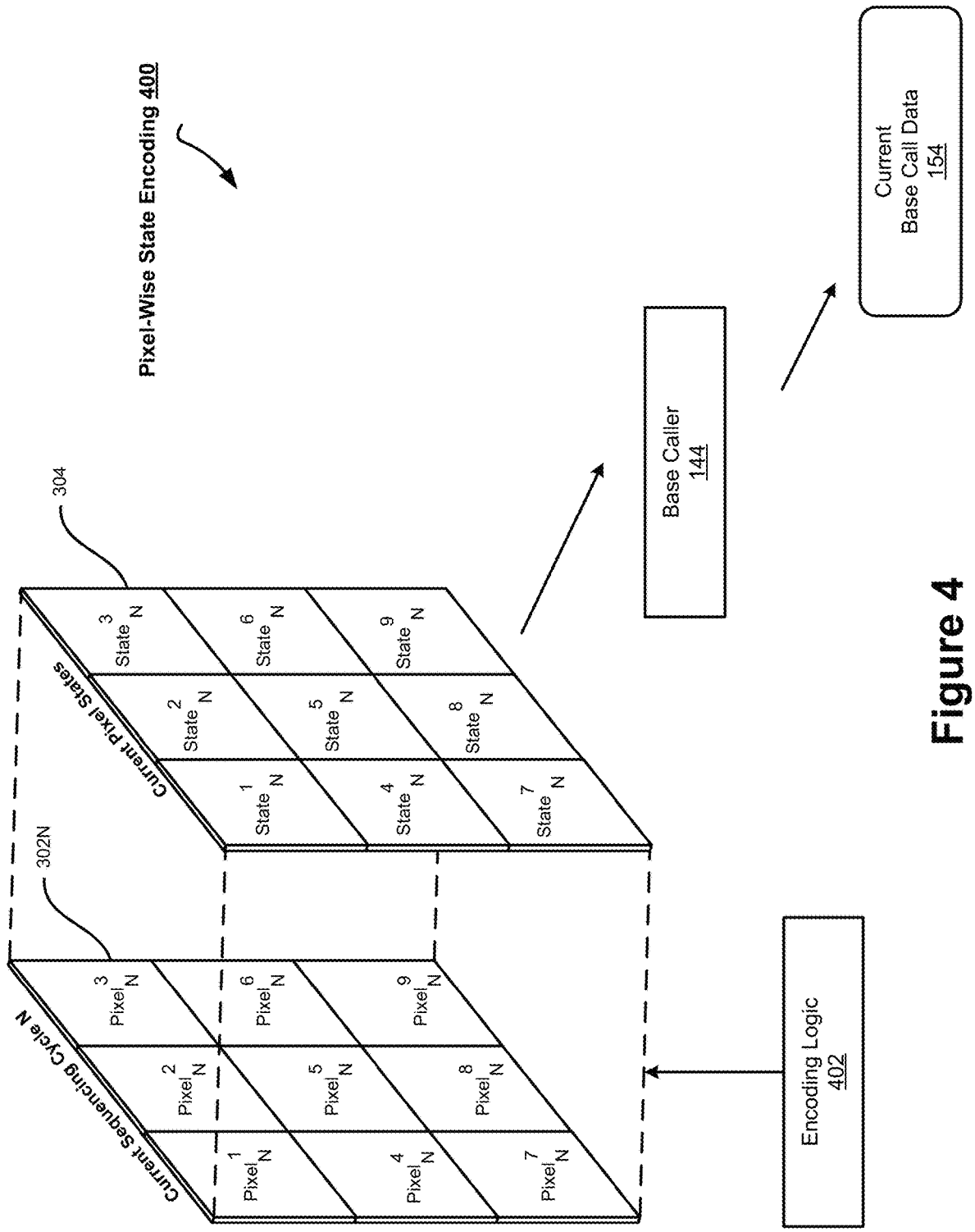
FIG. 4 illustrates one implementation of generating base calls based on the per-pixel states.

FIG. 4 illustrates one implementation of generating base calls based on the per-pixel states 304. In one implementation, an encoding logic 402 pixel-wise combines 400 the pixel grid 302N and the per-pixel state grid 304, for example, by summation, concatenation, element-wise multiplication, or element-wise multiplication and summation (convolution). The combination of the pixel grid 302N and the per-pixel state grid 304 is processed by the base caller 144 to generate the current base call data 154.

Per-Channel States

FIG. 5 illustrates one implementation of generating per-channel states 500 for pixels in sequencing images processed as input for base calling. FIG. 5 relates to an example pixel P. In FIG. 5, pixel P has intensity values across two example channels (or intensity channels): channel 1 502 and channel 2 506. In other implementations, pixel P can have fewer or greater number of channels. In the example illustrated in FIG. 5, the first channel 502 has a first set of intensity values 512, 513, ..., 516 for five sequencing cycles 1-5. Likewise, the second channel 506 has a second set of intensity values 522, 523, ..., 526 for the five sequencing cycles 1-5.

Then, a first channel state 532 is determined for the first channel 502 based on the first set of intensity values. Similarly, a second channel state 536 is determined for the second channel 506 based on the second set of intensity values. The first and second channel states 532 and 536 can be determined by the state generation logic, for example, by implementing a minimum value selection function, a maximum value selection function, an average function, an exponential weighting average function, a moving average function, an exponential moving average function, or a standard deviation function.

Then, at least one base call is generated for the fifth sequencing cycle (Cycle 5) based on the first channel state 532 and the second channel state 536. This includes, in one implementation, combining the channel 1 intensity value 516 for Cycle 5 with the first channel state 532 to generate a first combination for channel 1 502, and combining the channel 2 intensity value 526 for Cycle 5 with the second channel state 536 to generate a second combination for channel 2 506. Then, the base caller 144 processes the first combination for channel 1 502 and the second combination for channel 2 506 to generate one or more base calls for Cycle 5 (e.g., for one or more clusters).

In another implementation, the base caller 144 processes the channel 1 intensity value 516 for Cycle 5, the channel 2 intensity value 526 for Cycle 5, the first channel state 532 for Cycle 5, and the second channel state 536 for Cycle 5 as four separate input channels (e.g., RGB-style image channels) and generates the base call for Cycle 5. A person skilled in the art would appreciate that other contemporary or future methods of combining data/channels and processing them as a combination can be analogously applied and equivalently used within the scope of this disclosure.

In yet another implementation, the first and second channel states 532 and 536 are combined to generate a so-called "pan-channel state," for example, by applying an averaging function on the first and second channel states 532 and 536. Then, this pan-channel state for Cycle 5 is processed along with the channel 1 intensity value 516 for Cycle 5 and the channel 2 intensity value 526 for Cycle 5 to generate the base call for Cycle 5, i.e., a total of three separate input channels as opposed to four in the per-channel implementation.

Even though FIG. 5 relates to only one pixel P for purposes of illustration and simplicity, it is understood that the steps of state generation- and state encoding-responsive base calling are implemented for multiple pixels in the input sequencing images on a pixel-by-pixel basis and a channel-by-channel basis, partly because cluster intensity profiles and their states are defined by groups of contiguous pixels and therefore are analyzed as a group to generate a base call for a cluster.

Per-Channel MIN States

Figure 6:
FIG. 6 illustrates one implementation of generating per-channel MIN (minimum) states for pixels in sequencing images processed as input for base calling.

FIG. 6 illustrates one implementation of generating per-channel MIN (minimum) states 600 for pixels in sequencing images processed as input for base calling. In FIG. 6, column 601 indexes a plurality of pixels of an input sequencing image that is processed by the base caller 144 for base calling. The input sequencing image represents intensity profiles captured for a set of clusters at a current sequencing cycle N of a sequencing run. In FIG. 6, column 602 represents pixel-wise intensity values in a first channel (image channel) for the pixels indexed in the column 601 and for the current sequencing cycle N. In FIG. 6, column 603 represents pixel-wise intensity values in a second channel (image channel) for the pixels indexed in the column 601 and for the current sequencing cycle N.

In FIG. 6, column 604 represents pixel-wise minimum intensity values in the first channel selected from intensity values observed in the first channel between a first sequencing cycle 1 and the current sequencing cycle N for the pixels indexed in the column 601. In FIG. 6, column 605 represents pixel-wise minimum intensity values in the second channel selected from intensity values observed in the second channel between the first sequencing cycle 1 and the current sequencing cycle N for the pixels indexed in the column 601.

In one implementation, the base caller 144 processes columns 602, 603, 604, and 605 as separate input channels to generate one or more base calls for the current sequencing cycle N.

Pan-Channel MIN States

Figure 7:
FIG. 7 illustrates one implementation of generating pan-channel MIN (minimum) states for pixels in sequencing images processed as input for base calling.

FIG. 7 illustrates one implementation of generating pan-channel MIN (minimum) states 700 for pixels in sequencing images processed as input for base calling. In FIG. 7, column 708 pixel-wise averages the columns 604 and 605 of FIG. 6. In one implementation, the base caller 144 processes columns 602, 603, and 708 as separate input channels to generate one or more base calls for the current sequencing cycle N.

Per-Channel MAX States

Figure 8:
FIG. 8 illustrates one implementation of generating per-channel MAX (maximum) states for pixels in sequencing images processed as input for base calling.

FIG. 8 illustrates one implementation of generating per-channel MAX (maximum) states 800 for pixels in sequencing images processed as input for base calling. In FIG. 8, column 804 represents pixel-wise maximum intensity values in the first channel selected from intensity values observed in the first channel between the first sequencing cycle 1 and the current sequencing cycle N for the pixels indexed in the column 601. In FIG. 8, column 805 represents pixel-wise maximum intensity values in the second channel selected from intensity values observed in the second channel between the first sequencing cycle 1 and the current sequencing cycle N for the pixels indexed in the column 601.

In one implementation, the base caller 144 processes columns 602, 603, 804, and 805 as separate input channels to generate one or more base calls for the current sequencing cycle N.

Pan-Channel MAX States

Figure 9:
FIG. 9 illustrates one implementation of generating pan-channel MAX (maximum) states for pixels in sequencing images processed as input for base calling.

FIG. 9 illustrates one implementation of generating pan-channel MAX (maximum) states 900 for pixels in sequencing images processed as input for base calling. In FIG. 9, column 908 pixel-wise averages the columns 804 and 805 of FIG. 8. In one implementation, the base caller 144 processes columns 602, 603, and 908 as separate input channels to generate one or more base calls for the current sequencing cycle N.

Per-Channel AVG States

FIG. 10 illustrates one implementation of generating per-channel AVG (average) states 1000 for pixels in sequencing images processed as input for base calling. In FIG. 10, column 1004 represents pixel-wise average intensity values in the first channel calculated as respective per-pixel means of intensity values observed in the first channel between the first sequencing cycle 1 and the current sequencing cycle N for the pixels indexed in the column 601. In FIG. 10, column 1005 represents pixel-wise average intensity values in the second channel calculated as respective per-pixel means of intensity values observed in the second channel between the first sequencing cycle 1 and the current sequencing cycle N for the pixels indexed in the column 601.

In one implementation, the base caller 144 processes columns 602, 603, 1004, and 1005 as separate input channels to generate one or more base calls for the current sequencing cycle N.

Pan-Channel AVG States

Figure 11:
FIG. 11 illustrates one implementation of generating pan-channel AVG (average) states for pixels in sequencing images processed as input for base calling.

FIG. 11 illustrates one implementation of generating pan-channel AVG (average) states 1100 for pixels in sequencing images processed as input for base calling. In FIG. 11, column 1108 pixel-wise averages the columns 1004 and 1005 of FIG. 10. In one implementation, the base caller 144 processes columns 602, 603, and 1108 as separate input channels to generate one or more base calls for the current sequencing cycle N.

Per-Channel MIN MAX States

Figure 12:
FIG. 12 illustrates one implementation of generating per-channel MIN MAX (minimum and maximum) states 1200 for pixels in sequencing images processed as input for base calling.

FIG. 12 illustrates one implementation of generating per-channel MIN MAX (minimum and maximum) states 1200 for pixels in sequencing images processed as input for base calling. In one implementation, the base caller 144 processes columns 602, 603, 604, 605, 804, and 805 as separate input channels to generate one or more base calls for the current sequencing cycle N.

Per-Channel MIN AVG States

Figure 13:
FIG. 13 illustrates one implementation of generating per-channel MIN AVG (minimum and average) states 1300 for pixels in sequencing images processed as input for base calling.

FIG. 13 illustrates one implementation of generating per-channel MIN AVG (minimum and average) states 1300 for pixels in sequencing images processed as input for base calling. In one implementation, the base caller 144 processes columns 602, 603, 604, 605, 1004, and 1005 as separate input channels to generate one or more base calls for the current sequencing cycle N.

Per-Channel MAX AVG States

Figure 14:
FIG. 14 illustrates one implementation of generating per-channel MAX AVG (maximum and average) states 1400 for pixels in sequencing images processed as input for base calling.

FIG. 14 illustrates one implementation of generating per-channel MAX AVG (maximum and average) states 1400 for pixels in sequencing images processed as input for base calling. In one implementation, the base caller 144 processes columns 602, 603, 804, 805, 1004, and 1005 as separate input channels to generate one or more base calls for the current sequencing cycle N.

Per-Channel MIN MAX AVG States

Figure 15:
FIG. 15 illustrates one implementation of generating per-channel MIN MAX AVG (minimum, maximum, and average) states for pixels in sequencing images processed as input for base calling.

FIG. 15 illustrates one implementation of generating per-channel MIN MAX AVG (minimum, maximum, and average) states 1500 for pixels in sequencing images processed as input for base calling. In one implementation, the base caller 144 processes columns 602, 603, 604, 605, 804, 805, 1004, and 1005 as separate input channels to generate one or more base calls for the current sequencing cycle N.

A person skilled in the art will appreciate that any combination or ordering or arrangement of the channels and states discussed above can be provided as input to the base caller 144 for base calling. Other contemporaneous and future ways of combining, ordering, and arranging the channels and states discussed above are within the scope of this disclosure. For example, the pan-channel states can be generated by combining the per-channel states using other aggregation/accumulation functions like exponential weighted average, moving average, standard deviation, variance, and so on. In another example, the per-channel MIN states can be concatenated with the pan-channel AVG MAX states, and so on.

Base Call-Directed State Generation

Figure 16:
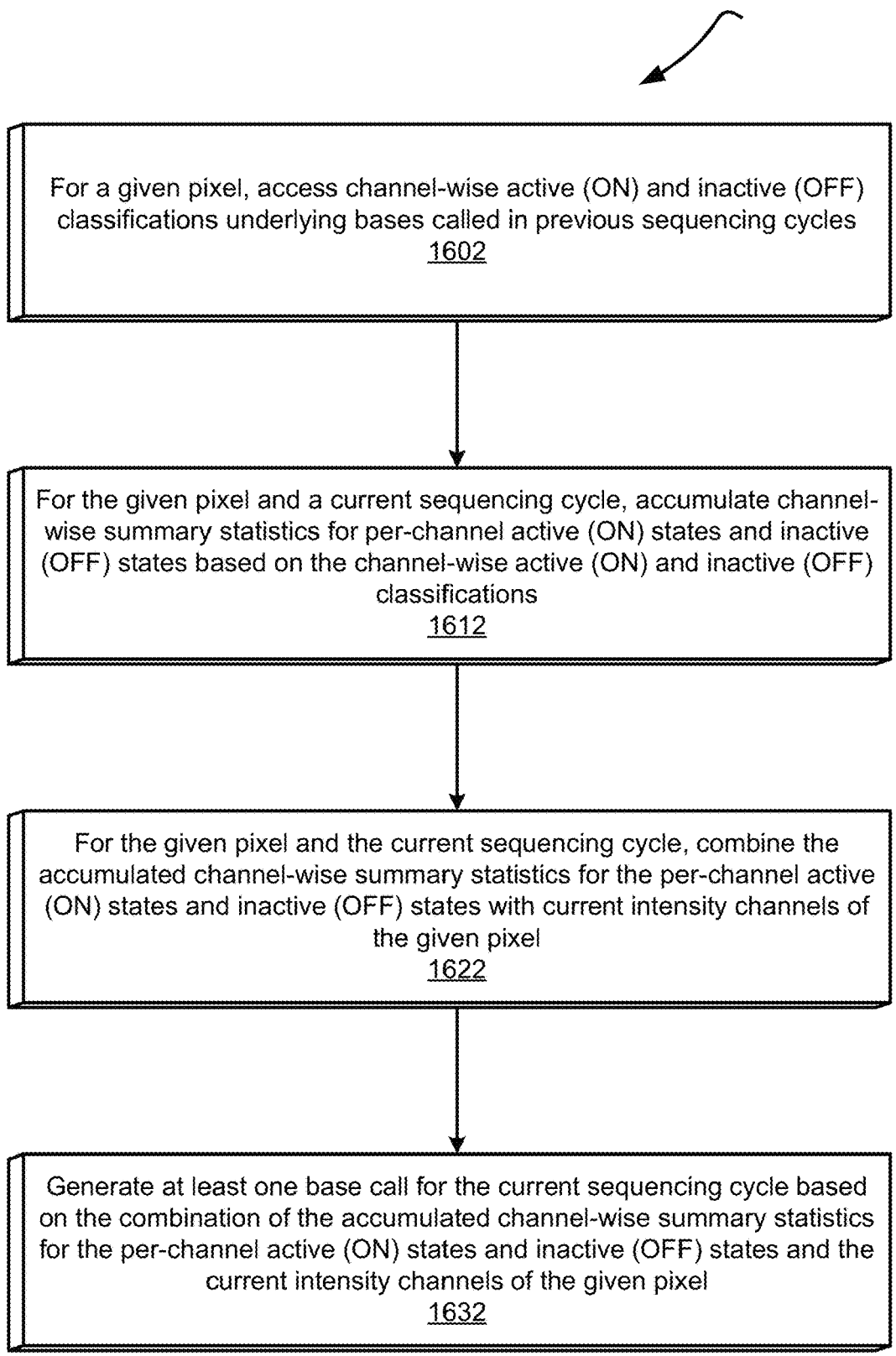
FIG. 16 illustrates one implementation of generating state information in dependence upon previously called bases for use in future base calling.

FIG. 16 illustrates one implementation of generating 1600 state information in dependence upon previously called bases for use in future base calling. FIGS. 17A, 17B, and 17C illustrate base call-directed ON and OFF state generation 1700 for a current sequencing cycle eleven (Cycle 11).

Figures 19A, 19B, 19C:
FIGS. 19A, 19B, and 19C further expand on FIGS. 18A, 18B, and 18C and illustrate how the ON state is updated at a yet next sequencing cycle thirteen (Cycle 13).

FIGS. 18A, 18B, and 18C expand on FIGS. 17A, 17B, and 17C and illustrate how the OFF state is updated 1800 at a next sequencing cycle twelve (Cycle 12). FIGS. 19A, 19B, and 19C further expand on FIGS. 18A, 18B, and 18C and illustrate how the ON state is updated 1900 at a yet next sequencing cycle thirteen (Cycle 13). FIGS. 20A, 20B, and 20C further expand on FIGS. 19A, 19B, and 19C and illustrate how both the ON and OFF states are updated 2000 at a yet next sequencing cycle fourteen (Cycle 14).

One avenue of differentiating between the different strategies for detecting nucleotide incorporation in a sequencing reaction using one fluorescent dye (or two or more dyes of same or similar excitation/emission spectra) is by characterizing the incorporations in terms of the presence or relative absence, or levels in between, of fluorescence transition that occurs during a sequencing cycle. As such, sequencing strategies can be exemplified by their fluorescent profile for a sequencing cycle. For strategies disclosed herein, "1" and "0" denotes a fluorescent state in which a nucleotide is in a signal state (e.g., detectable by fluorescence) (1)/(ON) or whether a nucleotide is in a dark state (e.g., not detected or minimally detected at an imaging step) (0)/OFF. A "0," "OFF," or "dark" state does not necessarily refer to a total lack, or absence of signal. Although in some implementations there may be a total lack or absence of signal (e.g., fluorescence), while in other implementation there may be some detectable signal even in the OFF state. Minimal or diminished fluorescence signal (e.g., background signal) is also contemplated to be included in the scope of a "0," "OFF," or "dark" state as long as a change in fluorescence from the first to the second image (or vice versa) can be reliably distinguished.

As used herein, the term "dark" or "OFF" is intended to refer to an amount of desired signal detected by a detector that is insignificant compared to background signal detected by the detector. For example, a feature of an object may be considered to be dark or OFF when the signal to noise ratio for the feature is substantially low, for example, being less than 1. In some implementations, a dark or OFF feature may not produce any amount of a desired signal (i.e., no signal is produced or detected). In other implementations, a very low amount of signal, relative to background, may be considered as dark or OFF.

In one implementation, an exemplary strategy for detecting and determining nucleotide incorporation in a sequencing reaction using one fluorescent dye (or two dyes of same or similar excitation/emission spectra) and two imaging events is exemplified by the following detection table:

|   | Image 1 | Image 2 |
|---|---------|---------|
| A | ON      | OFF     |
| C | OFF     | ON      |
| G | OFF     | OFF     |
| T | ON      | ON      |

Other strategies for detecting nucleotide incorporation, such as the four-channel chemistry and the one-channel chemistry, are within the scope of this disclosure and not discussed separately.

At action 1602, the technology disclosed accesses, for a given pixel, channel-wise active (ON) and inactive (OFF) classifications underlying bases called in previous sequencing cycles, i.e., previously called bases. This is illustrated by example in FIG. 17A. In FIG. 17A, pixel P depicts intensity emissions of a corresponding cluster for which bases are called for Cycles 1 to 10. In some implementations, pixel P contains a center of the corresponding cluster, as determined by location coordinates of the corresponding cluster's center. The called bases emanate from channel-wise active (ON) and inactive (OFF) classifications 1754 and 1756 for intensity values in a first channel (channel 1) and for intensity values in a second channel (channel 2).

At action 1612, the technology disclosed accumulates, for the given pixel and a current sequencing cycle, channel-wise summary statistics for per-channel active (ON) and inactive (OFF) states based on the channel-wise active (ON) and inactive (OFF) classifications 1754 and 1756. This is illustrated by example in FIG. 17B. In FIG. 17B, an inactive (OFF) state for the first channel 1702 is determined for the sequencing cycle eleven (Cycle 11) by applying an accumulation function to those intensity values in column 1754 that are classified to the inactive (OFF) state. Examples of the accumulation function include maximum value selection, minimum value selection, average (mean), exponential weighted average, moving (running) average, exponential moving average, mode, standard deviation, variance, skewness, kurtosis, percentiles, and entropy. In FIG. 17B, an active (ON) state for the first channel 1712 is determined for Cycle 11 by applying the accumulation function to those intensity values in column 1754 that are classified to the active (ON) state. In FIG. 17B, an inactive (OFF) state for the second channel 1722 is determined for Cycle 11 by applying the accumulation function to those intensity values in column 1756 that are classified to the inactive (OFF) state. In FIG. 17B, an active (ON) state for the second channel 1732 is determined for Cycle 11 by applying the accumulation function to those intensity values in column 1756 that are classified to the active (ON) state.

At action 1622, the technology disclosed combines, for the given pixel and the current sequencing cycle, the accumulated channel-wise summary statistics for the per-channel active (ON) states and inactive (OFF) states with current intensity channels of the given pixel. This is illustrated by example in FIG. 17C. In FIG. 17C, 1764 and 1766 are respective intensity values for the first and second channels that are registered for pixel P at Cycle 11. In FIG. 17C, the base caller 144 processes 1764, 1766, 1702, 1712, 1722, and 1732 as separate input channels to generate a base call for the corresponding cluster of pixel P at the sequencing cycle 11.

At action 1632, the technology disclosed generates, for the current sequencing cycle, at least one base call based on the combination of the accumulated channel-wise summary statistics for the per-channel active (ON) states and inactive (OFF) states and the intensity channels of the given pixel. This is illustrated by example in FIG. 18A. In FIG. 18A, a base call "G" is generated for the corresponding cluster of pixel P at Cycle 11 based on "OFF" and "OFF" channel-wise classifications 1854 and 1856, which in turn are made by the base caller 144 in response to processing 1764, 1766, 1702, 1712, 1722, and 1732 in FIG. 18C.

In FIG. 18B, in response to the "OFF" and "OFF" channel-wise classifications 1854 and 1856 at Cycle 11 (and lack of any "ON" classification), only the OFF channel states for the first and second channels 1802 and 1822 are updated at Cycle 12, such that the accumulation function is reapplied to now also consider channel-wise intensity values of Cycle 11 that both have "OFF" classifications 1854 and 1856. In some implementations, the channel-wise ON and OFF states are maintained in memory as single variables and reverse calculated at every update instance, for example, by multiplication with the divisor that was used to calculate the average when the accumulation function was an averaging function. The ON channel states for the first and second channels 1812 and 1832 are kept unchanged at Cycle 12 and inherit the same values from Cycle 11, i.e., 1712 and 1732, respectively.

In FIG. 18C, 1864 and 1866 are respective intensity values for the first and second channels that are registered for pixel P at Cycle 12. In FIG. 18C, the base caller 144 processes 1864, 1866, 1802, 1812, 1822, and 1832 as separate input channels to generate a base call for the corresponding cluster of pixel P at the sequencing cycle 12.

In FIG. 19A, a base call "T" is generated for the corresponding cluster of pixel P at Cycle 12 based on "ON" and "ON" channel-wise classifications 1954 and 1956, which in turn are made by the base caller 144 in response to processing 1864, 1866, 1802, 1812, 1822, and 1832 in FIG. 18C.

In FIG. 19B, in response to the "ON" and "ON" channel-wise classifications 1954 and 1956 at Cycle 12 (and lack of any "OFF" classification), only the ON channel states for the first and second channels 1912 and 1932 are updated at Cycle 13, such that the accumulation function is reapplied to now also consider channel-wise intensity values of Cycle 12 that both have "ON" classifications 1954 and 1956. The OFF channel states for the first and second channels 1902 and 1922 are kept unchanged at Cycle 13 and inherit the same values from Cycle 12, i.e., 1802 and 1822, respectively.

In FIG. 19C, 1964 and 1966 are respective intensity values for the first and second channels that are registered for pixel P at Cycle 13. In FIG. 19C, the base caller 144 processes 1964, 1966, 1902, 1912, 1922, and 1932 as separate input channels to generate a base call for the corresponding cluster of pixel P at the sequencing cycle 13.

In FIG. 20A, a base call "A" is generated for the corresponding cluster of pixel P at Cycle 13 based on "ON" and "OF" channel-wise classifications 2054 and 2056, which in turn are made by the base caller 144 in response to processing 1964, 1966, 1902, 1912, 1922, and 1932 in FIG. 19C.

In FIG. 20B, in response to the "ON" and "OFF" channel-wise classifications 2054 and 2056 at Cycle 13, both the ON and OFF channel states for the first and second channels 2002, 2012, 2022, and 2032, respectively, are updated at Cycle 14, such that the accumulation function is reapplied to now also consider channel-wise intensity values of Cycle 13 that have "ON" and "OFF" classifications 2054 and 2056.

In FIG. 20C, 2064 and 2066 are respective intensity values for the first and second channels that are registered for pixel P at Cycle 14. In FIG. 20C, the base caller 144 processes 2064, 2066, 2002, 2012, 2022, and 2032 as separate input channels to generate a base call for the corresponding cluster of pixel P at the sequencing cycle 14.

Note that with base call-directed state generation, the state information lags by one sequencing cycle. That is, the state information 1802, 1812, 1822, and 1832 used to base call Cycle 12 is based on Cycles 1-11 and does not include Cycle 12. Similarly, the state information 1902, 1912, 1922, and 1932 used to base call Cycle 13 is based on Cycles 1-12 and does not include Cycle 13.

Exponential Weighted Averaging

Figure 21:
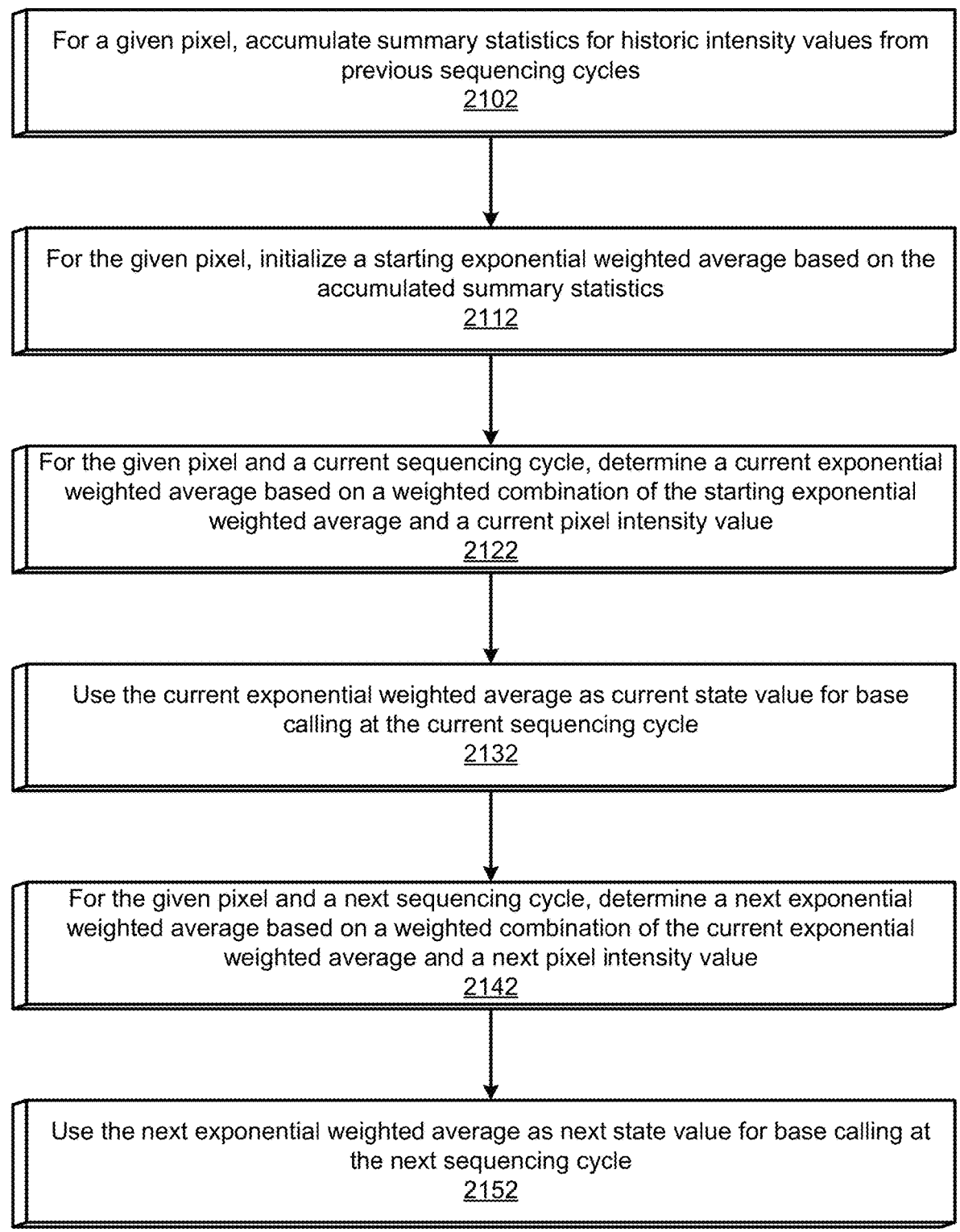
FIG. 21 illustrates one implementation of generating state information for base calling using exponential weighted averaging.

FIG. 21 illustrates one implementation of generating 2100 state information for base calling using exponential weighted averaging. In one implementation, exponential weighted averaging is used to give more weight to input signals (e.g., intensity values) from more recent sequencing cycles when calculating the state information. As a result, the state information estimates generated by exponential weighted averaging follow changes in the signals and are more robust to outliers.

At action 2102, the technology disclosed accumulates, for a given pixel, summary statistics for historic intensity values from previous sequencing cycles (e.g., the first ten or twenty sequencing cycles). Examples of an accumulation function that accumulates the summary statistics include maximum value selection, minimum value selection, average (mean), exponential weighted average, moving (running) average, exponential moving average, mode, standard deviation, variance, skewness, kurtosis, percentiles, and entropy.

At action 2112, the technology disclosed initializes, for the given pixel, a starting exponential weighted average based on the accumulated summary statistics. In one implementation, the starting exponential weighted average can be an average of the historic intensity values (e.g., an average of the historical intensity values of all other pixels or all other cluster pixels), a global maximum (global MAX) value selected from the historic intensity values (e.g., a global MAX of the historical intensity values of all other pixels or all other cluster pixels), or a global minimum (global MIN) selected from the historic intensity values (e.g., a global MIN of the historical intensity values of all other pixels or all other cluster pixels).

At action 2122, the technology disclosed determines, for the given pixel and a current sequencing cycle, a current exponential weighted average based on a weighted combination of the starting exponential weighted average and a current pixel intensity value.

At action 2132, the technology disclosed uses the current exponential weighted average as current state value for base calling at the current sequencing cycle (e.g., base calling a cluster corresponding to the given pixel). In one implementation, this includes the base caller 144 processing the current state value and the current pixel intensity value and generating at least one base call for the current sequencing cycle.

At action 2142, the technology disclosed determines, for the given pixel and a next sequencing cycle, a next exponential weighted average based on a weighted combination of the current exponential weighted average and a next pixel intensity value.

At action 2152, the technology disclosed uses the next exponential weighted average as next state value for base calling at the next sequencing cycle (e.g., base calling the cluster corresponding to the given pixel). In one implementation, this includes the base caller 144 processing the next state value and the next pixel intensity value and generating at least one base call for the next sequencing cycle.

In one implementation, the exponential weighted average logic is expressed as following:

$$y[k]=(1-alpha)*y[k-1]+alpha*x[k]$$

where
  y[k] is the exponential weighted average for the current sequencing cycle
  y[k−1] is the exponential weighted average for the previous sequencing cycle
  x[k] is the input signal (e.g., intensity value) for the current sequencing cycle
  alpha is the weighting parameter The weighting parameter "alpha" can be a value between zero and one $\{0 \leq alpha \leq 1\}$. When alpha is equal to zero $\{alpha=0\}$, the output is y[k−1] (no averaging). When alpha is equal to one $\{alpha=1\}$, the output is x[k]. At other alpha values, the output is an exponentially weighted average of the intensity. Alpha represents how quickly the filter reacts to updates; smaller values react slower and do more averaging, whereas larger values put more weight on the more recent input values.

Note that y[.] can be stored as a single variable and updated in place since historical values are not used except when updating the above-mentioned expression. y[k−1] can be initialized to, for example, an expected intensity (e.g., an average initial intensity over all the clusters/wells). In one implementation, the first twenty sequencing cycles (Cycles 1-20) can be used to estimate an initial average intensity with no online estimation. The initial average intensity can be plugged in as the initial estimate for y[k−1], and then online exponential weighted averaging can be used after sequencing cycle twenty (Cycle 20).

For implementation on CPU, the update can be efficiently implemented using one multiply by rewriting the above-mentioned expression as:

$$y[k]=y[k-1]*\text{alpha}\,(x[k]-y[k-1])$$

In some implementations, alpha can be a small value close to zero, so more averaging is performed. In other implementations, alpha can be varied to find the value that trade-offs averaging v/s response time that are most-suited for particular applications.

Per-Channel Exponential Weighted Averaging

Figure 22:
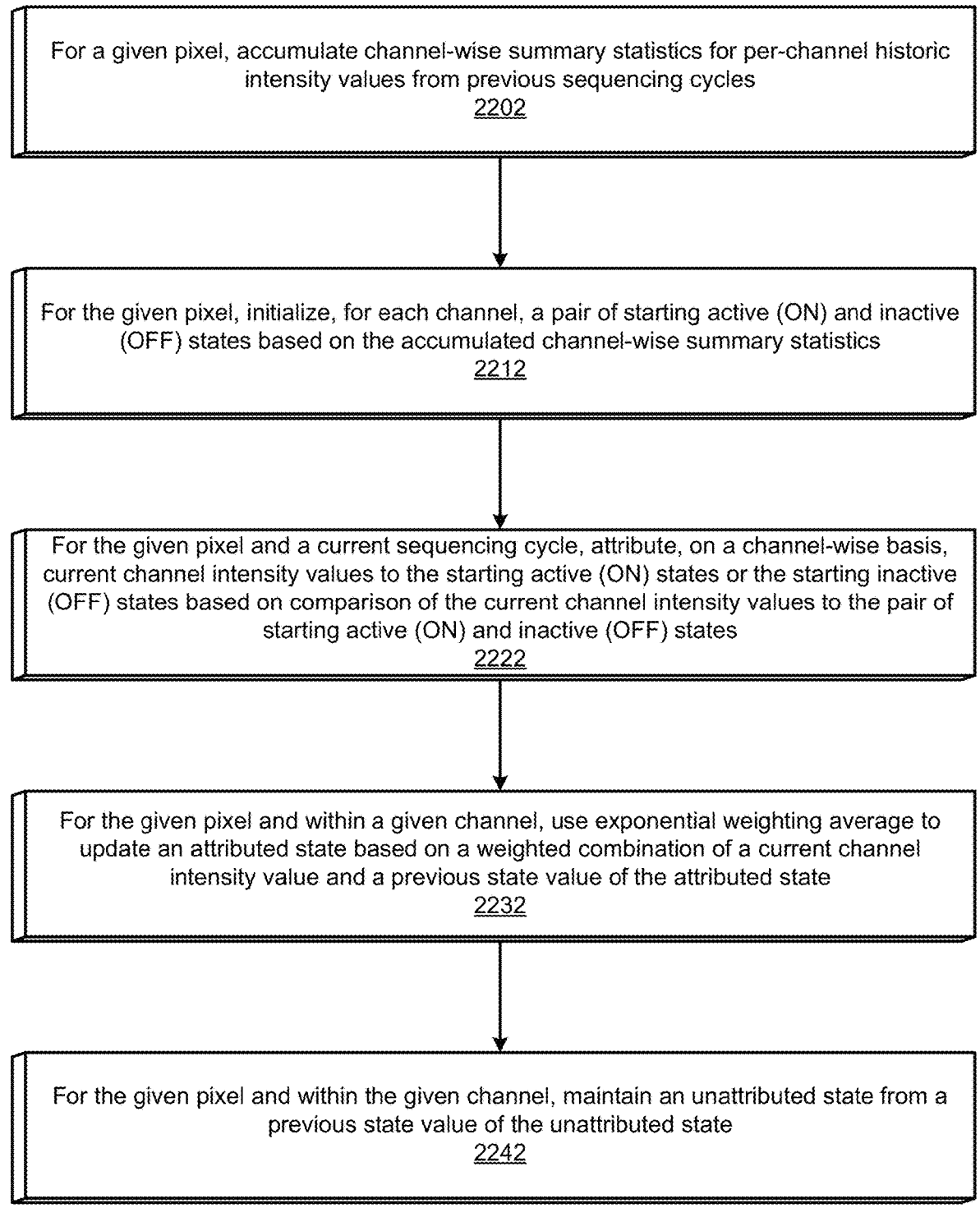
FIG. 22 illustrates one implementation of generating per-channel state information for base calling using exponential weighted averaging.

FIG. 22 illustrates one implementation of generating 2200 per-channel state information for base calling using exponential weighted averaging. FIG. 23 depicts an example of generating 2300 per-channel state information for base calling using exponential weighted averaging.

At action 2202, the technology disclosed accumulates, for a given pixel, channel-wise summary statistics for per-channel historic intensity values from previous sequencing cycles (e.g., the first ten or twenty sequencing cycles). Examples of a per-channel accumulation function that accumulates the channel-wise summary statistics include maximum/global maximum value selection, minimum/global minimum value selection, average (mean), exponential weighted average, moving (running) average, exponential moving average, mode, standard deviation, variance, skewness, kurtosis, percentiles, and entropy. This is illustrated by example in FIG. 23.

In FIG. 23, a first channel (channel 1) has historic intensity values 2374 for the first five sequencing cycles (Cycles 1-5). In FIG. 23, a second channel (channel 2) has historic intensity values 2376 for Cycles 1-5. Furthermore, a global maximum (global MAX) value 2312 is selected for channel 1 from the historic intensity values 2374, and a global minimum (global MIN) value 2314 is selected for channel 1 from the historic intensity values 2374. Similarly, a global MAX value 2316 is selected for channel 2 from the historic intensity values 2376, and a global MIN value 2318 is selected for channel 2 from the historic intensity values 2376.

At action 2212, the technology disclosed, initializes, for each channel, a pair of starting active (ON) and inactive (OFF) states based on the accumulated channel-wise summary statistics. This is illustrated by example in FIG. 23. In FIG. 23, for channel 1 and after Cycle 5, the global MAX 2312 is initialized as the active (ON) state for channel 1, and the global MIN 2314 is initialized as the inactive (OFF) state for channel 1. In FIG. 23, for channel 2 and after Cycle 5, the global MAX 2316 is initialized as the active (ON) state for channel 2, and the global MIN 2318 is initialized as the inactive (OFF) state for channel 2.

At action 2222, the technology disclosed attributes, for the given pixel and a current sequencing cycle, on a channel-wise basis, current channel intensity values to the starting active (ON) states or the starting inactive (OFF) states based on comparison of the current channel intensity values to the pair of starting active (ON) and inactive (OFF) states. This is illustrated by example in FIG. 23. In FIG. 23, for channel 1 and for Cycle 6, an intensity value 2322 is registered. Since intensity value 2322 is quantitatively closer to the global MAX 2312, the intensity value 2322 is attributed to the active (ON) state because the global MAX 2312 serves as the proxy for the active (ON) state for channel 1 and is used as the starting exponential weighted average for channel 1 in the active (ON) state. In FIG. 23, for channel 2 and for Cycle 6, an intensity value 2326 is registered.

Since intensity value 2326 is quantitatively closer to the global MIN 2318, the intensity value 2326 is attributed to the inactive (OFF) state because the global MIN 2318 serves as the proxy for the inactive (OFF) state for channel 2 and is used as the starting exponential weighted average for channel 2 in the inactive (OFF) state.

At action 2232, the technology disclosed uses, for the given pixel and within a given channel, exponential weighting average to update an attributed state based on a weighted combination of a current channel intensity value and a previous state value of the attributed state.

At action 2242, the technology disclosed maintains, for the given pixel and within the given channel, an unattributed state from a previous state value of the unattributed state.

Actions 2232 and 2242 are illustrated by example in FIG. 23. In FIG. 23, for Cycle 6, the state information is determined for channels 1 and 2 as follows. An active (ON) state 2342 for Cycle 6 and channel 1 is determined using an exponential weighted average 2332 because an intensity value 2322 for Cycle 6 and channel 1 is attributed to the active (ON) state for channel 1. The exponential weighted average 2332 uses "0.12" as the alpha value, as discussed with respect to the above-mentioned expression. An inactive (OFF) state 2344 for channel 1 is kept unchanged and is inherited from Cycle 5 as the global MIN 2314 for channel 1.

An inactive (OFF) state 2348 for Cycle 6 and channel 2 is determined using an exponential weighted average 2338 because an intensity value 2326 for Cycle 6 and channel 2 is attributed to the inactive (OFF) state for channel 2. The exponential weighted average 2338 also uses "0.12" as the alpha value, as discussed with respect to the above-mentioned expression. An active (ON) state 2346 for channel 2 is kept unchanged and is inherited from Cycle 5 as the global MAX 2316 for channel 2.

Then, the channel-wise active (ON) and inactive (OFF) states 2342, 2344, 2346, and 2348 for Cycle 6 are used along with the intensity values 2322 and 2326 registered for Cycle 6 to generate at least one base call for Cycle 6.

In FIG. 23, for Cycle 7, the state information is determined for channels 1 and 2 as follows. An inactive (OFF) state 2374 for Cycle 7 and channel 1 is determined using an exponential weighted average 2364 because an intensity value 2352 for Cycle 7 and channel 1 is attributed to the inactive (OFF) state for channel 1. The exponential weighted average 2364 also uses "0.12" as the alpha value, as discussed with respect to the above-mentioned expression. An active (ON) state 2372 for channel 1 is kept unchanged and is inherited from Cycle 6 as the exponential weighted average 2342 for channel 1.

An active (ON) state 2376 for Cycle 7 and channel 2 is determined using an exponential weighted average 2366 because an intensity value 2356 for Cycle 7 and channel 2 is attributed to the active (ON) state for channel 2. The exponential weighted average 2366 also uses "0.12" as the alpha value, as discussed in the above-mentioned expression. An inactive (OFF) state 2378 for channel 2 is kept unchanged and is inherited from Cycle 6 as the exponential weighted average 2348 for channel 2.

Then, the channel-wise active (ON) and inactive (OFF) states 2372, 2374, 2376, and 2378 for Cycle 7 are used along with the intensity values 2352 and 2356 registered for Cycle 7 to generate at least one base call for Cycle 7.

Note that, in FIG. 23, the channel-wise attributions to active (ON) and inactive (OFF) states at a given sequencing cycle are based on the per-channel intensity values registered for the given sequencing cycle (e.g., Cycles 6 and 7 in FIG. 23). The discussion now turns to base call-directed per-channel exponential weighted averaging in which the channel-wise attributions to active (ON) and inactive (OFF) states at the given sequencing cycle are based on a base call made a previous sequencing cycle.

Base Call-Directed Per-Channel Exponential Weighted Averaging

Figure 24:
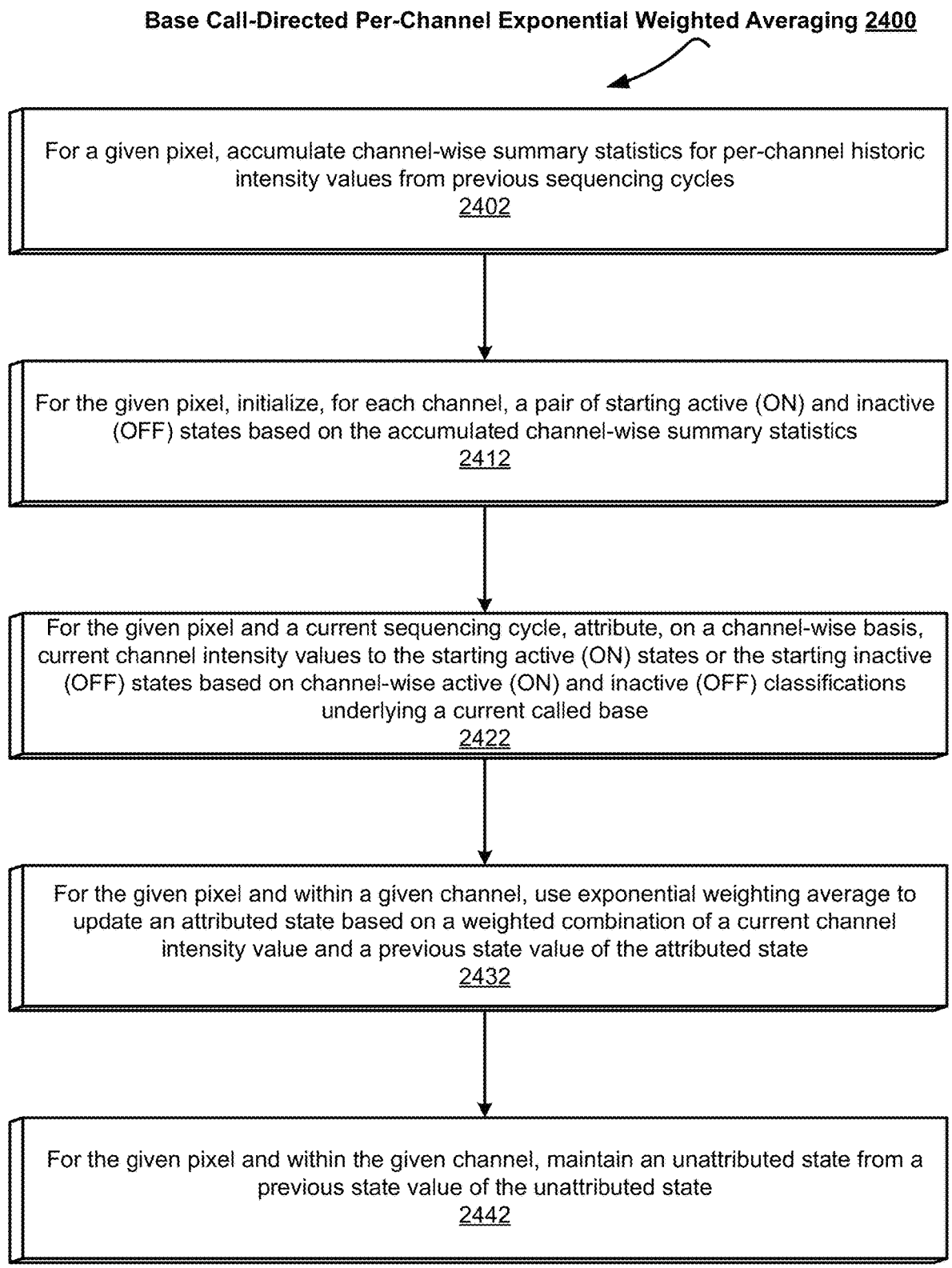
FIG. 24 illustrates one implementation of generating per-channel state information for base calling using exponential weighted averaging that is directed by previously called bases.

FIG. 24 illustrates one implementation of generating 2400 per-channel state information for base calling using exponential weighted averaging that is directed by previously called bases. FIG. 25 depicts an example of generating 2500 per-channel state information for base calling using exponential weighted averaging that is directed by previously called bases.

In FIG. 24, actions 2402 and 2412 are similar to actions 2202 and 2212 of FIG. 22. At action 2422, the channel-wise attributions to active (ON) and inactive (OFF) states lag by one sequencing cycle and are made based on a base called in a previous sequencing cycle. This is illustrated by example in FIG. 25. In FIG. 25, at Cycle 6, a base call "A" 2502 is made based on "ON" and "OFF" classifications 2504 and 2506 of channels 1 and 2, respectively.

At action 2432, the "ON" and "OFF" classifications 2504 and 2506 and the base call 2502 at Cycle 6 are used to determine the state information 2342, 2344, 2346, and 2348 for Cycle 7 by applying the exponential weighted averaging. At action 2442, unattributed states for Cycle 7 are also identified based on the base call 2502 at Cycle 6 and kept unchanged.

Note that, at Cycle 7, "OFF" and "ON" classifications 2514 and 2516 and in turn the base call "C" 2512 are generated based on the state information 2342, 2344, 2346, and 2348 determined at Cycle 6 and per-channel intensity values 2372 and 2376 registered at Cycle 7.

Continuing ahead, the "OFF" and "ON" classifications 2514 and 2516 and the base call 2512 at Cycle 7 are used to determine the state information 2372, 2374, 2376, and 2378 for Cycle 8 by applying the exponential weighted averaging. Unattributed states for Cycle 8 are also identified based on the base call 2512 at Cycle 7 and kept unchanged.

Though not shown, a base call for Cycle 8 is generated based on channel-wise intensity values registered for Cycle 8 and the state information 2372, 2374, 2376, and 2378 determined at Cycle 7 for Cycle 8.

In different implementations, state information determined using exponential weighted averages (EWAs) can be used instead of, in addition to, or in combination with state information determined using some other logic, such as the minimum value selection logic, the maximum value selection logic, the averaging logic, and so on.

Non-Cluster Pixels

The discussion now turns to the distinction between cluster pixels and non-cluster pixels. Cluster pixels are pixels that contain centers of clusters, as determined by location coordinates of cluster centers. Non-cluster pixels do not contain cluster centers. Note that non-cluster pixels do depict cluster intensities (or background intensities); they just do not coincide with cluster centers.

A brief discussion of cluster-to-pixel-to-base call relationship may also be helpful here. A cluster is depicted by a plurality of pixels, for example, by a pixel grid of 3×3 pixels. In some implementations, the base caller 144 processes sequencing images that have different intensity values for pixels in a given pixel grid to characterize respective intensity profiles of a given cluster at different sequencing cycles. In response to the processing, in one implementation, the base caller 144 generates outputs that specify respective base calls for the given cluster at the different sequencing cycles by referencing only a center pixel in the given pixel grid that contains a center of the given cluster. That is, the respective base calls are made with respect to only the center pixel even though the given pixel grid in its entirety characterizes the intensity profiles of the given cluster. The non-center pixels of the given pixel grid are analyzed by the base caller 144 to generate the base calls; however, only the center pixel is used to express the base calls.

In implementations in which only the center pixels are used to express the base calls, base call-directed state generation can be challenging because no base calls are available to determine the states of non-cluster pixels. This limitation can be compensated by techniques discussed below.

Figure 26:
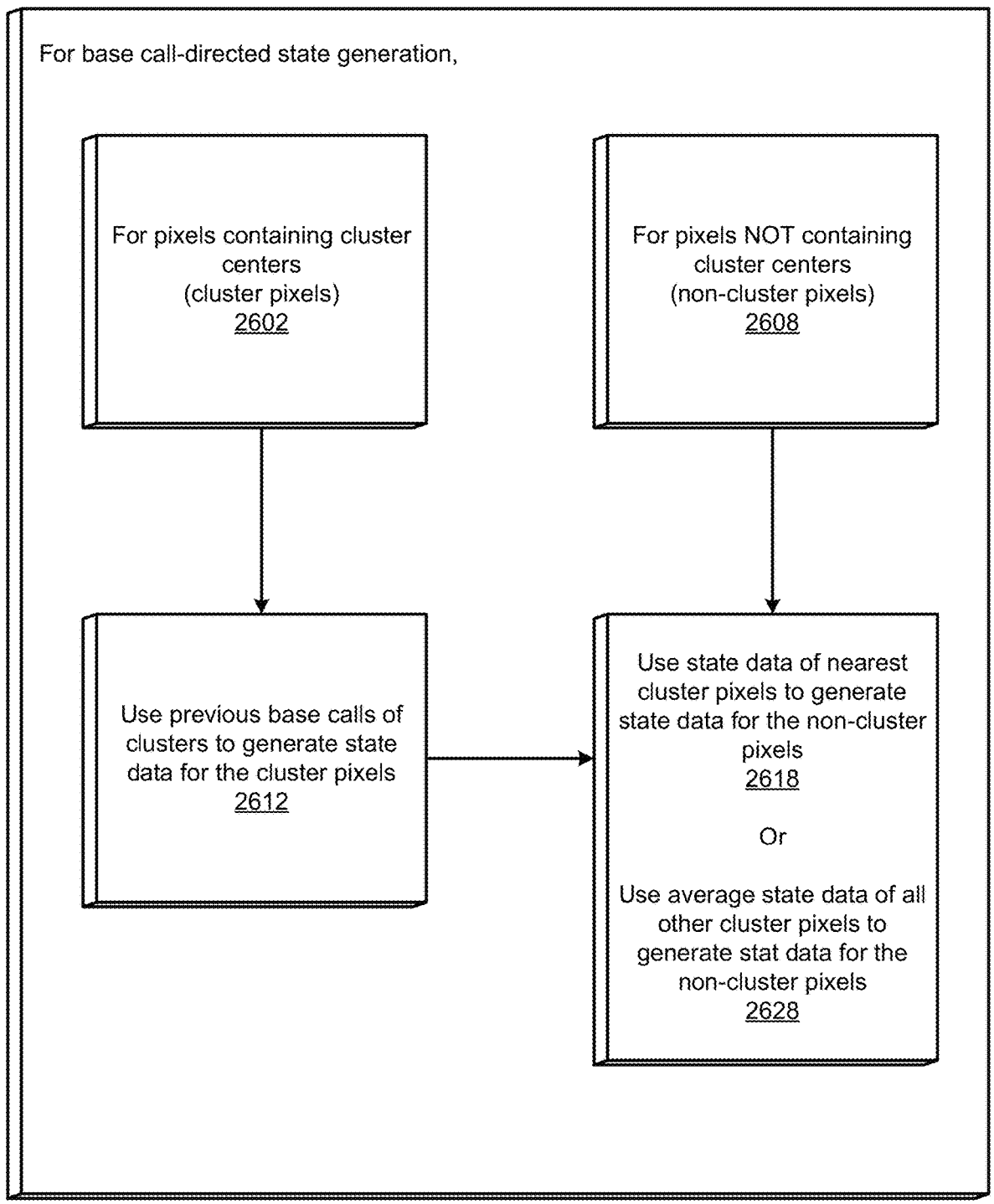
FIG. 26 illustrates one implementation of generating state information for non-cluster pixels using previously called bases.

FIG. 26 illustrates one implementation of generating 2600 state information for non-cluster pixels using previously called bases. For pixels that contain cluster centers, i.e., the cluster pixels 2602, previous base calls of clusters are used 2612 to generate state data, as discussed above, for example, with respect to FIG. 16 to FIG. 20C and FIGS. 24 and 25.

For pixels that do not contain cluster centers, i.e., the non-cluster pixels 2608, state data of nearest cluster pixels is used 2618 to generate state data, in accordance with one implementation. In another implementation, an average of state data of all other cluster pixels is used 2628 to generate state data for the non-cluster pixels 2608.

State Input

Figure 27:
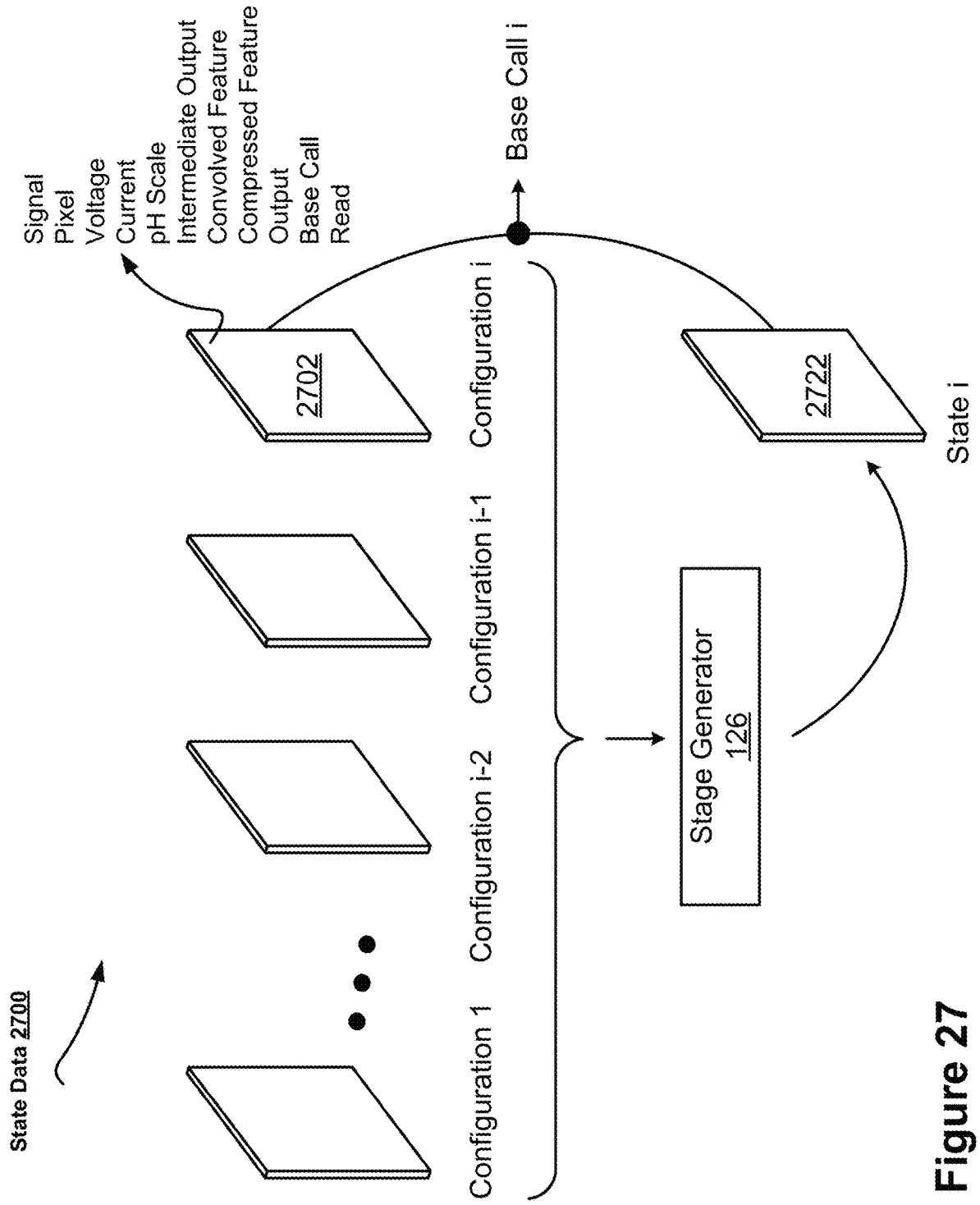
FIG. 27 illustrates different implementations of generating state data for base calling.

FIG. 27 illustrates different implementations of generating state data 2700 for base calling. The technology disclosed generates state information 2722 for an "entity" 2702 based on its current configuration i and past configurations i−1, i−2, . . . , 1. Examples of the entity 2702 include any type of signal measurements, pixel measurements, voltage measurements, current measurements, pH scale measurements, intermediate outputs of processing, convolved features (e.g., feature maps), compressed features (e.g., compressed feature maps), different types of outputs (e.g., softmax scores, sigmoid scores, regression scores), base calls, and reads. A current base call is then made in dependence upon the state information 2722 and the current configuration i of the entity 2702.

Note that to combine the state information 2722 with the entity 2702, in some implementations, the dimensionality of the state information 2722 may need to be reconciled with that of the entity 2702 (e.g., make compatible by matching), or vice-versa. In different implementations, this can be achieved by dimensionality-altering operations like cloning, padding (e.g., zero padding), concatenation, convolution, summing, transpose convolutions, etc. For example, when the state information 2722 has a dimensionality of 1×1 and the entity 2702 has a dimensionality of 3×3, nine clones of the state information 2722 can be concatenated with the entity 2702.

Feeding State Input

Figure 28:
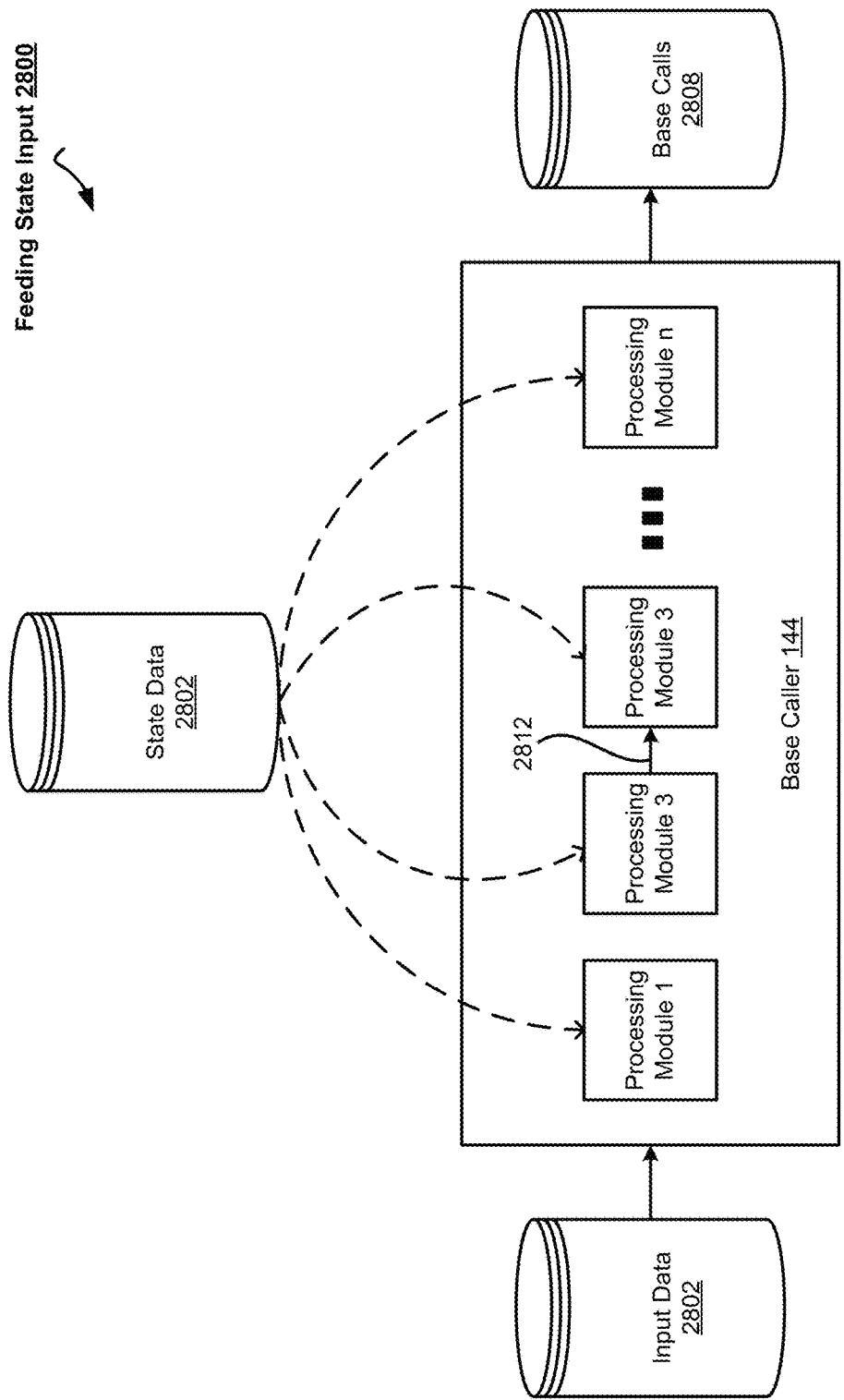
FIG. 28 illustrates different implementations of feeding state data at various aspects of processing of a base calling operation.

FIG. 28 illustrates different implementations of feeding 2800 state data at various aspects of processing of a base calling operation. In one implementation, the base caller 144 can have a variety of processing modules 1-n (e.g., pre-processing layers, neural network layers, post-processing layers, output layers). State data 2802 can be provided to any of the processing modules 1-n of the base caller 144 to generate base calls 2808. For example, the state data 2802 can be combined with input data 2802 (e.g., input image(s)) for processing by a first processing module (e.g., a first convolution layer) of the base caller 144. In another example, the state data 2802 can be combined with an intermediate output 2812 of the base caller 144 (e.g., intermediate feature map(s) produced by a preceding convolution layer). In yet another example (not depicted), the state data 2802 can be combined with a final output of the base caller 144 (e.g., final feature map(s) produced by a final convolution layer). In such an implementation, a combination of the state data 2802 and the final output can be processed by an output layer/base calling layer (e.g., a softmax layer, a regression layer, a sigmoid layer) to generate the base calls 2808.

State-Based and Neural Network-Based Base Caller

The following discussion focuses on a neural network-based base caller 2900 described herein. The neural network-based base caller 2900 is one implementation of the base caller 144, and collectively referred to herein as "Deep-RTA." First, the input to the neural network-based base caller 2900 is described, in accordance with one implementation. Then, examples of the structure and form of the neural network-based base caller 2900 are provided. Finally, the output of the neural network-based base caller 2900 is described, in accordance with one implementation.

A data flow logic provides sequencing images to the neural network-based base caller 2900 for base calling. The neural network-based base caller 2900 accesses the sequencing images on a patch-by-patch basis (or a tile-by-tile basis). Each of the patches is a sub-grid (or sub-array) of pixelated units in the grid of pixelated units that forms the sequencing images. The patches have dimensions q×r of the sub-grid of pixelated units, where q (width) and r (height) are any numbers ranging from 1 and 10000 (e.g., 3×3, 5×5, 7×7, 10×10, 15×15, 25×25, 64×64, 78×78, 115×115). In some implementations, q and r are the same. In other implementations, q and r are different. In some implementations, the patches extracted from a sequencing image are of the same size. In other implementations, the patches are of different sizes. In some implementations, the patches can have overlapping pixelated units (e.g., on the edges).

Sequencing produces m sequencing images per sequencing cycle for corresponding m image channels. That is, each of the sequencing images has one or more image (or intensity) channels (analogous to the red, green, blue (RGB) channels of a color image). In one implementation, each image channel corresponds to one of a plurality of filter wavelength bands. In another implementation, each image channel corresponds to one of a plurality of imaging events at a sequencing cycle. In yet another implementation, each image channel corresponds to a combination of illumination with a specific laser and imaging through a specific optical filter. The image patches are tiled (or accessed) from each of the m image channels for a particular sequencing cycle. In different implementations such as 4-, 2-, and 1-channel chemistries, m is 4 or 2. In other implementations, m is 1, 3, or greater than 4. In other implementations, the images can be in blue and violet color channels instead of or in addition to the red and green color channels.

Consider, for example, that a sequencing run is implemented using two different image channels: a blue channel and a green channel. Then, at each sequencing cycle, the sequencing run produces a blue image and a green image. This way, for a series of k sequencing cycles of the sequencing run, a sequence of k pairs of blue and green images is produced as output and stored as the sequencing images. Accordingly, a sequence of k pairs of blue and green image patches is generated for the patch-level processing by the neural network-based base caller 2900.

The input image data to the neural network-based base caller 2900 for a single iteration of base calling (or a single instance of forward pass or a single forward traversal) comprises data for a sliding window of multiple sequencing cycles. The sliding window can include, for example, a current sequencing cycle, one or more preceding sequencing cycles, and one or more successive sequencing cycles.

In one implementation, the input image data comprises data for three sequencing cycles, such that data for a current (time t) sequencing cycle to be base called is accompanied with (i) data for a left flanking/context/previous/preceding/prior (time t−1) sequencing cycle and (ii) data for a right flanking/context/next/successive/subsequent (time t+1) sequencing cycle.

In another implementation, the input image data comprises data for five sequencing cycles, such that data for a current (time t) sequencing cycle to be base called is accompanied with (i) data for a first left flanking/context/previous/preceding/prior (time t−1) sequencing cycle, (ii) data for a second left flanking/context/previous/preceding/prior (time t−2) sequencing cycle, (iii) data for a first right flanking/context/next/successive/subsequent (time t+1), and (iv) data for a second right flanking/context/next/successive/subsequent (time t+2) sequencing cycle.

In yet another implementation, the input image data comprises data for seven sequencing cycles, such that data for a current (time t) sequencing cycle to be base called is accompanied with (i) data for a first left flanking/context/previous/preceding/prior (time t−1) sequencing cycle, (ii) data for a second left flanking/context/previous/preceding/prior (time t−2) sequencing cycle, (iii) data for a third left flanking/context/previous/preceding/prior (time t−3) sequencing cycle, (iv) data for a first right flanking/context/next/successive/subsequent (time t+1), (v) data for a second right flanking/context/next/successive/subsequent (time t+2) sequencing cycle, and (vi) data for a third right flanking/context/next/successive/subsequent (time t+3) sequencing cycle. In other implementations, the input image data comprises data for a single sequencing cycle. In yet other implementations, the input image data comprises data for 10, 15, 20, 30, 58, 75, 92, 130, 168, 175, 209, 225, 230, 275, 318, 325, 330, 525, or 625 sequencing cycles.

The neural network-based base caller 2900 processes the image patches through its convolution layers and produces an alternative representation, according to one implementation. The alternative representation is then used by an output layer (e.g., a softmax layer) for generating a base call for either just the current (time t) sequencing cycle or each of the sequencing cycles, i.e., the current (time t) sequencing cycle, the first and second preceding (time t−1, time t−2) sequencing cycles, and the first and second succeeding (time t+1, time t+2) sequencing cycles. The resulting base calls form the sequencing reads.

In one implementation, the neural network-based base caller 2900 outputs a base call for a single target cluster for a particular sequencing cycle. In another implementation, the neural network-based base caller 2900 outputs a base call for each target cluster in a plurality of target clusters for the particular sequencing cycle. In yet another implementation, the neural network-based base caller 2900 outputs a base call for each target cluster in a plurality of target clusters for each sequencing cycle in a plurality of sequencing cycles, thereby producing a base call sequence for each target cluster.

In one implementation, the neural network-based base caller 2900 is a multilayer perceptron (MLP). In another implementation, the neural network-based base caller 2900 is a feedforward neural network. In yet another implementation, the neural network-based base caller 2900 is a fully-connected neural network. In a further implementation, the neural network-based base caller 2900 is a fully convolution neural network. In yet further implementation, the neural network-based base caller 2900 is a semantic segmentation neural network. In yet another further implementation, the neural network-based base caller 2900 is a generative adversarial network (GAN). In yet another implementation, the neural network-based base caller 2900 includes multi-headed attention mechanisms like Transformers, BERTs, and DETRs.

In one implementation, the neural network-based base caller 2900 is a convolution neural network (CNN) with a plurality of convolution layers. In another implementation, the neural network-based base caller 2900 is a recurrent neural network (RNN) such as a long short-term memory network (LS™), bi-directional LS™ (Bi-LS™), or a gated recurrent unit (GRU). In yet another implementation, the neural network-based base caller 2900 includes both a CNN and an RNN.

In yet other implementations, the neural network-based base caller 2900 can use 1D convolutions, 2D convolutions, 3D convolutions, 4D convolutions, 5D convolutions, dilated or atrous convolutions, transpose convolutions, depthwise separable convolutions, pointwise convolutions, 1×1 convolutions, group convolutions, flattened convolutions, spatial and cross-channel convolutions, shuffled grouped convolutions, Transformers, BERTs, spatial separable convolutions, and deconvolutions. The neural network-based base caller 2900 can use one or more loss functions such as logistic regression/log loss, multi-class cross-entropy/softmax loss, binary cross-entropy loss, mean-squared error loss, L1 loss, L2 loss, smooth L1 loss, and Huber loss. The neural network-based base caller 2900 can use any parallelism, efficiency, and compression schemes such TFRecords, compressed encoding (e.g., PNG), sharding, parallel calls for map transformation, batching, prefetching, model parallelism, data parallelism, and synchronous/asynchronous stochastic gradient descent (SGD). The neural network-based base caller 2900 can include upsampling layers, downsampling layers, recurrent connections, gates and gated memory units (like an LS™ or GRU), residual blocks, residual connections, highway connections, skip connections, peephole connections, activation functions (e.g., non-linear transformation functions like rectifying linear unit (ReLU), leaky ReLU, exponential liner unit (ELU), sigmoid and hyperbolic tangent (tanh)), batch normalization layers, regularization layers, dropout, pooling layers (e.g., max or average pooling), global average pooling layers, and attention mechanisms.

The neural network-based base caller 2900 is trained using backpropagation-based gradient update techniques. Example gradient descent techniques that can be used for training the neural network-based base caller 2900 include stochastic gradient descent, batch gradient descent, and mini-batch gradient descent. Some examples of gradient descent optimization algorithms that can be used to train the neural network-based base caller 2900 are Momentum, Nesterov accelerated gradient, Adagrad, Adadelta, RMSprop, Adam, AdaMax, Nadam, and AMSGrad.

In one implementation, the neural network-based base caller 2900 uses a specialized architecture to segregate processing of data for different sequencing cycles. The motivation for using the specialized architecture is described first. As discussed above, the neural network-based base caller 2900 processes image patches for a current sequencing cycle, one or more preceding sequencing cycles, and one or more successive sequencing cycles. Data for additional sequencing cycles provides sequence-specific context. The neural network-based base caller 2900 learns the sequence-specific context during training and base calls them. Furthermore, data for pre- and post-sequencing cycles provides second order contribution of pre-phasing and phasing signals to the current sequencing cycle.

However, images captured at different sequencing cycles and in different image channels are misaligned and have residual registration error with respect to each other. To account for this misalignment, the specialized architecture comprises spatial convolution layers that do not mix information between sequencing cycles and only mix information within a sequencing cycle.

Spatial convolution layers (or spatial logic) use so-called "segregated convolutions" that operationalize the segregation by independently processing data for each of a plurality of sequencing cycles through a "dedicated, non-shared" sequence of convolutions. The segregated convolutions convolve over data and resulting feature maps of only a given sequencing cycle, i.e., intra-cycle, without convolving over data and resulting feature maps of any other sequencing cycle.

Consider, for example, that the input image data comprises (i) current image patch for a current (time t) sequencing cycle to be base called, (ii) previous image patch for a previous (time t−1) sequencing cycle, and (iii) next image patch for a next (time t+1) sequencing cycle. The specialized architecture then initiates three separate convolution pipelines, namely, a current convolution pipeline, a previous convolution pipeline, and a next convolution pipeline. The current data processing pipeline receives as input the current image patch for the current (time t) sequencing cycle and independently processes it through a plurality of spatial convolution layers to produce a so-called "current spatially convolved representation" as the output of a final spatial convolution layer. The previous convolution pipeline receives as input the previous image patch for the previous (time t−1) sequencing cycle and independently processes it through the plurality of spatial convolution layers to produce a so-called "previous spatially convolved representation" as the output of the final spatial convolution layer. The next convolution pipeline receives as input the next image patch for the next (time t+1) sequencing cycle and independently processes it through the plurality of spatial convolution layers to produce a so-called "next spatially convolved representation" as the output of the final spatial convolution layer.

In some implementations, the current, previous, and next convolution pipelines are executed in parallel. In some implementations, the spatial convolution layers are part of a spatial convolution network (or subnetwork) within the specialized architecture.

The neural network-based base caller 2900 further comprises temporal convolution layers (or temporal logic) that mix information between sequencing cycles, i.e., inter-cycles. The temporal convolution layers receive their inputs from the spatial convolution network and operate on the spatially convolved representations produced by the final spatial convolution layer for the respective data processing pipelines.

The inter-cycle operability freedom of the temporal convolution layers emanates from the fact that the misalignment property, which exists in the image data fed as input to the spatial convolution network, is purged out from the spatially convolved representations by the stack, or cascade, of segregated convolutions performed by the sequence of spatial convolution layers.

Temporal convolution layers use so-called "combinatory convolutions" that groupwise convolve over input channels in successive inputs on a sliding window basis. In one implementation, the successive inputs are successive outputs produced by a previous spatial convolution layer or a previous temporal convolution layer.

In some implementations, the temporal convolution layers are part of a temporal convolution network (or subnetwork) within the specialized architecture. The temporal convolution network receives its inputs from the spatial convolution network. In one implementation, a first temporal convolution layer of the temporal convolution network groupwise combines the spatially convolved representations between the sequencing cycles. In another implementation, subsequent temporal convolution layers of the temporal convolution network combine successive outputs of previous temporal convolution layers. The output of the final temporal convolution layer is fed to an output layer that produces an output. The output is used to base call one or more clusters at one or more sequencing cycles.

Additional details about the neural network-based base caller 2900 can be found in U.S. Provisional Patent Application No. 62/821,766, titled "ARTIFICIAL INTELLIGENCE-BASED SEQUENCING,", filed on Mar. 21, 2019, which is incorporated herein by reference.

Per-Pixel State Input

Figure 29:
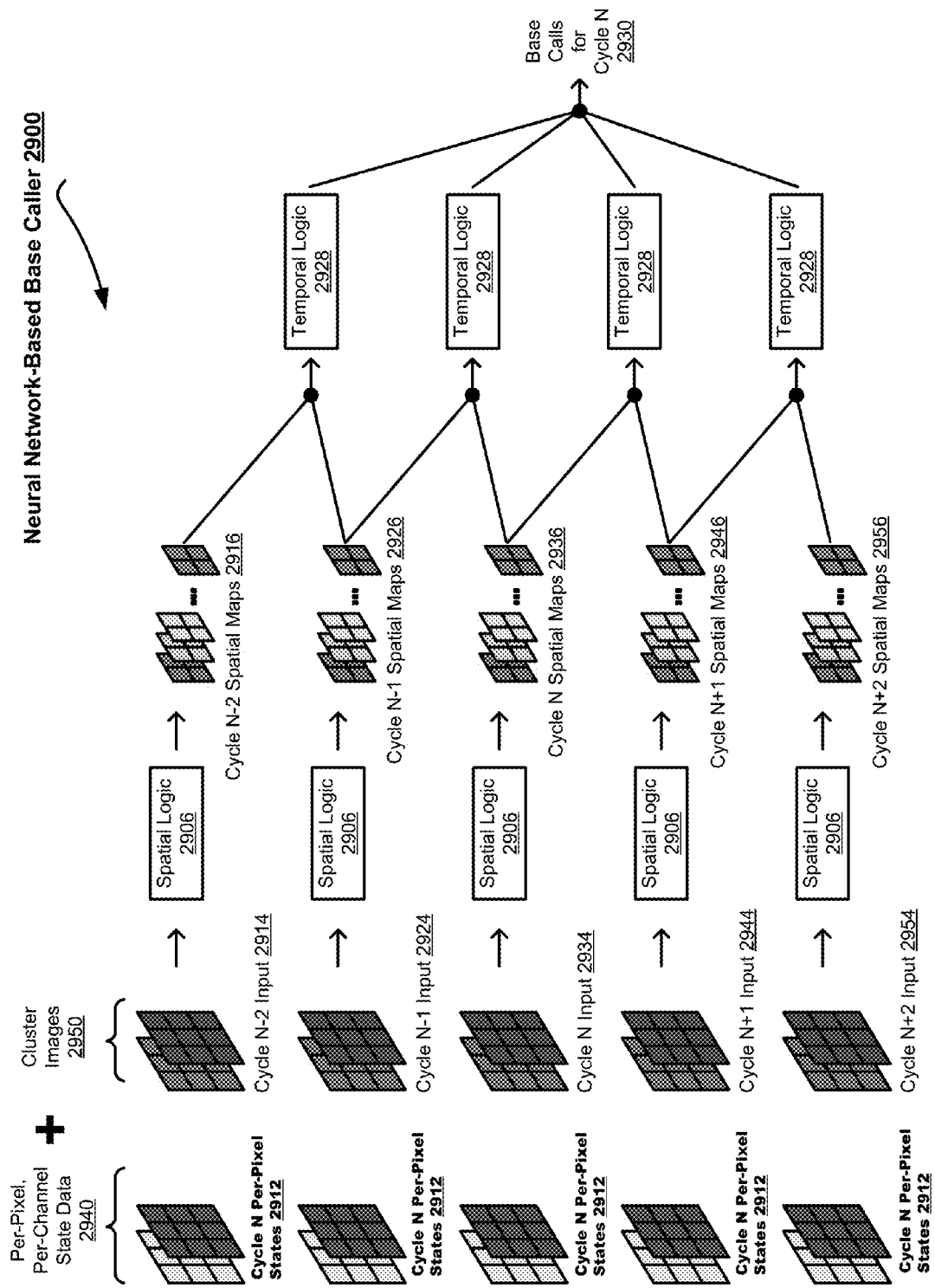
FIG. 29 illustrates one implementation of state-based and neural network-based base calling.

FIG. 29 illustrates one implementation of state-based and neural network-based base calling. In the example illustrated in FIG. 29, a first window of sequencing cycles includes sequencing cycles N−2, N−1, N, N+1, and N+2. In one implementation, respective image patches (sequencing images/cluster images) 2914, 2924, 2934, 2944, and 2954 for the respective sequencing cycles N−2, N−1, N, N+1, and N+2 are pixel-wise combined (e.g., concatenated) with state data 2912 for the current sequencing cycle N. State data 2912 can be determined using any of the techniques discussed above.

The image patches 2914, 2924, 2934, 2944, and 2954 are collectively referred to as cluster images (sequencing images) 2950. The per-pixel, per-channel state data 2940 includes five instances of the state data 2912 because there are five sequencing cycles N−2, N−1, N, N+1, and N+2.

State data 2912 has per-pixel state values for corresponding pixels in the cluster images 2950, similar to the implementation discussed above with respect to FIGS. 3 and 4. Also, in one implementation, because the cluster images 2950 have two channels (intensity channels), the state data 2912 also has two state channels. In other implementations, the state data 2912 can have only one channel or have more than two channels, as discussed above in different implementations.

At a high-level, per-pixel, per-channel state data 2940 is combined with the cluster images 2950 for processing by a spatial logic 106 (or spatial network or spatial subnetwork or spatial convolution neural network). The combination of the per-pixel, per-channel state data 2940 and the cluster images 2950 is separately processed through a spatial logic 106 to generate respective spatial maps 2916, 2926, 2936, 2946, and 2956 (or intermediate results or spatial output sets or spatial feature map sets) for the respective sequencing cycles N−2, N−1, N, N+1, and N+2. The spatial convolution network 106 can use 1D, 2D, or 3D convolutions.

The spatial logic 106 includes a sequence (or cascade) of spatial convolution layers. Each spatial convolution layer has a filter bank with a plurality of spatial convolution filters that implement segregated convolutions. Accordingly, each spatial convolution layer produces as output a plurality of spatial feature maps. The number of spatial feature maps produced by a subject spatial convolution layer is a function of the number of spatial convolution filters configured in the subject spatial convolution layer. For example, if the subject spatial convolution layer has fourteen spatial convolution filters, then the subject spatial convolution layer produces fourteen spatial feature maps. From an aggregate perspective, the fourteen spatial feature maps can be considered a spatial feature map volume (or tensor) with fourteen channels (or depth dimension=fourteen).

Furthermore, a next spatial convolution layer that follows the subject spatial convolution layer can also be configured with fourteen spatial convolution filters. In such a case, the next spatial convolution layer processes, as input, the fourteen spatial feature maps generated the subject spatial convolution layer, and itself generates fourteen new spatial feature maps as output. FIG. 29 shows the five spatial feature map sets 2916, 2926, 2936, 2946, and 2956 generated by a final spatial convolution layer of the spatial network 106 for the respective sequencing cycles N−2, N−1, N, N+1, and N+2. For example, each of the five spatial feature map sets 2916, 2926, 2936, 2946, and 2956 have fourteen feature maps.

In another example, a sequence of seven spatial feature map sets can be generated by a cascade of seven spatial convolution layers of the spatial network 106. A combination of per-cycle input patch data and state data for a subject sequencing cycle i can have, for example, a spatial dimensionality of 115×115 and a depth dimensionality of two (due to the two image channels in the original sequencing images). In one implementation, each of the seven spatial convolution layers uses 3×3 convolutions that reduce the spatial dimensionality of successive spatial feature map volumes by two, for example, from 10×10 to 8×8.

The first spatial feature map volume can have spatial dimensions 113×113 (i.e., reduced from 115×115 by the 3×3 convolutions of the first spatial convolution layer) and a depth dimension of 14 (i.e., fourteen feature maps or fourteen channels due to fourteen spatial convolution filters in the first spatial convolution layer). The second spatial feature map volume can have spatial dimensions 111×111 (i.e., reduced from 113×113 by the 3×3 convolutions of the second spatial convolution layer) and a depth dimension of 14 (i.e., fourteen feature maps or fourteen channels due to fourteen spatial convolution filters in the second spatial convolution layer). The third spatial feature map volume can have spatial dimensions 109×109 (i.e., reduced from 111×111 by the 3×3 convolutions of the third spatial convolution layer) and a depth dimension of 14 (i.e., fourteen feature maps or fourteen channels due to fourteen spatial convolution filters in the third spatial convolution layer). The fourth spatial feature map volume can have spatial dimensions 107×107 (i.e., reduced from 109×109 by the 3×3 convolutions of the fourth spatial convolution layer) and a depth dimension of 14 (i.e., fourteen feature maps or fourteen channels due to fourteen spatial convolution filters in the fourth spatial convolution layer). The fifth spatial feature map volume can have spatial dimensions 105×105 (i.e., reduced from 107×107 by the 3×3 convolutions of the fifth spatial convolution layer) and a depth dimension of 14 (i.e., fourteen feature maps or fourteen channels due to fourteen spatial convolution filters in the fifth spatial convolution layer). The sixth spatial feature map volume can have spatial dimensions 103×103 (i.e., reduced from 105×105 by the 3×3 convolutions of the sixth spatial convolution layer) and a depth dimension of 14 (i.e., fourteen feature maps or fourteen channels due to fourteen spatial convolution filters in the sixth spatial convolution layer). The seventh spatial feature map volume can have spatial dimensions 101×101 (i.e., reduced from 103×103 by the 3×3 convolutions of the seventh spatial convolution layer) and a depth dimension of 14 (i.e., fourteen feature maps or fourteen channels due to fourteen spatial convolution filters in the seventh spatial convolution layer).

Analogizing to the multi-cycle example illustrated in FIG. 29, for the five sequencing cycles N–2, N–1, N, N+1, and N+2 and the five per-cycle image patches 2914, 2924, 2934, 2944, and 2954 and the five instances of the state data 2912, the spatial logic 106 separately produces five respective sequences of the seven spatial feature map volumes, with the spatial maps 2916, 2926, 2936, 2946, and 2956 in FIG. 29 being equivalent to five separate instances of a final spatial feature map volume.

The spatial maps 2916, 2926, 2936, 2946, and 2956 are processed by a temporal logic 2928 to generate base calls 2930 for the current sequencing cycle N.

Per-Cluster/Per-Well States

Figure 30:
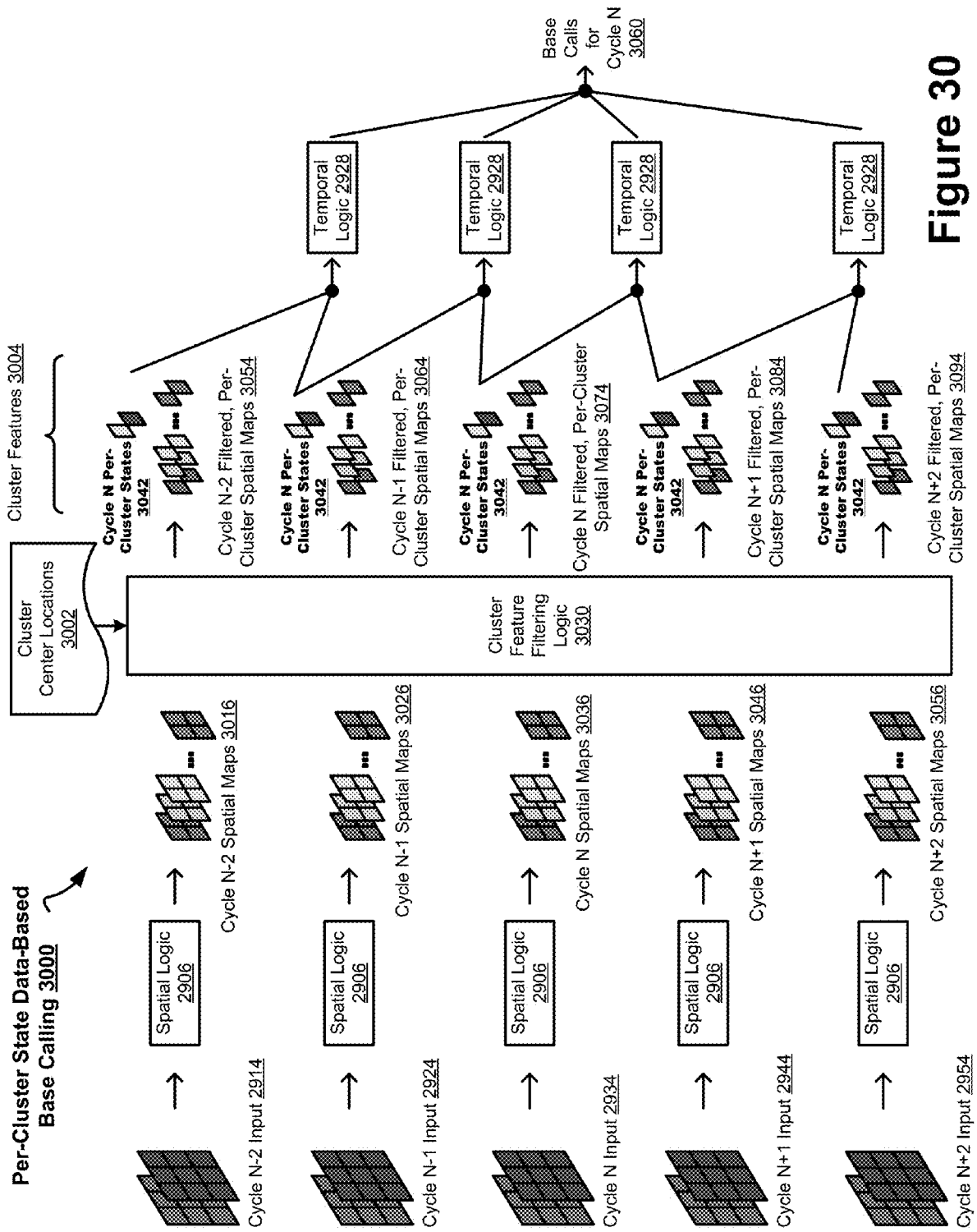
FIG. 30 illustrates one implementation of using per-cluster state data for base calling clusters.

FIG. 30 illustrates one implementation of using per-cluster state data for base calling clusters. Different than FIG. 29, in FIG. 30, the state data is not combined with the input cluster images 2914, 2924, 2934, 2944, and 2954. Instead, the state data is combined with the output of the spatial logic 106. Note that the cluster images 2914, 2924, 2934, 2944, and 2954 contain both cluster pixels and non-cluster pixels. As a result, the spatial maps 3016, 3026, 3036, 3046, and 3056 contain spatially convolved features emanating from both cluster pixels and non-cluster pixels.

In some implementations, a cluster feature filtering logic 3030 uses cluster center locations 3002 to filter out those features from the spatial maps 3016, 3026, 3036, 3046, and 3056 that correspond to non-cluster pixels. The resulting filtered, per-cluster spatial maps 3054, 3064, 3074, 3084, and 3094 contain only those features that correspond to cluster pixels, collectively referred to as cluster features 3004. In one implementation, the dimensionality of the spatial maps 3016, 3026, 3036, 3046, and 3056 is 101×101, and the dimensionality of the filtered, per-cluster spatial maps 3054, 3064, 3074, 3084, and 3094 is 25×25. In such an implementation, the 25×25 x k tensor includes spatial features that are produced as a result of applying successive convolution operations on data corresponding to cluster pixels, including the original cluster pixels and successively generated convolved features of the cluster pixels.

Unlike FIG. 29 in which the state data 2940 is combined with the cluster images 2950 at the starting input to the neural network-based base caller 2900, in FIG. 30, per-cluster states 3042 for the current sequencing cycle N are combined with intermediate outputs of the neural network-based base caller 2900, i.e., the filtered, per-cluster spatial maps 3054, 3064, 3074, 3084, and 3094.

In some implementations, the dimensionality of the per-cluster states 3042 is modified to conform with the dimensionality of the filtered, per-cluster spatial maps 3054, 3064, 3074, 3084, and 3094 (e.g., by trimming dimensions, adding dimensions, padding (e.g., zero padding), cloning, etc.). In different implementations, the respective five instances of the per-cluster states 3042 and the filtered, per-cluster spatial maps 3054, 3064, 3074, 3084, and 3094 can be respectively combined using techniques discussed above, such as concatenation, summation, element-wise multiplication, element-wise multiplication and summation (convolution), and so on.

Then, according to the illustrated example in FIG. 30, the respective five combinations of the respective filtered, per-cluster spatial maps 3054, 3064, 3074, 3084, and 3094 and the respective five instances of the per-cluster states 3042 are processed by the temporal logic 2928 to generate base calls 3060 for the current sequencing cycle N. The base calls 3060 are made for clusters corresponding to the cluster pixels and therefore the cluster features 3004.

The discussion now turns to different variations of the per-cluster states 3042 and how these variations are determined according to different implementations of the technology disclosed.

Figure 31:
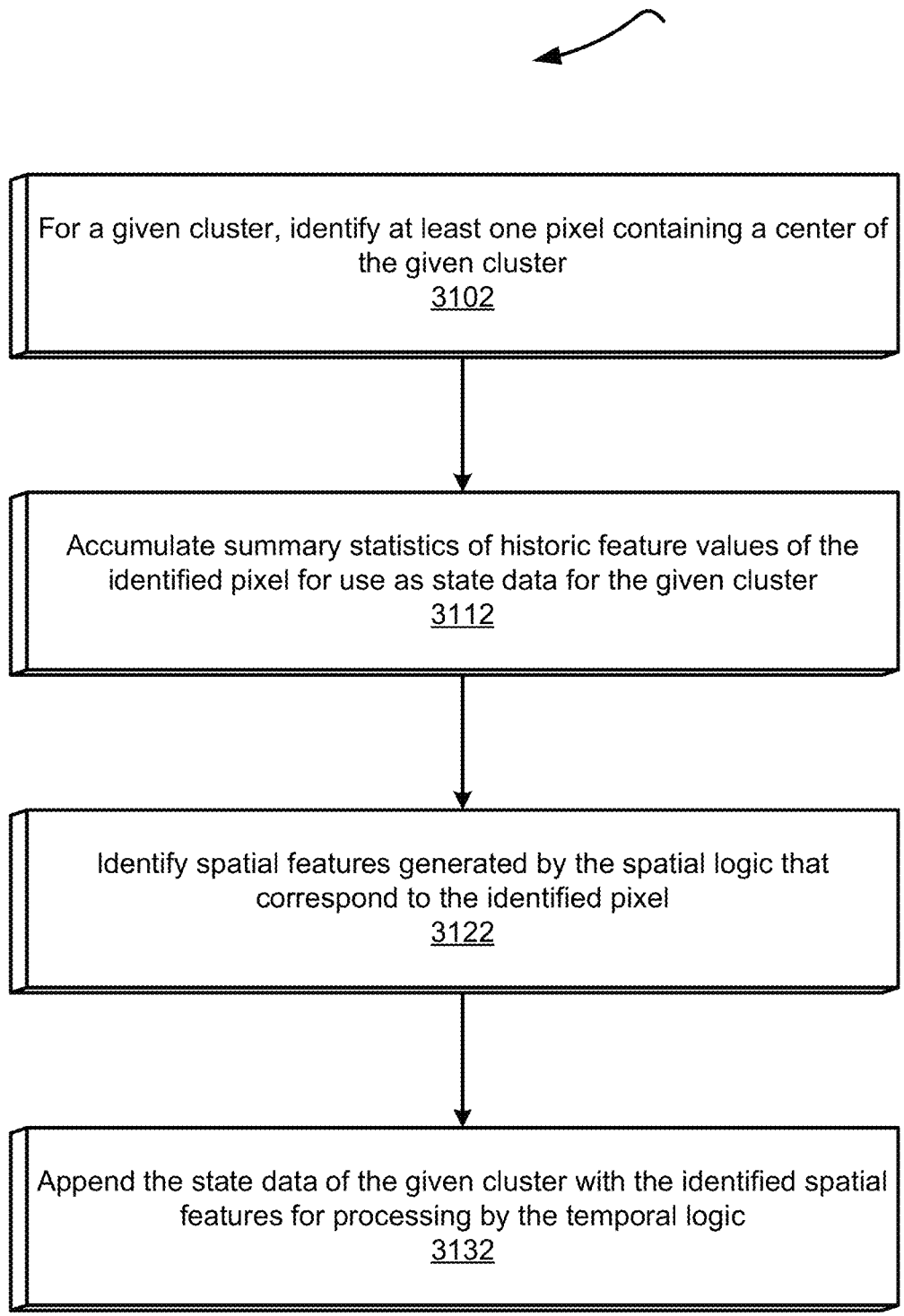
FIG. 31 illustrates one implementation of generating per-cluster states using historic intensity values of corresponding cluster pixels.

FIG. 31 illustrates one implementation of generating 3100 per-cluster states using historic intensity values of corresponding cluster pixels. In FIG. 31, the per-cluster states 3042 are determined by accumulating summary statistics of historic intensity values of the cluster pixels from the previous sequencing cycles and the current sequencing cycle, as discussed above, for example, using minimum value selection function, maximum value selection function, averaging function, exponential weighted averaging function, and so on. Then, the per-cluster states 3042 are combined with spatially convolved features of the cluster pixels and of a current base calling iteration/operation to generate base calls for the corresponding clusters. These steps are illustrated by actions 3102, 3112, 3122, and 3132 of FIG. 31.

Figure 32:
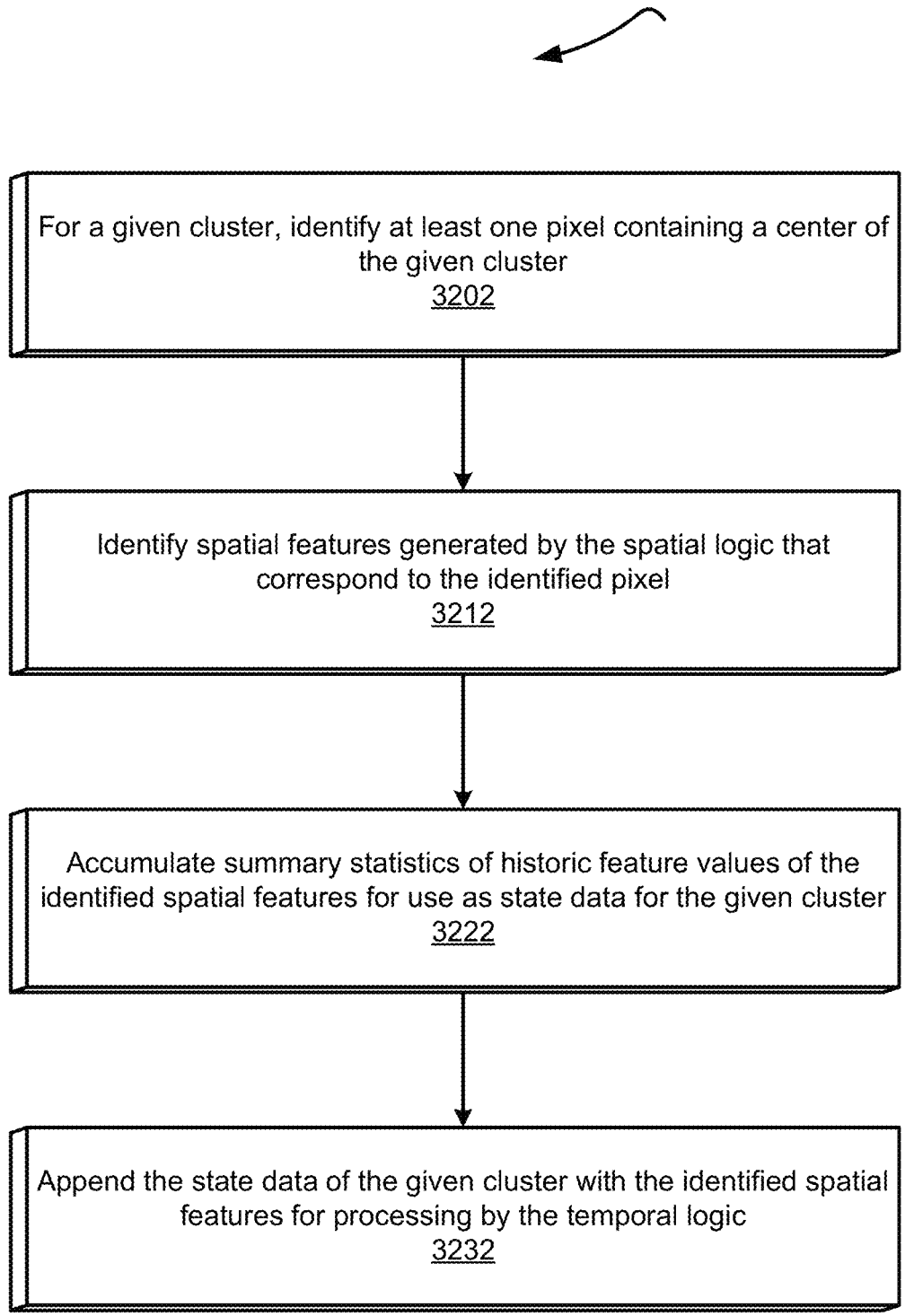
FIG. 32 illustrates one implementation of generating per-cluster states using historic feature values of spatially convolved features corresponding to cluster pixels.

FIG. 32 illustrates one implementation of generating 3200 per-cluster states using historic feature values of spatially convolved features corresponding to cluster pixels. In FIG. 31, the per-cluster states 3042 are determined by accumulating summary statistics of historic feature values of the spatially convolved features corresponding to the cluster pixels from the previous sequencing cycles and the current sequencing cycle, as discussed above, for example, using minimum value selection function, maximum value selection function, averaging function, exponential weighted averaging function, and so on. Then, the per-cluster states 3042 are combined with spatially convolved features of the cluster pixels and of the current base calling iteration/operation to generate base calls for the corresponding clusters. These steps are illustrated by actions 3202, 3212, 3222, and 3232 of FIG. 32.

Figure 33:
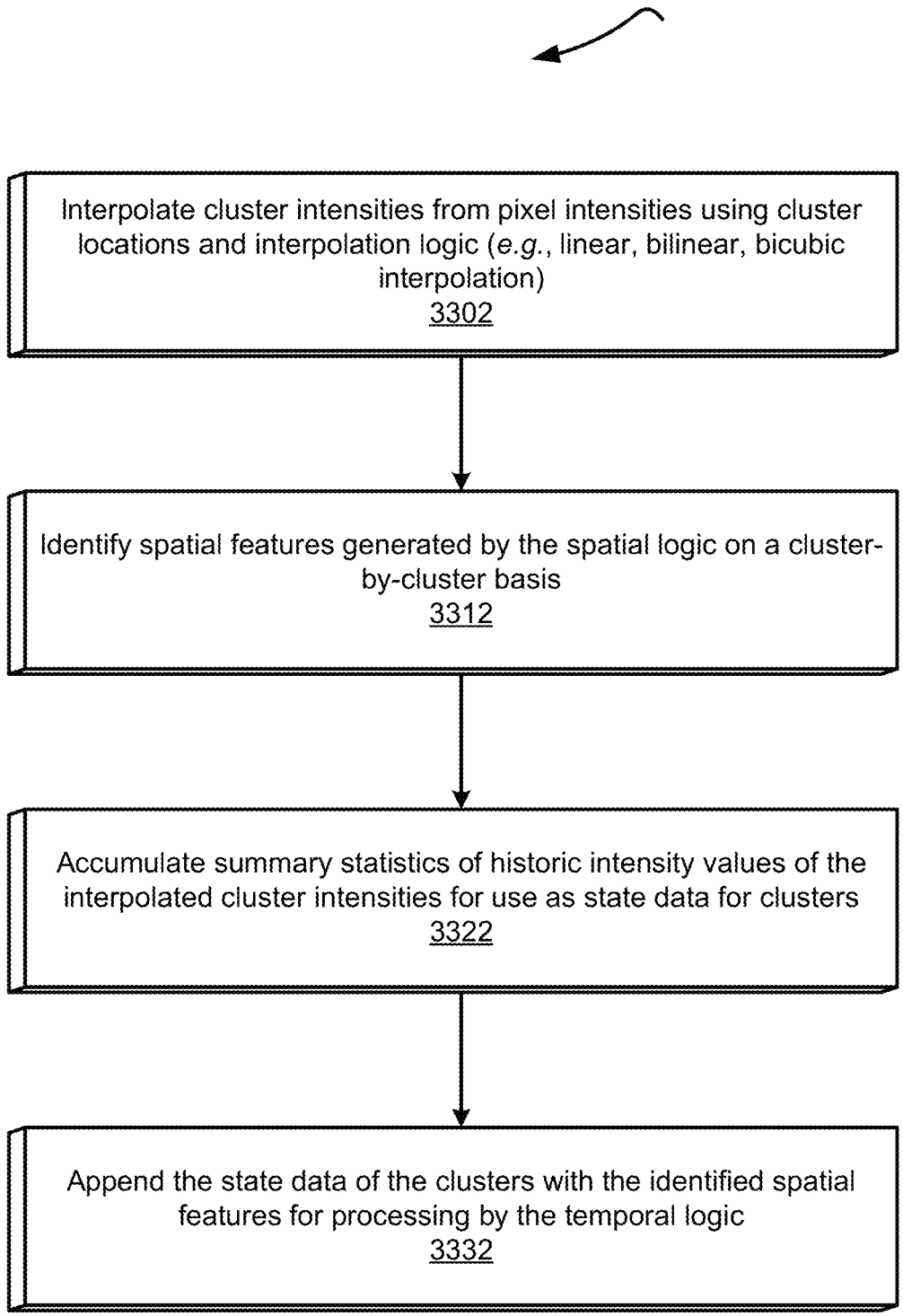
FIG. 33 illustrates one implementation of generating cluster intensities by interpolating pixel intensities, and using the interpolated cluster intensities to generate per-cluster states for base calling.

FIG. 33 illustrates one implementation of generating 3300 cluster intensities by interpolating pixel intensities, and using the interpolated cluster intensities to generate per-cluster states for base calling. In one implementation, intensity values of a group of pixels in the sequencing images can be interpolated (e.g., by using linear, bilinear, cubic interpolation) to estimate cluster intensities. In some implementations, cluster center locations and cluster shape data can be used to select a given group of pixels to interpolate cluster intensities for a corresponding cluster. In other implementations, cluster shape data can be used to use weighted intensities of partial pixels to determine the cluster intensities.

Summary statistics for cluster intensities interpolated at the previous sequencing cycles and the current sequencing cycle can be accumulated to generate the per-cluster states 3042 for the current sequencing cycle, as discussed above, for example, using minimum value selection function, maximum value selection function, averaging function, exponential weighted averaging function, and so on. Then, the per-cluster states 3042 are combined with spatially convolved features of the cluster pixels and of the current base calling iteration/operation to generate base calls for the corresponding clusters. These steps are illustrated by actions 3302, 3312, 3322, and 3332 of FIG. 32.

RTA Coefficients as Per-Cluster States

Figure 34:
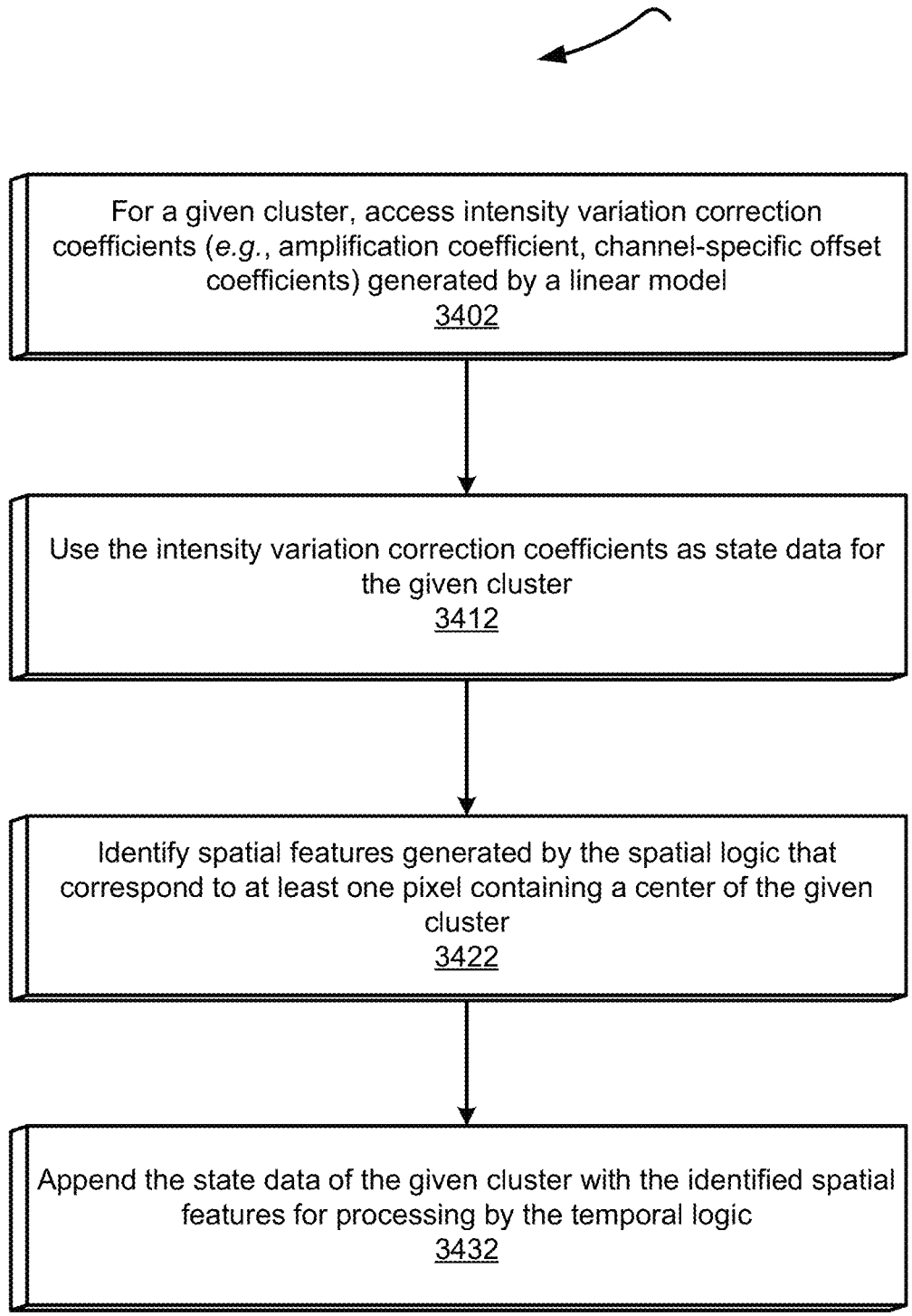
FIG. 34 illustrates one implementation of generating per-cluster states using a Real Time Analysis (RTA) base caller separate from the neural network-based base caller.

FIG. 34 illustrates one implementation of generating 3400 per-cluster states using a Real Time Analysis (RTA) base caller separate from the neural network-based base caller 2900.

Regarding the RTA base caller, The RTA is a base caller that can use linear intensity extractors to extract features from sequencing images for base calling. The following discussion describes one implementation of intensity extraction and base calling by RTA. In this implementation, RTA can perform a template generation step to produce a template image that identifies locations of clusters on a tile using sequencing images from some number of initial sequencing cycles called template cycles. The template image can be used as a reference for subsequent registration and intensity extraction steps. The template image can be generated by detecting and merging bright spots in each sequencing image of the template cycles, which in turn involves sharpening a sequencing image (e.g., using the Laplacian convolution), determining an "ON" threshold by a spatially segregated Otsu approach, and subsequent five-pixel local maximum detection with subpixel location interpolation. In another example, locations of clusters on a tile can be identified using fiducial markers. A solid support upon which a biological specimen is imaged can include such fiducial markers, to facilitate determination of the orientation of the specimen or the image thereof in relation to probes that are attached to the solid support. Exemplary fiducials can include but are not limited to beads (with or without fluorescent moieties or moieties such as nucleic acids to which labeled probes can be bound), fluorescent molecules attached at known or determinable features, or structures that combine morphological shapes with fluorescent moieties. Exemplary fiducials are set forth in U.S. Patent Publication No. 2002/0150909, which is incorporated herein by reference.

RTA can then register a current sequencing image against the template image. This can be achieved by using image correlation to align the current sequencing image to the template image on a sub-region, or by using non-linear transformations (e.g., a full six-parameter linear affine transformation).

RTA can generate a color matrix to correct cross-talk between color channels of the sequencing images. RTA can implement empirical phasing correction to compensate noise in the sequencing images caused by phase errors.

After different corrections are applied to the sequencing images, RTA can extract signal intensities for each spot location in the sequencing images. For example, for a given spot location, signal intensity may be extracted by determining a weighted average of the intensity of the pixels in a spot location. For example, a weighted average of the center pixel and neighboring pixels may be performed using bilinear or bicubic interpolation. In some implementations, each spot location in the image may comprise a few pixels (e.g., 1-5 pixels).

RTA can then spatially normalize the extracted signal intensities to account for variation in illumination across the sampled imaged. For example, intensity values may be normalized such that a 5th and 95th percentiles have values of 0 and 1, respectively. The normalized signal intensities for the image (e.g., normalized intensities for each channel) may be used to calculate mean chastity for the plurality of spots in the image.

In some implementations, RTA can use an equalizer to maximize the signal-to-noise ratio of the extracted signal intensities. The equalizer can be trained (e.g., using least square estimation, adaptive equalization algorithm) to maximize the signal-to-noise ratio of cluster intensity data in sequencing images. In one implementation, the equalizer can include trained coefficients to correct for spatial crosstalk and other forms of crosstalk and noises. In some implementations, the equalizer can be a single lookup table (LUT). In other implementations, the equalizer can be a LUT bank with a plurality of LUTs with subpixel resolution, also referred to as "equalizer filters" or "convolution kernels." In one implementation, the number of LUTs in the equalizer can depend on the number of subpixels into which pixels of the sequencing images can be divided. For example, if the pixels are divisible into n by n subpixels (e.g., 5×5 subpixels), then the equalizer can generate n2 LUTs (e.g., 25 LUTs). In yet implementations, the equalizer can be based on Fast Fourier Transforms (FFTs). In yet implementations, the equalizer can be based on Winograd convolutions.

In one implementation of training the equalizer, data from the sequencing images is binned by well subpixel location. For example, for a 5×5 LUT, $\frac{1}{25}$th of the wells have a center that is in bin (1,1) (e.g., the upper left corner of a sensor pixel), $\frac{1}{25}$th of the wells are in bin (1,2), and so on. In one implementation, the equalizer coefficients for each bin are determined using least squares estimation on the subset of data from the wells corresponding to the respective bins. This way the resulting estimated equalizer coefficients are different for each bin.

Each LUT/equalizer filter/convolution kernel has a plurality of coefficients that are learned from the training. In one implementation, the number of coefficients in a LUT corresponds to the number of pixels that are used for base calling a cluster. For example, if a local grid of pixels (image or pixel patch) that is used to base call a cluster is of size p×p (e.g., 9×9 pixel patch), then each LUT has p2 coefficients (e.g., 81 coefficients).

In one implementation, the training produces equalizer coefficients that are configured to mix/combine intensity values of pixels that depict intensity emissions from a target cluster being base called and intensity emissions from one or more adjacent clusters in a manner that maximizes the signal-to-noise ratio. The signal maximized in the signal-to-noise ratio is the intensity emissions from the target cluster, and the noise minimized in the signal-to-noise ratio is the intensity emissions from the adjacent clusters, i.e., spatial crosstalk, plus some random noise (e.g., to account for background intensity emissions). The equalizer coefficients are used as weights and the mixing/combining includes executing element-wise multiplication between the equalizer coefficients and the intensity values of the pixels to calculate a weighted sum of the intensity values of the pixels, i.e., a convolution operation.

RTA can perform base calling by fitting a mathematical model to the optimized intensity data. Suitable mathematical models that can be used include, for example, a k-means clustering algorithm, a k-means-like clustering algorithm, expectation maximization clustering algorithm, a histogram based method, and the like. Four Gaussian distributions may be fit to the set of two-channel intensity data such that one distribution is applied for each of the four nucleotides represented in the data set. In one particular implementation, an expectation maximization (EM) algorithm may be applied. As a result of the EM algorithm, for each X, Y value (referring to each of the two channel intensities respectively) a value can be generated which represents the likelihood that a certain X, Y intensity value belongs to one of four Gaussian distributions to which the data is fitted. Where four bases give four separate distributions, each X, Y intensity value will also have four associated likelihood values, one for each of the four bases. The maximum of the four likelihood values indicates the base call. For example, if a cluster is "OFF" in both channels, the base call is G. If the cluster is "OFF" in one channel and "ON" in another channel the base call is either C or T (depending on which channel is ON), and if the cluster is "ON" in both channels the base call is A.

Additional details about RTA can be found in U.S. Nonprovisional patent application Ser. No. 15/909,437, titled "OPTICAL DISTORTION CORRECTION FOR IMAGED SAMPLES," filed on Mar. 1, 2018; U.S. Nonprovisional patent application Ser. No. 14/530,299, titled "IMAGE ANALYSIS USEFUL FOR PATTERNED OBJECTS," filed on Oct. 31, 2014; U.S. Nonprovisional patent application Ser. No. 15/153,953, titled "METHODS AND SYSTEMS FOR ANALYZING IMAGE DATA," filed on Dec. 3, 2014; U.S. Nonprovisional patent application Ser. No. 13/006,206, titled "DATA PROCESSING SYSTEM AND METHODS," filed on Jan. 13, 2011; and U.S. Nonprovisional patent application Ser. No. 17/308,035, titled "EQUALIZATION-BASED IMAGE PROCESSING AND SPATIAL CROSS-TALK ATTENUATOR," filed May 4, 2021, all which are incorporated by reference as if fully set forth herein.

The inter-cluster intensity profile variation among intensity profiles of a large number (e.g., thousands, millions, billions, etc.) of clusters in the cluster population causes a drop in base calling throughput and an increase in base calling error rate. To correct the inter-cluster intensity profile variation, the RTA generates per-cluster variation correction coefficients on a cluster-by-cluster basis.

In the two-channel implementation, the per-cluster variation correction coefficients comprise an amplification coefficient that accounts for scale variation in the inter-cluster intensity profile variation, and two channel-specific offset coefficients that account for shift variation along the first and the second intensity channels in the inter-cluster intensity profile variation, respectively. In another implementation, the shift variation is accounted for by using a common offset coefficient for the different intensity channels (e.g., the first and the second intensity channels).

It would be apparent to one skilled in the art that the variation correction logic of the RTA can be analogously applied to sequencing images generated using one-channel implementation, four-channel implementation, and so on. For example, in the case of four-channel implementation, four channel-specific offset coefficients are determined to correct shift variations in four intensity channels, respectively.

The per-cluster variation correction coefficients for a target cluster are generated at a current sequencing cycle of the sequencing run based on combining analysis of historic intensity statistics determined for the target cluster at preceding sequencing cycles of the sequencing run with analysis of current intensity statistics determined for the target cluster at the current sequencing cycle. The per-cluster variation correction coefficients are used to correct next intensity readings registered for the target cluster a next sequencing cycle of the sequencing run. The corrected next intensity readings are used to base call the target cluster at the next sequencing cycle. The result of repeatedly applying respective per-cluster variation correction coefficients to respective intensity profiles of respective clusters at successive sequencing cycles of the sequencing run is that the intensity profiles become coincidental and anchored to the origin (e.g., at the bottom lower corner of the trapezoids).

Current Sequencing Cycle

At the current sequencing cycle i, the sequencer generates sequencing images. The sequencing images contain current intensity data registered for the target cluster at the current sequencing cycle i, along with containing current intensity data registered for multiple clusters in the cluster population.

The current intensity data is provided to the RTA. The RTA processes the current intensity data and generates a current base call for the target cluster at the current sequencing cycle i.

At the current sequencing cycle i, the intensity profile of the target cluster includes the current intensity data, and current historic intensity data registered for the target cluster at those sequencing cycles of the sequencing run that precede the current sequencing cycle i, i.e., preceding sequencing cycles 1 to i−1. We collectively refer to the current intensity data and the current historic intensity data as current available intensity data.

In the intensity profile, the four intensity distributions correspond to the four bases A, C, T, and G. In one implementation, the current base call is made by determining which of the four intensity distributions the current intensity data belongs to. In some implementations, this is accomplished by using an expectation maximization algorithm. The expectation maximization algorithm iteratively maximizes the likelihood of observing means (centroids) and distributions (covariances) that best fit the current available intensity data.

Once the four intensity distributions are determined at the current sequencing cycle i by using the expectation maximization algorithm, the likelihoods of the current intensity data belonging to each of the four intensity distributions are calculated. The greatest likelihood gives the current base call. As an example, consider that "m, n" are the intensity values of the current intensity data in the first and second intensity channels, respectively. The expectation maximization algorithm generates four values that represent the likelihoods of the "m, n" intensity values belonging to each of the four intensity distributions. The maximum of the four values identifies the called base.

In other implementations, a k-means clustering algorithm, a k-means-like clustering algorithm, a histogram based method, and the like can be used for base calling.

Next Sequencing Cycle

At the next sequencing cycle i+1, an intensity correction parameters determiner determines intensity correction parameters for the target cluster based on the current base call. In the two-channel implementation, the intensity correction parameters include distribution intensity in the first intensity channel, distribution intensity in the second intensity channel, intensity error in the first intensity channel, intensity error in the second intensity channel, distribution centroid-to-origin distance, and distribution intensity-to-intensity error similarity measure.

We define each of the intensity correction parameters as follows:
1) A distribution intensity in the first intensity channel is the intensity value in the first intensity channel at a centroid of a base-specific intensity distribution to which the target cluster belongs at the current sequencing cycle i. Note that the base-specific intensity distribution is the basis for calling the current base call.
2) A distribution intensity in the second intensity channel is the intensity value in the second intensity channel at the centroid of the base-specific intensity distribution.
3) An intensity error in the first intensity channel is the difference between the measured intensity value of the current intensity data in the first intensity channel and the distribution intensity in the first intensity channel.
4) An intensity error in the second intensity channel is the difference between the measured intensity value of the current intensity data in the second intensity channel and the distribution intensity in the second intensity channel.
5) A distribution centroid-to-origin distance is the Euclidean distance between the centroid of the base-specific intensity distribution and the origin of the multi-dimensional space in which the base-specific intensity distribution was fitted (e.g., by using the expectation maximization algorithm). In other implementations, distance metrics such as the Mahalanobis distance and the minimum covariance determinant (MCD) distances, and their associated centroid estimators can be used.
6) A distribution intensity-to-intensity error similarity measure is the summation of channel-wise dot products between the distribution intensities and the intensity errors in the first and second intensity channels.

An accumulated intensity correction parameter determiner accumulates the intensity correction parameters with historic accumulated intensity correction parameters from preceding sequencing cycle i−1 to determine accumulated intensity correction parameters. Examples of accumulation include summing and averaging.

A variation correction coefficients determiner determines variation correction coefficients based on the determine accumulated intensity correction parameters.

At the next sequencing cycle i+1, the sequencer generates sequencing images. The sequencing images contain next intensity data registered for the target cluster at the next sequencing cycle i+1, along with containing next intensity data registered for multiple clusters in the cluster population.

An intensity corrector applies the variation correction coefficients to the next intensity data to generate corrected next intensity data.

At the next sequencing cycle i+1, the intensity profile of the target cluster includes the corrected next intensity data, and next historic intensity data registered for the target cluster at those sequencing cycles of the sequencing run that precede the next sequencing cycle i+1, i.e., preceding sequencing cycles 1 to i. We collectively refer to the corrected next intensity data and the next historic intensity data as next available intensity data.

The corrected next intensity data is provided to the RTA. The RTA can process the corrected next intensity data and can generate a next base call for the target cluster at the next sequencing cycle i+1. To generate the next base call, the expectation maximization algorithm can observe the means (centroids) and the distributions (covariances) based on the corrected next intensity data to best fit the next available intensity data.

Once the four intensity distributions are determined at the next sequencing cycle i+1 by using the expectation maximization algorithm, the likelihoods of the corrected next intensity data belonging to each of the four intensity distributions are calculated. The greatest likelihood gives the next base call.

Note that the base calling pipeline is executed on a cluster-by-cluster basis and is executed in parallel for the multiple clusters in the cluster population. Also, the base calling pipeline is executed repeatedly for successive sequencing cycles of the sequencing run (e.g., for successive 150 sequencing cycles of read 1 and another successive 150 sequencing cycles of read 2 in a paired-end sequencing run).

Least-Squares Solution

A least-squares solution determines closed-form expressions for the accumulated intensity correction parameters and the variation correction coefficients. The least-squares solution determiner comprises an intensity modeler and a minimizer.

The intensity modeler models the relationship between the measured intensity for the target cluster and the variation correction coefficients according to the following expression:

$$y_{C,i} = ax_{C,i} + d_i + n_{C,i} \qquad \text{Equation (1)}$$

where
a is the amplification coefficient for the target cluster
$d_i$ is the channel-specific offset coefficient for intensity channel i
$x_{C,i}$ is the distribution intensity in the intensity channel i for the target cluster at the current sequencing cycle C
$Y_{C,i}$ is the measured intensity in the intensity channel i for the target cluster at the current sequencing cycle C
$n_{C,i}$ is the additive noise in the intensity channel i for the target cluster at the current sequencing cycle C The minimizer uses the least-squares solution to minimize the following expression:

$$errorf(\hat{a}, \hat{d}_i) = \sum_{c=1}^{C} \sum_{i=1}^{2} (\hat{a} x_{C,i} + \hat{d}_i - y_{C,i})^2 \qquad \text{Equation (2)}$$

where:
error f is the error function
$\hat{a}$ is the amplification coefficient for the target cluster
$\hat{d}_i$ is the channel-specific offset coefficient for the intensity channel i
C is the current sequencing cycle Using the chain rule, the minimizer calculates two partial derivatives of the error function with respect to the amplification coefficient $\hat{a}$ and the channel-specific offset coefficients $\hat{d}_i$. The partial derivatives set Equation 2 to zero to minimize the error function:

$$\frac{\partial errorf}{\partial \hat{a}} = \frac{\partial}{\partial \hat{a}} \left[ \sum_{c=1}^{C} \sum_{i=1}^{2} (\hat{a} x_{C,i} + \hat{d}_i - y_{C,i})^2 \right] = 0 \qquad \text{Equation (3)}$$

$$\frac{\partial errorf}{\partial \hat{d}_i} = \frac{\partial}{\partial \hat{d}_i} \left[ \sum_{c=1}^{C} \sum_{i=1}^{2} (\hat{a} x_{C,i} + \hat{d}_i - y_{C,i})^2 \right] = 0 \qquad \text{Equation (4)}$$

Channel-specific intensity error $e_{c,i}$ is defined as follows:

$$e_{C,i} = y_{C,i} - x_{C,i} \quad \text{Equation (5)}$$

Closed-Form Expressions

The first partial derivative determines a closed-form expression for the amplification coefficient â as follows:

$$\frac{\partial errorf}{\partial \hat{a}} = \sum_{c=1}^{C}\sum_{i=1}^{2} 2x_{C,i}(\hat{a}x_{C,i} + \hat{d}_i - y_{C,i}) = 0 \quad \text{Equation (6)}$$

$$= \sum_{c=1}^{C}\sum_{i=1}^{2} 2x_{C,i}(\hat{a}x_{C,i} - x_{C,i} + \hat{d}_i - y_{C,i} + x_{C,i}) = 0 \quad \text{Equation (7)}$$

$$= \sum_{c=1}^{C}\sum_{i=1}^{2} x_{C,i}^2(\hat{a}-1) + \hat{d}_i x_{C,i} - e_{C,i} x_{C,i}) = 0 \quad \text{Equation (8)}$$

$$= (a-1)\sum_{c=1}^{C}(x_{C,1}^2 + x_{C,2}^2) + d_1\sum_{c=1}^{C} x_{C,i} + d_2\sum_{c=1}^{C} x_{C,2} - \sum_{c=1}^{C} e_{C,1} x_{C,1} - \sum_{c=1}^{C} e_{C,2} x_{C,2} = 0 \quad \text{Equation (9)}$$

Closed-form expressions $\bar{x}_1$, $\bar{x}_2$, $\bar{e}_1$, $\bar{e}_2$, $\overline{xx}$, and $\overline{xe}$ for the accumulated intensity correction parameters recharacterize Equation 9 as follows:

$$= C(\hat{a}-1)\overline{xx} + C\bar{x}_1\hat{d}_1 + C\bar{x}_2\hat{d}_2 - C\overline{xe} = 0 \quad \text{Equation (10)}$$

$$= (\hat{a}-1)\overline{xx} + \bar{x}_1\hat{d}_1 + \bar{x}_2\hat{d}_2 - \overline{xe} = 0 \quad \text{Equation (11)}$$

where:

$$\bar{x}_1 = \sum_{c=1}^{C} x_{C,1} \quad \text{Intermediate Term (1)}$$

$$\bar{x}_2 = \sum_{c=1}^{C} x_{C,2} \quad \text{Intermediate Term (2)}$$

$$\bar{e}_1 = \sum_{c=1}^{C} e_{c,1} \quad \text{Intermediate Term (3)}$$

$$\bar{e}_2 = \sum_{c=1}^{C} e_{c,2} \quad \text{Intermediate Term (4)}$$

$$\overline{xx} = \sum_{c=1}^{C} (x_{C,1}^2 + x_{C,2}^2) \quad \text{Intermediate Term (5)}$$

$$\overline{xe} = \sum_{c=1}^{C} (x_{c,1} e_{c,1} + x_{c,2} e_{c,2}) \quad \text{Intermediate Term (6)}$$

We define each of the accumulated intensity correction parameters as follows:

1) The first accumulated intensity correction parameter $\bar{x}_1$ is the sum of distribution intensities in the first intensity channel measured for the target cluster at each of the preceding sequencing cycles 1 to i−1, and the current sequencing cycle i.
2) The second accumulated intensity correction parameter $\bar{x}_2$ is the sum of distribution intensities in the second intensity channel measured for the target cluster at each of the preceding sequencing cycles 1 to i−1, and the current sequencing cycle i.
3) The third accumulated intensity correction parameter $\bar{e}_1$ is the sum of intensity errors in the first intensity channel calculated for the target cluster at each of the preceding sequencing cycles 1 to i−1, and the current sequencing cycle i.
4) The fourth accumulated intensity correction parameter $\bar{e}_2$ is the sum of intensity errors in the second intensity channel calculated for the target cluster at each of the preceding sequencing cycles 1 to i−1, and the current sequencing cycle i.
5) The fifth accumulated intensity correction parameter $\overline{xx}$ is the sum of distribution centroid-to-origin distances calculated for the target cluster at each of the preceding sequencing cycles 1 to i−1, and the current sequencing cycle i.
6) The sixth accumulated intensity correction parameter $\overline{xe}$ is the sum of distribution intensity-to-intensity error similarity measures calculated for the target cluster at each of the preceding sequencing cycles 1 to i−1, and the current sequencing cycle i.

The second partial derivative determines a closed-form expression for the offset coefficients $\hat{d}_i$ as follows:

$$\frac{\partial errorf}{\partial \hat{a}} = \sum_{c=1}^{C}\sum_{i=1}^{2} 2(\hat{a}x_{C,i} + \hat{d}_i - y_{C,i}) = 0 \quad \text{Equation (12)}$$

$$= \sum_{c=1}^{C}\sum_{i=1}^{2} (\hat{a}x_{C,i} - x_{C,i} + \hat{d}_i - y_{C,i} + x_{C,i}) = 0 \quad \text{Equation (13)}$$

$$= \sum_{c=1}^{C}\sum_{i=1}^{2} x_{C,i}^2\left((\hat{a}-1) + \sum_{i=1}^{2}\hat{d}_i + \sum_{C=1}^{C} x_{C,i}\right) = 0 \quad \text{Equation (14)}$$

Then, for each intensity channel:

$$= C(\hat{a}-1)\bar{x}_i + C\hat{d}_i - C\bar{e}_i = 0 \quad \text{Equation (15)}$$

$$= (\hat{a}-1)\bar{x}_i + \hat{d}_i - \bar{e}_i = 0 \quad \text{Equation (16)}$$

For the first intensity channel, i.e., i=1:

$$\hat{d}_1 = \bar{e}_1 + (1-\hat{a})\bar{x}_1 \quad \text{Equation (17)}$$

where:
$\hat{d}_1$ is the offset coefficient for the first intensity channel
For the second intensity channel, i.e., i=2:

$$\hat{d}_2 = \bar{e}_2 + (1-\hat{a})\bar{x}_2 \quad \text{Equation (18)}$$

where:
$\hat{d}_2$ is the offset coefficient for the second intensity channel
Substituting Equations 17 and 18 in Equation 11:

$$\frac{\partial errorf}{\partial \hat{a}} = (a-1)\overline{xx} + \bar{x}_1[\bar{e}_1 + (1-\hat{a})\hat{x}_1] + \quad \text{Equation (19)}$$

$$\hat{x}_2[\hat{e}_2 + (1-\hat{a})\bar{x}_2] - \overline{xe} = 0$$

$$= (\hat{a}-1)\overline{xx} + (1-\hat{a})\hat{x}_1^2 + (1-\hat{a})\hat{x}_2^2 + \quad \text{Equation (20)}$$

$$\bar{x}_1\bar{e}_1 + \bar{x}_2\bar{e}_2 - \overline{xe} = 0$$

$$= (\hat{a}-1)(\overline{xx} - \hat{x}_1^2 - \hat{x}_2^2) + \hat{x}_1\hat{e}_1 + \bar{x}_2\bar{e}_2 - \overline{xe} = 0 \quad \text{Equation (21)}$$

$$\hat{a} - 1 = \frac{\bar{x}_1\bar{e}_1 + \bar{x}_2\bar{e}_2 - \overline{xe}}{\overline{xx} - \bar{x}_1^2 - \bar{x}_2^2} \quad \text{Equation (22)}$$

$$\hat{a} = 1 + \frac{\bar{x}_1\bar{e}_1 + \bar{x}_2\bar{e}_2 - \overline{xe}}{\overline{xx} - \bar{x}_1^2 - \bar{x}_2^2} \quad \text{Equation (23)}$$

where:
â is the amplification coefficient for the target cluster
In another implementation, to reduce the memory requirements per cluster, the common offset coefficient for the different intensity channels (e.g., the first and the second intensity channels) is determined as follows by introducing the constraint $\hat{d}_1 = \hat{d}_2$:

$$\bar{x} = \frac{1}{2C}\sum_{c=1}^{C}(x_{C,1} + x_{C,2})$$ Intermediate Term (1.1)

$$\overline{xx} = \frac{1}{C}\sum_{c=1}^{C}(x_{C,1}^2 + x_{C,2}^2)$$ Intermediate Term (2.1)

$$\bar{e} = \frac{1}{2C}\sum_{c=1}^{C}(e_{C,1} + e_{C,2})$$ Intermediate Term (3.1)

$$\overline{xe} = \frac{1}{C}\sum_{c=1}^{C}(x_{C,1}e_{C,1} + x_{C,2}e_{C,2})$$ Intermediate Term (4.1)

$$\hat{a} = 1 + \frac{\overline{xe} + 2\bar{x}\,\bar{e}}{\overline{xx} - 2\bar{x}^2}$$ Equation (24)

$$\hat{d}_1 = \bar{e} + \bar{x}(1 - \hat{a})$$ Equation (25)

$$\hat{d}_2 = \bar{e} + \bar{x}(1 - \hat{a})$$ Equation (26)

It would be apparent to one skilled in the art that the least-squares solution is executed in advance of the sequencing run to determine the closed-form expressions. Once determined, the closed-form expressions are applied to the intensity values generated during the sequencing run on a cluster-by-cluster and iteratively at each sequencing cycle of the sequencing run.

Additional details about the per-cluster variation correction coefficients and how they are determined can be found in U.S. Provisional Patent Application No. 63/106,256, titled "SYSTEMS AND METHODS FOR PER-CLUSTER INTENSITY CORRECTION AND BASE CALLING," filed 27 Oct. 2021, which is incorporated herein by reference in its entirety.

In FIG. 34, the per-cluster states 3042 are the per-cluster variation correction coefficients determined by the RTA for the current sequencing cycle, in accordance with one implementation. Then, the per-cluster states 3042 are combined with spatially convolved features of the cluster pixels and of the current base calling iteration/operation to generate base calls for the corresponding clusters. These steps are illustrated by actions 3402, 3412, 3422, and 3432 of FIG. 34.

Compression Network

As discussed above, the specialized architecture of the neural network-based base caller 2900 processes sliding windows of image patches for corresponding sequencing cycles. Overlap exists between sequencing cycles of successive sliding windows. This causes the neural network-based base caller 2900 to redundantly process image patches for the overlapping sequencing cycles. This in turn results in waste of compute resources. For example, in one implementation, each spatial convolution layer of the neural network-based base caller 2900 has nearly 100 million multiplication operations. Then, for a window of five sequencing cycles and a cascade (or sequence) of seven spatial convolution layers, the spatial convolution neural network executes about 620 million multiplication operations. Furthermore, the temporal convolution neural network executes about 10 million multiplication operations.

Since the image data for cycle N−1 in a current sliding window (or a current iteration of base calling) is processed as cycle N in the previous sliding window (or a previous iteration of base calling), an opportunity arises to store the intermediate results of the processing done in the current sliding window and the intermediate results them in subsequent sliding windows, and thereby bypass (or obviate) redundant processing (or reprocessing) of input image data for overlapping sequencing cycles between successive sliding windows.

However, the intermediate results are several terabytes of data that require impractical amount of storage. To overcome this technical problem, the technology disclosed proposes compressing the intermediate results the first time the intermediate results are generated by the neural network-based base caller 2900 and repurposing the compressed intermediate results in subsequent sliding windows to avoid redundant computation, and thereby not regenerating (or only-once generating) the intermediate results.

Figure 35:
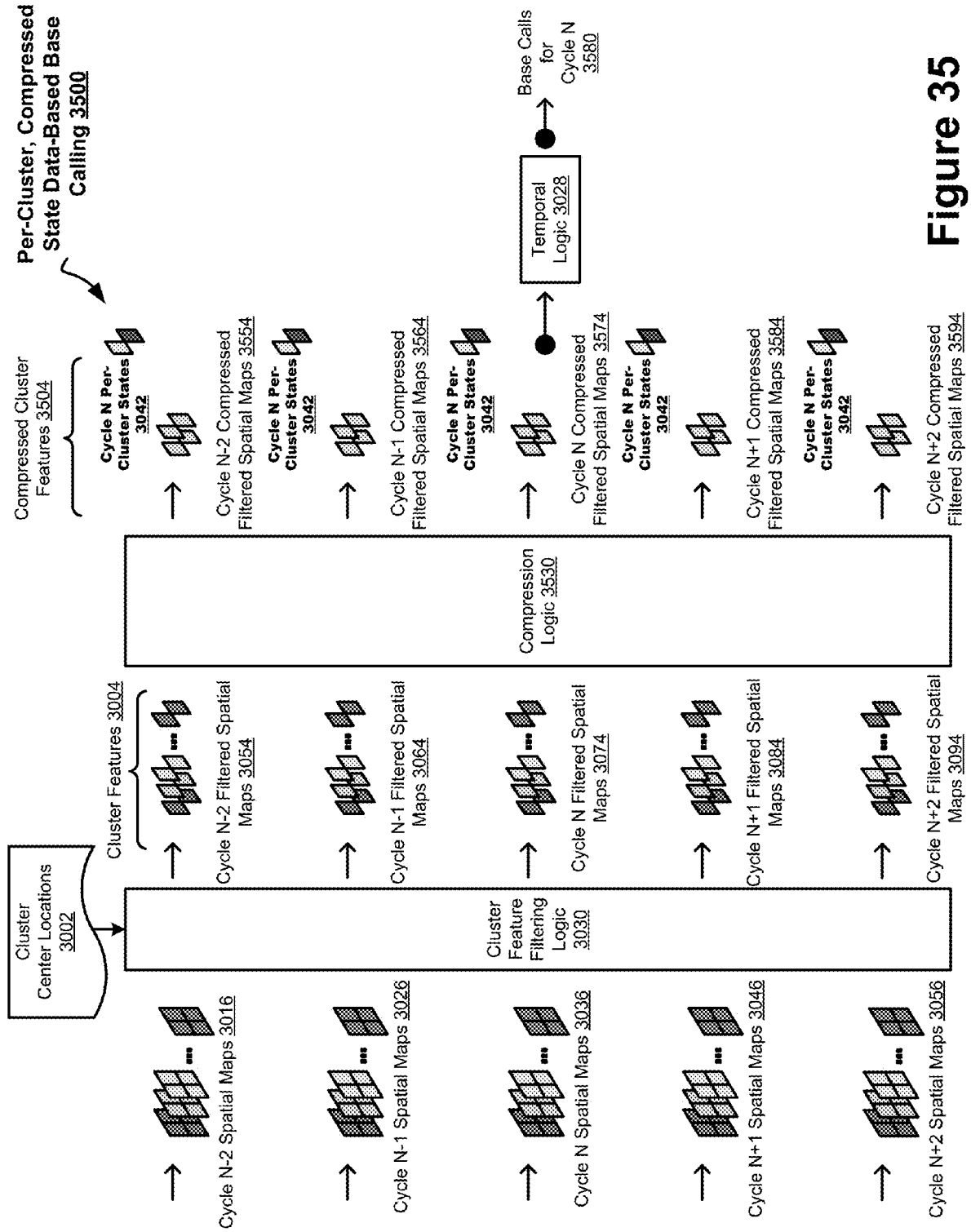
FIG. 35 illustrates one implementation of a compression logic that generates compressed features.

In FIG. 35, a compression logic 3530 (or compression network or compression subnetwork or compression layer or squeezing layer) processes the outputs of the cluster feature filtering logic 3030 and generates a compressed representation of the outputs, in accordance with one implementation. In one implementation, the compression network 3530 comprises a compression convolution layer that reduces the depth dimensionality of feature maps generated by the cluster feature filtering logic 3030.

For example, consider that the depth dimensionality of the filtered, per-cluster spatial maps 3054, 3064, 3074, 3084, and 3094 is 14 (i.e., fourteen feature maps or fourteen channels per spatial output). The compression network 3530 attenuates the filtered, per-cluster spatial maps 3054, 3064, 3074, 3084, and 3094 into respective compressed filtered, per-cluster spatial maps 3554, 3564, 3574, 3584, and 3594 for the respective sequencing cycles N−2, N−1, N, N+1, and N+2, collectively referred to as compressed cluster features 3504. In one implementation, each of the compressed filtered, per-cluster spatial maps 3554, 3564, 3574, 3584, and 3594 has a depth dimensionality of 2 (i.e., two feature maps or two channels per compressed spatial output). In other implementations, the compressed filtered, per-cluster spatial maps 3554, 3564, 3574, 3584, and 3594 can have a depth dimensionality of 3 or 4 (i.e., three or fourth feature maps or three or fourth channels per compressed spatial output). In yet other implementations, the compressed filtered, per-cluster spatial maps 3554, 3564, 3574, 3584, and 3594 can have a depth dimensionality of 1 (i.e., one feature map or one channel per compressed spatial output). In one implementation, the compression layer 3530 does not include an activation function like ReLU. In other implementations, it can include an activation function. In other implementations, the compression logic 3530 can configure the corresponding compressed spatial map sets to each have more than four feature maps.

The discussion now turns to how the compression logic 3530 generates the compressed outputs.

In one implementation, the compression logic 3530 uses 1×1 convolutions to reduce the number of feature maps (i.e., the depth dimension or the number of channels) while introducing non-linearity. The 1×1 convolutions have a kernel size of 1. The 1×1 convolutions can transform a volume depth into another squeezed or expanded representation without changing the spatial dimensions. A 1×1 convolution operates like a fully connected linear layer across the input channels. This is useful in mapping from feature maps with many channels to fewer feature maps. A single 1×1 convolution can be applied to an input tensor with two feature maps. The 1×1 convolution compresses the two-channel input to a single-channel output.

The number of compressed outputs (or compressed feature maps or compressed spatial maps or compressed temporal maps) generated by the compression layer 108 is a function of the number of 1×1 convolution filters (or compression convolution filters or compression filters) configured in the compression layer 3530. In one implementation, the compression layer 3530 can have two 1×1 convolution filters. The first 1×1 convolution filter can process a spatial feature volume with the fourteen feature maps and generate a first feature map while preserving the spatial dimensionality of 101×101. The second 1×1 convolution filter can also process the spatial feature volume with the fourteen feature maps and generate a second feature map while preserving the spatial dimensionality of 101×101. Accordingly, the compression layer 3530 reduces the spatial feature volume with the fourteen feature maps into a compressed output with two spatial feature maps (i.e., compression ratio=7).

In some implementations, the technology disclosed saves about 80% of convolutions in the spatial network of the neural network-based base caller 2900. In one implementation, the 80% savings are observed in the spatial convolutions when a compression logic and repurposing of the compressed feature maps in subsequent sequencing cycles is used for an input window of five sequencing cycles (e.g., cycle N, cycle N+1, cycle N−1, cycle N+2, and cycle N−2). In another implementation, 90% savings are observed in the spatial convolutions when the compression logic and repurposing of the compressed feature maps in subsequent sequencing cycles is used for an input window of ten sequencing cycles (e.g., cycle N, cycle N+1, cycle N−1, cycle N+2, cycle N−2, cycle N+3, and cycle N−3). That is, the larger the window size, the bigger the savings from the use of the compression logic and repurposing of the compressed feature maps, and the larger the window size, the better the base calling performance due to incorporation of greater context from additional flanking cycles. So bigger savings for bigger windows improves overall performance for a given compute capability.

The compute efficiency and compact compute footprint brought about by the compression logic facilitates hardware implementation of the neural network-based base caller 2900 on resource-constrained processors like Central Processing Units (CPUs), Graphics Processing Units (GPUs), Field Programmable Gate Arrays (FPGAs), Coarse-Grained Reconfigurable Architectures (CGRAs), Application-Specific Integrated Circuits (ASICs), Application Specific Instruction-set Processor (ASIP), and Digital Signal Processors (DSPs).

The compute saved by the compression logic allows for incorporating more convolution operators in the neural network-based base caller 2900. Examples include adding more convolution filters in the spatial and temporal convolution layers, increasing the size of the convolution filters, and increasing the number of spatial and temporal convolution layers. Additional convolution operations improve intensity pattern detection and overall base calling accuracy of the neural network-based base caller 2900.

Additional details about the compression logic and its compressed outputs can be found in U.S. Nonprovisional patent application Ser. No. 17/179,395, titled "DATA COMPRESSION FOR ARTIFICIAL INTELLIGENCE-BASED BASE CALLING," filed 18 Feb. 2021 which is incorporated herein by reference in its entirety.

In FIG. 35, per-cluster states 3042 for the current sequencing cycle N are combined with intermediate outputs of the neural network-based base caller 2900, i.e., the compressed filtered, per-cluster spatial maps 3554, 3564, 3574, 3584, and 3594.

In some implementations, the dimensionality of the per-cluster states 3042 is modified to conform with the dimensionality of the compressed filtered, per-cluster spatial maps 3554, 3564, 3574, 3584, and 3594 (e.g., by trimming dimensions, adding dimensions, padding (e.g., zero padding), cloning, etc.). In different implementations, the respective five instances of the per-cluster states 3042 and the compressed filtered, per-cluster spatial maps 3554, 3564, 3574, 3584, and 3594 can be respectively combined using techniques discussed above, such as concatenation, summation, element-wise multiplication, element-wise multiplication and summation (convolution), and so on.

Then, according to the illustrated example in FIG. 35, the respective five combinations of the respective compressed filtered, per-cluster spatial maps 3554, 3564, 3574, 3584, and 3594 and the respective five instances of the per-cluster states 3042 are processed by the temporal logic 2928 to generate base calls 3080 for the current sequencing cycle N. The base calls 3080 are made for clusters corresponding to the cluster pixels and therefore the cluster features 3004.

The discussion now turns to different variations of the per-cluster states 3042 and how these variations are determined according to different implementations of the technology disclosed.

Figure 36:
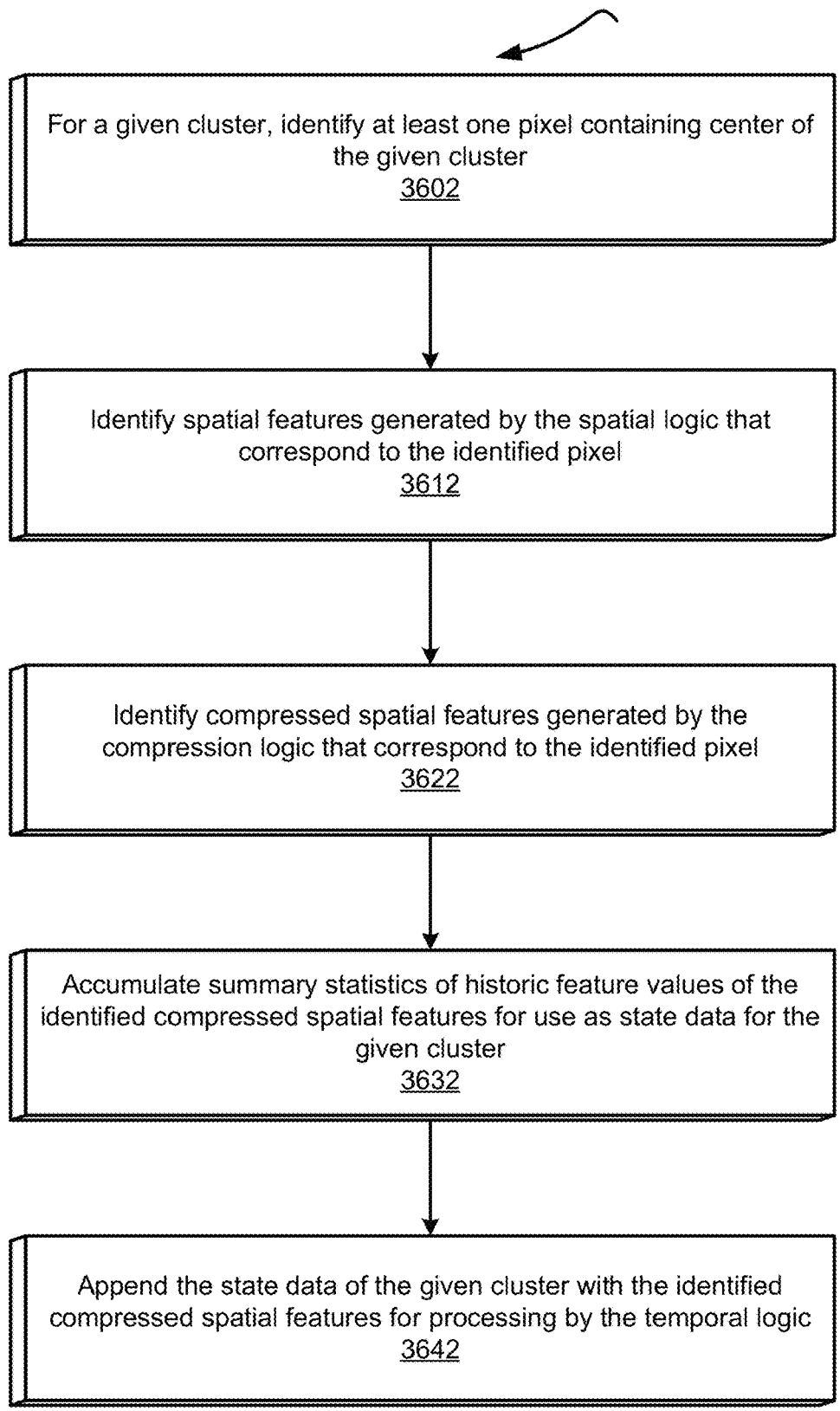
FIG. 36 illustrates one implementation of generating per-cluster states using historic feature values of compressed spatially convolved features corresponding to cluster pixels.

FIG. 36 illustrates one implementation of generating 3600 per-cluster states using historic feature values of compressed spatially convolved features corresponding to cluster pixels. In FIG. 36, the per-cluster states 3042 are determined by accumulating summary statistics of historic feature values of the compressed spatially convolved features corresponding to the cluster pixels from the previous sequencing cycles and the current sequencing cycle, as discussed above, for example, using minimum value selection function, maximum value selection function, averaging function, exponential weighted averaging function, and so on. Then, the per-cluster states 3042 are combined with compressed spatially convolved features of the cluster pixels and of the current base calling iteration/operation to generate base calls for the corresponding clusters. These steps are illustrated by actions 3602, 3612, 3622, 3632, and 3642 of FIG. 36.

Figure 37:
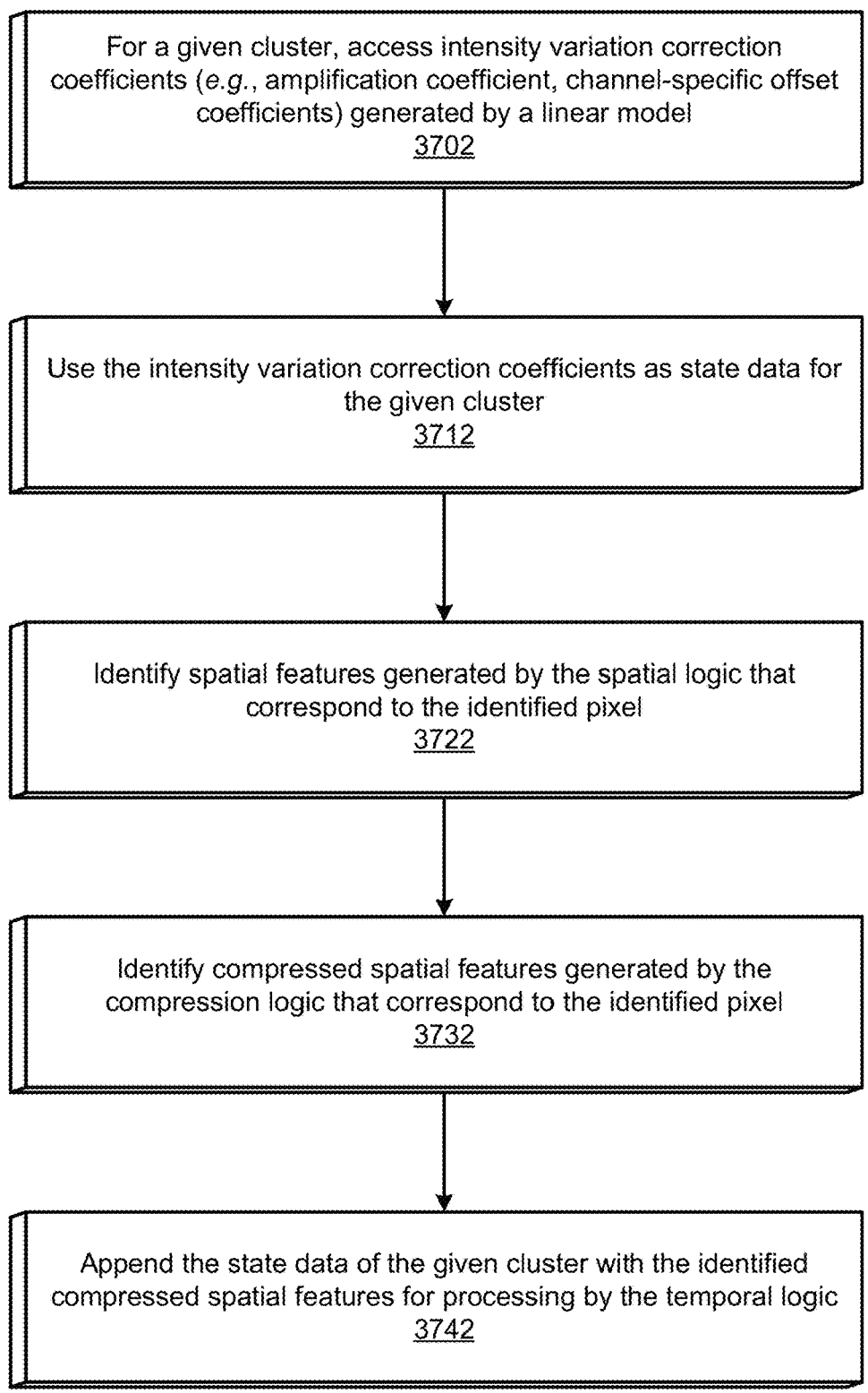
FIG. 37 illustrates one implementation of generating per-cluster states using the RTA base caller separate from the neural network-based base caller for incorporation of the per-cluster states with compressed feature.

In FIG. 37, the per-cluster states 3042 are the per-cluster variation correction coefficients determined by the RTA for the current sequencing cycle, in accordance with one implementation. Then, the per-cluster states 3042 are combined with compressed spatially convolved features of the cluster pixels and of the current base calling iteration/operation to generate base calls for the corresponding clusters. These steps are illustrated by actions 3702, 3712, 3722, 3732, and 3742 of FIG. 37.

Figure 38:
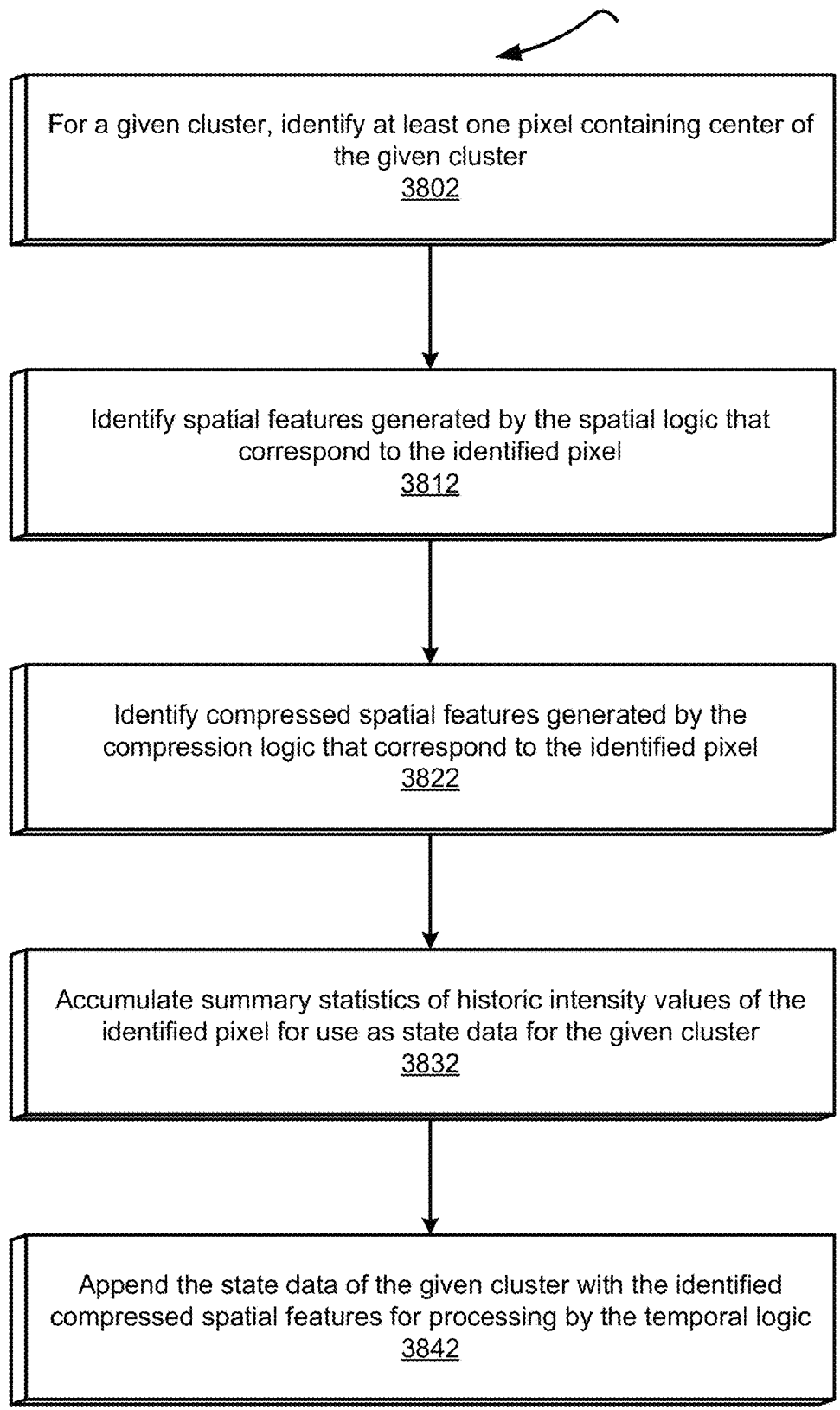
FIG. 38 illustrates one implementation of generating per-cluster states using historic intensity values of corresponding cluster pixels for incorporation of the per-cluster states with compressed features.

FIG. 38 illustrates one implementation of generating 3800 per-cluster states 3042 using historic intensity values of corresponding cluster pixels for incorporation of the per-cluster states 3042 with compressed features. In FIG. 38, the per-cluster states 3042 are determined by accumulating summary statistics of historic intensity values of the cluster pixels from the previous sequencing cycles and the current sequencing cycle, as discussed above, for example, using minimum value selection function, maximum value selection function, averaging function, exponential weighted averaging function, and so on. Then, the per-cluster states 3042 are combined with compressed spatially convolved features of the cluster pixels and of a current base calling iteration/operation to generate base calls for the corresponding clusters. These steps are illustrated by actions 3802, 3812, 3822, 3832, and 3842 of FIG. 38.

Well State Data to Pixel State Data Transformation

Figure 39:
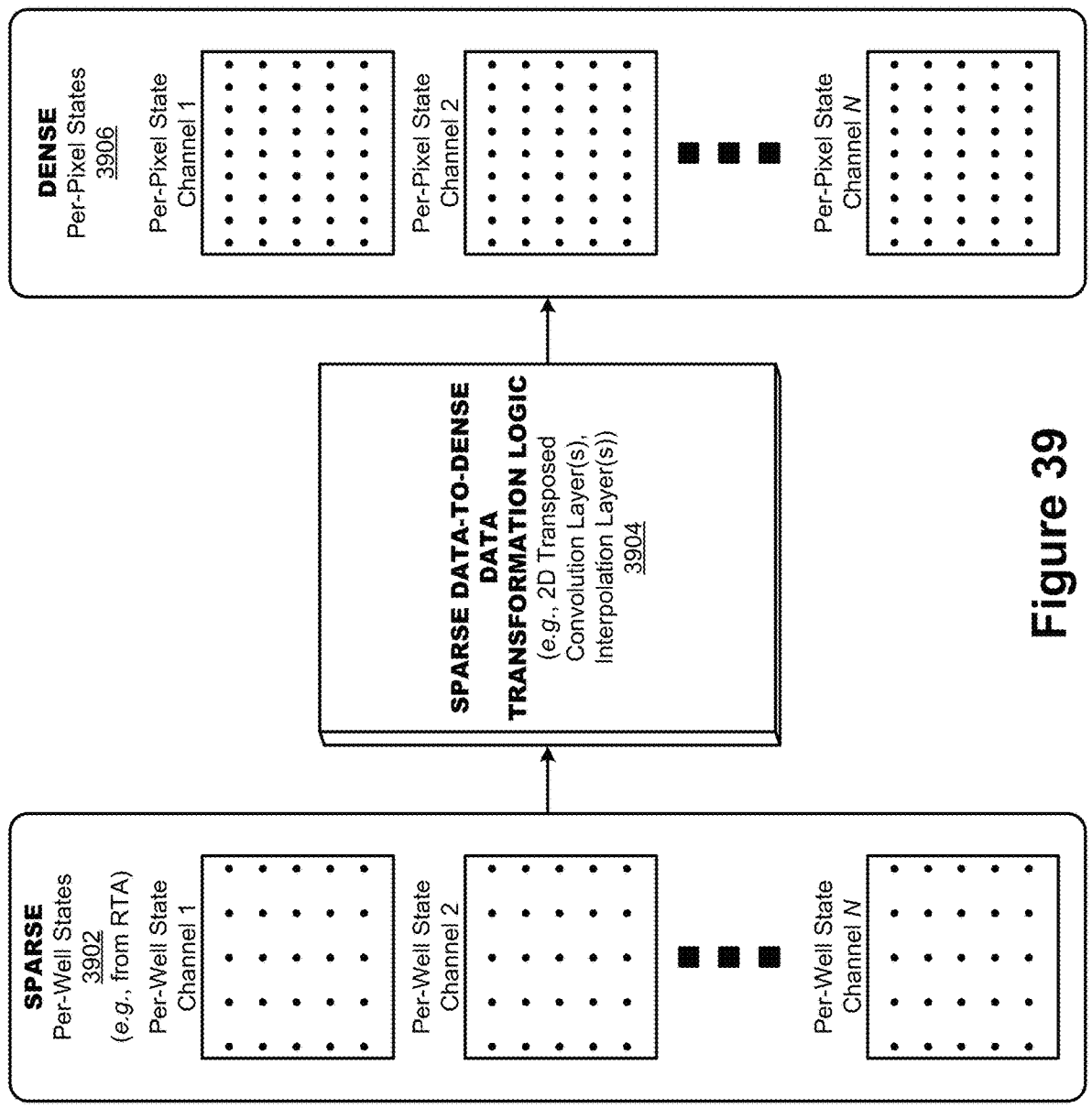
FIG. 39 illustrates one implementation of generating dense, per-pixel states from sparse, per-well states.

FIG. 39 illustrates one implementation of generating dense, per-pixel states from sparse, per-well states. In FIG. 39, the per-well states 3902 are sparse and can be transformed into dense, per-pixels states 3906 using transpose convolutions or interpolation (e.g., linear, bilinear, cubic interpolation) 3904.

"Sparse" and "dense" refer to the number of zero versus non-zero elements in an array (e.g., vector or matrix). A sparse array is one that contains mostly zeros and few non-zero entries. A dense array contains mostly non-zeros. In a dense array, in one implementation, each per-pixel state can be surrounded by at least two, four, or eight neighboring per-pixel states. In a sparse array, in one implementation, each per-well state is not surrounded by even two, four, or eight neighboring per-well states. A collection of states is called dense if all rows between the first row and the last row are defined with non-zero elements and given a value. A collection of states is called sparse if there are gaps or zero elements in the rows. Sparseness can mean that many elements (e.g., every other, every third, or every fourth) are zero or very close to zero.

Figure 40:
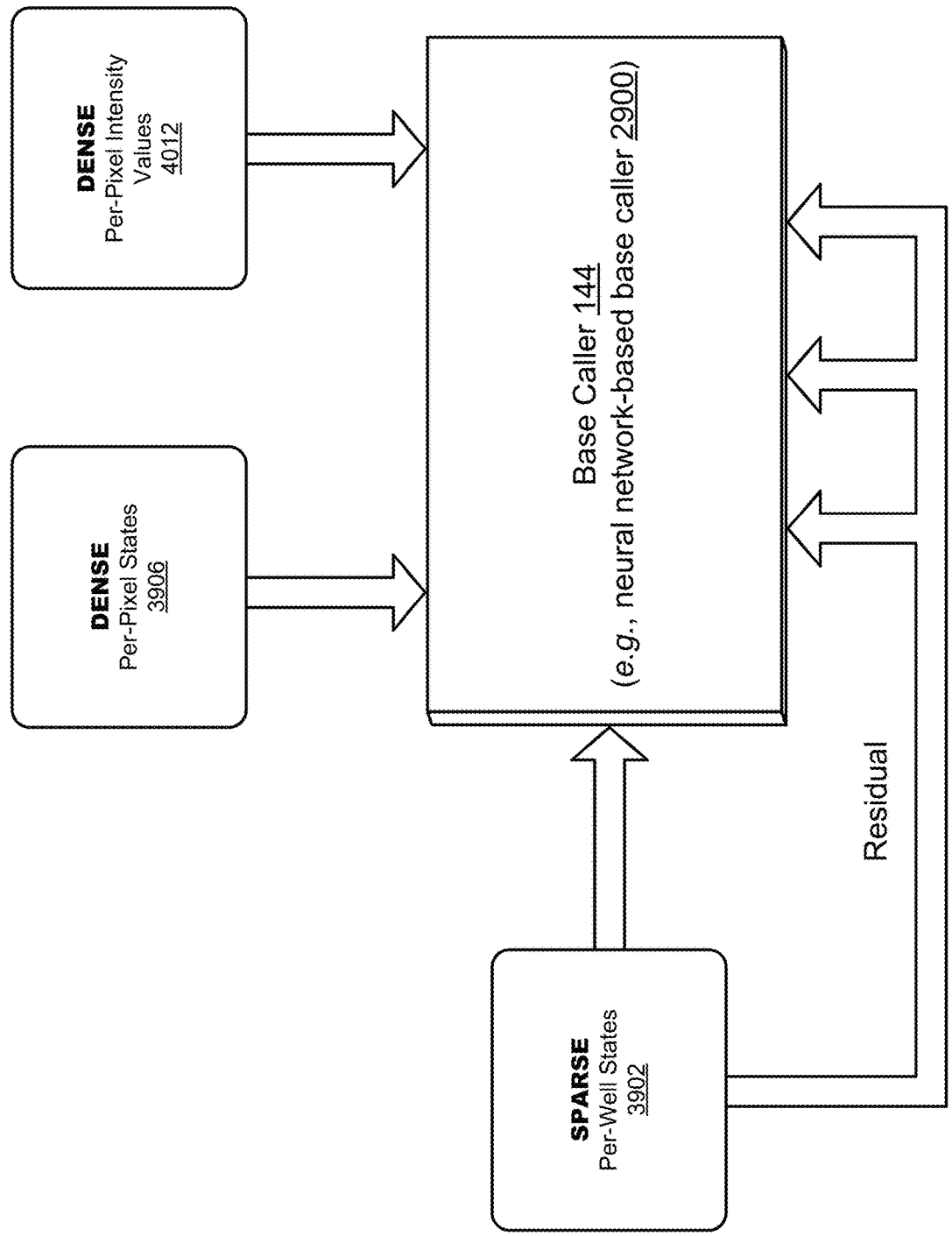
FIG. 40 illustrates one implementation of providing the sparse, per-well states, the dense, per-pixel states, and per-pixel intensity values as input to the base caller for executing base calling operations.

FIG. 40 illustrates one implementation of providing the sparse, per-well states, the dense, per-pixel states, and per-pixel intensity values as input to the base caller for executing base calling operations. In FIG. 40, the sparse, per-well states 3902 can be provided as input to the base caller 144, e.g., the neural network-based base caller 2900, as a direct input as well as redundant inputs using, for example, residual connections and/or skip connections. In some implementations, the sparse, per-well states 3902 are provided as supplemental input along with the dense, per-pixel states 3906 and dense per-pixel intensity values 4012 (i.e., cluster images), which are processed by the base caller 144 to generate base calls.

Figure 41:
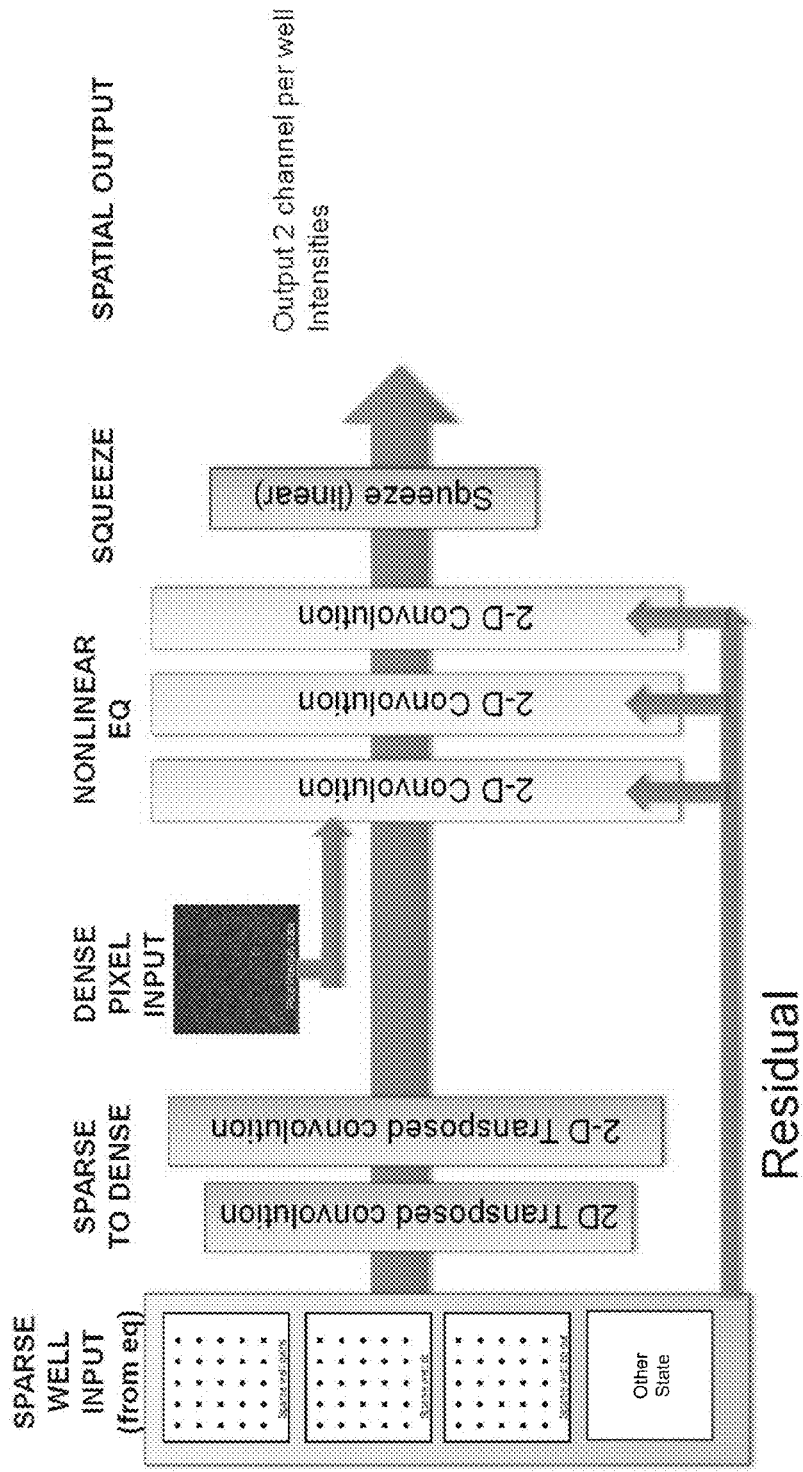
FIG. 41 illustrates one implementation of using the sparse, per-well states, the dense, per-pixel states, and per-pixel intensity values as input to the neural network-based base caller for executing base calling operations.

FIG. 41 illustrates one implementation of using the sparse, per-well states, the dense, per-pixel states, and per-pixel intensity values as input to the neural network-based base caller 2900 for executing base calling operations. The input to the neural network-based base caller 2900 are the dense, per-pixel states 3906 and the dense per-pixel intensity values 4012 (i.e., cluster images).

Sequencing System

Figure 42A:
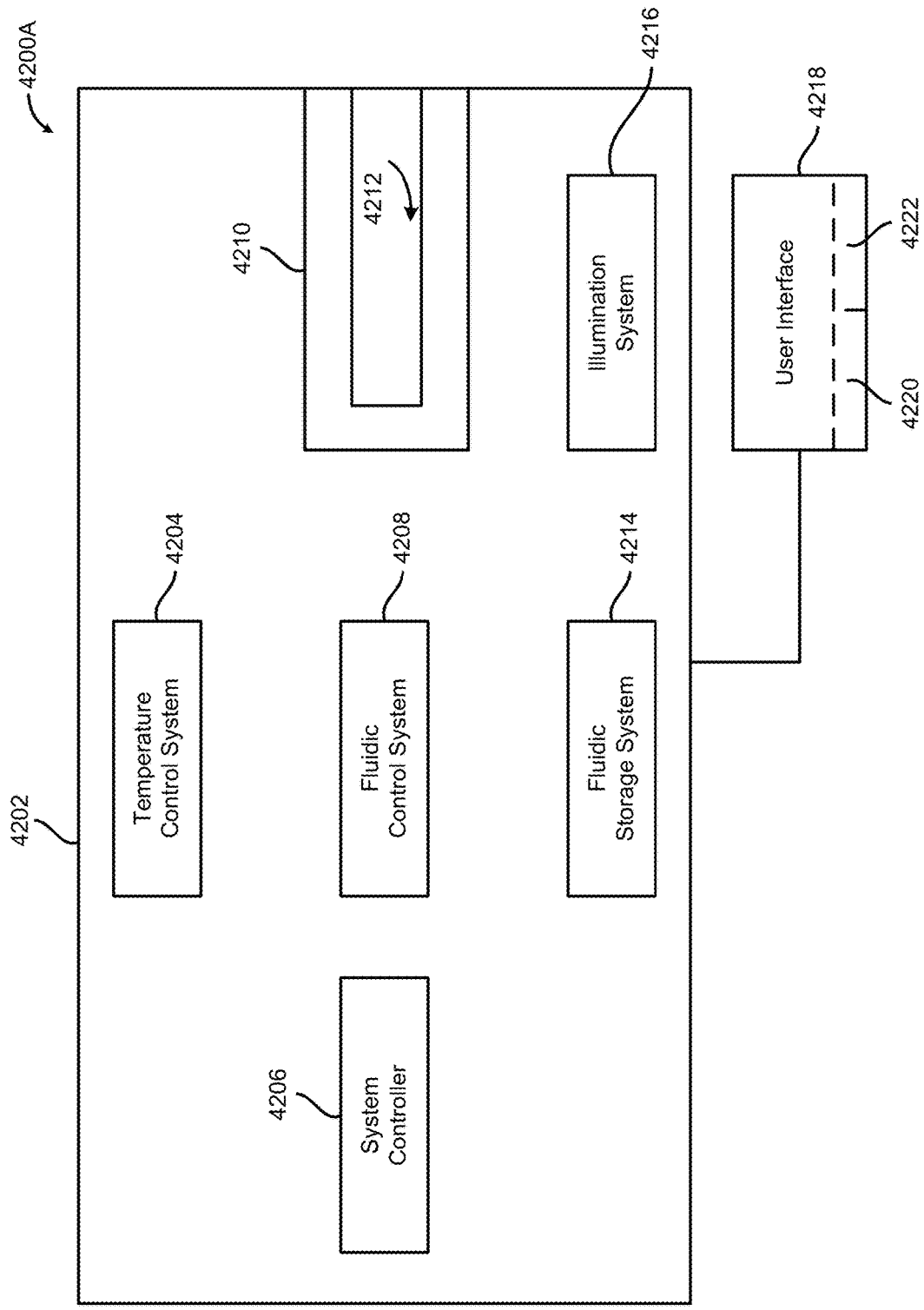
FIGS. 42A and 42B depict one implementation of a sequencing system that comprises a configurable processor.
Figure 42B:
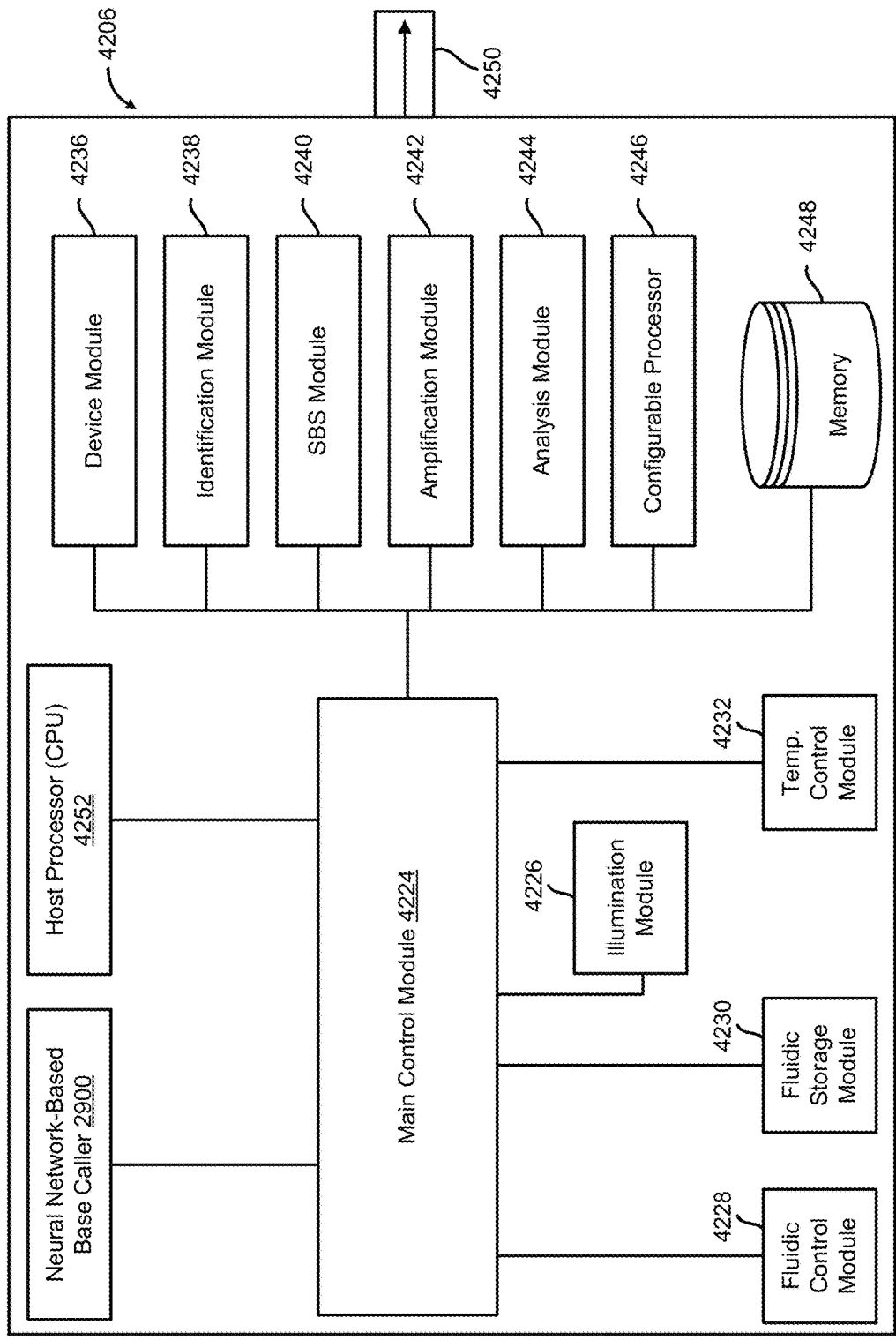

FIGS. 42A and 42B depict one implementation of a sequencing system 4200A. The sequencing system 4200A comprises a configurable processor 4246. The configurable processor 4246 implements the base calling techniques disclosed herein. The sequencing system is also referred to as a "sequencer."

The sequencing system 4200A can operate to obtain any information or data that relates to at least one of a biological or chemical substance. In some implementations, the sequencing system 4200A is a workstation that may be similar to a bench-top device or desktop computer. For example, a majority (or all) of the systems and components for conducting the desired reactions can be within a common housing 4202.

In particular implementations, the sequencing system 4200A is a nucleic acid sequencing system configured for various applications, including but not limited to de novo sequencing, resequencing of whole genomes or target genomic regions, and metagenomics. The sequencer may also be used for DNA or RNA analysis. In some implementations, the sequencing system 4200A may also be configured to generate reaction sites in a biosensor. For example, the sequencing system 4200A may be configured to receive a sample and generate surface attached clusters of clonally amplified nucleic acids derived from the sample. Each cluster may constitute or be part of a reaction site in the biosensor.

The exemplary sequencing system 4200A may include a system receptacle or interface 4210 that is configured to interact with a biosensor 4212 to perform desired reactions within the biosensor 4212. In the following description with respect to FIG. 42A, the biosensor 4212 is loaded into the system receptacle 4210. However, it is understood that a cartridge that includes the biosensor 4212 may be inserted into the system receptacle 4210 and in some states the cartridge can be removed temporarily or permanently. As described above, the cartridge may include, among other things, fluidic control and fluidic storage components.

In particular implementations, the sequencing system 4200A is configured to perform a large number of parallel reactions within the biosensor 4212. The biosensor 4212 includes one or more reaction sites where desired reactions can occur. The reaction sites may be, for example, immobilized to a solid surface of the biosensor or immobilized to beads (or other movable substrates) that are located within corresponding reaction chambers of the biosensor. The reaction sites can include, for example, clusters of clonally amplified nucleic acids. The biosensor 4212 may include a solid-state imaging device (e.g., CCD or CMOS imager) and a flow cell mounted thereto. The flow cell may include one or more flow channels that receive a solution from the sequencing system 4200A and direct the solution toward the reaction sites. Optionally, the biosensor 4212 can be configured to engage a thermal element for transferring thermal energy into or out of the flow channel.

The sequencing system 4200A may include various components, assemblies, and systems (or sub-systems) that interact with each other to perform a predetermined method or assay protocol for biological or chemical analysis. For example, the sequencing system 4200A includes a system controller 4206 that may communicate with the various components, assemblies, and sub-systems of the sequencing system 4200A and also the biosensor 4212. For example, in addition to the system receptacle 4210, the sequencing system 4200A may also include a fluidic control system 4208 to control the flow of fluid throughout a fluid network of the sequencing system 4200A and the biosensor 4212; a fluid storage system 4214 that is configured to hold all fluids (e.g., gas or liquids) that may be used by the bioassay system; a temperature control system 4204 that may regulate the temperature of the fluid in the fluid network, the fluid storage system 4214, and/or the biosensor 4212; and an illumination system 4216 that is configured to illuminate the biosensor 4212. As described above, if a cartridge having the biosensor 4212 is loaded into the system receptacle 4210, the cartridge may also include fluidic control and fluidic storage components.

Also shown, the sequencing system 4200A may include a user interface 4218 that interacts with the user. For example, the user interface 4218 may include a display 4220 to display or request information from a user and a user input device 4222 to receive user inputs. In some implementations, the display 4220 and the user input device 4222 are the same device. For example, the user interface 4218 may include a touch-sensitive display configured to detect the presence of an individual's touch and also identify a location of the touch on the display. However, other user input devices 4222 may be used, such as a mouse, touchpad, keyboard, keypad, handheld scanner, voice-recognition system, motion-recognition system, and the like. As will be discussed in greater detail below, the sequencing system 4200A may communicate with various components, including the biosensor 4212 (e.g., in the form of a cartridge), to perform the desired reactions. The sequencing system 4200A may also be configured to analyze data obtained from the biosensor to provide a user with desired information.

The system controller 4206 may include any processor-based or microprocessor-based system, including systems using microcontrollers, reduced instruction set computers (RISC), application specific integrated circuits (ASICs), field programmable gate array (FPGAs), coarse-grained reconfigurable architectures (CGRAs), logic circuits, and any other circuit or processor capable of executing functions described herein. The above examples are exemplary only, and are thus not intended to limit in any way the definition and/or meaning of the term system controller. In the exemplary implementation, the system controller 4206 executes a set of instructions that are stored in one or more storage elements, memories, or modules in order to at least one of obtain and analyze detection data. Detection data can include a plurality of sequences of pixel signals, such that a sequence of pixel signals from each of the millions of sensors (or pixels) can be detected over many base calling cycles. Storage elements may be in the form of information sources or physical memory elements within the sequencing system 4200A.

The set of instructions may include various commands that instruct the sequencing system 4200A or biosensor 4212 to perform specific operations such as the methods and processes of the various implementations described herein. The set of instructions may be in the form of a software program, which may form part of a tangible, non-transitory computer readable medium or media. As used herein, the terms "software" and "firmware" are interchangeable, and include any computer program stored in memory for execution by a computer, including RAM memory, ROM memory, EPROM memory, EEPROM memory, and non-volatile RAM (NVRAM) memory. The above memory types are exemplary only, and are thus not limiting as to the types of memory usable for storage of a computer program.

The software may be in various forms such as system software or application software. Further, the software may be in the form of a collection of separate programs, or a program module within a larger program or a portion of a program module. The software also may include modular programming in the form of object-oriented programming. After obtaining the detection data, the detection data may be automatically processed by the sequencing system 4200A, processed in response to user inputs, or processed in response to a request made by another processing machine (e.g., a remote request through a communication link). In the illustrated implementation, the system controller 4206 includes an analysis module 4244. In other implementations, system controller 4206 does not include the analysis module 4244 and instead has access to the analysis module 4244 (e.g., the analysis module 4244 may be separately hosted on cloud).

The system controller 4206 may be connected to the biosensor 4212 and the other components of the sequencing system 4200A via communication links. The system controller 4206 may also be communicatively connected to off-site systems or servers. The communication links may be hardwired, corded, or wireless. The system controller 4206 may receive user inputs or commands, from the user interface 4218 and the user input device 4222.

The fluidic control system 4208 includes a fluid network and is configured to direct and regulate the flow of one or more fluids through the fluid network. The fluid network may be in fluid communication with the biosensor 4212 and the fluid storage system 4214. For example, select fluids may be drawn from the fluid storage system 4214 and directed to the biosensor 4212 in a controlled manner, or the fluids may be drawn from the biosensor 4212 and directed toward, for example, a waste reservoir in the fluid storage system 4214. Although not shown, the fluidic control system 4208 may include flow sensors that detect a flow rate or pressure of the fluids within the fluid network. The sensors may communicate with the system controller 4206.

The temperature control system 4204 is configured to regulate the temperature of fluids at different regions of the fluid network, the fluid storage system 4214, and/or the biosensor 4212. For example, the temperature control system 4204 may include a thermocycler that interfaces with the biosensor 4212 and controls the temperature of the fluid that flows along the reaction sites in the biosensor 4212. The temperature control system 4204 may also regulate the temperature of solid elements or components of the sequencing system 4200A or the biosensor 4212. Although not shown, the temperature control system 4204 may include sensors to detect the temperature of the fluid or other components. The sensors may communicate with the system controller 4206.

The fluid storage system 4214 is in fluid communication with the biosensor 4212 and may store various reaction components or reactants that are used to conduct the desired reactions therein. The fluid storage system 4214 may also store fluids for washing or cleaning the fluid network and biosensor 4212 and for diluting the reactants. For example, the fluid storage system 4214 may include various reservoirs to store samples, reagents, enzymes, other biomolecules, buffer solutions, aqueous, and non-polar solutions, and the like. Furthermore, the fluid storage system 4214 may also include waste reservoirs for receiving waste products from the biosensor 4212. In implementations that include a cartridge, the cartridge may include one or more of a fluid storage system, fluidic control system or temperature control system. Accordingly, one or more of the components set forth herein as relating to those systems can be contained within a cartridge housing. For example, a cartridge can have various reservoirs to store samples, reagents, enzymes, other biomolecules, buffer solutions, aqueous, and non-polar solutions, waste, and the like. As such, one or more of a fluid storage system, fluidic control system or temperature control system can be removably engaged with a bioassay system via a cartridge or other biosensor.

The illumination system 4216 may include a light source (e.g., one or more LEDs) and a plurality of optical components to illuminate the biosensor. Examples of light sources may include lasers, arc lamps, LEDs, or laser diodes. The optical components may be, for example, reflectors, dichroics, beam splitters, collimators, lenses, filters, wedges, prisms, mirrors, detectors, and the like. In implementations that use an illumination system, the illumination system 4216 may be configured to direct an excitation light to reaction sites. As one example, fluorophores may be excited by green wavelengths of light, as such the wavelength of the excitation light may be approximately 4232 nm. In one implementation, the illumination system 4216 is configured to produce illumination that is parallel to a surface normal of a surface of the biosensor 4212. In another implementation, the illumination system 4216 is configured to produce illumination that is off-angle relative to the surface normal of the surface of the biosensor 4212. In yet another implementation, the illumination system 4216 is configured to produce illumination that has plural angles, including some parallel illumination and some off-angle illumination.

The system receptacle or interface 4210 is configured to engage the biosensor 4212 in at least one of a mechanical, electrical, and fluidic manner. The system receptacle 4210 may hold the biosensor 4212 in a desired orientation to facilitate the flow of fluid through the biosensor 4212. The system receptacle 4210 may also include electrical contacts that are configured to engage the biosensor 4212 so that the sequencing system 4200A may communicate with the biosensor 4212 and/or provide power to the biosensor 4212. Furthermore, the system receptacle 4210 may include fluidic ports (e.g., nozzles) that are configured to engage the biosensor 4212. In some implementations, the biosensor 4212 is removably coupled to the system receptacle 4210 in a mechanical manner, in an electrical manner, and also in a fluidic manner.

In addition, the sequencing system 4200A may communicate remotely with other systems or networks or with other bioassay systems 4200A. Detection data obtained by the bioassay system(s) 4200A may be stored in a remote database.

FIG. 42B is a block diagram of a system controller 4206 that can be used in the system of FIG. 42A. In one implementation, the system controller 4206 includes one or more processors or modules that can communicate with one another. Each of the processors or modules may include an algorithm (e.g., instructions stored on a tangible and/or non-transitory computer readable storage medium) or sub-algorithms to perform particular processes. The system controller 4206 is illustrated conceptually as a collection of modules, but may be implemented utilizing any combination of dedicated hardware boards, DSPs, processors, etc. Alternatively, the system controller 4206 may be implemented utilizing an off-the-shelf PC with a single processor or multiple processors, with the functional operations distributed between the processors. As a further option, the modules described below may be implemented utilizing a hybrid configuration in which certain modular functions are performed utilizing dedicated hardware, while the remaining modular functions are performed utilizing an off-the-shelf PC and the like. The modules also may be implemented as software modules within a processing unit.

During operation, a communication port 4250 may transmit information (e.g., commands) to or receive information (e.g., data) from the biosensor 4212 (FIG. 42A) and/or the sub-systems 4208, 4214, 4204 (FIG. 42A). In implementations, the communication port 4250 may output a plurality of sequences of pixel signals. A communication link 4234 may receive user input from the user interface 4218 (FIG. 42A) and transmit data or information to the user interface 4218. Data from the biosensor 4212 or sub-systems 4208, 4214, 4204 may be processed by the system controller 4206 in real-time during a bioassay session. Additionally or alternatively, data may be stored temporarily in a system memory during a bioassay session and processed in slower than real-time or off-line operation.

As shown in FIG. 42B, the system controller 4206 may include a plurality of modules 4226-4248 that communicate with a main control module 4224, along with a central processing unit (CPU) 4252. The main control module 4224 may communicate with the user interface 4218 (FIG. 42A). Although the modules 4226-4248 are shown as communicating directly with the main control module 4224, the modules 4226-4248 may also communicate directly with each other, the user interface 4218, and the biosensor 4212. Also, the modules 4226-4248 may communicate with the main control module 4224 through the other modules.

The plurality of modules 4226-4248 include system modules 4228-4232, 4226 that communicate with the sub-systems 4208, 4214, 4204, and 4216, respectively. The fluidic control module 4228 may communicate with the fluidic control system 4208 to control the valves and flow sensors of the fluid network for controlling the flow of one or more fluids through the fluid network. The fluid storage module 4230 may notify the user when fluids are low or when the waste reservoir is at or near capacity. The fluid storage module 4230 may also communicate with the temperature control module 4232 so that the fluids may be stored at a desired temperature. The illumination module 4226 may communicate with the illumination system 4216 to illuminate the reaction sites at designated times during a protocol, such as after the desired reactions (e.g., binding events) have occurred. In some implementations, the illumination module 4226 may communicate with the illumination system 4216 to illuminate the reaction sites at designated angles.

The plurality of modules 4226-4248 may also include a device module 4236 that communicates with the biosensor 4212 and an identification module 4238 that determines identification information relating to the biosensor 4212. The device module 4236 may, for example, communicate with the system receptacle 4210 to confirm that the biosensor has established an electrical and fluidic connection with the sequencing system 4200A. The identification module 4238 may receive signals that identify the biosensor 4212. The identification module 4238 may use the identity of the biosensor 4212 to provide other information to the user. For example, the identification module 4238 may determine and then display a lot number, a date of manufacture, or a protocol that is recommended to be run with the biosensor 4212.

The plurality of modules 4226-4248 also includes an analysis module 4244 (also called signal processing module or signal processor) that receives and analyzes the signal data (e.g., image data) from the biosensor 4212. Analysis module 4244 includes memory (e.g., RAM or Flash) to store detection/image data. Detection data can include a plurality of sequences of pixel signals, such that a sequence of pixel signals from each of the millions of sensors (or pixels) can be detected over many base calling cycles. The signal data may be stored for subsequent analysis or may be transmitted to the user interface 4218 to display desired information to the user. In some implementations, the signal data may be processed by the solid-state imager (e.g., CMOS image sensor) before the analysis module 4244 receives the signal data.

The analysis module 4244 is configured to obtain image data from the light detectors at each of a plurality of sequencing cycles. The image data is derived from the emission signals detected by the light detectors and process the image data for each of the plurality of sequencing cycles through the neural network-based base caller 2900 and produce a base call for at least some of the clusters at each of the plurality of sequencing cycle. The light detectors can be part of one or more over-head cameras (e.g., Illumina's GAIIx's CCD camera taking images of the clusters on the biosensor 4212 from the top), or can be part of the biosensor 4212 itself (e.g., Illumina's iSeq's CMOS image sensors underlying the clusters on the biosensor 4212 and taking images of the clusters from the bottom).

The output of the light detectors is the sequencing images, each depicting intensity emissions of the clusters and their surrounding background. The sequencing images depict intensity emissions generated as a result of nucleotide incorporation in the sequences during the sequencing. The intensity emissions are from associated clusters and their surrounding background. The sequencing images are stored in memory 4248.

Protocol modules 4240 and 4242 communicate with the main control module 4224 to control the operation of the sub-systems 4208, 4214, and 4204 when conducting predetermined assay protocols. The protocol modules 4240 and 4242 may include sets of instructions for instructing the sequencing system 4200A to perform specific operations pursuant to predetermined protocols. As shown, the protocol module may be a sequencing-by-synthesis (SBS) module 4240 that is configured to issue various commands for performing sequencing-by-synthesis processes. In SBS, extension of a nucleic acid primer along a nucleic acid template is monitored to determine the sequence of nucleotides in the template. The underlying chemical process can be polymerization (e.g., as catalyzed by a polymerase enzyme) or ligation (e.g., catalyzed by a ligase enzyme). In a particular polymerase-based SBS implementation, fluorescently labeled nucleotides are added to a primer (thereby extending the primer) in a template dependent fashion such that detection of the order and type of nucleotides added to the primer can be used to determine the sequence of the template. For example, to initiate a first SBS cycle, commands can be given to deliver one or more labeled nucleotides, DNA polymerase, etc., into/through a flow cell that houses an array of nucleic acid templates. The nucleic acid templates may be located at corresponding reaction sites. Those reaction sites where primer extension causes a labeled nucleotide to be incorporated can be detected through an imaging event. During an imaging event, the illumination system 4216 may provide an excitation light to the reaction sites. Optionally, the nucleotides can further include a reversible termination property that terminates further primer extension once a nucleotide has been added to a primer. For example, a nucleotide analog having a reversible terminator moiety can be added to a primer such that subsequent extension cannot occur until a deblocking agent is delivered to remove the moiety. Thus, for implementations that use reversible termination a command can be given to deliver a deblocking reagent to the flow cell (before or after detection occurs). One or more commands can be given to effect wash(es) between the various delivery steps. The cycle can then be repeated n times to extend the primer by n nucleotides, thereby detecting a sequence of length n. Exemplary sequencing techniques are described, for example, in Bentley et al., Nature 456:53-59 (2008); WO 04/018497; U.S. Pat. No. 7,057,026; WO 91/06678; WO 07/123744; U.S. Pat. Nos. 7,329,492; 7,211,414; 7,315,019; 7,405,281, and US 2008/014708082, each of which is incorporated herein by reference.

For the nucleotide delivery step of an SBS cycle, either a single type of nucleotide can be delivered at a time, or multiple different nucleotide types (e.g., A, C, T and G together) can be delivered. For a nucleotide delivery configuration where only a single type of nucleotide is present at a time, the different nucleotides need not have distinct labels since they can be distinguished based on temporal separation inherent in the individualized delivery. Accordingly, a sequencing method or apparatus can use single color detection. For example, an excitation source need only provide excitation at a single wavelength or in a single range of wavelengths. For a nucleotide delivery configuration where delivery results in multiple different nucleotides being present in the flow cell at one time, sites that incorporate different nucleotide types can be distinguished based on different fluorescent labels that are attached to respective nucleotide types in the mixture. For example, four different nucleotides can be used, each having one of four different fluorophores. In one implementation, the four different fluorophores can be distinguished using excitation in four different regions of the spectrum. For example, four different excitation radiation sources can be used. Alternatively, fewer than four different excitation sources can be used, but optical filtration of the excitation radiation from a single source can be used to produce different ranges of excitation radiation at the flow cell.

In some implementations, fewer than four different colors can be detected in a mixture having four different nucleotides. For example, pairs of nucleotides can be detected at the same wavelength, but distinguished based on a difference in intensity for one member of the pair compared to the other, or based on a change to one member of the pair (e.g., via chemical modification, photochemical modification or physical modification) that causes apparent signal to appear or disappear compared to the signal detected for the other member of the pair. Exemplary apparatus and methods for distinguishing four different nucleotides using detection of fewer than four colors are described for example in US Pat. App. Ser. Nos. 61/538,294 and 61/619,878, which are incorporated herein by reference in their entireties. U.S. application Ser. No. 13/624,200, which was filed on Sep. 21, 2012, is also incorporated by reference in its entirety.

The plurality of protocol modules may also include a sample-preparation (or generation) module 4242 that is configured to issue commands to the fluidic control system 4208 and the temperature control system 4204 for amplifying a product within the biosensor 4212. For example, the biosensor 4212 may be engaged to the sequencing system 4200A. The amplification module 4242 may issue instructions to the fluidic control system 4208 to deliver necessary amplification components to reaction chambers within the biosensor 4212. In other implementations, the reaction sites may already contain some components for amplification, such as the template DNA and/or primers. After delivering the amplification components to the reaction chambers, the amplification module 4242 may instruct the temperature control system 4204 to cycle through different temperature stages according to known amplification protocols. In some implementations, the amplification and/or nucleotide incorporation is performed isothermally.

The SBS module 4240 may issue commands to perform bridge PCR where clusters of clonal amplicons are formed on localized areas within a channel of a flow cell. After generating the amplicons through bridge PCR, the amplicons may be "linearized" to make single stranded template DNA, or sstDNA, and a sequencing primer may be hybridized to a universal sequence that flanks a region of interest. For example, a reversible terminator-based sequencing by synthesis method can be used as set forth above or as follows.

Each base calling or sequencing cycle can extend an sstDNA by a single base which can be accomplished for example by using a modified DNA polymerase and a mixture of four types of nucleotides. The different types of nucleotides can have unique fluorescent labels, and each nucleotide can further have a reversible terminator that allows only a single-base incorporation to occur in each cycle. After a single base is added to the sstDNA, excitation light may be incident upon the reaction sites and fluorescent emissions may be detected. After detection, the fluorescent label and the terminator may be chemically cleaved from the sstDNA. Another similar base calling or sequencing cycle may follow. In such a sequencing protocol, the SBS module 4240 may instruct the fluidic control system 4208 to direct a flow of reagent and enzyme solutions through the biosensor 4212. Exemplary reversible terminator-based SBS methods which can be utilized with the apparatus and methods set forth herein are described in US Patent Application Publication No. 2007/0166705 A1, US Patent Application Publication No. 2006/0188901 A1, U.S. Pat. No. 7,057,026, US Patent Application Publication No. 2006/0240439 A1, US Patent Application Publication No. 2006/02814714709 A1, PCT Publication No. WO 05/065814, US Patent Application Publication No. 2005/014700900 A1, PCT Publication No. WO 06/08B199 and PCT Publication No. WO 07/01470251, each of which is incorporated herein by reference in its entirety. Exemplary reagents for reversible terminator-based SBS are described in U.S. Pat. Nos. 7,541,444; 7,057,026; 7,414,14716; U.S. Pat. Nos. 7,427,673; 7,566,537; 7,592,435 and WO 07/14835368, each of which is incorporated herein by reference in its entirety.

In some implementations, the amplification and SBS modules may operate in a single assay protocol where, for example, template nucleic acid is amplified and subsequently sequenced within the same cartridge.

The sequencing system 4200A may also allow the user to reconfigure an assay protocol. For example, the sequencing system 4200A may offer options to the user through the user interface 4218 for modifying the determined protocol. For example, if it is determined that the biosensor 4212 is to be used for amplification, the sequencing system 4200A may request a temperature for the annealing cycle. Furthermore, the sequencing system 4200A may issue warnings to a user if a user has provided user inputs that are generally not acceptable for the selected assay protocol.

In implementations, the biosensor 4212 includes millions of sensors (or pixels), each of which generates a plurality of sequences of pixel signals over successive base calling cycles. The analysis module 4244 detects the plurality of sequences of pixel signals and attributes them to corresponding sensors (or pixels) in accordance to the row-wise and/or column-wise location of the sensors on an array of sensors.

Figure 42C:
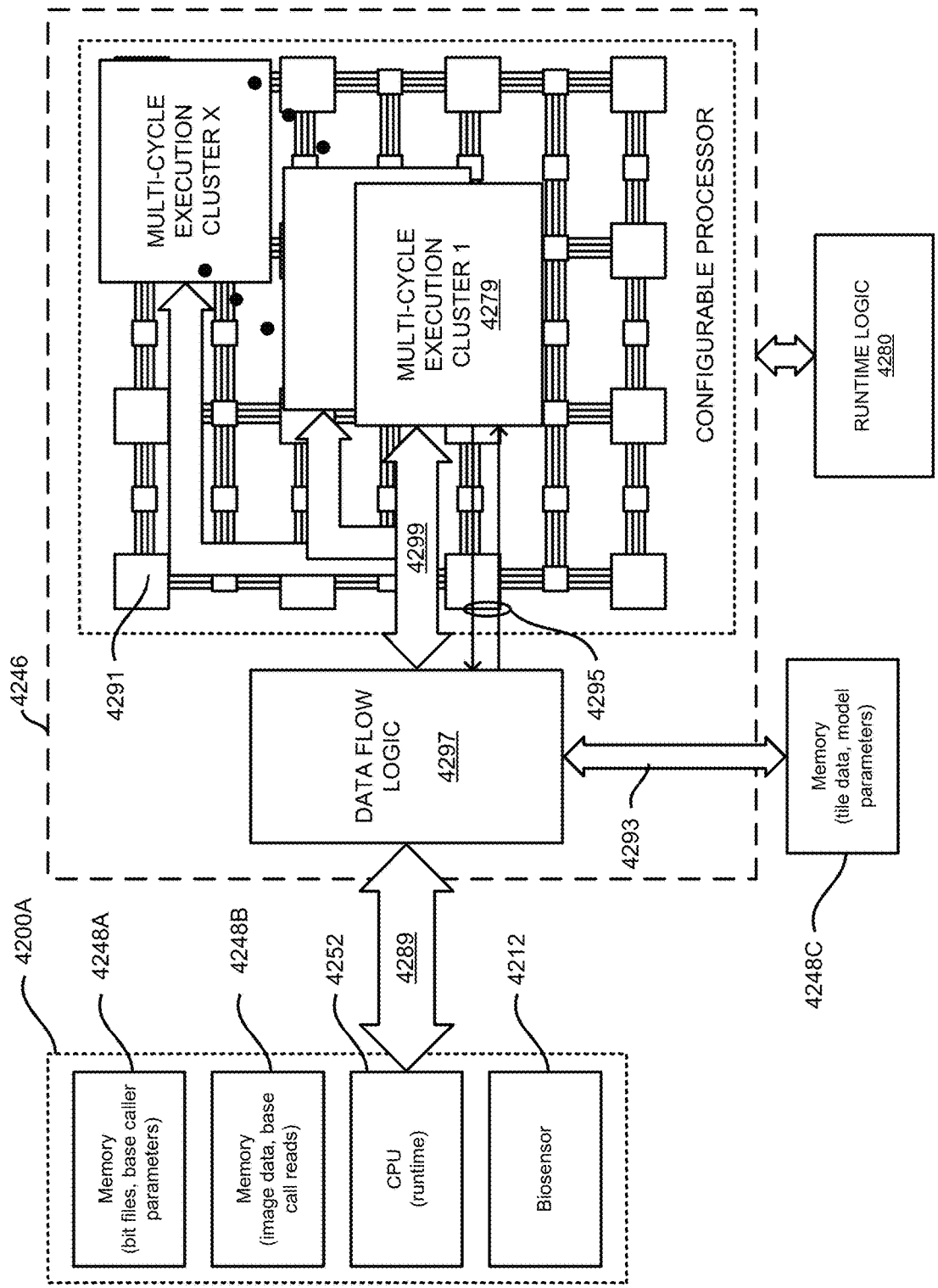
FIG. 42C is a simplified block diagram of a system for analysis of sensor data from the sequencing system, such as base call sensor outputs.

FIG. 42C is a simplified block diagram of a system for analysis of sensor data from the sequencing system 4200A, such as base call sensor outputs. In the example of FIG. 42C, the system includes the configurable processor 4246. The configurable processor 4246 can execute a base caller (e.g., the neural network-based base caller 2900) in coordination with a runtime program/logic 4280 executed by the central processing unit (CPU) 4252 (i.e., a host processor). The sequencing system 4200A comprises the biosensor 4212 and flow cells. The flow cells can comprise one or more tiles in which clusters of genetic material are exposed to a sequence of cluster flows used to cause reactions in the clusters to identify the bases in the genetic material. The sensors sense the reactions for each cycle of the sequence in each tile of the flow cell to provide tile data. Genetic sequencing is a data intensive operation, which translates base call sensor data into sequences of base calls for each cluster of genetic material sensed in during a base call operation.

The system in this example includes the CPU 4252, which executes a runtime program/logic 4280 to coordinate the base call operations, memory 4248B to store sequences of arrays of tile data, base call reads produced by the base calling operation, and other information used in the base call operations. Also, in this illustration the system includes memory 4248A to store a configuration file (or files), such as FPGA bit files, and model parameters for the neural networks used to configure and reconfigure the configurable processor 4246, and execute the neural networks. The sequencing system 4200A can include a program for configuring a configurable processor and in some implementations a reconfigurable processor to execute the neural networks.

The sequencing system 4200A is coupled by a bus 4289 to the configurable processor 4246. The bus 4289 can be implemented using a high throughput technology, such as in one example bus technology compatible with the PCIe standards (Peripheral Component Interconnect Express) currently maintained and developed by the PCI-SIG (PCI Special Interest Group). Also in this example, a memory 4248A is coupled to the configurable processor 4246 by bus 4293. The memory 4248A can be on-board memory, disposed on a circuit board with the configurable processor 4246. The memory 4248A is used for high speed access by the configurable processor 4246 of working data used in the base call operation. The bus 4293 can also be implemented using a high throughput technology, such as bus technology compatible with the PCIe standards.

Configurable processors, including field programmable gate arrays FPGAs, coarse grained reconfigurable arrays CGRAs, and other configurable and reconfigurable devices, can be configured to implement a variety of functions more efficiently or faster than might be achieved using a general purpose processor executing a computer program. Configuration of configurable processors involves compiling a functional description to produce a configuration file, referred to sometimes as a bitstream or bit file, and distributing the configuration file to the configurable elements on the processor. The configuration file defines the logic functions to be executed by the configurable processor, by configuring the circuit to set data flow patterns, use of distributed memory and other on-chip memory resources, lookup table contents, operations of configurable logic blocks and configurable execution units like multiply-and-accumulate units, configurable interconnects and other elements of the configurable array. A configurable processor is reconfigurable if the configuration file may be changed in the field, by changing the loaded configuration file. For example, the configuration file may be stored in volatile SRAM elements, in non-volatile read-write memory elements, and in combinations of the same, distributed among the array of configurable elements on the configurable or reconfigurable processor. A variety of commercially available configurable processors are suitable for use in a base calling operation as described herein. Examples include Google's Tensor Processing Unit (TPU)™, rackmount solutions like GX4 Rackmount Series™, GX9 Rackmount Series™, NVIDIA DGX-1™, Microsoft' Stratix V FPGA™, Graphcore's Intelligent Processor Unit (IPU)™, Qualcomm's Zeroth Platform™ with Snapdragon Processors™, NVIDIA's Volta™, NVIDIA's DRIVE PX™, NVIDIA's JETSON TX1/TX2 MODULE™, Intel's Nirvana™, Movidius VPU™, Fujitsu DPI™, ARM's DynamicIQ™, IBM TrueNorth™, Lambda GPU Server with Testa V100s™, Xilinx Alveo™ U200, Xilinx Alveo™ U2190, Xilinx Alveo™ U280, Intel/Altera Stratix™ GX2800, Intel/Altera Stratix™ GX2800, and Intel Stratix™ GX10M. In some examples, a host CPU can be implemented on the same integrated circuit as the configurable processor.

Implementations described herein implement the neural network-based base caller 2900 using the configurable processor 4246. The configuration file for the configurable processor 4246 can be implemented by specifying the logic functions to be executed using a high level description language HDL or a register transfer level RTL language specification. The specification can be compiled using the resources designed for the selected configurable processor to generate the configuration file. The same or similar specification can be compiled for the purposes of generating a design for an application-specific integrated circuit which may not be a configurable processor.

Alternatives for the configurable processor configurable processor 4246, in all implementations described herein, therefore include a configured processor comprising an application specific ASIC or special purpose integrated circuit or set of integrated circuits, or a system-on-a-chip SOC device, or a graphics processing unit (GPU) processor or a coarse-grained reconfigurable architecture (CGRA) processor, configured to execute a neural network based base call operation as described herein.

In general, configurable processors and configured processors described herein, as configured to execute runs of a neural network, are referred to herein as neural network processors.

The configurable processor 4246 is configured in this example by a configuration file loaded using a program executed by the CPU 4252, or by other sources, which configures the array of configurable elements 4291 (e.g., configuration logic blocks (CLB) such as look up tables (LUTs), flip-flops, compute processing units (PMUs), and compute memory units (CMUs), configurable I/O blocks, programmable interconnects), on the configurable processor to execute the base call function. In this example, the configuration includes data flow logic 4297 which is coupled to the buses 4289 and 4293 and executes functions for distributing data and control parameters among the elements used in the base call operation.

Also, the configurable processor 4246 is configured with data flow logic 4297 to execute the neural network-based base caller 2900. The logic 4297 comprises multi-cycle execution clusters (e.g., 4279) which, in this example, includes execution cluster 1 through execution cluster X. The number of multi-cycle execution clusters can be selected according to a trade-off involving the desired throughput of the operation, and the available resources on the configurable processor 4246.

The multi-cycle execution clusters are coupled to the data flow logic 4297 by data flow paths 4299 implemented using configurable interconnect and memory resources on the configurable processor 4246. Also, the multi-cycle execution clusters are coupled to the data flow logic 4297 by control paths 4295 implemented using configurable interconnect and memory resources for example on the configurable processor 4246, which provide control signals indicating available execution clusters, readiness to provide input units for execution of a run of the neural network-based base caller 2900 to the available execution clusters, readiness to provide trained parameters for the neural network-based base caller 2900, readiness to provide output patches of base call classification data, and other control data used for execution of the neural network-based base caller 2900.

The configurable processor 4246 is configured to execute runs of the neural network-based base caller 2900 using trained parameters to produce classification data for the sensing cycles of the base calling operation. A run of the neural network-based base caller 2900 is executed to produce classification data for a subject sensing cycle of the base calling operation. A run of the neural network-based base caller 2900 operates on a sequence including a number N of arrays of tile data from respective sensing cycles of N sensing cycles, where the N sensing cycles provide sensor data for different base call operations for one base position per operation in time sequence in the examples described herein. Optionally, some of the N sensing cycles can be out of sequence if needed according to a particular neural network model being executed. The number N can be any number greater than one. In some examples described herein, sensing cycles of the N sensing cycles represent a set of sensing cycles for at least one sensing cycle preceding the subject sensing cycle and at least one sensing cycle following the subject cycle in time sequence. Examples are described herein in which the number N is an integer equal to or greater than five.

The data flow logic 4297 is configured to move tile data and at least some trained parameters of the model parameters from the memory 4248A to the configurable processor 4246 for runs of the neural network-based base caller 2900, using input units for a given run including tile data for spatially aligned patches of the N arrays. The input units can be moved by direct memory access operations in one DMA operation, or in smaller units moved during available time slots in coordination with the execution of the neural network deployed.

Tile data for a sensing cycle as described herein can comprise an array of sensor data having one or more features. For example, the sensor data can comprise two images which are analyzed to identify one of four bases at a base position in a genetic sequence of DNA, RNA, or other genetic material. The tile data can also include metadata about the images and the sensors. For example, in implementations of the base calling operation, the tile data can comprise information about alignment of the images with the clusters such as distance from center information indicating the distance of each pixel in the array of sensor data from the center of a cluster of genetic material on the tile.

During execution of the neural network-based base caller 2900 as described below, tile data can also include data produced during execution of the neural network-based base caller 2900, referred to as intermediate data, which can be reused rather than recomputed during a run of the neural network-based base caller 2900. For example, during execution of the neural network-based base caller 2900, the data flow logic 4297 can write intermediate data to the memory 4248A in place of the sensor data for a given patch of an array of tile data. Implementations like this are described in more detail below.

As illustrated, a system is described for analysis of base call sensor output, comprising memory (e.g., 4248A) accessible by the runtime program/logic 4280 storing tile data including sensor data for a tile from sensing cycles of a base calling operation. Also, the system includes a neural network processor, such as configurable processor 4246 having access to the memory. The neural network processor is configured to execute runs of a neural network using trained parameters to produce classification data for sensing cycles. As described herein, a run of the neural network is operating on a sequence of N arrays of tile data from respective sensing cycles of N sensing cycles, including a subject cycle, to produce the classification data for the subject cycle. The data flow logic 4297 is provided to move tile data and the trained parameters from the memory to the neural network processor for runs of the neural network using input units including data for spatially aligned patches of the N arrays from respective sensing cycles of N sensing cycles.

Also, a system is described in which the neural network processor has access to the memory, and includes a plurality of execution clusters, the execution clusters in the plurality of execution clusters configured to execute a neural network. The data flow logic 1997 has access to the memory and to execution clusters in the plurality of execution clusters, to provide input units of tile data to available execution clusters in the plurality of execution clusters, the input units including a number N of spatially aligned patches of arrays of tile data from respective sensing cycles, including a subject sensing cycle, and to cause the execution clusters to apply the N spatially aligned patches to the neural network to produce output patches of classification data for the spatially aligned patch of the subject sensing cycle, where N is greater than 1.

Figure 43A:
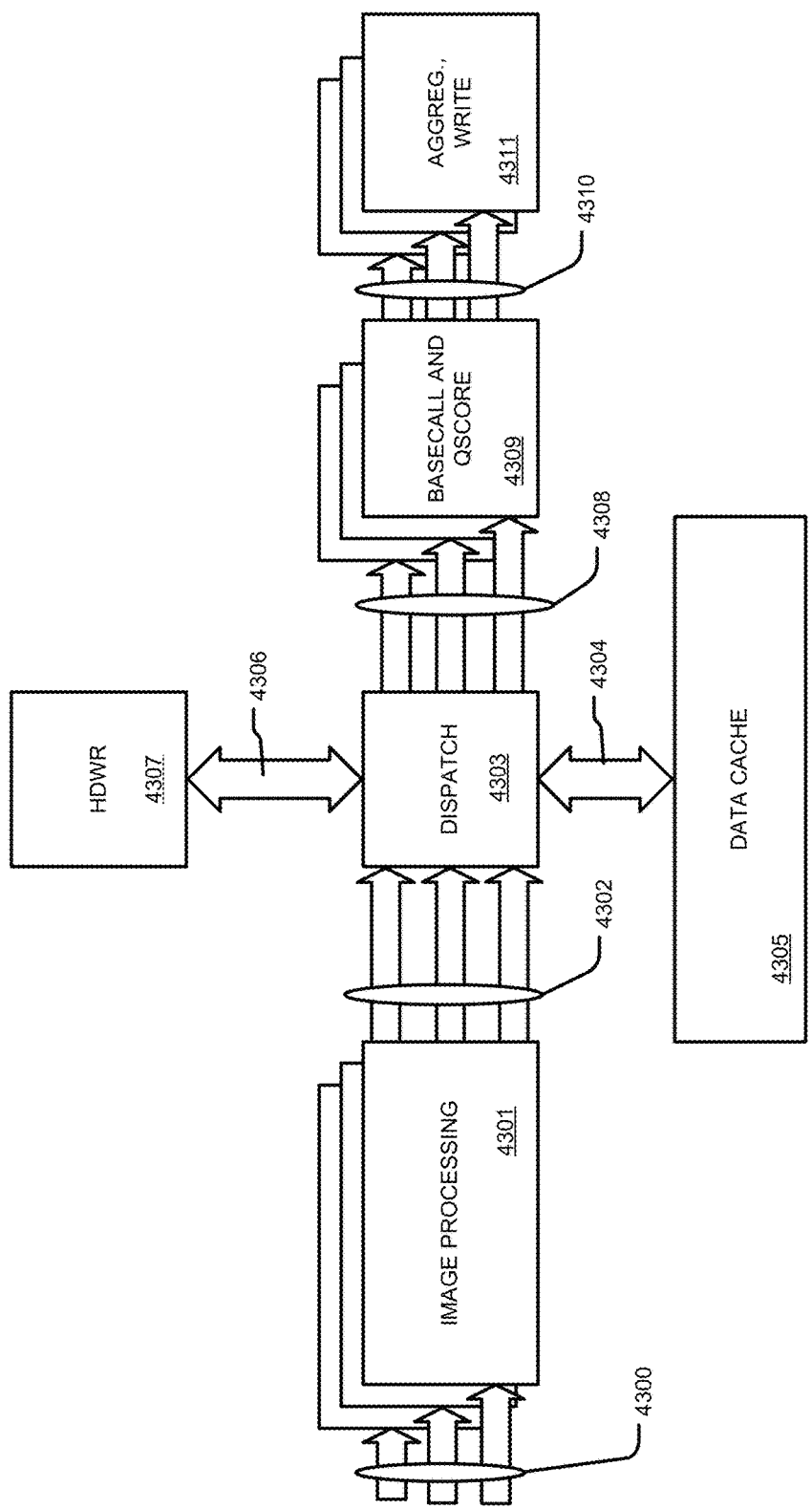
FIG. 43A is a simplified diagram showing aspects of the base calling operation, including functions of a runtime program executed by a host processor.

FIG. 43A is a simplified diagram showing aspects of the base calling operation, including functions of a runtime program (e.g., the runtime logic 4280) executed by a host processor. In this diagram, the output of image sensors from a flow cell are provided on lines 4300 to image processing threads 4301, which can perform processes on images such as alignment and arrangement in an array of sensor data for the individual tiles and resampling of images, and can be used by processes which calculate a tile cluster mask for each tile in the flow cell, which identifies pixels in the array of sensor data that correspond to clusters of genetic material on the corresponding tile of the flow cell. The outputs of the image processing threads 4301 are provided on lines 4302 to a dispatch logic 4303 in the CPU which routes the arrays of tile data to a data cache 4305 (e.g., SSD storage) on a high-speed bus 4304, or on high-speed bus 4306 to the neural network processor hardware 4307, such as the configurable processor 1946 of FIG. 19C, according to the state of the base calling operation. The processed and transformed images can be stored on the data cache 4305 for sensing cycles that were previously used. The hardware 4307 returns classification data output by the neural network to the dispatch logic 4303, which passes the information to the data cache 4305, or on lines 4308 to threads 4309 that perform base call and quality score computations using the classification data, and can arrange the data in standard formats for base call reads. The outputs of the threads 4309 that perform base calling and quality score computations are provided on lines 4310 to threads 4311 that aggregate the base call reads, perform other operations such as data compression, and write the resulting base call outputs to specified destinations for utilization by the customers.

In some implementations, the host can include threads (not shown) that perform final processing of the output of the hardware 4307 in support of the neural network. For example, the hardware 4307 can provide outputs of classification data from a final layer of the multi-cluster neural network. The host processor can execute an output activation function, such as a softmax function, over the classification data to configure the data for use by the base call and quality score threads 4302. Also, the host processor can execute input operations (not shown), such as batch normalization of the tile data prior to input to the hardware 4307.

Figure 43B:
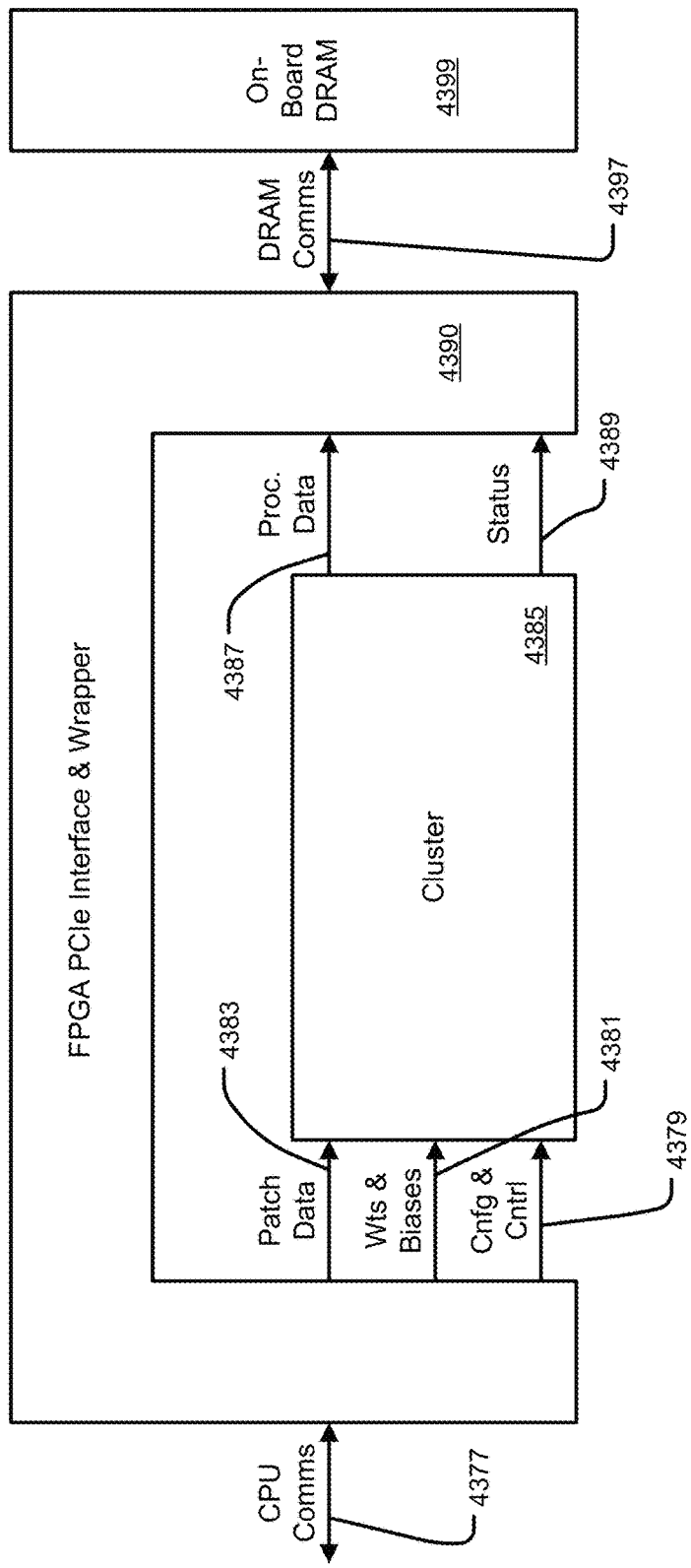
FIG. 43B is a simplified diagram of a configuration of a configurable processor.

FIG. 43B is a simplified diagram of a configuration of a configurable processor 1946 such as that of FIG. 19C. In FIG. 43B, the configurable processor 1946 comprises an FPGA with a plurality of high speed PCIe interfaces. The FPGA is configured with a wrapper 4390 which comprises the data flow logic 1997 described with reference to FIG. 19C. The wrapper 4390 manages the interface and coordination with a runtime program in the CPU across the CPU communication link 4377 and manages communication with the on-board DRAM 4399 (e.g., memory 1448A) via DRAM communication link 4397. The data flow logic 1997 in the wrapper 4390 provides patch data retrieved by traversing the arrays of tile data on the on-board DRAM 4399 for the number N cycles to a cluster 4385, and retrieves process data 4387 from the cluster 4385 for delivery back to the on-board DRAM 4399. The wrapper 4390 also manages transfer of data between the on-board DRAM 4399 and host memory, for both the input arrays of tile data, and for the output patches of classification data. The wrapper transfers patch data on line 4383 to the allocated cluster 4385. The wrapper provides trained parameters, such as weights and biases on line 4381 to the cluster 4385 retrieved from the on-board DRAM 4399. The wrapper provides configuration and control data on line 4379 to the cluster 4385 provided from, or generated in response to, the runtime program on the host via the CPU communication link 4377. The cluster can also provide status signals on line 4389 to the wrapper 4390, which are used in cooperation with control signals from the host to manage traversal of the arrays of tile data to provide spatially aligned patch data, and to execute the multi-cycle neural network over the patch data using the resources of the cluster 4385.

As mentioned above, there can be multiple clusters on a single configurable processor managed by the wrapper 4390 configured for executing on corresponding ones of multiple patches of the tile data. Each cluster can be configured to provide classification data for base calls in a subject sensing cycle using the tile data of multiple sensing cycles described herein.

In examples of the system, model data, including kernel data like filter weights and biases can be sent from the host CPU to the configurable processor, so that the model can be updated as a function of cycle number. A base calling operation can comprise, for a representative example, on the order of hundreds of sensing cycles. Base calling operation can include paired end reads in some implementations. For example, the model trained parameters may be updated once every 20 cycles (or other number of cycles), or according to update patterns implemented for particular systems and neural network models. In some implementations including paired end reads in which a sequence for a given string in a genetic cluster on a tile includes a first part extending from a first end down (or up) the string, and a second part extending from a second end up (or down) the string, the trained parameters can be updated on the transition from the first part to the second part.

In some examples, image data for multiple cycles of sensing data for a tile can be sent from the CPU to the wrapper 4390. The wrapper 4390 can optionally do some pre-processing and transformation of the sensing data and write the information to the on-board DRAM 4399. The input tile data for each sensing cycle can include arrays of sensor data including on the order of 4000×3000 pixels per sensing cycle per tile or more, with two features representing colors of two images of the tile, and one or two bytes per feature per pixel. For an implementation in which the number N is three sensing cycles to be used in each run of the multi-cycle neural network, the array of tile data for each run of the multi-cycle neural network can consume on the order of hundreds of megabytes per tile. In some implementations of the system, the tile data also includes an array of distance-from-cluster center (DFC) data, stored once per tile, or other type of metadata about the sensor data and the tiles.

In operation, when a multi-cycle cluster is available, the wrapper allocates a patch to the cluster. The wrapper fetches a next patch of tile data in the traversal of the tile and sends it to the allocated cluster along with appropriate control and configuration information. The cluster can be configured with enough memory on the configurable processor to hold a patch of data including patches from multiple cycles in some systems, that is being worked on in place, and a patch of data that is to be worked on when the current patch of processing is finished using a ping-pong buffer technique or raster scanning technique in various implementations.

When an allocated cluster completes its run of the neural network for the current patch and produces an output patch, it will signal the wrapper. The wrapper will read the output patch from the allocated cluster, or alternatively the allocated cluster will push the data out to the wrapper. Then the wrapper will assemble output patches for the processed tile in the DRAM 4399. When the processing of the entire tile has been completed, and the output patches of data transferred to the DRAM, the wrapper sends the processed output array for the tile back to the host/CPU in a specified format. In some implementations, the on-board DRAM 4399 is managed by memory management logic in the wrapper 4390. The runtime program can control the sequencing operations to complete analysis of all the arrays of tile data for all the cycles in the run in a continuous flow to provide real time analysis.

Figure 44:
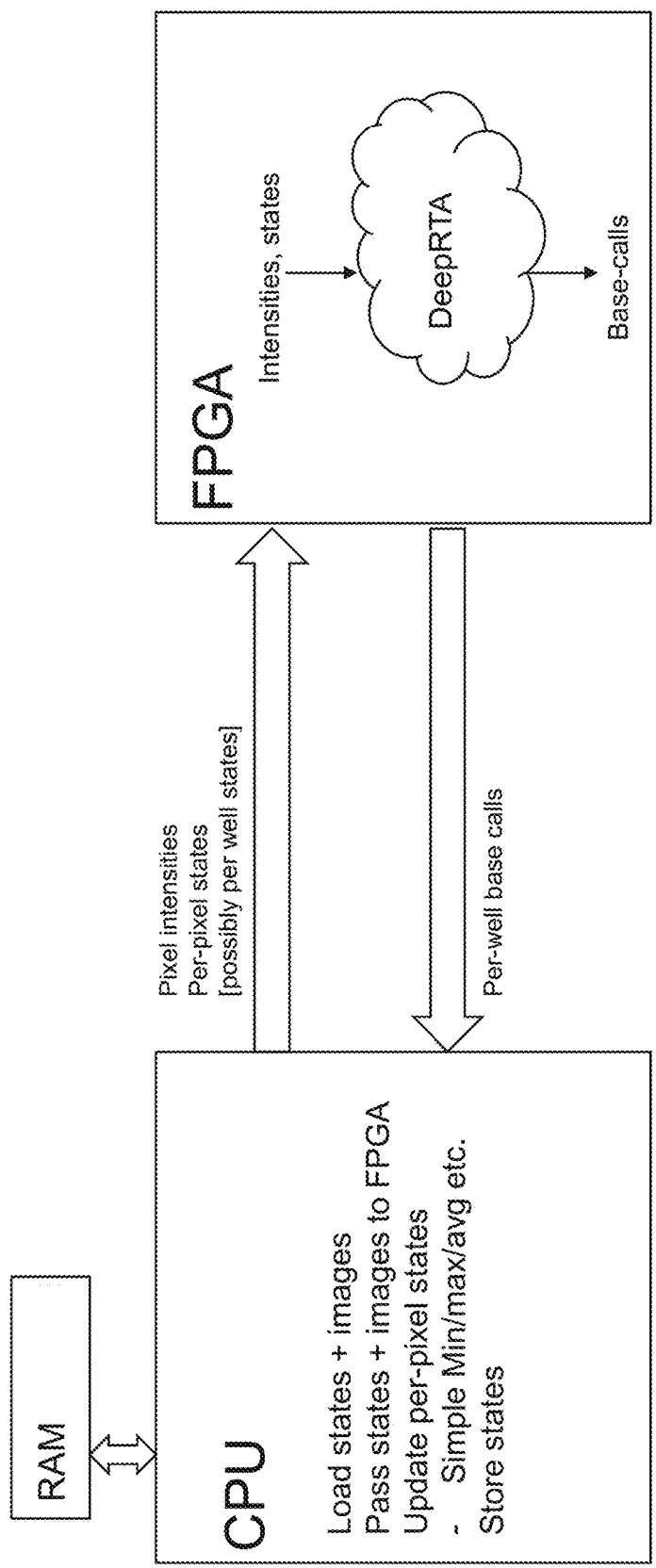
FIG. 44 illustrates one implementation of determining state data on a CPU, and loading the state data from the CPU to an FPGA for base calling.

FIG. 44 illustrates one implementation of determining state data on a CPU, and loading the state data from the CPU to an FPGA for base calling.

Terminology and Additional Implementations

Base calling includes incorporation or attachment of a fluorescently-labeled tag with an analyte. The analyte can be a nucleotide or an oligonucleotide, and the tag can be for a particular nucleotide type (A, C, T, or G). Excitation light is directed toward the analyte having the tag, and the tag emits a detectable fluorescent signal or intensity emission. The intensity emission is indicative of photons emitted by the excited tag that is chemically attached to the analyte.

Throughout this application, including the claims, when phrases such as or similar to "images, image data, or image regions depicting intensity emissions of analytes and their surrounding background" are used, they refer to the intensity emissions of the tags attached to the analytes. A person skilled in the art will appreciate that the intensity emissions of the attached tags are representative of or equivalent to the intensity emissions of the analytes to which the tags are attached, and are therefore used interchangeably. Similarly, properties of the analytes refer to properties of the tags attached to the analytes or of the intensity emissions from the attached tags. For example, a center of an analyte refers to the center of the intensity emissions emitted by a tag attached to the analyte. In another example, the surrounding background of an analyte refers to the surrounding background of the intensity emissions emitted by a tag attached to the analyte.

All literature and similar material cited in this application, including, but not limited to, patents, patent applications, articles, books, treatises, and web pages, regardless of the format of such literature and similar materials, are expressly incorporated by reference in their entirety. In the event that one or more of the incorporated literature and similar materials differs from or contradicts this application, including but not limited to defined terms, term usage, described techniques, or the like, this application controls.

The technology disclosed uses neural networks to improve the quality and quantity of nucleic acid sequence information that can be obtained from a nucleic acid sample such as a nucleic acid template or its complement, for instance, a DNA or RNA polynucleotide or other nucleic acid sample. Accordingly, certain implementations of the technology disclosed provide higher throughput polynucleotide sequencing, for instance, higher rates of collection of DNA or RNA sequence data, greater efficiency in sequence data collection, and/or lower costs of obtaining such sequence data, relative to previously available methodologies.

The technology disclosed uses neural networks to identify the center of a solid-phase nucleic acid cluster and to analyze optical signals that are generated during sequencing of such clusters, to discriminate unambiguously between adjacent, abutting or overlapping clusters in order to assign a sequencing signal to a single, discrete source cluster. These and related implementations thus permit retrieval of meaningful information, such as sequence data, from regions of high-density cluster arrays where useful information could not previously be obtained from such regions due to confounding effects of overlapping or very closely spaced adjacent clusters, including the effects of overlapping signals (e.g., as used in nucleic acid sequencing) emanating therefrom.

As described in greater detail below, in certain implementations there is provided a composition that comprises a solid support having immobilized thereto one or a plurality of nucleic acid clusters as provided herein. Each cluster comprises a plurality of immobilized nucleic acids of the same sequence and has an identifiable center having a detectable center label as provided herein, by which the identifiable center is distinguishable from immobilized nucleic acids in a surrounding region in the cluster. Also described herein are methods for making and using such clusters that have identifiable centers.

The presently disclosed implementations will find uses in numerous situations where advantages are obtained from the ability to identify, determine, annotate, record or otherwise assign the position of a substantially central location within a cluster, such as high-throughput nucleic acid sequencing, development of image analysis algorithms for assigning optical or other signals to discrete source clusters, and other applications where recognition of the center of an immobilized nucleic acid cluster is desirable and beneficial.

In certain implementations, the present invention contemplates methods that relate to high-throughput nucleic acid analysis such as nucleic acid sequence determination (e.g., "sequencing"). Exemplary high-throughput nucleic acid analyses include without limitation de novo sequencing, re-sequencing, whole genome sequencing, gene expression analysis, gene expression monitoring, epigenetic analysis, genome methylation analysis, allele specific primer extension (APSE), genetic diversity profiling, whole genome polymorphism discovery and analysis, single nucleotide polymorphism analysis, hybridization based sequence determination methods, and the like. One skilled in the art will appreciate that a variety of different nucleic acids can be analyzed using the methods and compositions of the present invention.

Although the implementations of the present invention are described in relation to nucleic acid sequencing, they are applicable in any field where image data acquired at different time points, spatial locations or other temporal or physical perspectives is analyzed. For example, the methods and systems described herein are useful in the fields of molecular and cell biology where image data from microarrays, biological specimens, cells, organisms and the like is acquired and at different time points or perspectives and analyzed. Images can be obtained using any number of techniques known in the art including, but not limited to, fluorescence microscopy, light microscopy, confocal microscopy, optical imaging, magnetic resonance imaging, tomography scanning or the like. As another example, the methods and systems described herein can be applied where image data obtained by surveillance, aerial or satellite imaging technologies and the like is acquired at different time points or perspectives and analyzed. The methods and systems are particularly useful for analyzing images obtained for a field of view in which the analytes being viewed remain in the same locations relative to each other in the field of view. The analytes may however have characteristics that differ in separate images, for example, the analytes may appear different in separate images of the field of view. For example, the analytes may appear different with regard to the color of a given analyte detected in different images, a change in the intensity of signal detected for a given analyte in different images, or even the appearance of a signal for a given analyte in one image and disappearance of the signal for the analyte in another image.

Examples described herein may be used in various biological or chemical processes and systems for academic or commercial analysis. More specifically, examples described herein may be used in various processes and systems where it is desired to detect an event, property, quality, or characteristic that is indicative of a designated reaction. For example, examples described herein include light detection devices, biosensors, and their components, as well as bioassay systems that operate with biosensors. In some examples, the devices, biosensors and systems may include a flow cell and one or more light sensors that are coupled together (removably or fixedly) in a substantially unitary structure.

The devices, biosensors and bioassay systems may be configured to perform a plurality of designated reactions that may be detected individually or collectively. The devices, biosensors and bioassay systems may be configured to perform numerous cycles in which the plurality of designated reactions occurs in parallel. For example, the devices, biosensors and bioassay systems may be used to sequence a dense array of DNA features through iterative cycles of enzymatic manipulation and light or image detection/acquisition. As such, the devices, biosensors and bioassay systems (e.g., via one or more cartridges) may include one or more microfluidic channel that delivers reagents or other reaction components in a reaction solution to a reaction site of the devices, biosensors and bioassay systems. In some examples, the reaction solution may be substantially acidic, such as comprising a pH of less than or equal to about 5, or less than or equal to about 4, or less than or equal to about 3. In some other examples, the reaction solution may be substantially alkaline/basic, such as comprising a pH of greater than or equal to about 8, or greater than or equal to about 9, or greater than or equal to about 10. As used herein, the term "acidity" and grammatical variants thereof refer to a pH value of less than about 7, and the terms "basicity," "alkalinity" and grammatical variants thereof refer to a pH value of greater than about 7.

In some examples, the reaction sites are provided or spaced apart in a predetermined manner, such as in a uniform or repeating pattern. In some other examples, the reaction sites are randomly distributed. Each of the reaction sites may be associated with one or more light guides and one or more light sensors that detect light from the associated reaction site. In some examples, the reaction sites are located in reaction recesses or chambers, which may at least partially compartmentalize the designated reactions therein.

As used herein, a "designated reaction" includes a change in at least one of a chemical, electrical, physical, or optical property (or quality) of a chemical or biological substance of interest, such as an analyte-of-interest. In particular examples, a designated reaction is a positive binding event, such as incorporation of a fluorescently labeled biomolecule with an analyte-of-interest, for example. More generally, a designated reaction may be a chemical transformation, chemical change, or chemical interaction. A designated reaction may also be a change in electrical properties. In particular examples, a designated reaction includes the incorporation of a fluorescently-labeled molecule with an analyte. The analyte may be an oligonucleotide and the fluorescently-labeled molecule may be a nucleotide. A designated reaction may be detected when an excitation light is directed toward the oligonucleotide having the labeled nucleotide, and the fluorophore emits a detectable fluorescent signal. In alternative examples, the detected fluorescence is a result of chemiluminescence or bioluminescence. A designated reaction may also increase fluorescence (or Förster) resonance energy transfer (FRET), for example, by bringing a donor fluorophore in proximity to an acceptor fluorophore, decrease FRET by separating donor and acceptor fluorophores, increase fluorescence by separating a quencher from a fluorophore, or decrease fluorescence by co-locating a quencher and fluorophore.

As used herein, a "reaction solution," "reaction component" or "reactant" includes any substance that may be used to obtain at least one designated reaction. For example, potential reaction components include reagents, enzymes, samples, other biomolecules, and buffer solutions, for example. The reaction components may be delivered to a reaction site in a solution and/or immobilized at a reaction site. The reaction components may interact directly or indirectly with another substance, such as an analyte-of-interest immobilized at a reaction site. As noted above, the reaction solution may be substantially acidic (i.e., include a relatively high acidity) (e.g., comprising a pH of less than or equal to about 5, a pH less than or equal to about 4, or a pH less than or equal to about 3) or substantially alkaline/basic (i.e., include a relatively high alkalinity/basicity) (e.g., comprising a pH of greater than or equal to about 8, a pH of greater than or equal to about 9, or a pH of greater than or equal to about 10).

As used herein, the term "reaction site" is a localized region where at least one designated reaction may occur. A reaction site may include support surfaces of a reaction structure or substrate where a substance may be immobilized thereon. For example, a reaction site may include a surface of a reaction structure (which may be positioned in a channel of a flow cell) that has a reaction component thereon, such as a colony of nucleic acids thereon. In some such examples, the nucleic acids in the colony have the same sequence, being for example, clonal copies of a single stranded or double stranded template. However, in some examples a reaction site may contain only a single nucleic acid molecule, for example, in a single stranded or double stranded form.

A plurality of reaction sites may be randomly distributed along the reaction structure or arranged in a predetermined manner (e.g., side-by-side in a matrix, such as in microarrays). A reaction site can also include a reaction chamber or recess that at least partially defines a spatial region or volume configured to compartmentalize the designated reaction. As used herein, the term "reaction chamber" or "reaction recess" includes a defined spatial region of the support structure (which is often in fluid communication with a flow channel). A reaction recess may be at least partially separated from the surrounding environment other or spatial regions. For example, a plurality of reaction recesses may be separated from each other by shared walls, such as a detection surface. As a more specific example, the reaction recesses may be nanowells comprising an indent, pit, well, groove, cavity or depression defined by interior surfaces of a detection surface and have an opening or aperture (i.e., be open-sided) so that the nanowells can be in fluid communication with a flow channel.

In some examples, the reaction recesses of the reaction structure are sized and shaped relative to solids (including semi-solids) so that the solids may be inserted, fully or partially, therein. For example, the reaction recesses may be sized and shaped to accommodate a capture bead. The capture bead may have clonally amplified DNA or other substances thereon. Alternatively, the reaction recesses may be sized and shaped to receive an approximate number of beads or solid substrates. As another example, the reaction recesses may be filled with a porous gel or substance that is configured to control diffusion or filter fluids or solutions that may flow into the reaction recesses.

In some examples, light sensors (e.g., photodiodes) are associated with corresponding reaction sites. A light sensor that is associated with a reaction site is configured to detect light emissions from the associated reaction site via at least one light guide when a designated reaction has occurred at the associated reaction site. In some cases, a plurality of light sensors (e.g. several pixels of a light detection or camera device) may be associated with a single reaction site. In other cases, a single light sensor (e.g. a single pixel) may be associated with a single reaction site or with a group of reaction sites. The light sensor, the reaction site, and other features of the biosensor may be configured so that at least some of the light is directly detected by the light sensor without being reflected.

As used herein, a "biological or chemical substance" includes biomolecules, samples-of-interest, analytes-of-interest, and other chemical compound(s). A biological or chemical substance may be used to detect, identify, or analyze other chemical compound(s), or function as intermediaries to study or analyze other chemical compound(s). In particular examples, the biological or chemical substances include a biomolecule. As used herein, a "biomolecule" includes at least one of a biopolymer, nucleoside, nucleic acid, polynucleotide, oligonucleotide, protein, enzyme, polypeptide, antibody, antigen, ligand, receptor, polysaccharide, carbohydrate, polyphosphate, cell, tissue, organism, or fragment thereof or any other biologically active chemical compound(s) such as analogs or mimetics of the aforementioned species. In a further example, a biological or chemical substance or a biomolecule includes an enzyme or reagent used in a coupled reaction to detect the product of another reaction such as an enzyme or reagent, such as an enzyme or reagent used to detect pyrophosphate in a pyrosequencing reaction. Enzymes and reagents useful for pyrophosphate detection are described, for example, in U.S. Patent Publication No. 2005/0244870 A1, which is incorporated by reference in its entirety.

Biomolecules, samples, and biological or chemical substances may be naturally occurring or synthetic and may be suspended in a solution or mixture within a reaction recess or region. Biomolecules, samples, and biological or chemical substances may also be bound to a solid phase or gel material. Biomolecules, samples, and biological or chemical substances may also include a pharmaceutical composition. In some cases, biomolecules, samples, and biological or chemical substances of interest may be referred to as targets, probes, or analytes.

As used herein, a "biosensor" includes a device that includes a reaction structure with a plurality of reaction sites that is configured to detect designated reactions that occur at or proximate to the reaction sites. A biosensor may include a solid-state light detection or "imaging" device (e.g., CCD or CMOS light detection device) and, optionally, a flow cell mounted thereto. The flow cell may include at least one flow channel that is in fluid communication with the reaction sites. As one specific example, the biosensor is configured to fluidically and electrically couple to a bioassay system. The bioassay system may deliver a reaction solution to the reaction sites according to a predetermined protocol (e.g., sequencing-by-synthesis) and perform a plurality of imaging events. For example, the bioassay system may direct reaction solutions to flow along the reaction sites. At least one of the reaction solutions may include four types of nucleotides having the same or different fluorescent labels. The nucleotides may bind to the reaction sites, such as to corresponding oligonucleotides at the reaction sites. The bioassay system may then illuminate the reaction sites using an excitation light source (e.g., solid-state light sources, such as light-emitting diodes (LEDs)). The excitation light may have a predetermined wavelength or wavelengths, including a range of wavelengths. The fluorescent labels excited by the incident excitation light may provide emission signals (e.g., light of a wavelength or wavelengths that differ from the excitation light and, potentially, each other) that may be detected by the light sensors.

As used herein, the term "immobilized," when used with respect to a biomolecule or biological or chemical substance, includes substantially attaching the biomolecule or biological or chemical substance at a molecular level to a surface, such as to a detection surface of a light detection device or reaction structure. For example, a biomolecule or biological or chemical substance may be immobilized to a surface of the reaction structure using adsorption techniques including non-covalent interactions (e.g., electrostatic forces, van der Waals, and dehydration of hydrophobic interfaces) and covalent binding techniques where functional groups or linkers facilitate attaching the biomolecules to the surface. Immobilizing biomolecules or biological or chemical substances to the surface may be based upon the properties of the surface, the liquid medium carrying the biomolecule or biological or chemical substance, and the properties of the biomolecules or biological or chemical substances themselves. In some cases, the surface may be functionalized (e.g., chemically or physically modified) to facilitate immobilizing the biomolecules (or biological or chemical substances) to the surface.

In some examples, nucleic acids can be immobilized to the reaction structure, such as to surfaces of reaction recesses thereof. In particular examples, the devices, biosensors, bioassay systems and methods described herein may include the use of natural nucleotides and also enzymes that are configured to interact with the natural nucleotides. Natural nucleotides include, for example, ribonucleotides or deoxyribonucleotides. Natural nucleotides can be in the mono-, di-, or tri-phosphate form and can have a base selected from adenine (A), Thymine (T), uracil (U), guanine (G) or cytosine (C). It will be understood, however, that non-natural nucleotides, modified nucleotides or analogs of the aforementioned nucleotides can be used.

As noted above, a biomolecule or biological or chemical substance may be immobilized at a reaction site in a reaction recess of a reaction structure. Such a biomolecule or biological substance may be physically held or immobilized within the reaction recesses through an interference fit, adhesion, covalent bond, or entrapment. Examples of items or solids that may be disposed within the reaction recesses include polymer beads, pellets, agarose gel, powders, quantum dots, or other solids that may be compressed and/or held within the reaction chamber. In certain implementations, the reaction recesses may be coated or filled with a hydrogel layer capable of covalently binding DNA oligonucleotides. In particular examples, a nucleic acid superstructure, such as a DNA ball, can be disposed in or at a reaction recess, for example, by attachment to an interior surface of the reaction recess or by residence in a liquid within the reaction recess. A DNA ball or other nucleic acid superstructure can be performed and then disposed in or at a reaction recess. Alternatively, a DNA ball can be synthesized in situ at a reaction recess. A substance that is immobilized in a reaction recess can be in a solid, liquid, or gaseous state.

As used herein, the term "analyte" is intended to mean a point or area in a pattern that can be distinguished from other points or areas according to relative location. An individual analyte can include one or more molecules of a particular type. For example, an analyte can include a single target nucleic acid molecule having a particular sequence or an analyte can include several nucleic acid molecules having the same sequence (and/or complementary sequence, thereof). Different molecules that are at different analytes of a pattern can be differentiated from each other according to the locations of the analytes in the pattern. Example analytes include without limitation, wells in a substrate, beads (or other particles) in or on a substrate, projections from a substrate, ridges on a substrate, pads of gel material on a substrate, or channels in a substrate.

Any of a variety of target analytes that are to be detected, characterized, or identified can be used in an apparatus, system or method set forth herein. Exemplary analytes include, but are not limited to, nucleic acids (e.g., DNA, RNA or analogs thereof), proteins, polysaccharides, cells, antibodies, epitopes, receptors, ligands, enzymes (e.g. kinases, phosphatases or polymerases), small molecule drug candidates, cells, viruses, organisms, or the like.

The terms "analyte", "nucleic acid", "nucleic acid molecule", and "polynucleotide" are used interchangeably herein. In various implementations, nucleic acids may be used as templates as provided herein (e.g., a nucleic acid template, or a nucleic acid complement that is complementary to a nucleic acid nucleic acid template) for particular types of nucleic acid analysis, including but not limited to nucleic acid amplification, nucleic acid expression analysis, and/or nucleic acid sequence determination or suitable combinations thereof. Nucleic acids in certain implementations include, for instance, linear polymers of deoxyribonucleotides in 3'-5' phosphodiester or other linkages, such as deoxyribonucleic acids (DNA), for example, single- and double-stranded DNA, genomic DNA, copy DNA or complementary DNA (cDNA), recombinant DNA, or any form of synthetic or modified DNA. In other implementations, nucleic acids include for instance, linear polymers of ribonucleotides in 3'-5' phosphodiester or other linkages such as ribonucleic acids (RNA), for example, single- and double-stranded RNA, messenger (mRNA), copy RNA or complementary RNA (cRNA), alternatively spliced mRNA, ribosomal RNA, small nucleolar RNA (snoRNA), microRNAs (miRNA), small interfering RNAs (sRNA), piwi RNAs (piRNA), or any form of synthetic or modified RNA. Nucleic acids used in the compositions and methods of the present invention may vary in length and may be intact or full-length molecules or fragments or smaller parts of larger nucleic acid molecules. In particular implementations, a nucleic acid may have one or more detectable labels, as described elsewhere herein.

The terms "analyte", "cluster", "nucleic acid cluster", "nucleic acid colony", and "DNA cluster" are used interchangeably and refer to a plurality of copies of a nucleic acid template and/or complements thereof attached to a solid support. Typically and in certain preferred implementations, the nucleic acid cluster comprises a plurality of copies of template nucleic acid and/or complements thereof, attached via their 5' termini to the solid support. The copies of nucleic acid strands making up the nucleic acid clusters may be in a single or double stranded form. Copies of a nucleic acid template that are present in a cluster can have nucleotides at corresponding positions that differ from each other, for example, due to presence of a label moiety. The corresponding positions can also contain analog structures having different chemical structure but similar Watson-Crick base-pairing properties, such as is the case for uracil and thymine.

Colonies of nucleic acids can also be referred to as "nucleic acid clusters". Nucleic acid colonies can optionally be created by cluster amplification or bridge amplification techniques as set forth in further detail elsewhere herein. Multiple repeats of a target sequence can be present in a single nucleic acid molecule, such as a concatamer created using a rolling circle amplification procedure.

The nucleic acid clusters of the invention can have different shapes, sizes and densities depending on the conditions used. For example, clusters can have a shape that is substantially round, multi-sided, donut-shaped or ring-shaped. The diameter of a nucleic acid cluster can be designed to be from about 0.2 µm to about 6 µm, about 0.3 µm to about 4 µm, about 0.4 µm to about 3 µm, about 0.5 µm to about 2 µm, about 0.75 µm to about 1.5 µm, or any intervening diameter. In a particular implementation, the diameter of a nucleic acid cluster is about 0.5 µm, about 1 µm, about 1.5 µm, about 2 µm, about 2.5 µm, about 3 µm, about 4 m, about 5 µm, or about 6 µm. The diameter of a nucleic acid cluster may be influenced by a number of parameters, including, but not limited to the number of amplification cycles performed in producing the cluster, the length of the nucleic acid template or the density of primers attached to the surface upon which clusters are formed. The density of nucleic acid clusters can be designed to typically be in the range of $0.1/mm^2$, $1/mm^2$, $10/mm^2$, $100/mm^2$, $1,000/mm^2$, $10,000/mm^2$ to $100,000/mm^2$. The present invention further contemplates, in part, higher density nucleic acid clusters, for example, $100,000/mm^2$ to $1,000,000/mm^2$ and $1,000,000/mm^2$ to $10,000,000/mm^2$.

As used herein, an "analyte" is an area of interest within a specimen or field of view. When used in connection with microarray devices or other molecular analytical devices, an analyte refers to the area occupied by similar or identical molecules. For example, an analyte can be an amplified oligonucleotide or any other group of a polynucleotide or polypeptide with a same or similar sequence. In other implementations, an analyte can be any element or group of elements that occupy a physical area on a specimen. For example, an analyte could be a parcel of land, a body of water or the like. When an analyte is imaged, each analyte will have some area. Thus, in many implementations, an analyte is not merely one pixel.

The distances between analytes can be described in any number of ways. In some implementations, the distances between analytes can be described from the center of one analyte to the center of another analyte. In other implementations, the distances can be described from the edge of one analyte to the edge of another analyte, or between the outer-most identifiable points of each analyte. The edge of an analyte can be described as the theoretical or actual physical boundary on a chip, or some point inside the boundary of the analyte. In other implementations, the distances can be described in relation to a fixed point on the specimen or in the image of the specimen.

Generally several implementations will be described herein with respect to a method of analysis. It will be understood that systems are also provided for carrying out the methods in an automated or semi-automated way. Accordingly, this disclosure provides neural network-based template generation and base calling systems, wherein the systems can include a processor; a storage device; and a program for image analysis, the program including instructions for carrying out one or more of the methods set forth herein. Accordingly, the methods set forth herein can be carried out on a computer, for example, having components set forth herein or otherwise known in the art.

The methods and systems set forth herein are useful for analyzing any of a variety of objects. Particularly useful objects are solid supports or solid-phase surfaces with attached analytes. The methods and systems set forth herein provide advantages when used with objects having a repeating pattern of analytes in an xy plane. An example is a microarray having an attached collection of cells, viruses, nucleic acids, proteins, antibodies, carbohydrates, small molecules (such as drug candidates), biologically active molecules or other analytes of interest.

An increasing number of applications have been developed for arrays with analytes having biological molecules such as nucleic acids and polypeptides. Such microarrays typically include deoxyribonucleic acid (DNA) or ribonucleic acid (RNA) probes. These are specific for nucleotide sequences present in humans and other organisms. In certain applications, for example, individual DNA or RNA probes can be attached at individual analytes of an array. A test sample, such as from a known person or organism, can be exposed to the array, such that target nucleic acids (e.g., gene fragments, mRNA, or amplicons thereof) hybridize to complementary probes at respective analytes in the array. The probes can be labeled in a target specific process (e.g., due to labels present on the target nucleic acids or due to enzymatic labeling of the probes or targets that are present in hybridized form at the analytes). The array can then be examined by scanning specific frequencies of light over the analytes to identify which target nucleic acids are present in the sample.

Biological microarrays may be used for genetic sequencing and similar applications. In general, genetic sequencing comprises determining the order of nucleotides in a length of target nucleic acid, such as a fragment of DNA or RNA. Relatively short sequences are typically sequenced at each analyte, and the resulting sequence information may be used in various bioinformatics methods to logically fit the sequence fragments together so as to reliably determine the sequence of much more extensive lengths of genetic material from which the fragments were derived. Automated, computer-based algorithms for characteristic fragments have been developed, and have been used more recently in genome mapping, identification of genes and their function, and so forth. Microarrays are particularly useful for characterizing genomic content because a large number of variants are present and this supplants the alternative of performing many experiments on individual probes and targets. The microarray is an ideal format for performing such investigations in a practical manner.

Any of a variety of analyte arrays (also referred to as "microarrays") known in the art can be used in a method or system set forth herein. A typical array contains analytes, each having an individual probe or a population of probes. In the latter case, the population of probes at each analyte is typically homogenous having a single species of probe. For example, in the case of a nucleic acid array, each analyte can have multiple nucleic acid molecules each having a common sequence. However, in some implementations the populations at each analyte of an array can be heterogeneous. Similarly, protein arrays can have analytes with a single protein or a population of proteins typically, but not always, having the same amino acid sequence. The probes can be attached to the surface of an array for example, via covalent linkage of the probes to the surface or via non-covalent interaction(s) of the probes with the surface. In some implementations, probes, such as nucleic acid molecules, can be attached to a surface via a gel layer as described, for example, in U.S. patent application Ser. No. 13/784,368 and US Pat. App. Pub. No. 2011/0059865 A1, each of which is incorporated herein by reference.

Example arrays include, without limitation, a BeadChip Array available from Illumina, Inc. (San Diego, Calif.) or others such as those where probes are attached to beads that are present on a surface (e.g. beads in wells on a surface) such as those described in U.S. Pat. Nos. 6,266,459; 6,355,431; 6,770,441; 6,859,570; or 7,622,294; or PCT Publication No. WO 00/63437, each of which is incorporated herein by reference. Further examples of commercially available microarrays that can be used include, for example, an Affymetrix® GeneChip® microarray or other microarray synthesized in accordance with techniques sometimes referred to as VLSIPS™ (Very Large Scale Immobilized Polymer Synthesis) technologies. A spotted microarray can also be used in a method or system according to some implementations of the present disclosure. An example spotted microarray is a CodeLink™ Array available from Amersham Biosciences. Another microarray that is useful is one that is manufactured using inkjet printing methods such as SurePrint™ Technology available from Agilent Technologies.

Other useful arrays include those that are used in nucleic acid sequencing applications. For example, arrays having amplicons of genomic fragments (often referred to as clusters) are particularly useful such as those described in Bentley et al., Nature 456:53-59 (2008), WO 04/018497; WO 91/06678; WO 07/123744; U.S. Pat. Nos. 7,329,492; 7,211,414; 7,315,019; 7,405,281, or 7,057,026; or US Pat. App. Pub. No. 2008/0108082 A1, each of which is incorporated herein by reference. Another type of array that is useful for nucleic acid sequencing is an array of particles produced from an emulsion PCR technique. Examples are described in Dressman et al., Proc. Natl. Acad. Sci. USA 100:8817-8822 (2003), WO 05/010145, US Pat. App. Pub. No. 2005/0130173 or US Pat. App. Pub. No. 2005/0064460, each of which is incorporated herein by reference in its entirety.

Arrays used for nucleic acid sequencing often have random spatial patterns of nucleic acid analytes. For example, HiSeq or MiSeq sequencing platforms available from Illumina Inc. (San Diego, Calif.) utilize flow cells upon which nucleic acid arrays are formed by random seeding followed by bridge amplification. However, patterned arrays can also be used for nucleic acid sequencing or other analytical applications. Example patterned arrays, methods for their manufacture and methods for their use are set forth in U.S. Ser. No. 13/787,396; U.S. Ser. No. 13/783,043; U.S. Ser. No. 13/784,368; US Pat. App. Pub. No. 2013/0116153 A1; and US Pat. App. Pub. No. 2012/0316086 A1, each of which is incorporated herein by reference. The analytes of such patterned arrays can be used to capture a single nucleic acid template molecule to seed subsequent formation of a homogenous colony, for example, via bridge amplification. Such patterned arrays are particularly useful for nucleic acid sequencing applications.

The size of an analyte on an array (or other object used in a method or system herein) can be selected to suit a particular application. For example, in some implementations, an analyte of an array can have a size that accommodates only a single nucleic acid molecule. A surface having a plurality of analytes in this size range is useful for constructing an array of molecules for detection at single molecule resolution. Analytes in this size range are also useful for use in arrays having analytes that each contain a colony of nucleic acid molecules. Thus, the analytes of an array can each have an area that is no larger than about 1 $mm^2$, no larger than about 500 $\mu m^2$, no larger than about 100 $\mu m^2$, no larger than about 10 $\mu m^2$, no larger than about 1 $m^2$, no larger than about 500 $nm^2$, or no larger than about 100 $nm^2$, no larger than about 10 $nm^2$, no larger than about 5 $nm^2$, or no larger than about 1 $nm^2$. Alternatively or additionally, the analytes of an array will be no smaller than about 1 $mm^2$, no smaller than about 500 $\mu m^2$, no smaller than about 100 $\mu m^2$, no smaller than about 10 $\mu m^2$, no smaller than about 1 $\mu m^2$, no smaller than about 500 $nm^2$, no smaller than about 100 $nm^2$, no smaller than about 10 $nm^2$, no smaller than about 5 $nm^2$, or no smaller than about 1 $nm^2$. Indeed, an analyte can have a size that is in a range between an upper and lower limit selected from those exemplified above. Although several size ranges for analytes of a surface have been exemplified with respect to nucleic acids and on the scale of nucleic acids, it will be understood that analytes in these size ranges can be used for applications that do not include nucleic acids. It will be further understood that the size of the analytes need not necessarily be confined to a scale used for nucleic acid applications.

For implementations that include an object having a plurality of analytes, such as an array of analytes, the analytes can be discrete, being separated with spaces between each other. An array useful in the invention can have analytes that are separated by edge to edge distance of at most 100 $\mu m$, 50 $\mu m$, 10 $\mu m$, 5 $\mu m$, 1 $\mu m$, 0.5 $\mu m$, or less. Alternatively or additionally, an array can have analytes that are separated by an edge to edge distance of at least 0.5 m, 1 $\mu m$, 5 m, 10 $\mu m$, 50 $\mu m$, 100 pm, or more. These ranges can apply to the average edge to edge spacing for analytes as well as to the minimum or maximum spacing.

In some implementations the analytes of an army need not be discrete and instead neighboring analytes can abut each other. Whether or not the analytes are discrete, the size of the analytes and/or pitch of the analytes can vary such that arrays can have a desired density. For example, the average analyte pitch in a regular pattern can be at most 100 $\mu m$, 50 $\mu m$, 10 $\mu m$, 5 $\mu m$, 1 $\mu m$, 0.5 $\mu m$, or less. Alternatively or additionally, the average analyte pitch in a regular pattern can be at least 0.5 $\mu m$, 1 $\mu m$, 5 $\mu m$, 10 $\mu m$, 50 $\mu m$, 100 $\mu m$, or more. These ranges can apply to the maximum or minimum pitch for a regular pattern as well. For example, the maximum analyte pitch for a regular pattern can be at most 100 $\mu m$, 50 $\mu m$, 10 $\mu m$, 5 $\mu m$, 1 $\mu m$, 0.5 $\mu m$, or less; and/or the minimum analyte pitch in a regular pattern can be at least 0.5 $\mu m$, 1 $\mu m$, 5 $\mu m$, 10 $\mu m$, 50 $\mu m$, 100 $\mu m$, or more.

The density of analytes in an array can also be understood in terms of the number of analytes present per unit area. For example, the average density of analytes for an array can be at least about $1 \times 10^3$ analytes/$mm^2$, $1 \times 10^4$ analytes/$mm^2$, $1 \times 10^5$ analytes/$mm^2$, $1 \times 10^6$ analytes/$mm^2$, $1 \times 10^7$ analytes/$mm^2$, $1 \times 10^8$ analytes/$mm^2$, or $1 \times 10^9$ analytes/$mm^2$, or higher. Alternatively or additionally the average density of analytes for an array can be at most about $1 \times 10^9$ analytes/$mm^2$, $1 \times 10^8$ analytes/$mm^2$, $1 \times 10^7$ analytes/$mm^2$, $1 \times 10^6$ analytes/$mm^2$, $1 \times 10^5$ analytes/$mm^2$, $1 \times 10^4$ analytes/$mm^2$, or $1 \times 10^3$ analytes/$mm^2$, or less.

The above ranges can apply to all or part of a regular pattern including, for example, all or part of an array of analytes.

The analytes in a pattern can have any of a variety of shapes. For example, when observed in a two dimensional plane, such as on the surface of an array, the analytes can appear rounded, circular, oval, rectangular, square, symmetric, asymmetric, triangular, polygonal, or the like. The analytes can be arranged in a regular repeating pattern including, for example, a hexagonal or rectilinear pattern. A pattern can be selected to achieve a desired level of packing. For example, round analytes are optimally packed in a hexagonal arrangement. Of course other packing arrangements can also be used for round analytes and vice versa.

A pattern can be characterized in terms of the number of analytes that are present in a subset that forms the smallest geometric unit of the pattern. The subset can include, for example, at least about 2, 3, 4, 5, 6, 10 or more analytes. Depending upon the size and density of the analytes the geometric unit can occupy an area of less than 1 $mm^2$, 500 $\mu m^2$, 100 $\mu m^2$, 50 $\mu m^2$, 10 $\mu m^2$, 1 $\mu m^2$, 500 $nm^2$, 100 $nm^2$, 50 $nm^2$, 10 $nm^2$, or less. Alternatively or additionally, the geometric unit can occupy an area of greater than 10 $nm^2$, 50 $nm^2$, 100 $nm^2$, 500 $nm^2$, 1 $\mu m^2$, 10 $\mu m^2$, 50 $\mu m^2$, 100 $\mu m^2$, 500 $\mu m^2$, 1 $mm^2$, or more. Characteristics of the analytes in a geometric unit, such as shape, size, pitch and the like, can be selected from those set forth herein more generally with regard to analytes in an array or pattern.

An array having a regular pattern of analytes can be ordered with respect to the relative locations of the analytes but random with respect to one or more other characteristic of each analyte. For example, in the case of a nucleic acid array, the nuclei acid analytes can be ordered with respect to their relative locations but random with respect to one's knowledge of the sequence for the nucleic acid species present at any particular analyte. As a more specific example, nucleic acid arrays formed by seeding a repeating pattern of analytes with template nucleic acids and amplifying the template at each analyte to form copies of the template at the analyte (e.g., via cluster amplification or bridge amplification) will have a regular pattern of nucleic acid analytes but will be random with regard to the distribution of sequences of the nucleic acids across the array. Thus, detection of the presence of nucleic acid material generally on the array can yield a repeating pattern of analytes, whereas sequence specific detection can yield non-repeating distribution of signals across the array.

It will be understood that the description herein of patterns, order, randomness and the like pertain not only to analytes on objects, such as analytes on arrays, but also to analytes in images. As such, patterns, order, randomness and the like can be present in any of a variety of formats that are used to store, manipulate or communicate image data including, but not limited to, a computer readable medium or computer component such as a graphical user interface or other output device.

As used herein, the term "image" is intended to mean a representation of all or part of an object. The representation can be an optically detected reproduction. For example, an image can be obtained from fluorescent, luminescent, scatter, or absorption signals. The part of the object that is present in an image can be the surface or other xy plane of the object. Typically, an image is a 2 dimensional representation, but in some cases information in the image can be derived from 3 or more dimensions. An image need not include optically detected signals. Non-optical signals can be present instead. An image can be provided in a computer readable format or medium such as one or more of those set forth elsewhere herein.

As used herein, "image" refers to a reproduction or representation of at least a portion of a specimen or other object. In some implementations, the reproduction is an optical reproduction, for example, produced by a camera or other optical detector. The reproduction can be a non-optical reproduction, for example, a representation of electrical signals obtained from an array of nanopore analytes or a representation of electrical signals obtained from an ion-sensitive CMOS detector. In particular implementations non-optical reproductions can be excluded from a method or apparatus set forth herein. An image can have a resolution capable of distinguishing analytes of a specimen that are present at any of a variety of spacings including, for example, those that are separated by less than 100 µm, 50 µm, 10 µm, 5 µm, 1 µm or 0.5 µm.

As used herein, "acquiring", "acquisition" and like terms refer to any part of the process of obtaining an image file. In some implementations, data acquisition can include generating an image of a specimen, looking for a signal in a specimen, instructing a detection device to look for or generate an image of a signal, giving instructions for further analysis or transformation of an image file, and any number of transformations or manipulations of an image file.

As used herein, the term "template" refers to a representation of the location or relation between signals or analytes. Thus, in some implementations, a template is a physical grid with a representation of signals corresponding to analytes in a specimen. In some implementations, a template can be a chart, table, text file or other computer file indicative of locations corresponding to analytes. In implementations presented herein, a template is generated in order to track the location of analytes of a specimen across a set of images of the specimen captured at different reference points. For example, a template could be a set of x,y coordinates or a set of values that describe the direction and/or distance of one analyte with respect to another analyte.

As used herein, the term "specimen" can refer to an object or area of an object of which an image is captured. For example, in implementations where images are taken of the surface of the earth, a parcel of land can be a specimen. In other implementations where the analysis of biological molecules is performed in a flow cell, the flow cell may be divided into any number of subdivisions, each of which may be a specimen. For example, a flow cell may be divided into various flow channels or lanes, and each lane can be further divided into 2, 3, 4, 5, 6, 7, 8, 9, 10, 20, 30, 40, 50, 60 70, 80, 90, 100, 110, 120, 140, 160, 180, 200, 400, 600, 800, 1000 or more separate regions that are imaged. One example of a flow cell has 8 lanes, with each lane divided into 120 specimens or tiles. In another implementation, a specimen may be made up of a plurality of tiles or even an entire flow cell. Thus, the image of each specimen can represent a region of a larger surface that is imaged.

It will be appreciated that references to ranges and sequential number lists described herein include not only the enumerated number but all real numbers between the enumerated numbers.

As used herein, a "reference point" refers to any temporal or physical distinction between images. In a preferred implementation, a reference point is a time point. In a more preferred implementation, a reference point is a time point or cycle during a sequencing reaction. However, the term "reference point" can include other aspects that distinguish or separate images, such as angle, rotational, temporal, or other aspects that can distinguish or separate images.

As used herein, a "subset of images" refers to a group of images within a set. For example, a subset may contain 1, 2, 3, 4, 6, 8, 10, 12, 14, 16, 18, 20, 30, 40, 50, 60 or any number of images selected from a set of images. In particular implementations, a subset may contain no more than 1, 2, 3, 4, 6, 8, 10, 12, 14, 16, 18, 20, 30, 40, 50, 60 or any number of images selected from a set of images. In a preferred implementation, images are obtained from one or more sequencing cycles with four images correlated to each cycle. Thus, for example, a subset could be a group of 16 images obtained through four cycles.

A base refers to a nucleotide base or nucleotide, A (adenine), C (cytosine), T (thymine), or G (guanine). This application uses "base(s)" and "nucleotide(s)" interchangeably.

The term "chromosome" refers to the heredity-bearing gene carrier of a living cell, which is derived from chromatin strands comprising DNA and protein components (especially histones). The conventional internationally recognized individual human genome chromosome numbering system is employed herein.

The term "site" refers to a unique position (e.g., chromosome ID, chromosome position and orientation) on a reference genome. In some implementations, a site may be a residue, a sequence tag, or a segment's position on a sequence. The term "locus" may be used to refer to the specific location of a nucleic acid sequence or polymorphism on a reference chromosome.

The term "sample" herein refers to a sample, typically derived from a biological fluid, cell, tissue, organ, or organism containing a nucleic acid or a mixture of nucleic acids containing at least one nucleic acid sequence that is to be sequenced and/or phased. Such samples include, but are not limited to sputum/oral fluid, amniotic fluid, blood, a blood fraction, fine needle biopsy samples (e.g., surgical biopsy, fine needle biopsy, etc.), urine, peritoneal fluid, pleural fluid, tissue explant, organ culture and any other tissue or cell preparation, or fraction or derivative thereof or isolated therefrom. Although the sample is often taken from a human subject (e.g., patient), samples can be taken from any organism having chromosomes, including, but not limited to dogs, cats, horses, goats, sheep, cattle, pigs, etc. The sample may be used directly as obtained from the biological source or following a pretreatment to modify the character of the sample. For example, such pretreatment may include preparing plasma from blood, diluting viscous fluids and so forth. Methods of pretreatment may also involve, but are not limited to, filtration, precipitation, dilution, distillation, mixing, centrifugation, freezing, lyophilization, concentration, amplification, nucleic acid fragmentation, inactivation of interfering components, the addition of reagents, lysing, etc.

The term "sequence" includes or represents a strand of nucleotides coupled to each other. The nucleotides may be based on DNA or RNA. It should be understood that one sequence may include multiple sub-sequences. For example, a single sequence (e.g., of a PCR amplicon) may have 350 nucleotides. The sample read may include multiple sub-sequences within these 350 nucleotides. For instance, the sample read may include first and second flanking subsequences having, for example, 20-50 nucleotides. The first and second flanking sub-sequences may be located on either side of a repetitive segment having a corresponding sub-sequence (e.g., 40-100 nucleotides). Each of the flanking sub-sequences may include (or include portions of) a primer sub-sequence (e.g., 10-30 nucleotides). For ease of reading, the term "sub-sequence" will be referred to as "sequence," but it is understood that two sequences are not necessarily separate from each other on a common strand. To differentiate the various sequences described herein, the sequences may be given different labels (e.g., target sequence, primer sequence, flanking sequence, reference sequence, and the like). Other terms, such as "allele," may be given different labels to differentiate between like objects. The application uses "read(s)" and "sequence read(s)" interchangeably.

The term "paired-end sequencing" refers to sequencing methods that sequence both ends of a target fragment. Paired-end sequencing may facilitate detection of genomic rearrangements and repetitive segments, as well as gene fusions and novel transcripts. Methodology for paired-end sequencing are described in PCT publication WO07010252, PCT application Serial No. PCTGB2007/003798 and US patent application publication US 2009/0088327, each of which is incorporated by reference herein. In one example, a series of operations may be performed as follows; (a) generate clusters of nucleic acids; (b) linearize the nucleic acids; (c) hybridize a first sequencing primer and carry out repeated cycles of extension, scanning and deblocking, as set forth above; (d) "invert" the target nucleic acids on the flow cell surface by synthesizing a complimentary copy; (e) linearize the resynthesized strand; and (f) hybridize a second sequencing primer and carry out repeated cycles of extension, scanning and deblocking, as set forth above. The inversion operation can be carried out be delivering reagents as set forth above for a single cycle of bridge amplification.

The term "reference genome" or "reference sequence" refers to any particular known genome sequence, whether partial or complete, of any organism which may be used to reference identified sequences from a subject. For example, a reference genome used for human subjects as well as many other organisms is found at the National Center for Biotechnology Information at ncbi.nlm.nih.gov. A "genome" refers to the complete genetic information of an organism or virus, expressed in nucleic acid sequences. A genome includes both the genes and the noncoding sequences of the DNA. The reference sequence may be larger than the reads that are aligned to it. For example, it may be at least about 100 times larger, or at least about 1000 times larger, or at least about 10,000 times larger, or at least about 105 times larger, or at least about 106 times larger, or at least about 107 times larger. In one example, the reference genome sequence is that of a full length human genome. In another example, the reference genome sequence is limited to a specific human chromosome such as chromosome 13. In some implementations, a reference chromosome is a chromosome sequence from human genome version hg19. Such sequences may be referred to as chromosome reference sequences, although the term reference genome is intended to cover such sequences. Other examples of reference sequences include genomes of other species, as well as chromosomes, sub-chromosomal regions (such as strands), etc., of any species. In various implementations, the reference genome is a consensus sequence or other combination derived from multiple individuals. However, in certain applications, the reference sequence may be taken from a particular individual. In other implementations, the "genome" also covers so-called "graph genomes", which use a particular storage format and representation of the genome sequence. In one implementation, graph genomes store sequence data in a linear file. In another implementation, the graph genomes refer to a representation where alternative sequences (e.g., different copies of a chromosome with small differences) are stored as different paths in a graph. Additional information regarding graph genome implementations can be found in https://www.biorxiv.org/content/biorxiv/early/2018/03/20/194530.full.pdf, the content of which is hereby incorporated herein by reference in its entirety.

The term "read" refer to a collection of sequence data that describes a fragment of a nucleotide sample or reference. The term "read" may refer to a sample read and/or a reference read. Typically, though not necessarily, a read represents a short sequence of contiguous base pairs in the sample or reference. The read may be represented symbolically by the base pair sequence (in ACTG) of the sample or reference fragment. It may be stored in a memory device and processed as appropriate to determine whether the read matches a reference sequence or meets other criteria. A read may be obtained directly from a sequencing apparatus or indirectly from stored sequence information concerning the sample. In some cases, a read is a DNA sequence of sufficient length (e.g., at least about 25 bp) that can be used to identify a larger sequence or region, e.g., that can be aligned and specifically assigned to a chromosome or genomic region or gene.

Next-generation sequencing methods include, for example, sequencing by synthesis technology (Illumina), pyrosequencing (454), ion semiconductor technology (Ion Torrent sequencing), single-molecule real-time sequencing and sequencing by ligation (SOLD sequencing). Depending on the sequencing methods, the length of each read may vary from about 30 bp to more than 10,000 bp. For example, the DNA sequencing method using SOLID sequencer generates nucleic acid reads of about 50 bp. For another example, Ion Torrent Sequencing generates nucleic acid reads of up to 400 bp and 454 pyrosequencing generates nucleic acid reads of about 700 bp. For yet another example, single-molecule real-time sequencing methods may generate reads of 10,000 bp to 15,000 bp. Therefore, in certain implementations, the nucleic acid sequence reads have a length of 30-100 bp, 50-200 bp, or 50-400 bp.

The terms "sample read", "sample sequence" or "sample fragment" refer to sequence data for a genomic sequence of interest from a sample. For example, the sample read comprises sequence data from a PCR amplicon having a forward and reverse primer sequence. The sequence data can be obtained from any select sequence methodology. The sample read can be, for example, from a sequencing-by-synthesis (SBS) reaction, a sequencing-by-ligation reaction, or any other suitable sequencing methodology for which it is desired to determine the length and/or identity of a repetitive element. The sample read can be a consensus (e.g., averaged or weighted) sequence derived from multiple sample reads. In certain implementations, providing a reference sequence comprises identifying a locus-of-interest based upon the primer sequence of the PCR amplicon.

The term "raw fragment" refers to sequence data for a portion of a genomic sequence of interest that at least partially overlaps a designated position or secondary position of interest within a sample read or sample fragment. Non-limiting examples of raw fragments include a duplex stitched fragment, a simplex stitched fragment, a duplex un-stitched fragment and a simplex un-stitched fragment. The term "raw" is used to indicate that the raw fragment includes sequence data having some relation to the sequence data in a sample read, regardless of whether the raw fragment exhibits a supporting variant that corresponds to and authenticates or confirms a potential variant in a sample read. The term "raw fragment" does not indicate that the fragment necessarily includes a supporting variant that validates a variant call in a sample read. For example, when a sample read is determined by a variant call application to exhibit a first variant, the variant call application may determine that one or more raw fragments lack a corresponding type of "supporting" variant that may otherwise be expected to occur given the variant in the sample read.

The terms "mapping", "aligned," "alignment," or "aligning" refer to the process of comparing a read or tag to a reference sequence and thereby determining whether the reference sequence contains the read sequence. If the reference sequence contains the read, the read may be mapped to the reference sequence or, in certain implementations, to a particular location in the reference sequence. In some cases, alignment simply tells whether or not a read is a member of a particular reference sequence (i.e., whether the read is present or absent in the reference sequence). For example, the alignment of a read to the reference sequence for human chromosome 13 will tell whether the read is present in the reference sequence for chromosome 13. A tool that provides this information may be called a set membership tester. In some cases, an alignment additionally indicates a location in the reference sequence where the read or tag maps to. For example, if the reference sequence is the whole human genome sequence, an alignment may indicate that a read is present on chromosome 13, and may further indicate that the read is on a particular strand and/or site of chromosome 13.

The term "indel" refers to the insertion and/or the deletion of bases in the DNA of an organism. A micro-indel represents an indel that results in a net change of 1 to 50 nucleotides. In coding regions of the genome, unless the length of an indel is a multiple of 3, it will produce a frameshift mutation. Indels can be contrasted with point mutations. An indel inserts and deletes nucleotides from a sequence, while a point mutation is a form of substitution that replaces one of the nucleotides without changing the overall number in the DNA. Indels can also be contrasted with a Tandem Base Mutation (TBM), which may be defined as substitution at adjacent nucleotides (primarily substitutions at two adjacent nucleotides, but substitutions at three adjacent nucleotides have been observed.

The term "variant" refers to a nucleic acid sequence that is different from a nucleic acid reference. Typical nucleic acid sequence variant includes without limitation single nucleotide polymorphism (SNP), short deletion and insertion polymorphisms (Indel), copy number variation (CNV), microsatellite markers or short tandem repeats and structural variation. Somatic variant calling is the effort to identify variants present at low frequency in the DNA sample. Somatic variant calling is of interest in the context of cancer treatment. Cancer is caused by an accumulation of mutations in DNA. A DNA sample from a tumor is generally heterogeneous, including some normal cells, some cells at an early stage of cancer progression (with fewer mutations), and some late-stage cells (with more mutations). Because of this heterogeneity, when sequencing a tumor (e.g., from an FFPE sample), somatic mutations will often appear at a low frequency. For example, a SNV might be seen in only 10% of the reads covering a given base. A variant that is to be classified as somatic or germline by the variant classifier is also referred to herein as the "variant under test".

The term "noise" refers to a mistaken variant call resulting from one or more errors in the sequencing process and/or in the variant call application.

The term "variant frequency" represents the relative frequency of an allele (variant of a gene) at a particular locus in a population, expressed as a fraction or percentage. For example, the fraction or percentage may be the fraction of all chromosomes in the population that carry that allele. By way of example, sample variant frequency represents the relative frequency of an allele/variant at a particular locus/position along a genomic sequence of interest over a "population" corresponding to the number of reads and/or samples obtained for the genomic sequence of interest from an individual. As another example, a baseline variant frequency represents the relative frequency of an allele/variant at a particular locus/position along one or more baseline genomic sequences where the "population" corresponding to the number of reads and/or samples obtained for the one or more baseline genomic sequences from a population of normal individuals.

The term "variant allele frequency (VAF)" refers to the percentage of sequenced reads observed matching the variant divided by the overall coverage at the target position. VAF is a measure of the proportion of sequenced reads carrying the variant.

The terms "position", "designated position", and "locus" refer to a location or coordinate of one or more nucleotides within a sequence of nucleotides. The terms "position", "designated position", and "locus" also refer to a location or coordinate of one or more base pairs in a sequence of nucleotides.

The term "haplotype" refers to a combination of alleles at adjacent sites on a chromosome that are inherited together. A haplotype may be one locus, several loci, or an entire chromosome depending on the number of recombination events that have occurred between a given set of loci, if any occurred.

The term "threshold" herein refers to a numeric or non-numeric value that is used as a cutoff to characterize a sample, a nucleic acid, or portion thereof (e.g., a read). A threshold may be varied based upon empirical analysis. The threshold may be compared to a measured or calculated value to determine whether the source giving rise to such value suggests should be classified in a particular manner. Threshold values can be identified empirically or analytically. The choice of a threshold is dependent on the level of confidence that the user wishes to have to make the classification. The threshold may be chosen for a particular purpose (e.g., to balance sensitivity and selectivity). As used herein, the term "threshold" indicates a point at which a course of analysis may be changed and/or a point at which an action may be triggered. A threshold is not required to be a predetermined number. Instead, the threshold may be, for instance, a function that is based on a plurality of factors. The threshold may be adaptive to the circumstances. Moreover, a threshold may indicate an upper limit, a lower limit, or a range between limits.

In some implementations, a metric or score that is based on sequencing data may be compared to the threshold. As used herein, the terms "metric" or "score" may include values or results that were determined from the sequencing data or may include functions that are based on the values or results that were determined from the sequencing data. Like a threshold, the metric or score may be adaptive to the circumstances. For instance, the metric or score may be a normalized value. As an example of a score or metric, one or more implementations may use count scores when analyzing the data. A count score may be based on number of sample reads. The sample reads may have undergone one or more filtering stages such that the sample reads have at least one common characteristic or quality. For example, each of the sample reads that are used to determine a count score may have been aligned with a reference sequence or may be assigned as a potential allele. The number of sample reads having a common characteristic may be counted to determine a read count. Count scores may be based on the read count. In some implementations, the count score may be a value that is equal to the read count. In other implementations, the count score may be based on the read count and other information. For example, a count score may be based on the read count for a particular allele of a genetic locus and a total number of reads for the genetic locus. In some implementations, the count score may be based on the read count and previously-obtained data for the genetic locus. In some implementations, the count scores may be normalized scores between predetermined values. The count score may also be a function of read counts from other loci of a sample or a function of read counts from other samples that were concurrently run with the sample-of-interest. For instance, the count score may be a function of the read count of a particular allele and the read counts of other loci in the sample and/or the read counts from other samples. As one example, the read counts from other loci and/or the read counts from other samples may be used to normalize the count score for the particular allele.

The terms "coverage" or "fragment coverage" refer to a count or other measure of a number of sample reads for the same fragment of a sequence. A read count may represent a count of the number of reads that cover a corresponding fragment. Alternatively, the coverage may be determined by multiplying the read count by a designated factor that is based on historical knowledge, knowledge of the sample, knowledge of the locus, etc.

The term "read depth" (conventionally a number followed by "x") refers to the number of sequenced reads with overlapping alignment at the target position. This is often expressed as an average or percentage exceeding a cutoff over a set of intervals (such as exons, genes, or panels). For example, a clinical report might say that a panel average coverage is 1,105x with 98% of targeted bases covered >100x.

The terms "base call quality score" or "Q score" refer to a PHRED-scaled probability ranging from 0-50 inversely proportional to the probability that a single sequenced base is correct. For example, a T base call with Q of 20 is considered likely correct with a probability of 99.99%. Any base call with Q<20 should be considered low quality, and any variant identified where a substantial proportion of sequenced reads supporting the variant are of low quality should be considered potentially false positive.

The terms "variant reads" or "variant read number" refer to the number of sequenced reads supporting the presence of the variant.

Regarding "strandedness" (or DNA strandedness), the genetic message in DNA can be represented as a string of the letters A, G, C, and T. For example, 5'-AGGACA-3'. Often, the sequence is written in the direction shown here, i.e., with the 5' end to the left and the 3' end to the right. DNA may sometimes occur as single-stranded molecule (as in certain viruses), but normally we find DNA as a double-stranded unit. It has a double helical structure with two antiparallel strands. In this case, the word "antiparallel" means that the two strands run in parallel, but have opposite polarity. The double-stranded DNA is held together by pairing between bases and the pairing is always such that adenine (A) pairs with thymine (T) and cytosine (C) pairs with guanine (G). This pairing is referred to as complementarity, and one strand of DNA is said to be the complement of the other. The double-stranded DNA may thus be represented as two strings, like this: 5'-AGGACA-3' and 3'-TCCTGT-5'. Note that the two strands have opposite polarity. Accordingly, the strandedness of the two DNA strands can be referred to as the reference strand and its complement, forward and reverse strands, top and bottom strands, sense and antisense strands, or Watson and Crick strands.

The reads alignment (also called reads mapping) is the process of figuring out where in the genome a sequence is from. Once the alignment is performed, the "mapping quality" or the "mapping quality score (MAPQ)" of a given read quantifies the probability that its position on the genome is correct. The mapping quality is encoded in the phred scale where P is the probability that the alignment is not correct. The probability is calculated as: $P=10^{(-MAPQ/10)}$, where MAPQ is the mapping quality. For example, a mapping quality of 40=10 to the power of −4, meaning that there is a 0.01% chance that the read was aligned incorrectly. The mapping quality is therefore associated with several alignment factors, such as the base quality of the read, the complexity of the reference genome, and the paired-end information. Regarding the first, if the base quality of the read is low, it means that the observed sequence might be wrong and thus its alignment is wrong. Regarding the second, the mappability refers to the complexity of the genome. Repeated regions are more difficult to map and reads falling in these regions usually get low mapping quality. In this context, the MAPQ reflects the fact that the reads are not uniquely aligned and that their real origin cannot be determined. Regarding the third, in case of paired-end sequencing data, concordant pairs are more likely to be well aligned. The higher is the mapping quality, the better is the alignment. A read aligned with a good mapping quality usually means that the read sequence was good and was aligned with few mismatches in a high mappability region. The MAPQ value can be used as a quality control of the alignment results. The proportion of reads aligned with an MAPQ higher than 20 is usually for downstream analysis.

As used herein, a "signal" refers to a detectable event such as an emission, preferably light emission, for example, in an image. Thus, in preferred implementations, a signal can represent any detectable light emission that is captured in an image (i.e., a "spot"). Thus, as used herein, "signal" can refer to both an actual emission from an analyte of the specimen, and can refer to a spurious emission that does not correlate to an actual analyte. Thus, a signal could arise from noise and could be later discarded as not representative of an actual analyte of a specimen.

As used herein, the term "clump" refers to a group of signals. In particular implementations, the signals are derived from different analytes. In a preferred implementation, a signal clump is a group of signals that cluster together. In a more preferred implementation, a signal clump represents a physical region covered by one amplified oligonucleotide. Each signal clump should be ideally observed as several signals (one per template cycle, and possibly more due to cross-talk). Accordingly, duplicate signals are detected where two (or more) signals are included in a template from the same clump of signals.

As used herein, terms such as "minimum," "maximum," "minimize," "maximize" and grammatical variants thereof can include values that are not the absolute maxima or minima. In some implementations, the values include near maximum and near minimum values. In other implementations, the values can include local maximum and/or local minimum values. In some implementations, the values include only absolute maximum or minimum values.

As used herein, "cross-talk" refers to the detection of signals in one image that are also detected in a separate image. In a preferred implementation, cross-talk can occur when an emitted signal is detected in two separate detection channels. For example, where an emitted signal occurs in one color, the emission spectrum of that signal may overlap with another emitted signal in another color. In a preferred implementation, fluorescent molecules used to indicate the presence of nucleotide bases A, C, G and T are detected in separate channels. However, because the emission spectra of A and C overlap, some of the C color signal may be detected during detection using the A color channel. Accordingly, cross-talk between the A and C signals allows signals from one color image to appear in the other color image. In some implementations, G and T cross-talk. In some implementations, the amount of cross-talk between channels is asymmetric. It will be appreciated that the amount of cross-talk between channels can be controlled by, among other things, the selection of signal molecules having an appropriate emission spectrum as well as selection of the size and wavelength range of the detection channel.

As used herein, "register", "registering", "registration" and like terms refer to any process to correlate signals in an image or data set from a first time point or perspective with signals in an image or data set from another time point or perspective. For example, registration can be used to align signals from a set of images to form a template. In another example, registration can be used to align signals from other images to a template. One signal may be directly or indirectly registered to another signal. For example, a signal from image "S" may be registered to image "G" directly. As another example, a signal from image "N" may be directly registered to image "G", or alternatively, the signal from image "N" may be registered to image "S", which has previously been registered to image "G". Thus, the signal from image "N" is indirectly registered to image "G".

As used herein, the term "fiducial" is intended to mean a distinguishable point of reference in or on an object. The point of reference can be, for example, a mark, second object, shape, edge, area, irregularity, channel, pit, post or the like. The point of reference can be present in an image of the object or in another data set derived from detecting the object. The point of reference can be specified by an x and/or y coordinate in a plane of the object. Alternatively or additionally, the point of reference can be specified by a z coordinate that is orthogonal to the xy plane, for example, being defined by the relative locations of the object and a detector. One or more coordinates for a point of reference can be specified relative to one or more other analytes of an object or of an image or other data set derived from the object.

As used herein, the term "optical signal" is intended to include, for example, fluorescent, luminescent, scatter, or absorption signals. Optical signals can be detected in the ultraviolet (UV) range (about 200 to 390 inn), visible (VIS) range (about 391 to 770 nm), infrared (IR) range (about 0.771 to 25 microns), or other range of the electromagnetic spectrum. Optical signals can be detected in a way that excludes all or part of one or more of these ranges.

As used herein, the term "signal level" is intended to mean an amount or quantity of detected energy or coded information that has a desired or predefined characteristic. For example, an optical signal can be quantified by one or more of intensity, wavelength, energy, frequency, power, luminance or the like. Other signals can be quantified according to characteristics such as voltage, current, electric field strength, magnetic field strength, frequency, power, temperature, etc. Absence of signal is understood to be a signal level of zero or a signal level that is not meaningfully distinguished from noise.

As used herein, the term "simulate" is intended to mean creating a representation or model of a physical thing or action that predicts characteristics of the thing or action. The representation or model can in many cases be distinguishable from the thing or action. For example, the representation or model can be distinguishable from a thing with respect to one or more characteristic such as color, intensity of signals detected from all or part of the thing, size, or shape. In particular implementations, the representation or model can be idealized, exaggerated, muted, or incomplete when compared to the thing or action. Thus, in some implementations, a representation of model can be distinguishable from the thing or action that it represents, for example, with respect to at least one of the characteristics set forth above. The representation or model can be provided in a computer readable format or medium such as one or more of those set forth elsewhere herein.

As used herein, the term "specific signal" is intended to mean detected energy or coded information that is selectively observed over other energy or information such as background energy or information. For example, a specific signal can be an optical signal detected at a particular intensity, wavelength or color; an electrical signal detected at a particular frequency, power or field strength; or other signals known in the art pertaining to spectroscopy and analytical detection.

As used herein, the term "swath" is intended to mean a rectangular portion of an object. The swath can be an elongated strip that is scanned by relative movement between the object and a detector in a direction that is parallel to the longest dimension of the strip. Generally, the width of the rectangular portion or strip will be constant along its full length. Multiple swaths of an object can be parallel to each other. Multiple swaths of an object can be adjacent to each other, overlapping with each other, abutting each other, or separated from each other by an interstitial area.

As used herein, the term "variance" is intended to mean a difference between that which is expected and that which is observed or a difference between two or more observations. For example, variance can be the discrepancy between an expected value and a measured value. Variance can be represented using statistical functions such as standard deviation, the square of standard deviation, coefficient of variation or the like.

As used herein, the term "xy coordinates" is intended to mean information that specifies location, size, shape, and/or orientation in an xy plane. The information can be, for example, numerical coordinates in a Cartesian system. The coordinates can be provided relative to one or both of the x and y axes or can be provided relative to another location in the xy plane. For example, coordinates of an analyte of an object can specify the location of the analyte relative to location of a fiducial or other analyte of the object.

As used herein, the term "xy plane" is intended to mean a 2 dimensional area defined by straight line axes x and y. When used in reference to a detector and an object observed by the detector, the area can be further specified as being orthogonal to the direction of observation between the detector and object being detected.

As used herein, the term "z coordinate" is intended to mean information that specifies the location of a point, line or area along an axes that is orthogonal to an xy plane. In particular implementations, the z axis is orthogonal to an area of an object that is observed by a detector. For example, the direction of focus for an optical system may be specified along the z axis.

In some implementations, acquired signal data is transformed using an affine transformation. In some such implementations, template generation makes use of the fact that the affine transforms between color channels are consistent between runs. Because of this consistency, a set of default offsets can be used when determining the coordinates of the analytes in a specimen. For example, a default offsets file can contain the relative transformation (shift, scale, skew) for the different channels relative to one channel, such as the A channel. In other implementations, however, the offsets between color channels drift during a run and/or between runs, making offset-driven template generation difficult. In such implementations, the methods and systems provided herein can utilize offset-less template generation, which is described further below.

In some implementations of the above implementations, the system can comprise a flow cell. In some implementations, the flow cell comprises lanes, or other configurations, of tiles, wherein at least some of the tiles comprise one or more arrays of analytes. In some implementations, the analytes comprise a plurality of molecules such as nucleic acids. In certain aspects, the flow cell is configured to deliver a labeled nucleotide base to an array of nucleic acids, thereby extending a primer hybridized to a nucleic acid within an analyte so as to produce a signal corresponding to an analyte comprising the nucleic acid. In preferred implementations, the nucleic acids within an analyte are identical or substantially identical to each other.

In some of the systems for image analysis described herein, each image in the set of images includes color signals, wherein a different color corresponds to a different nucleotide base. In some implementations, each image of the set of images comprises signals having a single color selected from at least four different colors. In some implementations, each image in the set of images comprises signals having a single color selected from four different colors. In some of the systems described herein, nucleic acids can be sequenced by providing four different labeled nucleotide bases to the array of molecules so as to produce four different images, each image comprising signals having a single color, wherein the signal color is different for each of the four different images, thereby producing a cycle of four color images that corresponds to the four possible nucleotides present at a particular position in the nucleic acid. In certain aspects, the system comprises a flow cell that is configured to deliver additional labeled nucleotide bases to the array of molecules, thereby producing a plurality of cycles of color images.

In preferred implementations, the methods provided herein can include determining whether a processor is actively acquiring data or whether the processor is in a low activity state. Acquiring and storing large numbers of high-quality images typically requires massive amounts of storage capacity. Additionally, once acquired and stored, the analysis of image data can become resource intensive and can interfere with processing capacity of other functions, such as ongoing acquisition and storage of additional image data. Accordingly, as used herein, the term low activity state refers to the processing capacity of a processor at a given time. In some implementations, a low activity state occurs when a processor is not acquiring and/or storing data. In some implementations, a low activity state occurs when some data acquisition and/or storage is taking place, but additional processing capacity remains such that image analysis can occur at the same time without interfering with other functions.

As used herein, "identifying a conflict" refers to identifying a situation where multiple processes compete for resources. In some such implementations, one process is given priority over another process. In some implementations, a conflict may relate to the need to give priority for allocation of time, processing capacity, storage capacity or any other resource for which priority is given. Thus, in some implementations, where processing time or capacity is to be distributed between two processes such as either analyzing a data set and acquiring and/or storing the data set, a conflict between the two processes exists and can be resolved by giving priority to one of the processes.

Also provided herein are systems for performing image analysis. The systems can include a processor; a storage capacity; and a program for image analysis, the program comprising instructions for processing a first data set for storage and the second data set for analysis, wherein the processing comprises acquiring and/or storing the first data set on the storage device and analyzing the second data set when the processor is not acquiring the first data set. In certain aspects, the program includes instructions for identifying at least one instance of a conflict between acquiring and/or storing the first data set and analyzing the second data set; and resolving the conflict in favor of acquiring and/or storing image data such that acquiring and/or storing the first data set is given priority. In certain aspects, the first data set comprises image files obtained from an optical imaging device. In certain aspects, the system further comprises an optical imaging device. In some implementations, the optical imaging device comprises a light source and a detection device.

As used herein, the term "program" refers to instructions or commands to perform a task or process. The term "program" can be used interchangeably with the term module. In certain implementations, a program can be a compilation of various instructions executed under the same set of commands. In other implementations, a program can refer to a discrete batch or file.

Set forth below are some of the surprising effects of utilizing the methods and systems for performing image analysis set forth herein. In some sequencing implementations, an important measure of a sequencing system's utility is its overall efficiency. For example, the amount of mappable data produced per day and the total cost of installing and running the instrument are important aspects of an economical sequencing solution. To reduce the time to generate mappable data and to increase the efficiency of the system, real-time base calling can be enabled on an instrument computer and can run in parallel with sequencing chemistry and imaging. This allows much of the data processing and analysis to be completed before the sequencing chemistry finishes. Additionally, it can reduce the storage required for intermediate data and limit the amount of data that needs to travel across the network.

While sequence output has increased, the data per run transferred from the systems provided herein to the network and to secondary analysis processing hardware has substantially decreased. By transforming data on the instrument computer (acquiring computer), network loads are dramatically reduced. Without these on-instrument, off-network data reduction techniques, the image output of a fleet of DNA sequencing instruments would cripple most networks.

The widespread adoption of the high-throughput DNA sequencing instruments has been driven in part by ease of use, support for a range of applications, and suitability for virtually any lab environment. The highly efficient algorithms presented herein allow significant analysis functionality to be added to a simple workstation that can control sequencing instruments. This reduction in the requirements for computational hardware has several practical benefits that will become even more important as sequencing output levels continue to increase. For example, by performing image analysis and base calling on a simple tower, heat production, laboratory footprint, and power consumption are kept to a minimum. In contrast, other commercial sequencing technologies have recently ramped up their computing infrastructure for primary analysis, with up to five times more processing power, leading to commensurate increases in heat output and power consumption. Thus, in some implementations, the computational efficiency of the methods and systems provided herein enables customers to increase their sequencing throughput while keeping server hardware expenses to a minimum.

Accordingly, in some implementations, the methods and/or systems presented herein act as a state machine, keeping track of the individual state of each specimen, and when it detects that a specimen is ready to advance to the next state, it does the appropriate processing and advances the specimen to that state. A more detailed example of how the state machine monitors a file system to determine when a specimen is ready to advance to the next state according to a preferred implementation is set forth in Example 1 below.

In preferred implementations, the methods and systems provided herein are multi-threaded and can work with a configurable number of threads. Thus, for example in the context of nucleic acid sequencing, the methods and systems provided herein are capable of working in the background during a live sequencing run for real-time analysis, or it can be run using a pre-existing set of image data for off-line analysis. In certain preferred implementations, the methods and systems handle multi-threading by giving each thread its own subset of specimen for which it is responsible. This minimizes the possibility of thread contention.

A method of the present disclosure can include a step of obtaining a target image of an object using a detection apparatus, wherein the image includes a repeating pattern of analytes on the object. Detection apparatus that are capable of high resolution imaging of surfaces are particularly useful. In particular implementations, the detection apparatus will have sufficient resolution to distinguish analytes at the densities, pitches, and/or analyte sizes set forth herein. Particularly useful are detection apparatus capable of obtaining images or image data from surfaces. Example detectors are those that are configured to maintain an object and detector in a static relationship while obtaining an area image. Scanning apparatus can also be used. For example, an apparatus that obtains sequential area images (e.g., so called 'step and shoot' detectors) can be used. Also useful are devices that continually scan a point or line over the surface of an object to accumulate data to construct an image of the surface. Point scanning detectors can be configured to scan a point (i.e., a small detection area) over the surface of an object via a raster motion in the x-y plane of the surface. Line scanning detectors can be configured to scan a line along the y dimension of the surface of an object, the longest dimension of the line occurring along the x dimension. It will be understood that the detection device, object or both can be moved to achieve scanning detection. Detection apparatus that are particularly useful, for example in nucleic acid sequencing applications, are described in US Pat App. Pub. Nos. 2012/0270305 A1; 2013/0023422 A1; and 2013/0260372 A1; and U.S. Pat. Nos. 5,528,050; 5,719,391; 8,158,926 and 8,241,573, each of which is incorporated herein by reference.

The implementations disclosed herein may be implemented as a method, apparatus, system, or article of manufacture using programming or engineering techniques to produce software, firmware, hardware, or any combination thereof. The term "article of manufacture" as used herein refers to code or logic implemented in hardware or computer readable media such as optical storage devices, and volatile or non-volatile memory devices. Such hardware may include, but is not limited to, field programmable gate arrays (FPGAs), coarse grained reconfigurable architectures (CGRAs), application-specific integrated circuits (ASICs), complex programmable logic devices (CPLDs), programmable logic arrays (PLAs), microprocessors, or other similar processing devices. In particular implementations, information or algorithms set forth herein are present in non-transient storage media.

In particular implementations, a computer implemented method set forth herein can occur in real time while multiple images of an object are being obtained. Such real time analysis is particularly useful for nucleic acid sequencing applications wherein an array of nucleic acids is subjected to repeated cycles of fluidic and detection steps. Analysis of the sequencing data can often be computationally intensive such that it can be beneficial to perform the methods set forth herein in real time or in the background while other data acquisition or analysis algorithms are in process. Example real time analysis methods that can be used with the present methods are those used for the MiSeq and HiSeq sequencing devices commercially available from Illumina, Inc. (San Diego, Calif.) and/or described in US Pat. App. Pub. No. 2012/0020537 A1, which is incorporated herein by reference.

An example data analysis system, formed by one or more programmed computers, with programming being stored on one or more machine readable media with code executed to carry out one or more steps of methods described herein. In one implementation, for example, the system includes an interface designed to permit networking of the system to one or more detection systems (e.g., optical imaging systems) that are configured to acquire data from target objects. The interface may receive and condition data, where appropriate. In particular implementations the detection system will output digital image data, for example, image data that is representative of individual picture elements or pixels that, together, form an image of an array or other object. A processor processes the received detection data in accordance with a one or more routines defined by processing code. The processing code may be stored in various types of memory circuitry.

In accordance with the presently contemplated implementations, the processing code executed on the detection data includes a data analysis routine designed to analyze the detection data to determine the locations and metadata of individual analytes visible or encoded in the data, as well as locations at which no analyte is detected (i.e., where there is no analyte, or where no meaningful signal was detected from an existing analyte). In particular implementations, analyte locations in an array will typically appear brighter than non-analyte locations due to the presence of fluorescing dyes attached to the imaged analytes. It will be understood that the analytes need not appear brighter than their surrounding area, for example, when a target for the probe at the analyte is not present in an array being detected. The color at which individual analytes appear may be a function of the dye employed as well as of the wavelength of the light used by the imaging system for imaging purposes. Analytes to which targets are not bound or that are otherwise devoid of a particular label can be identified according to other characteristics, such as their expected location in the microarray.

Once the data analysis routine has located individual analytes in the data, a value assignment may be carried out. In general, the value assignment will assign a digital value to each analyte based upon characteristics of the data represented by detector components (e.g., pixels) at the corresponding location. That is, for example when imaging data is processed, the value assignment routine may be designed to recognize that a specific color or wavelength of light was detected at a specific location, as indicated by a group or cluster of pixels at the location. In a typical DNA imaging application, for example, the four common nucleotides will be represented by four separate and distinguishable colors. Each color, then, may be assigned a value corresponding to that nucleotide.

As used herein, the terms "module", "system," or "system controller" may include a hardware and/or software system and circuitry that operates to perform one or more functions. For example, a module, system, or system controller may include a computer processor, controller, or other logic-based device that performs operations based on instructions stored on a tangible and non-transitory computer readable storage medium, such as a computer memory. Alternatively, a module, system, or system controller may include a hard-wired device that performs operations based on hard-wired logic and circuitry. The module, system, or system controller shown in the attached figures may represent the hardware and circuitry that operates based on software or hardwired instructions, the software that directs hardware to perform the operations, or a combination thereof. The module, system, or system controller can include or represent hardware circuits or circuitry that include and/or are connected with one or more processors, such as one or computer microprocessors.

As used herein, the terms "software" and "firmware" are interchangeable and include any computer program stored in memory for execution by a computer, including RAM memory, ROM memory, EPROM memory, EEPROM memory, and non-volatile RAM (NVRAM) memory. The above memory types are examples only and are thus not limiting as to the types of memory usable for storage of a computer program.

In the molecular biology field, one of the processes for nucleic acid sequencing in use is sequencing-by-synthesis. The technique can be applied to massively parallel sequencing projects. For example, by using an automated platform, it is possible to carry out hundreds of thousands of sequencing reactions simultaneously. Thus, one of the implementations of the present invention relates to instruments and methods for acquiring, storing, and analyzing image data generated during nucleic acid sequencing.

Enormous gains in the amount of data that can be acquired and stored make streamlined image analysis methods even more beneficial. For example, the image analysis methods described herein permit both designers and end users to make efficient use of existing computer hardware. Accordingly, presented herein are methods and systems which reduce the computational burden of processing data in the face of rapidly increasing data output. For example, in the field of DNA sequencing, yields have scaled 15-fold over the course of a recent year and can now reach hundreds of gigabases in a single run of a DNA sequencing device. If computational infrastructure requirements grew proportionately, large genome-scale experiments would remain out of reach to most researchers. Thus, the generation of more raw sequence data will increase the need for secondary analysis and data storage, making optimization of data transport and storage extremely valuable. Some implementations of the methods and systems presented herein can reduce the time, hardware, networking, and laboratory infrastructure requirements needed to produce usable sequence data.

The present disclosure describes various methods and systems for carrying out the methods. Examples of some of the methods are described as a series of steps. However, it should be understood that implementations are not limited to the particular steps and/or order of steps described herein. Steps may be omitted, steps may be modified, and/or other steps may be added. Moreover, steps described herein may be combined, steps may be performed simultaneously, steps may be performed concurrently, steps may be split into multiple sub-steps, steps may be performed in a different order, or steps (or a series of steps) may be re-performed in an iterative fashion. In addition, although different methods are set forth herein, it should be understood that the different methods (or steps of the different methods) may be combined in other implementations.

In some implementations, a processing unit, processor, module, or computing system that is "configured to" perform a task or operation may be understood as being particularly structured to perform the task or operation (e.g., having one or more programs or instructions stored thereon or used in conjunction therewith tailored or intended to perform the task or operation, and/or having an arrangement of processing circuitry tailored or intended to perform the task or operation). For the purposes of clarity and the avoidance of doubt, a general purpose computer (which may become "configured to" perform the task or operation if appropriately programmed) is not "configured to" perform a task or operation unless or until specifically programmed or structurally modified to perform the task or operation.

Moreover, the operations of the methods described herein can be sufficiently complex such that the operations cannot be mentally performed by an average human being or a person of ordinary skill in the art within a commercially reasonable time period. For example, the methods may rely on relatively complex computations such that such a person cannot complete the methods within a commercially reasonable time.

Throughout this application various publications, patents or patent applications have been referenced. The disclosures of these publications in their entireties are hereby incorporated by reference in this application in order to more fully describe the state of the art to which this invention pertains.

The term "comprising" is intended herein to be open-ended, including not only the recited elements, but further encompassing any additional elements.

As used herein, the term "each", when used in reference to a collection of items, is intended to identify an individual item in the collection but does not necessarily refer to every item in the collection. Exceptions can occur if explicit disclosure or context clearly dictates otherwise.

Although the invention has been described with reference to the examples provided above, it should be understood that various modifications can be made without departing from the invention.

The modules in this application can be implemented in hardware or software and need not be divided up in precisely the same blocks as shown in the figures. Some can also be implemented on different processors or computers or spread among a number of different processors or computers. In addition, it will be appreciated that some of the modules can be combined, operated in parallel or in a different sequence than that shown in the figures without affecting the functions achieved. Also as used herein, the term "module" can include "sub-modules", which themselves can be considered herein to constitute modules. The blocks in the figures designated as modules can also be thought of as flowchart steps in a method.

As used herein, the "identification" of an item of information does not necessarily require the direct specification of that item of information. Information can be "identified" in a field by simply referring to the actual information through one or more layers of indirection, or by identifying one or more items of different information which are together sufficient to determine the actual item of information. In addition, the term "specify" is used herein to mean the same as "identify".

As used herein, a given signal, event or value is "in dependence upon" a predecessor signal, event or value of the predecessor signal, event or value influenced by the given signal, event, or value. If there is an intervening processing element, step or time period, the given signal, event, or value can still be "in dependence upon" the predecessor signal, event, or value. If the intervening processing element or step combines more than one signal, event or value, the signal output of the processing element or step is considered "in dependence upon" each of the signal, event, or value inputs. If the given signal, event, or value is the same as the predecessor signal, event, or value, this is merely a degenerate case in which the given signal, event or value is still considered to be "in dependence upon" or "dependent on" or "based on" the predecessor signal, event, or value. "Responsiveness" of a given signal, event or value upon another signal, event or value is defined similarly.

As used herein, "concurrently" or "in parallel" does not require exact simultaneity. It is sufficient if the evaluation of one of the individuals begins before the evaluation of another of the individuals completes.

This application refers to "sequencing images," "cluster images" and "cluster intensity images" interchangeably.
Other Implementations In one implementation, for the current sequencing cycle, the state data can be redundantly provided as input to the base caller 144 using residual connections and/or skip connections, for example, to intermediate layers of the neural network-based base caller 2900. In some implementations, the residual connections and/or skip connections provide the state data as input in addition to the state data being provided as input to a first layer of the neural network-based base caller 2900.

In one implementation, for the current sequencing cycle, the state data can be determined from a subset of previous sequencing cycles, as opposed to all the previous sequencing cycles.

In one implementation, for the current sequencing cycle, multiple instances of the state data can be determined such that each instance is determined from a different subset of the previous sequencing cycles.

In one implementation, for the current sequencing cycle, multiple copies of the state data can be provided as input to the base caller 144, for example, as multiple input channels.

Figure 45:
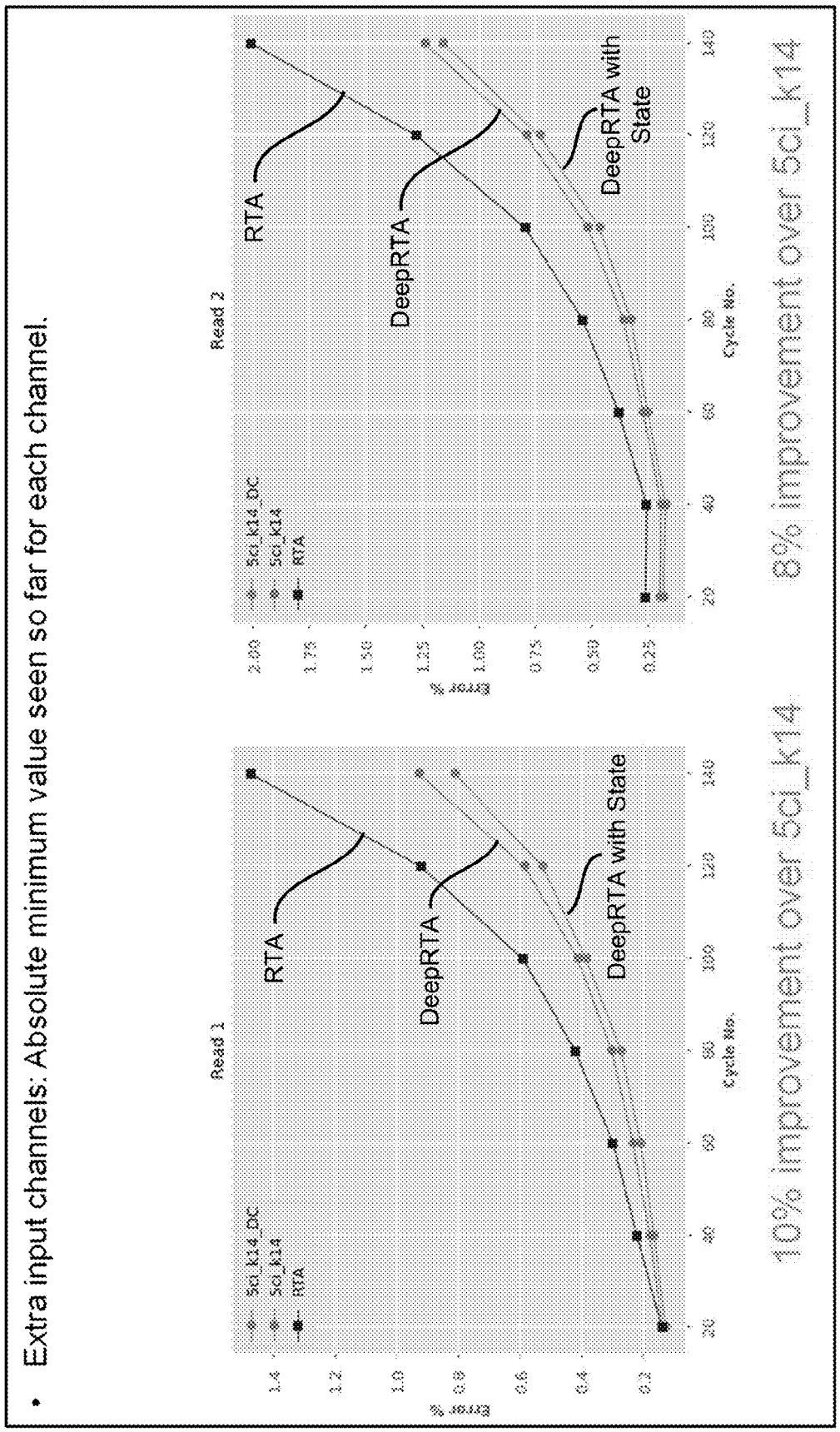
FIG. 45 compares base calling performance of a non-neural network-based base caller RTA, a neural network-based base caller DeepRTA (5ci_k14) without state information, and the disclosed state-based and neural network-based base caller DeepRTA with State (5ci_k14_DC) that uses per-pixel MIN state information as additional/supplemental input.

In some implementations, the state information can be provided as input to the temporal layers.
Performance Results as Objective Indicia of Inventiveness and Non-Obviousness FIG. 45 compares base calling performance of a non-neural network-based base caller RTA, a neural network-based base caller DeepRTA (5ci_k14) without state information, and the disclosed state-based and neural network-based base caller DeepRTA with State (5ci_k14_DC) that uses per-pixel MIN state information as additional/supplemental input. In FIG. 45, the x-axis denotes the progression of sequencing cycles of a sequencing run, and the y-axis denotes the base calling error rate. Also, FIG. 45 has two charts for sequencing of a first read (Read 1) and sequencing of a second read (Read 2).

As demonstrated, DeepRTA with State's base call accuracy exhibits 10% improvement over DeepRTA without state information in Read 1, and 8% improvement in Read 2. DeepRTA with State also significantly outperforms RTA.

Figure 46:
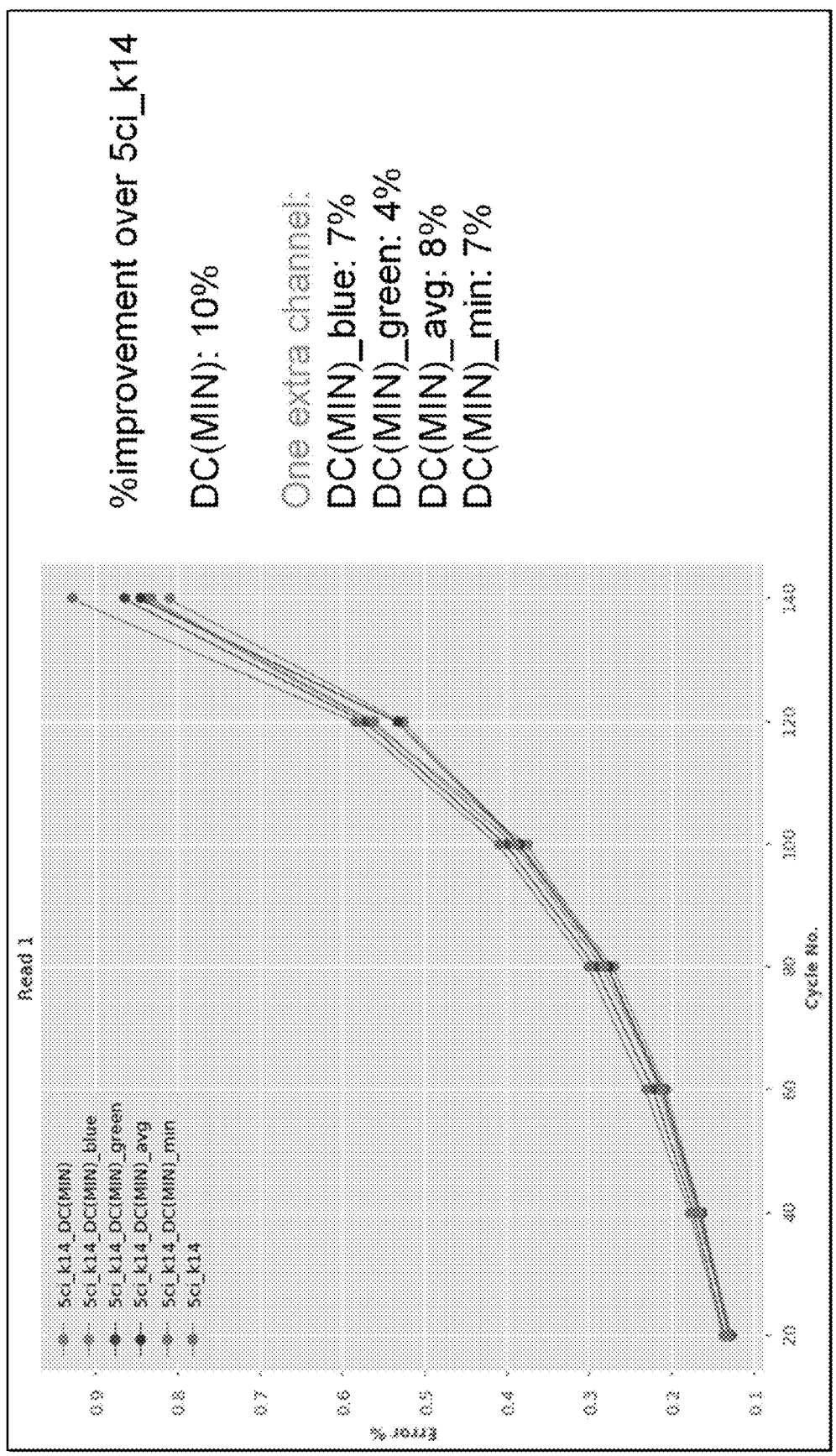
FIG. 46 compares base calling performance of the disclosed state-based and neural network-based base caller DeepRTA with State (5ci_k14_DC) across different state channels.

FIG. 46 compares base calling performance of the disclosed state-based and neural network-based base caller DeepRTA with State (5ci_k14_DC) across different state channels. In FIG. 46, the different state channels are DC(MIN) blue, DC(MIN)_green, DC(MIN)_avg, DC(MIN)_min, and DC(MIN). The DC(MIN) blue state channel is a single channel that includes per-pixel MIN state values only for the blue channel. The DC(MIN)_green state channel is a single channel that includes per-pixel MIN state values only for the green channel. The DC(MIN)_avg state channel is a single channel that includes per-pixel and pan-channel AVG state values determined as an average of the MIN state values of the blue and green channels. The DC(MIN)_min state channel is a single channel that includes per-pixel and pan-channel MIN state values selected from the MIN state values of the blue and green channels. The DC(MIN) state channels are two channels-one that includes per-pixel and per-channel MIN state values for the blue channel and another that includes per-pixel and per-channel MIN state values for the green channel.

With the DC(MIN) state channels as supplemental input, DeepRTA with State's base call accuracy exhibits 10% improvement over DeepRTA in Read 1. With the DC(MIN)_blue state channel as supplemental input, DeepRTA with State's base call accuracy exhibits 7% improvement over DeepRTA in Read 1. With the DC(MIN)_green state channel as supplemental input, DeepRTA with State's base call accuracy exhibits 4% improvement over DeepRTA in Read 1. With the DC(MIN)_avg state channel as supplemental input, DeepRTA with State's base call accuracy exhibits 8% improvement over DeepRTA in Read 1. With the DC(MIN)_min state channel as supplemental input, DeepRTA with State's base call accuracy exhibits 7% improvement over DeepRTA in Read 1.

Figure 47:
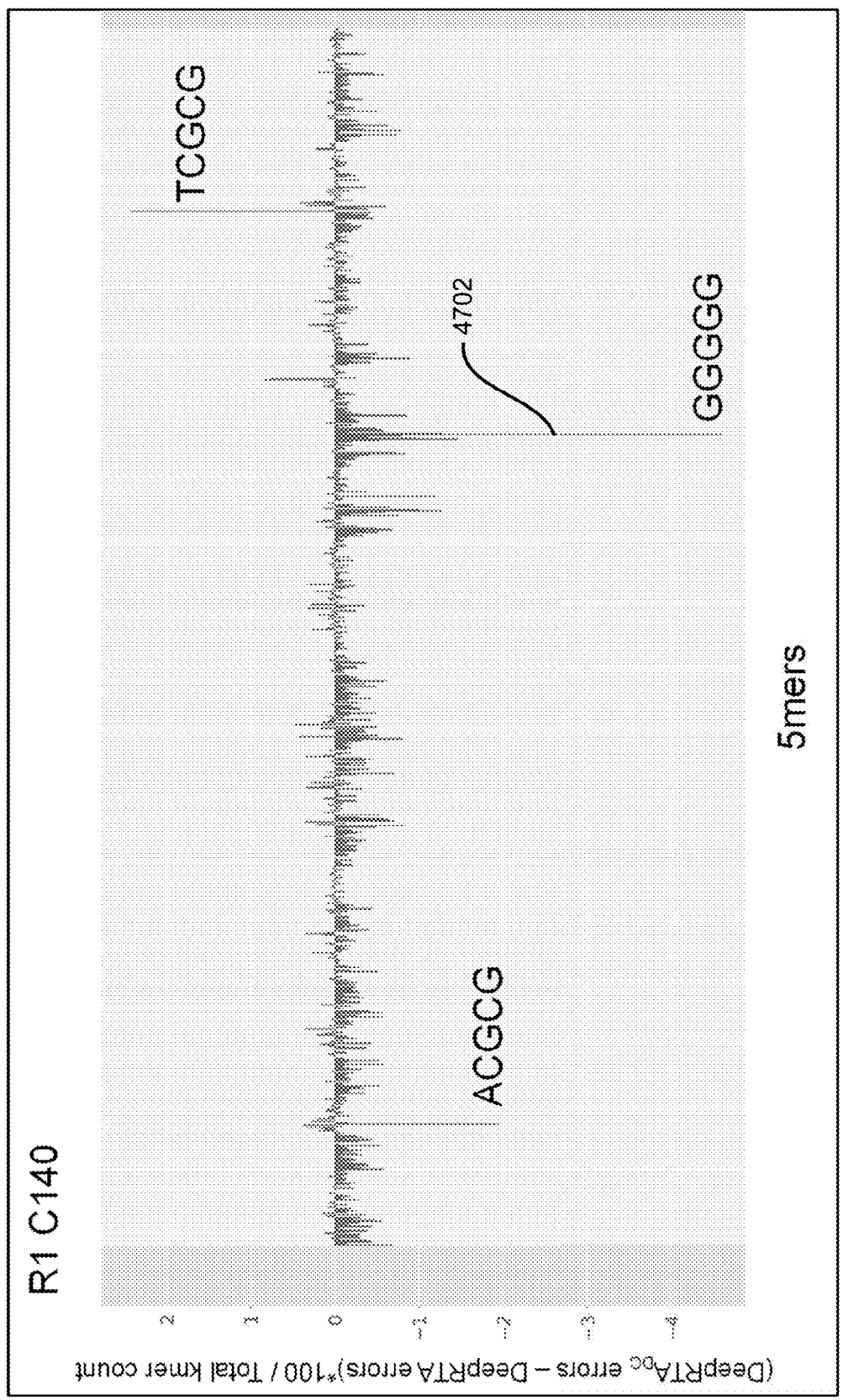
FIG. 47 illustrates base calling performance of the disclosed state-based and neural network-based base caller DeepRTA with State (DC) on k-mers, specifically 5mers. 5mers refers to repetitive base patterns for five base positions (e.g., ACGCG, GGGGG, TCGCG).

FIG. 47 illustrates base calling performance of the disclosed state-based and neural network-based base caller DeepRTA with State (DC) on k-mers, specifically 5mers. 5mers refers to repetitive base patterns for five base positions (e.g., ACGCG, GGGGG, TCGCG). In FIG. 47, the x-axis denotes all 1024 combinations of the 5mers, and the y-axis denotes base calling performance of the disclosed state-based and neural network-based base caller DeepRTA with State (DC).

In particular, the y-axis compares the base calling errors of the disclosed state-based and neural network-based base caller DeepRTA with State (DC) against the base calling errors of the DeepRTA without state information, such that the smaller the base calling errors of the disclosed state-based and neural network-based base caller DeepRTA with State (DC), the larger the negative values along the y-axis. As shown, the highly error-prone k-mer of Gs (due to lack of active states (i.e., only dark states of Gs)) experiences a small base calling error rate 4702 with the disclosed state-based and neural network-based base caller DeepRTA with State (DC).

Figure 48:
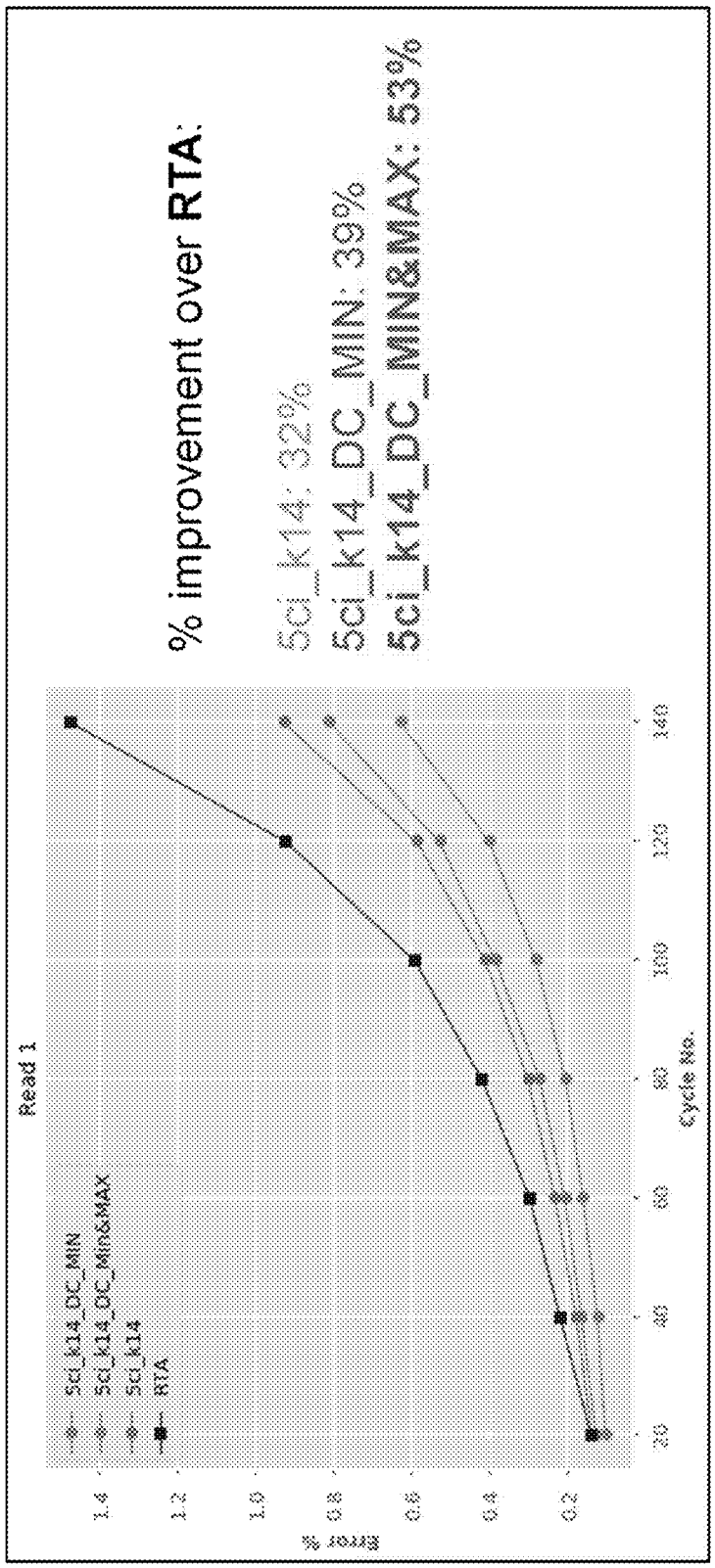
FIG. 48 compares base calling performance of a non-neural network-based base caller RTA, a neural network-based base caller DeepRTA without state information (5ci_k14), the disclosed state-based and neural network-based base caller DeepRTA with State (5ci_k14_DC_MIN) that uses per-pixel MIN state information as additional/supplemental input, and the disclosed state-based and neural network-based base caller DeepRTA with State (5ci_k14_DC_MIN_MAX) that uses per-pixel MIN and MAX state information as additional/supplemental input.

FIG. 48 compares base calling performance of a non-neural network-based base caller RTA, a neural network-based base caller DeepRTA without state information (5ci_k14), the disclosed state-based and neural network-based base caller DeepRTA with State (5ci_k14_DC_MIN) that uses per-pixel MIN state information as additional/supplemental input, and the disclosed state-based and neural network-based base caller DeepRTA with State (5ci_k14_DC_MIN_MAX) that uses per-pixel MIN and MAX state information as additional/supplemental input.

FIG. 48 shows that the DeepRTA without state information (5ci_k14) demonstrates 32% improvement over the RTA, the disclosed state-based and neural network-based base caller DeepRTA with State (5ci_k14_DC_MIN) that uses per-pixel MIN state information as additional/supplemental input demonstrates 39% improvement over the RTA, and the disclosed state-based and neural network-based base caller DeepRTA with State (5ci_k14_DC_MIN_MAX) that uses per-pixel MIN and MAX state information as additional/supplemental input demonstrates 53% improvement over the RTA.

Figure 49:
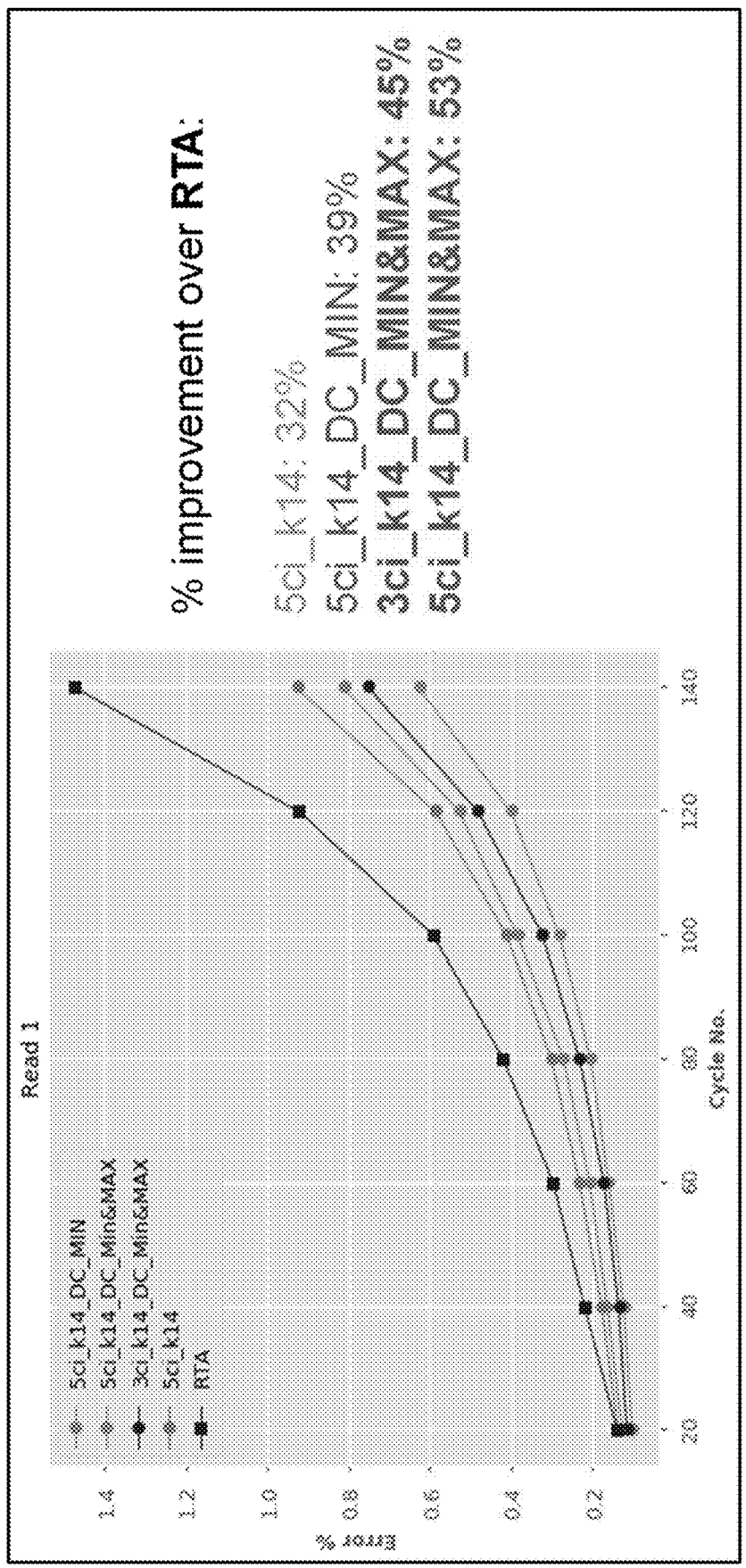
FIG. 49 compares base calling performance of a non-neural network-based base caller RTA, the neural network-based base caller DeepRTA without state information and 5-cycle flanking input window (5ci_k14), the disclosed state-based and neural network-based base caller DeepRTA with State (5ci_k14_DC_MIN) that uses per-pixel MIN state information as additional/supplemental input along with 5-cycle flanking input window, the disclosed state-based and neural network-based base caller DeepRTA with State (3ci_k14_DC_MIN_MAX) that uses per-pixel MIN and MAX state information as additional/supplemental input along with 3-cycle flanking input window, and the disclosed state-based and neural network-based base caller DeepRTA with State (5ci_k14_DC_MIN_MAX) that uses per-pixel MIN and MAX state information as additional/supplemental input along with 5-cycle flanking input window.

FIG. 49 compares base calling performance of a non-neural network-based base caller RTA, the neural network-based base caller DeepRTA without state information and 5-cycle flanking input window (5ci_k14), the disclosed state-based and neural network-based base caller DeepRTA with State (5ci_k14_DC_MIN) that uses per-pixel MIN state information as additional/supplemental input along with 5-cycle flanking input window, the disclosed state-based and neural network-based base caller DeepRTA with State (3ci_k14_DC_MIN_MAX) that uses per-pixel MIN and MAX state information as additional/supplemental input along with 3-cycle flanking input window, and the disclosed state-based and neural network-based base caller DeepRTA with State (5ci_k14_DC_MIN_MAX) that uses per-pixel MIN and MAX state information as additional/supplemental input along with 5-cycle flanking input window.

FIG. 49 shows that the disclosed state-based and neural network-based base caller DeepRTA with State (3ci_k14_DC_MIN_MAX) that uses per-pixel MIN and MAX state information as additional/supplemental input along with 3-cycle flanking input window demonstrates 45% improvement over the RTA. This shows that even with a smaller input window compared to the DeepRTA without state information (5ci_k14) (and the DeepRTA with State (5ci_k14_DC_MIN) (both with 5-cycle flanking input window), the DeepRTA with State (3ci_k14_DC_MIN_MAX) (3-cycle flanking input window) performs better. That is, with the state information, we get better base calling accuracy with processing lesser image data and thereby saving compute.

Figure 50:
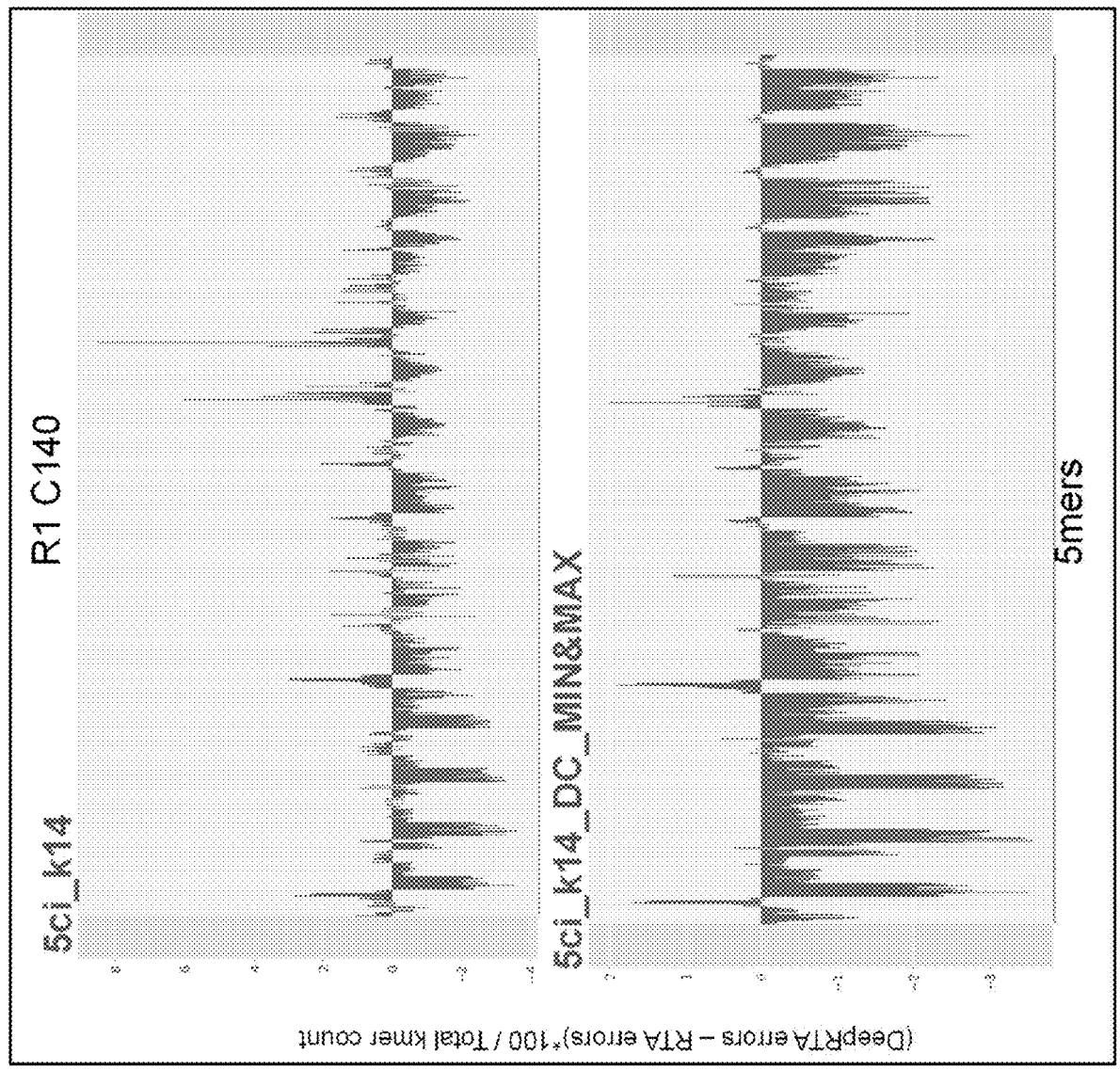
FIG. 50 compares base calling performance of the disclosed state-based and neural network-based base caller DeepRTA with State (5ci_k14_DC_MIN_MAX) that uses per-pixel MIN and MAX state information as additional/supplemental input along with 5-cycle flanking input window on k-mers (specifically 5mers) against that of the neural network-based base caller DeepRTA without state information and 5-cycle flanking input window (5ci_k14). 5mers refers to repetitive base patterns for five base positions (e.g., ACGCG, GGGGG, TCGCG).

FIG. 50 compares base calling performance of the disclosed state-based and neural network-based base caller DeepRTA with State (5ci_k14_DC_MIN_MAX) that uses per-pixel MIN and MAX state information as additional/supplemental input along with 5-cycle flanking input window on k-mers (specifically 5mers) against that of the neural network-based base caller DeepRTA without state information and 5-cycle flanking input window (5ci_k14). 5mers refers to repetitive base patterns for five base positions (e.g., ACGCG, GGGGG, TCGCG). In FIG. 50, the x-axis denotes all 1024 combinations of the 5mers, and the y-axis denotes base calling performance of the disclosed state-based and neural network-based base caller DeepRTA with State (DC).

In particular, in FIG. 50, the disclosed state-based and neural network-based base caller DeepRTA with State (5ci_k14_DC_MIN_MAX) that uses per-pixel MIN and MAX state information as additional/supplemental input along with 5-cycle flanking input window has longer negative lines than the neural network-based base caller DeepRTA without state information and 5-cycle flanking input window (5ci_k14), which indicates the disclosed state-based and neural network-based base caller DeepRTA with State (5ci_k14_DC_MIN_MAX) that uses per-pixel MIN and MAX state information as additional/supplemental input along with 5-cycle flanking input window has a lower base calling error rate for the 5mers along the x-axis.

Figure 51:
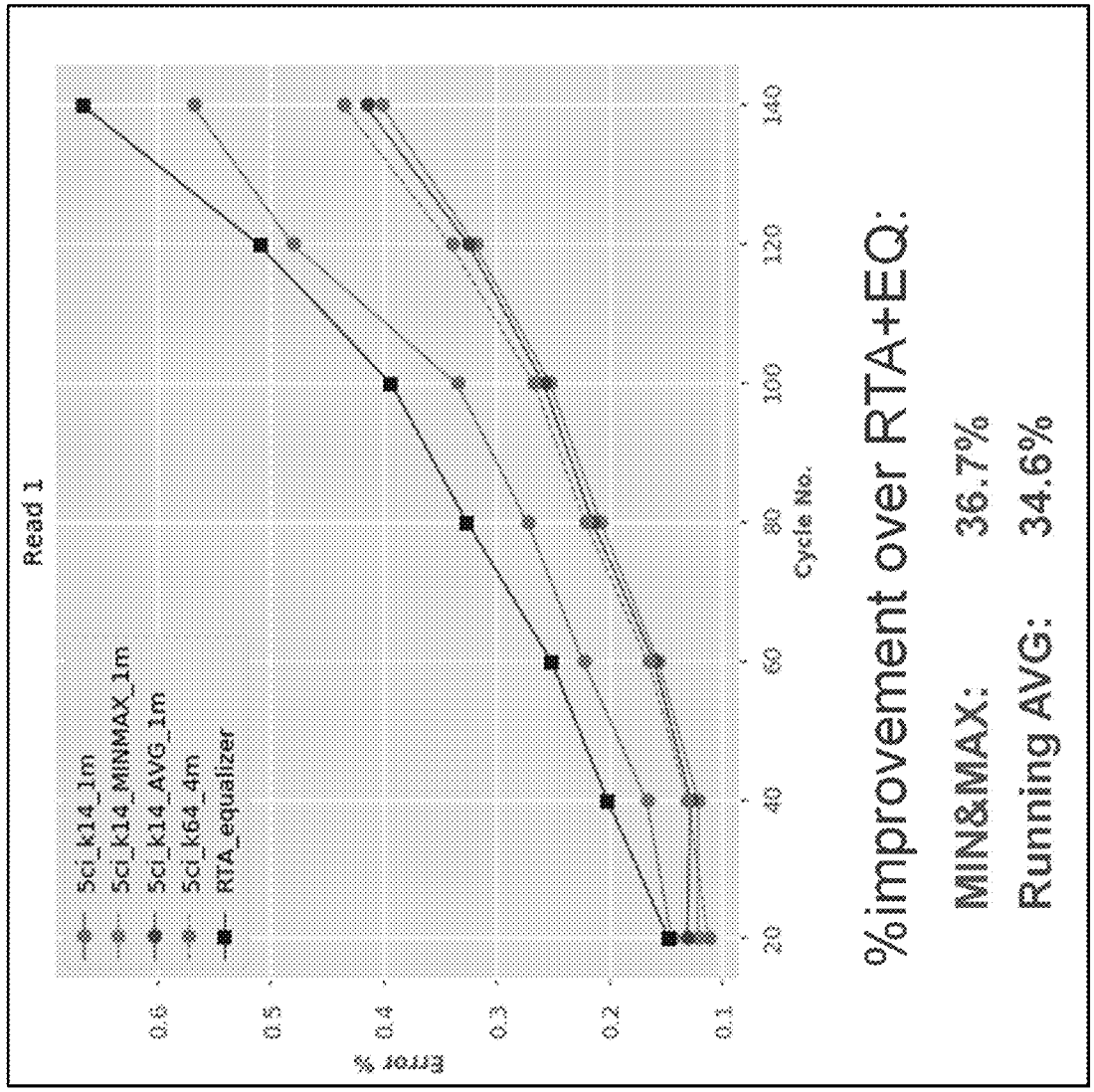
FIG. 51 compares base calling performance of a non-neural network-based base caller RTA with an Equalizer implementation, the disclosed state-based and neural network-based base caller DeepRTA with State (5ci_k14_DC_MIN_MAX) that uses per-pixel MIN and MAX state information as additional/supplemental input along with 5-cycle flanking input window, and the disclosed state-based and neural network-based base caller DeepRTA with State (5ci_k14_DC_AVG) that uses per-pixel AVG state information as additional/supplemental input along with 5-cycle flanking input window.

FIG. 51 compares base calling performance of a non-neural network-based base caller RTA with an Equalizer implementation, the disclosed state-based and neural network-based base caller DeepRTA with State (5ci_k14_DC_MIN_MAX) that uses per-pixel MIN and MAX state information as additional/supplemental input along with 5-cycle flanking input window, and the disclosed state-based and neural network-based base caller DeepRTA with State (5ci_k14_DC_AVG) that uses per-pixel AVG state information as additional/supplemental input along with 5-cycle flanking input window.

FIG. 51 shows that the disclosed state-based and neural network-based base caller DeepRTA with State (5ci_k14_DC_MIN_MAX) that uses per-pixel MIN and MAX state information as additional/supplemental input along with 5-cycle flanking input window demonstrates 36.7% improvement over the RTA with the Equalizer implementation. FIG. 51 also shows that the disclosed state-based and neural network-based base caller DeepRTA with State (5ci_k14_DC_AVG) that uses per-pixel AVG state information as additional/supplemental input along with 5-cycle flanking input window demonstrates 34.6% improvement over the RTA with the Equalizer implementation.

Figure 52:
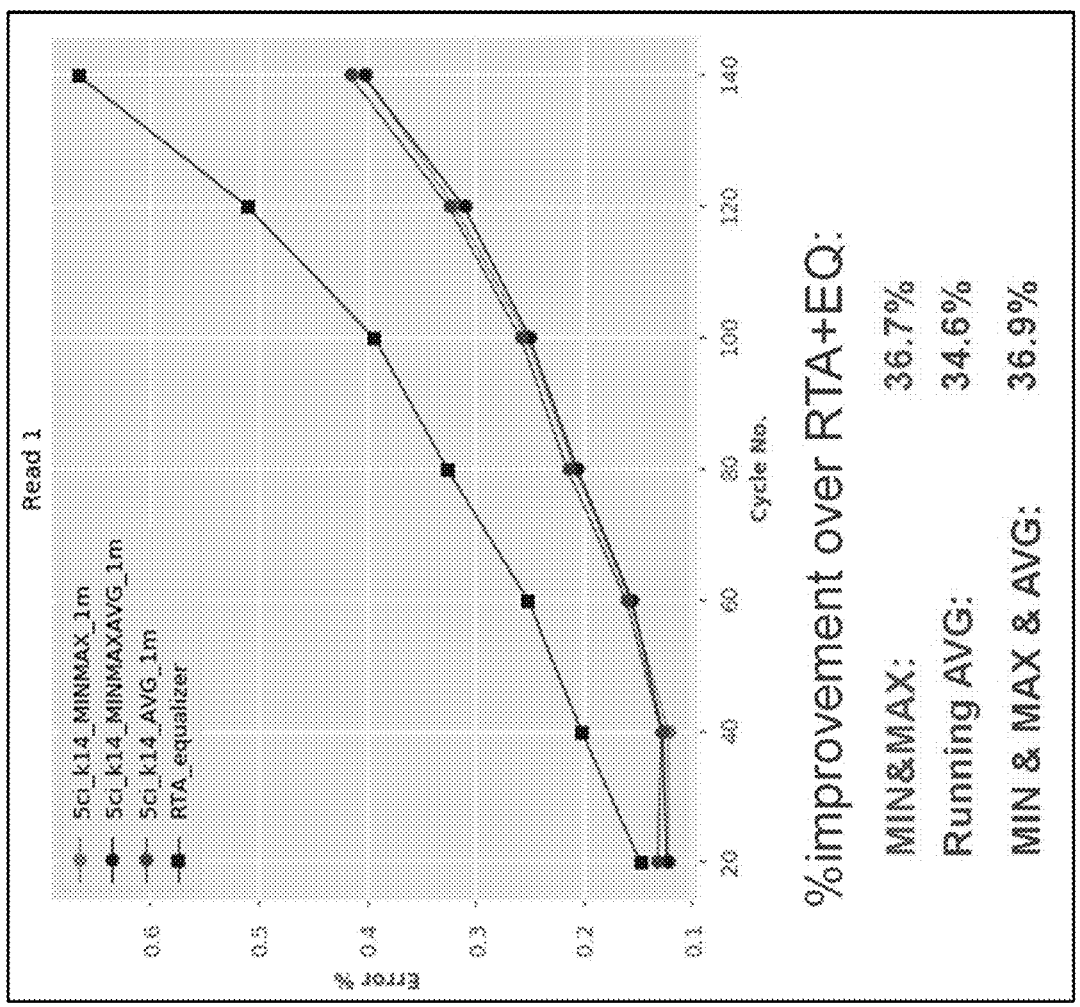
FIG. 52 compares base calling performance of the non-neural network-based base caller RTA with the Equalizer implementation and the disclosed state-based and neural network-based base caller DeepRTA with State (5ci_k14_DC_MIN_MAX_AVG) that uses per-pixel MIN, MAX, and AVG state information as additional/supplemental input along with 5-cycle flanking input window.

FIG. 52 compares base calling performance of the non-neural network-based base caller RTA with the Equalizer implementation and the disclosed state-based and neural network-based base caller DeepRTA with State (5ci_k14_DC_MIN_MAX_AVG) that uses per-pixel MIN, MAX, and AVG state information as additional/supplemental input along with 5-cycle flanking input window.

FIG. 52 shows that the disclosed state-based and neural network-based base caller DeepRTA with State (5ci_k14_DC_MIN_MAX_AVG) that uses per-pixel MIN, MAX, and AVG state information as additional/supplemental input along with 5-cycle flanking input window demonstrates 36.9% improvement over the RTA with the Equalizer implementation.

Figure 53:
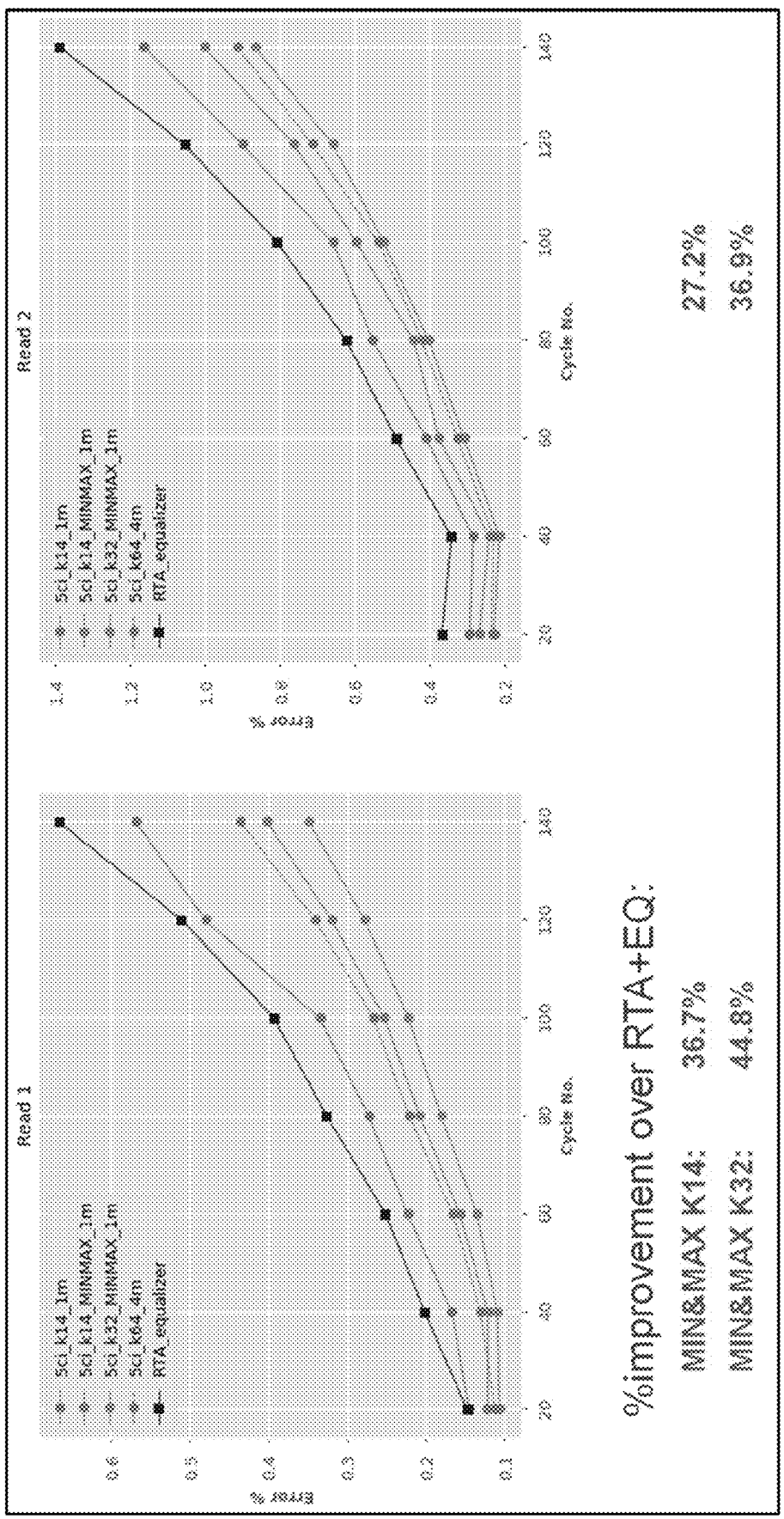
FIG. 53 compares base calling performance of the non-neural network-based base caller RTA with the Equalizer implementation, the disclosed state-based and neural network-based base caller DeepRTA with State (5ci_k14_DC_MIN_MAX) that uses per-pixel MIN and MAX state information as additional/supplemental input along with 5-cycle flanking input window and filter banks of size 14 (K=14), and the disclosed state-based and neural network-based base caller DeepRTA with State (5ci_k14_DC_MIN_MAX) that uses per-pixel MIN and MAX state information as additional/supplemental input along with 5-cycle flanking input window and filter banks of size 32 (K=32).

FIG. 53 compares base calling performance of the non-neural network-based base caller RTA with the Equalizer implementation, the disclosed state-based and neural network-based base caller DeepRTA with State (5ci_k14_DC_MIN_MAX) that uses per-pixel MIN and MAX state information as additional/supplemental input along with 5-cycle flanking input window and filter banks of size 14 (K=14), and the disclosed state-based and neural network-based base caller DeepRTA with State (5ci_k14_DC_MIN_MAX) that uses per-pixel MIN and MAX state information as additional/supplemental input along with 5-cycle flanking input window and filter banks of size 32 (K=32).

FIG. 53 shows that the disclosed state-based and neural network-based base caller DeepRTA with State (5ci_k14_DC_MIN_MAX) that uses per-pixel MIN and MAX state information as additional/supplemental input along with 5-cycle flanking input window and filter banks of size 14 (K=14) demonstrates 36.7% improvement over the RTA with the Equalizer implementation for Read 1 and 27.2% improvement for Read 2. FIG. 53 also shows that the disclosed state-based and neural network-based base caller DeepRTA with State (5ci_k14_DC_MIN_MAX) that uses per-pixel MIN and MAX state information as additional/supplemental input along with 5-cycle flanking input window and filter banks of size 32 (K=32) demonstrates 44.8% improvement over the RTA with the Equalizer implementation for Read 1 and 36.9% improvement for Read 2.

Figure 54:
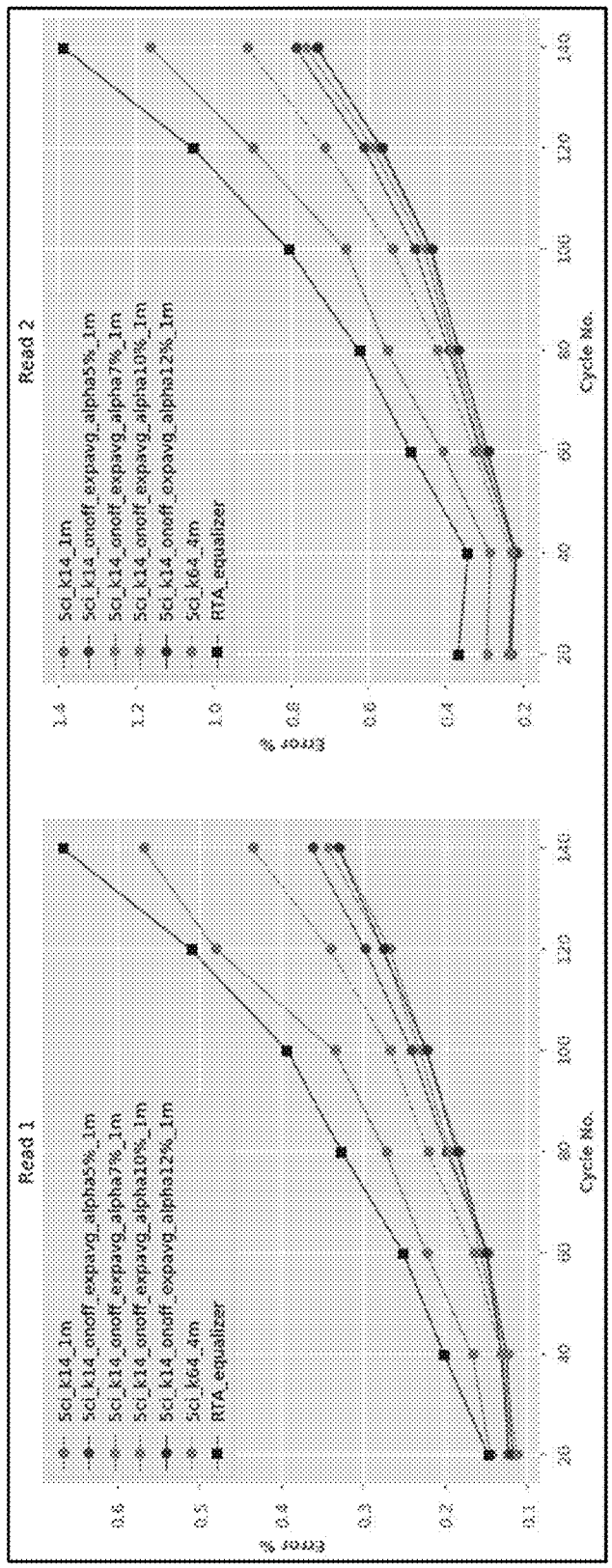
FIG. 54 compares base calling performance of the disclosed state-based and neural network-based base caller DeepRTA with State for different alpha parameter configurations (e.g., 0.05, 0.07, 0.10, 0.12) of exponential weighted averaging implementations, as discussed above.

FIG. 54 compares base calling performance of the disclosed state-based and neural network-based base caller DeepRTA with State for different alpha parameter configurations (e.g., 0.05, 0.07, 0.10, 0.12) of exponential weighted averaging implementations, as discussed above. As shown, the alpha parameter of 0.12 has the best base calling accuracy for both Read 1 and Read 2.

Figure 55:
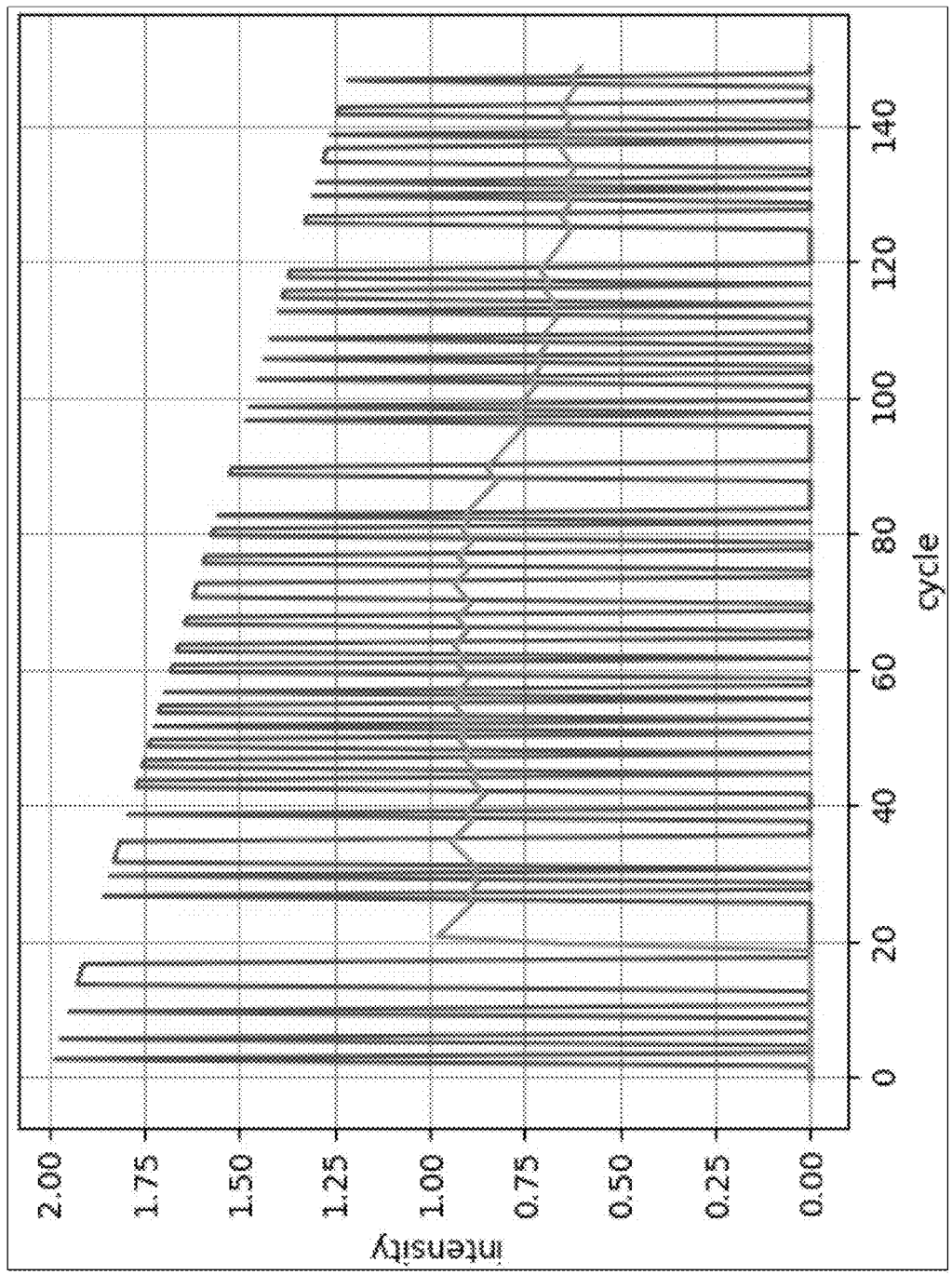
FIGS. 55 and 56 are graphs that track the state values determined by exponential weighted averages according to one implementation of the technology disclosed.
Figure 56:
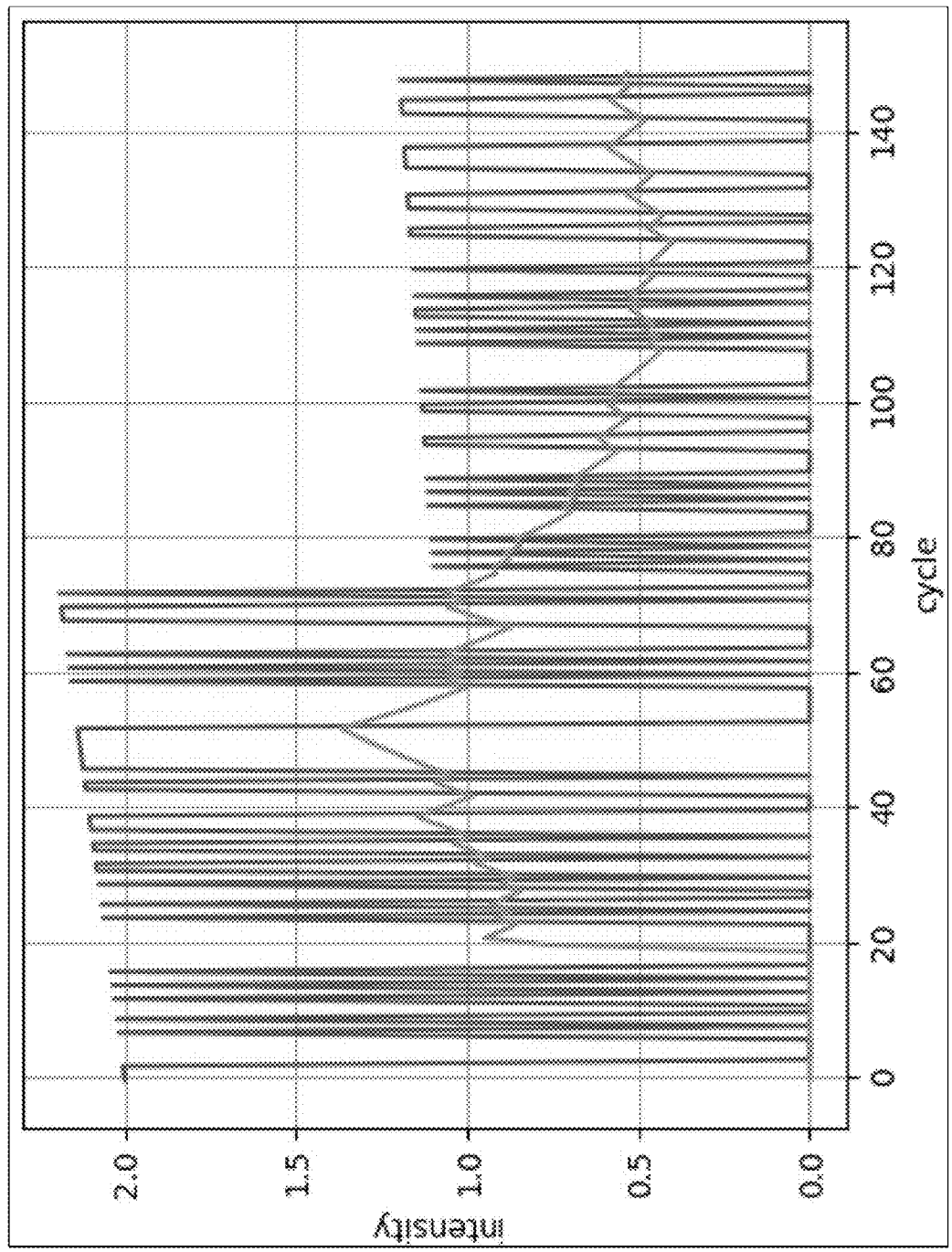

FIGS. 55 and 56 are graphs that track the state values determined by exponential weighted averages according to one implementation of the technology disclosed. In FIGS. 55 and 56, the blue lines are the raw intensity, and the exponentially weighted average estimate is initialized at cycle 21 using the average intensity from cycles 1-20 and an alpha=0.02. The x-axis is the cycle index, and the y-axis is measured amplitude (blue) plus estimated average intensity (orange). The estimated amplitude in orange follows the envelope of the intensity/average intensity as desired. It is moderately noisy, due to the need to average over ON/OFF intensities to recover average intensity. In the next example, the amplitude suddenly steps down at cycle 75. The exponential moving average is able to estimate this amplitude change quite quickly. The pixel intensity average is quite a noisy statistic since it has to average over the large ON/OFF steps as well as smaller amplitude variations.

FIG. 57 compares base calling performance of RTA with the Equalizer implementation (RTA+Eq), the DeepRTA without state information (DeepRTA (k14_1m)), and the disclosed DeepRTA with State (DeepRTA_extrachannels (k14_1,_onoff_expavg)) from the perspective of secondary analysis tasks and metrics like number of called reads, read mismatch error rate for Read 1 and Read 1 and their average, single nucleotide polymorphism (SNP) recall, SNO precision, SNP calling accuracy (F1 score), insertion/deletion (Indel) recall, Indel precision, and Indel calling accuracy (F1 score). The disclosed DeepRTA_extrachannels (k14_1,_onoff_expavg) model uses state information determined from exponential weighted average implementations discussed above. As demonstrated, the disclosed DeepRTA_extrachannels (k14_1,_onoff_expavg) model outperforms others on a variety of secondary analysis tasks and metrics.

CLAUSES

The technology disclosed can be practiced as a system, method, or article of manufacture. One or more features of an implementation can be combined with the base implementation. Implementations that are not mutually exclusive are taught to be combinable. One or more features of an implementation can be combined with other implementations. This disclosure periodically reminds the user of these options. Omission from some implementations of recitations that repeat these options should not be taken as limiting the combinations taught in the preceding sections—these recitations are hereby incorporated forward by reference into each of the following implementations.

One or more implementations and clauses of the technology disclosed or elements thereof can be implemented in the form of a computer product, including a non-transitory computer readable storage medium with computer usable program code for performing the method steps indicated. Furthermore, one or more implementations and clauses of the technology disclosed or elements thereof can be implemented in the form of an apparatus including a memory and at least one processor that is coupled to the memory and operative to perform exemplary method steps. Yet further, in another aspect, one or more implementations and clauses of the technology disclosed or elements thereof can be implemented in the form of means for carrying out one or more of the method steps described herein; the means can include (i) hardware module(s), (ii) software module(s) executing on one or more hardware processors, or (iii) a combination of hardware and software modules; any of (i)-(iii) implement the specific techniques set forth herein, and the software modules are stored in a computer readable storage medium (or multiple such media).

The clauses described in this section can be combined as features. In the interest of conciseness, the combinations of features are not individually enumerated and are not repeated with each base set of features. The reader will understand how features identified in the clauses described in this section can readily be combined with sets of base features identified as implementations in other sections of this application. These clauses are not meant to be mutually exclusive, exhaustive, or restrictive; and the technology disclosed is not limited to these clauses but rather encompasses all possible combinations, modifications, and variations within the scope of the claimed technology and its equivalents.

Other implementations of the clauses described in this section can include a non-transitory computer readable storage medium storing instructions executable by a processor to perform any of the clauses described in this section. Yet another implementation of the clauses described in this section can include a system including memory and one or more processors operable to execute instructions, stored in the memory, to perform any of the clauses described in this section.

We disclose the following clauses:

Clauses Set 1—Per-Pixel State Channels

1. A system, comprising:
    memory storing, for a current sequencing cycle of a sequencing run, respective current intensity values for respective pixels in a plurality of pixels;
    the memory storing, for one or more previous sequencing cycles of the sequencing run that precede the current sequencing cycle, sequences of respective previous intensity values for the respective pixels;
    a state generator, having access to the memory, configured to generate respective current state values for the respective pixels in dependence upon
        (i) the respective current intensity values, and
        (ii) respective previous intensity values in the sequences of respective previous intensity values, and to store the respective current state values in the memory; and
    a base caller, having access to the memory, configured to generate base calls for the current sequencing cycle in response to processing
        (i) the respective current intensity values, and
        (ii) the respective current state values.

2. The system of clause 1, wherein respective intensity values for the respective pixels are each characterized by channel-specific intensity values for a plurality of channels.
3. The system of clause 2, wherein respective state values for the respective pixels are each characterized by channel-specific state values for the plurality of channels.
4. The system of clause 3, wherein the respective current state values are pixel-wise encoded with the respective current intensity values.
5. The system of clause 3, wherein channel-specific state values for a subset of channels in the plurality of channels are pixel-wise encoded with the respective current intensity values.
6. The system of clause 3, wherein the channel-specific state values are averaged across channels in the plurality of channels to generate respective pan-channel current state values, wherein the respective pan-channel current state values are pixel-wise encoded with the respective current intensity values.
7. The system of clause 4, wherein the pixel-wise encoding includes pixel-wise concatenation.
8. The system of clause 4, wherein the pixel-wise encoding includes pixel-wise summing.
9. The system of clause 1, wherein the respective current state values are respective current average intensities determined for the respective pixels at the current sequencing cycle from
   (i) the respective previous intensity values, and
   (ii) the respective current intensity values.
10. The system of clause 9, wherein the respective current average intensities are each characterized by channel-specific current average intensities.
11. The system of clause 10, wherein the respective current state values are respective current maximum intensities determined for the respective pixels at the current sequencing cycle from
    (i) the respective previous intensity values, and
    (ii) the respective current intensity values.
12. The system of clause 11, wherein the respective current maximum intensities are each characterized by channel-specific current maximum intensities.
13. The system of clause 12, wherein the respective current state values are respective current minimum intensities determined for the respective pixels at the current sequencing cycle from
    (i) the respective previous intensity values, and
    (ii) the respective current intensity values.
14. The system of clause 13, wherein the respective current minimum intensities are each characterized by channel-specific current minimum intensities.
15. The system of clause 14, wherein the respective current state values are respective current exponentially weighted average intensities determined for the respective pixels at the current sequencing cycle from
    (i) the respective previous intensity values, and
    (ii) the respective current intensity values.
16. The system of clause 15, wherein the respective current exponentially weighted average intensities are determined based on weighting recent sequencing cycles more than earlier sequencing cycles.
17. The system of clause 16, wherein the respective current exponentially weighted average intensities are each characterized by channel-specific current exponentially weighted average intensities.
18. The system of clause 17, wherein the respective current state values are respective current moving average intensities determined for the respective pixels at the current sequencing cycle from
    (i) the respective current intensity values, and
    (ii) a rolling subset of the respective previous intensity values.
19. The system of clause 18, wherein the respective current moving average intensities are each characterized by channel-specific current moving average intensities.
20. The system of clause 19, wherein each of the respective current intensity values is attributed to an active state bucket or an inactive state bucket based on comparison of the respective current intensity values to respective current active state intensities and respective current inactive state intensities.
21. The system of clause 20, wherein the respective current active state intensities are respective current global maximum intensities determined for the respective pixels at the current sequencing cycle from
    (i) the respective previous intensity values.
22. The system of clause 21, wherein the respective current global maximum intensities are each characterized by channel-specific current global maximum intensities.
23. The system of clause 22, wherein the respective current inactive state intensities are respective current global minimum intensities determined for the respective pixels at the current sequencing cycle from
    (i) the respective previous intensity values.
24. The system of clause 23, wherein the respective current global minimum intensities are each characterized by channel-specific current global minimum intensities.
25. The system of clause 24, wherein the respective current state values further include respective current active state values and respective current inactive state values generated for the respective pixels at the current sequencing cycle.
26. The system of clause 25, wherein the respective current active state values are each characterized by channel-specific current active state values.
27. The system of clause 26, wherein the respective current inactive state values are each characterized by channel-specific current inactive state values.
28. The system of clause 27, wherein a current active state value for a pixel in a subject channel is determined at the current sequencing cycle from
    (i) a current intensity value for the pixel in the subject channel that is detected and attributed to the active state bucket at the current sequencing cycle, and
    (ii) previous intensity values for the pixel in the subject channel that were detected at the previous sequencing cycles.
29. The system of clause 28, wherein the current intensity value is attributed to the active state bucket based on comparison of the current intensity value to a global maximum value and a global minimum value determined from the previous intensity values in the subject channel.
30. The system of clause 29, wherein the current intensity value is attributed to the active state bucket based on comparison of the current intensity value to a previous active state value and a previous inactive state value determined at a preceding sequencing cycle in the subject channel.

31. The system of clause 30, wherein the current active state value is an exponentially weighted average determined from the current intensity value and the previous intensity values.
32. The system of clause 31, wherein the current active state value is an average determined from the current intensity value and the previous intensity values.
33. The system of clause 32, wherein the current active state value is a moving average determined from the current intensity value and a rolling subset of the previous intensity values.
34. The system of clause 33, wherein the current active state value is a minimum value determined from the current intensity value and the previous intensity values.
35. The system of clause 34, wherein the current active state value is a maximum value determined from the current intensity value and the previous intensity values.
36. The system of clause 35, wherein the current active state value is carried from the preceding sequencing cycle and not redetermined at the current sequencing cycle when the current intensity value is attributed to the inactive state bucket at the current sequencing cycle.
37. The system of clause 36, wherein a current inactive state value for the pixel in the subject channel is determined at the current sequencing cycle from
    (i) a current intensity value for the pixel in the subject channel that is detected and attributed to the inactive state bucket at the current sequencing cycle, and
    (ii) previous intensity values for the pixel in the subject channel that were detected at the previous sequencing cycles.
38. The system of clause 37, wherein the current intensity value is attributed to the inactive state bucket based on comparison of the current intensity value to a global maximum value and a global minimum value determined from the previous intensity values in the subject channel.
39. The system of clause 38, wherein the current intensity value is attributed to the inactive state bucket based on comparison of the current intensity value to a previous inactive state value and a previous inactive state value determined at a preceding sequencing cycle in the subject channel.
40. The system of clause 39, wherein the current inactive state value is an exponentially weighted average determined from the current intensity value and the previous intensity values.
41. The system of clause 40, wherein the current inactive state value is an average determined from the current intensity value and the previous intensity values.
42. The system of clause 41, wherein the current inactive state value is a moving average determined from the current intensity value and a rolling subset of the previous intensity values.
43. The system of clause 42, wherein the current inactive state value is a minimum value determined from the current intensity value and the previous intensity values.
44. The system of clause 43, wherein the current inactive state value is a maximum value determined from the current intensity value and the previous intensity values.
45. The system of clause 44, wherein the current inactive state value is carried from the preceding sequencing cycle and not redetermined at the current sequencing cycle when the current intensity value is attributed to the active state bucket at the current sequencing cycle.
46. The system of clause 1, wherein the respective current state values are iteratively generated at each sequencing cycle of the sequencing run.
47. The system of clause 1, wherein the memory is further configured to store, for next sequencing cycles of the sequencing run, sequences of respective next intensity values for the respective pixels.
48. The system of clause 47, wherein the base caller is further configured to generate the base calls for the current sequencing cycle in response to processing
    (i) the respective current intensity values,
    (ii) respective previous intensity values in the sequences of respective previous intensity values for one or more of the previous sequencing cycles,
    (iii) respective next intensity values in the sequences of respective next intensity values for one or more of the next sequencing cycles, and
    (iv) the respective state values.
49. The system of clause 48, wherein the respective state values are pixel-wise encoded with respective previous intensity values and the respective next intensity values.
50. The system of clause 3, wherein the channels correspond to a combination of illumination with a specific laser and imaging through a specific optical filter.
51. The system of clause 49, wherein the channels correspond to filter wavelength bands.
52. The system of clause 51, wherein the channels correspond to imaging events at a sequencing cycle.
53. The system of clause 1, wherein the base caller is a neural network.
54. The system of clause 53, wherein the neural network is a convolutional neural network.
55. The system of clause 54, wherein the convolutional neural network includes a plurality of spatial convolution layers and a plurality of temporal convolution layers.
56. The system of clause 3, wherein the respective state values are configured to characterize historic intensity patterns of the respective pixels.
57. The system of clause 56, wherein the historic intensity patterns are configured to compensate for losses in base calling accuracy of the base caller.
58. The system of clause 57, wherein the historic intensity patterns are configured to compensate for losses in base calling accuracy of the base caller when base calling bases for k-mers.
59. The system of clause 1, wherein the base calls for the current sequencing cycle include base calls for one or more clusters for which the respective current signal values and the respective previous signal values are detected.
60. The system of clause 59, wherein the respective state values are configured to discern respective signal profiles of the clusters.
61. The system of clause 1, wherein the base caller is trained using sequencing images generated offline for an already-executed sequencing run.
62. The system of clause 61, wherein the respective state values for the respective pixels are calculated offline for each sequencing cycle of the already-executed sequencing run in advance of base calling by the base caller.

63. The system of clause 62, wherein the base caller is trained to use the respective state values to compensate for losses in base calling accuracy.

64. A system, comprising:
memory storing, for a current sequencing cycle of a sequencing run, respective current signal values for respective signal units in a plurality of signal units;
the memory storing, for one or more previous sequencing cycles of the sequencing run that precede the current sequencing cycle, sequences of respective previous signal values for the respective signal units;
a state generator, having access to the memory, configured to generate respective current state values for the respective signal units in dependence upon
 (i) the respective current signal values, and
 (ii) respective previous intensity values in the sequences of respective previous intensity values,
and to store the respective current state values in the memory; and
a base caller, having access to the memory, configured to generate base calls for the current sequencing cycle in response to processing
 (i) the respective current signal values, and
 (ii) the respective current state values.

65. The system of clause 64, wherein the respective signal units are respective pixels of an image.

66. The system of clause 65, wherein the respective current signal values are respective current pixel intensities of the respective pixels detected at the current sequencing cycle.

67. The system of clause 66, wherein the respective previous signal values are respective previous pixel intensities of the respective pixels detected at the previous sequencing cycles.

68. The system of clause 67, wherein the base calls for the current sequencing cycle include base calls for one or more clusters for which the respective current signal values and the respective previous signal values are detected.

69. The system of clause 68, wherein the respective current state values are configured to discern respective signal profiles of the clusters.

70. The system of clause 69, wherein the memory is further configured to store, for next sequencing cycles of the sequencing run, sequences of respective next signal values for the respective signal units.

71. The system of clause 70, wherein the base caller is further configured to generate the base calls for the current sequencing cycle in response to processing
 (i) the respective current signal values,
 (ii) respective previous signal values in the sequences of respective previous signal values for one or more of the previous sequencing cycles,
 (iii) respective next signal values in the sequences of respective next signal values for one or more of the next sequencing cycles, and
 (iv) the respective state values.

72. The system of clause 64, wherein the respective current signal values are respective current voltage values detected at the current sequencing cycle.

73. The system of clause 72, wherein the respective previous signal values are respective previous voltage values detected at the previous sequencing cycles.

74. The system of clause 64, wherein the respective current signal values are respective current current values detected at the current sequencing cycle.

75. The system of clause 74, wherein the respective previous signal values are respective previous current values detected at the previous sequencing cycles.

76. A system, comprising:
a neural network-based base caller configured to process a first sliding window of sequencing cycles including sequencing images for a center sequencing cycle, one or more right flanking sequencing cycles, and one or more left flanking sequencing cycles;
a state generator configured to determine per-pixel states of the sequencing images in the first sliding window of sequencing cycles based on (i) pixel intensities in a sequencing image for the center sequencing cycle in the first sliding window of sequencing cycles, and (ii) pixel intensities in sequencing images for sequencing cycles preceding the center sequencing cycle in the first sliding window of sequencing cycles; and
the neural network-based base caller further configured to process the sequencing images in the first sliding window of sequencing cycles along with the per-pixel states to base call the center sequencing cycle in the first sliding window of sequencing cycles.

77. The system of clause 76, wherein a second sliding window of sequencing cycles includes sequencing images for a center sequencing cycle, one or more right flanking sequencing cycles, and one or more left flanking sequencing cycles,
wherein the state generator configured to determine per-pixel states of the sequencing images in the second sliding window of sequencing cycles based on (i) pixel intensities in a sequencing image for the center sequencing cycle in the second sliding window of sequencing cycles, and (ii) pixel intensities in sequencing images for sequencing cycles preceding the center sequencing cycle in the second sliding window of sequencing cycles, and
wherein the neural network-based base caller is further configured to process the sequencing images in the second sliding window of sequencing cycles along with the per-pixel states to base call the center sequencing cycle in the second sliding window of sequencing cycles.

78. The system of clause 77, wherein a third sliding window of sequencing cycles includes sequencing images for a center sequencing cycle, one or more right flanking sequencing cycles, and one or more left flanking sequencing cycles,
wherein the state generator configured to determine per-pixel states of the sequencing images in the third sliding window of sequencing cycles based on (i) pixel intensities in a sequencing image for the center sequencing cycle in the third sliding window of sequencing cycles, and (ii) pixel intensities in sequencing images for sequencing cycles preceding the center sequencing cycle in the third sliding window of sequencing cycles, and
wherein the neural network-based base caller is further configured to process the sequencing images in the third sliding window of sequencing cycles along with the per-pixel states to base call the center sequencing cycle in the third sliding window of sequencing cycles.

79. A system, comprising:
a neural network-based base caller having a plurality of intensity pattern detectors, intensity pattern detectors in the plurality of intensity pattern detectors configured to execute a subject base calling operation based on intensity pattern detection from intensity values of pixels in a current sliding window of sequencing images with losses in base calling accuracy due to confinement of the intensity pattern detectors to the current window of sequencing images;

intensity contextualization logic configured to determine intensity context data based on (i) past intensity values of the pixels in sequencing images preceding sequencing images in the current sliding window of sequencing images, and (ii) target intensity values of the pixels in a target sequencing image in the current sliding window of sequencing images;

data flow logic configured to append the intensity context data with the intensity values of the pixels to generate intensity contextualized pixels; and the neural network-based base caller further configured to apply the intensity pattern detectors on the intensity contextualized pixels and generate base calls for the subject base calling operation, the intensity context data in the intensity contextualized pixels compensating for the losses in the base calling accuracy.

80. A computer-implemented method, including:
accessing current window sequenced signal data for a first plurality of sequencing cycles in a current sliding window of sequencing cycles;
accessing previous sequenced signal data for a second plurality of sequencing cycles that precede sequencing cycles in the first plurality of sequencing cycles;
generating state signal data based on the current window sequenced signal data and the previous sequenced signal data; and
base calling at least one sequencing cycle in the first plurality of sequencing cycles in response to processing the current window sequenced signal data and the state signal data.

81. A computer-implemented method, including:
base calling a current sequencing cycle of a sequencing run based on state information determined from one or more previous sequencing cycles of the sequencing run that precede the current sequencing cycle.

82. A system, comprising:
memory storing current sequencing images for clusters for a current sequencing cycle of a sequencing run, and previous sequencing images for the clusters for one or more previous sequencing cycles of the sequencing run that precede the current sequencing cycle;
a host processor having access to the memory and configured to generate, for the current sequencing cycle, current per-pixel states for pixels in the sequencing images based on the current sequencing images and the previous sequencing images;
a configurable processor having access to the memory and configured to execute a neural network to produce base call classification scores; and
a data flow logic having access to the memory, the host processor, and the configurable processor and configured
to provide the current per-pixel states and the current sequencing images to the neural network and cause the neural network to produce current base call classification scores for the clusters for the current sequencing cycle in response to processing the current per-pixel states and the current sequencing images, and
to provide the current base call classification scores to the host.

83. The system of clause 82, wherein the memory further stores previous per-pixel states for the pixels generated by the host processor in a previous sequencing cycle.

84. The system of clause 83, wherein the host processor is further configured to generate the current per-pixel states based on the current sequencing images and the previous per-pixel states.

Clauses Set 2—Per-Well State Channels

1. A system, comprising:
a spatial convolutional neural network configured to process sequencing images of analytes, and produce spatially convolved features;
filtering logic configured to select, from the spatially convolved features, a subset of spatially convolved features that contain centers of the analytes;
state generation logic configured to generate per-analyte states for the subset of spatially convolved features; temporal processing logic configured to process the subset of spatially convolved features and the per-analyte states, and produce a temporally compact output; and
base calling logic configured to produce base calls based on the temporally compact output.

2. The system of clause 1, wherein the per-analyte states are intensity variation correction coefficients generated on an analyte-by-analyte basis by a linear model in response to independently processing the sequencing images.

3. The system of clause 2, wherein the intensity variation correction coefficients include an amplification coefficient that compensates for scale variation between the intensity profiles of the analytes.

4. The system of clause 3, wherein the intensity variation correction coefficients include channel-specific offset coefficients that compensate for shift variation between the intensity profiles of the analytes along a plurality of channels.

5. The system of clause 4, wherein the intensity variation correction coefficients include a common offset coefficient that compensates for the shift variation.

6. The system of clause 5, wherein the intensity variation correction coefficients are generated on the analyte-by-analyte basis based on combining analysis of current intensity statistics determined at a current sequencing cycle of a sequencing run with analysis of historic intensity statistics determined at one or more previous sequencing cycles of the sequencing run that precede the current sequencing cycle.

7. The system of clause 1, wherein the intensity profiles of the analytes are characterized by channel-specific intensity values for channels in the plurality of channels.

8. The system of clause 7, wherein the per-analyte states are characterized by channel-specific state values for the channels.

9. The system of clause 8, wherein the per-analyte states are encoded with the subset of spatially convolved features on a central feature-by-central feature basis.

10. The system of clause 8, wherein channel-specific state values for a subset of the channels are encoded with the subset of spatially convolved features on the central feature-by-central feature basis.

11. The system of clause 8, wherein the channel-specific state values are averaged across the channels to generate pan-channel state values, wherein the pan-channel state values are encoded with the subset of spatially convolved features on the central feature-by-central feature basis.
12. The system of clause 9, wherein the per-analyte states are concatenated with the subset of spatially convolved features on the central feature-by-central feature basis.
13. The system of clause 9, wherein the per-analyte states are summed with the subset of spatially convolved features on the central feature-by-central feature basis.
14. The system of clause 1, wherein the per-analyte states are based on feature values of the subset of spatially convolved features produced by the spatial processing logic at the current sequencing cycle and at the previous sequencing cycles.
15. The system of clause 14, wherein the per-analyte states are averages of the feature values.
16. The system of clause 14, wherein the per-analyte states are maximum ones of the feature values.
17. The system of clause 14, wherein the per-analyte states are minimum ones of the feature values.
18. The system of clause 14, wherein the per-analyte states are exponentially weighted averages of the feature values.
19. The system of clause 18, wherein the exponentially weighted averages are determined based on weighting recent sequencing cycles more than earlier sequencing cycles.
20. The system of clause 14, wherein the per-analyte states are moving averages of the feature values.
21. The system of clause 20, wherein the moving averages use rolling subsets of feature values from the previous sequencing cycles.
22. The system of clause 14, wherein the per-analyte states include active state values and inactive state values.
23. The system of clause 22, wherein the active state values and inactive state values are channel-specific.
24. The system of clause 23, wherein the active state values and inactive state values are determined from a preceding base call.
25. The system of clause 23, wherein the active state values and inactive state values are determined based on global maximums and global minimums of the feature values.
26. The system of clause 23, wherein the active state values and inactive state values are determined based on exponentially weighted averages of the feature values.
27. The system of clause 1, wherein the input includes a sliding window of sequencing images for a current sequencing cycle, one or more previous sequencing cycles, and one or more next sequencing cycles.
28. The system of clause 27, wherein feature sets are extracted from pixels of sequencing images in the sliding window of sequencing images for the current sequencing cycle, the previous sequencing cycles, and the next flanking sequencing cycles.
29. The system of clause 28, wherein central feature sets are culled from the feature sets for the current sequencing cycle, the previous sequencing cycles, and the next sequencing cycles.
30. The system of clause 29, wherein per-analyte state sets are generated for and encoded with the central feature sets for the current sequencing cycle, the previous sequencing cycles, and the next flanking sequencing cycles.
31. The system of clause 1, wherein the spatial processing logic and the temporal processing logic are neural networks.
32. The system of clause 31, wherein the neural networks are convolutional neural networks.
33. The system of clause 1, wherein the per-analyte states are configured to characterize historic intensity patterns of the pixels.
34. The system of clause 33, wherein the historic intensity patterns are configured to compensate for losses in base calling accuracy.
35. The system of clause 34, wherein the historic intensity patterns are configured to compensate for losses in base calling accuracy when base calling bases for k-mers.
36. The system of clause 1, wherein the per-analyte states are configured to discern the intensity profiles of the analytes.
37. The system of clause 1, wherein the spatial processing logic and the temporal processing logic are trained using sequencing images generated offline for an already-executed sequencing run.
38. The system of clause 37, wherein the per-analyte states are calculated offline for each sequencing cycle of the already-executed sequencing run in advance of base calling.
39. The system of clause 38, wherein the spatial processing logic and the temporal processing logic are trained to use the per-analyte states to compensate for losses in base calling accuracy.
40. A system, comprising:
spatial processing logic configured to process an input in which intensity profiles of analytes are dispersed across pixels of sequencing images, and produce a spatially compact output in which the intensity profiles of the analytes are aggregated into features extracted from the pixels;
analyte focusing logic configured to cull those per-analyte, central features from the features that characterize peak intensities detected at centers of the analytes;
state generation logic configured to generate per-analyte states for the per-analyte, central features;
temporal processing logic configured to process the per-analyte, central features and the per-analyte states, and produce a temporally compact output; and
base calling logic configured to produce base calls based on the temporally compact output.

Clauses Set 3—Per-Compressed Feature State Channels
1. A system, comprising:
a spatial convolutional neural network configured to process sequencing images of clusters, and produce spatially convolved features;
filtering logic configured to select, from the spatially convolved features, a subset of spatially convolved features that contain centers of the clusters;
compression logic configured to compress the subset of spatially convolved features into a set of compressed features, wherein the subset of spatially convolved features has A channels, and the set of compressed features has N channels, and wherein M>N;
contextualization logic configured to access state information for compressed features in the set of compressed features, and to append the state information with the compressed features to generate a set of stateful compressed features;

a temporal convolutional neural network configured to process the set of stateful compressed features, and produce temporally convolved stateful features; and
base calling logic configured to generate base calls for the clusters based on the temporally convolved stateful features.
2. The system of clause 1, wherein the per-channel states are intensity variation correction coefficients generated on an analyte-by-analyte basis by a linear model in response to independently processing the sequencing images.
3. The system of clause 2, wherein the intensity variation correction coefficients include an amplification coefficient that compensates for scale variation between the intensity profiles of the analytes.
4. The system of clause 3, wherein the intensity variation correction coefficients include channel-specific offset coefficients that compensate for shift variation between the intensity profiles of the analytes along a plurality of channels.
5. The system of clause 4, wherein the intensity variation correction coefficients include a common offset coefficient that compensates for the shift variation.
6. The system of clause 5, wherein the intensity variation correction coefficients are generated on the analyte-by-analyte basis based on combining analysis of current intensity statistics determined at a current sequencing cycle of a sequencing run with analysis of historic intensity statistics determined at one or more previous sequencing cycles of the sequencing run that precede the current sequencing cycle.
7. The system of clause 1, wherein the intensity profiles of the analytes are characterized by channel-specific intensity values for channels in the plurality of channels.
8. The system of clause 7, wherein the per-channel states are characterized by channel-specific state values for the channels.
9. The system of clause 8, wherein the per-channel states are encoded with the per-analyte, channel-specific bits on a bit-by-bit basis.
10. The system of clause 8, wherein channel-specific state values for a subset of the channels are encoded with the per-analyte, channel-specific bits on the bit-by-bit basis.
11. The system of clause 8, wherein the channel-specific state values are averaged across the channels to generate pan-channel state values, wherein the pan-channel state values are encoded with the per-analyte, channel-specific bits on the bit-by-bit basis.
12. The system of clause 9, wherein the per-channel states are concatenated with the per-analyte, channel-specific bits on the bit-by-bit basis.
13. The system of clause 9, wherein the per-channel states are summed with the per-analyte, channel-specific bits on the bit-by-bit basis.
14. The system of clause 1, wherein the per-channel states are based on compressed values of the per-analyte, channel-specific bits produced by the spatial processing logic at the current sequencing cycle and at the previous sequencing cycles.
15. The system of clause 14, wherein the per-channel states are averages of the compressed values.
16. The system of clause 14, wherein the per-channel states are maximum ones of the compressed values.
17. The system of clause 14, wherein the per-channel states are minimum ones of the compressed values.
18. The system of clause 14, wherein the per-channel states are exponentially weighted averages of the compressed values.
19. The system of clause 18, wherein the exponentially weighted averages are determined based on weighting recent sequencing cycles more than earlier sequencing cycles.
20. The system of clause 14, wherein the per-channel states are moving averages of the compressed values.
21. The system of clause 20, wherein the moving averages use rolling subsets of compressed values from the previous sequencing cycles.
22. The system of clause 14, wherein the per-channel states include active state values and inactive state values.
23. The system of clause 22, wherein the active state values and inactive state values are channel-specific.
24. The system of clause 23, wherein the active state values and inactive state values are determined from a preceding base call.
25. The system of clause 23, wherein the active state values and inactive state values are determined based on global maximums and global minimums of the compressed values.
26. The system of clause 23, wherein the active state values and inactive state values are determined based on exponentially weighted averages of the compressed values.
27. The system of clause 1, wherein the input includes a sliding window of sequencing images for a current sequencing cycle, one or more previous sequencing cycles, and one or more next sequencing cycles.
28. The system of clause 27, wherein feature sets are extracted from channel-specific pixels of sequencing images in the sliding window of sequencing images for the current sequencing cycle, the previous sequencing cycles, and the next flanking sequencing cycles, wherein per-analyte, central feature sets are culled from the feature sets for the current sequencing cycle, the previous sequencing cycles, and the next sequencing cycles.
29. The system of clause 28, wherein channel-specific bit sets are compressed from the per-analyte, central feature sets for the current sequencing cycle, the previous sequencing cycles, and the next sequencing cycles.
30. The system of clause 29, wherein per-channel state sets are generated for and encoded with the channel-specific bit sets for the current sequencing cycle, the previous sequencing cycles, and the next flanking sequencing cycles.
31. The system of clause 1, wherein the spatial processing logic and the temporal processing logic are neural networks.
32. The system of clause 31, wherein the neural networks are convolutional neural networks.
33. The system of clause 1, wherein the per-channel states are configured to characterize historic intensity patterns of the channel-specific pixels.
34. The system of clause 33, wherein the historic intensity patterns are configured to compensate for losses in base calling accuracy.
35. The system of clause 34, wherein the historic intensity patterns are configured to compensate for losses in base calling accuracy when base calling bases for k-mers.
36. The system of clause 1, wherein the per-analyte states are configured to discern the intensity profiles of the analytes.

37. The system of clause 1, wherein the spatial processing logic and the temporal processing logic are trained using sequencing images generated offline for an already-executed sequencing run.
38. The system of clause 37, wherein the per-channel states are calculated offline for each sequencing cycle of the already-executed sequencing run in advance of base calling.
39. The system of clause 38, wherein the spatial processing logic and the temporal processing logic are trained to use the per-channel states to compensate for losses in base calling accuracy.
40. A system, comprising:
    spatial processing logic configured to process an input in which intensity profiles of analytes are dispersed across channel-specific pixels of sequencing images, and produce a spatially compact output in which the intensity profiles of the analytes are aggregated into features extracted from the channel-specific pixels;
    analyte focusing logic configured to cull those per-analyte, central features from the features that characterize peak intensities detected at centers of the analytes;
    compression logic configured to distill the per-analyte, central features into per-analyte, channel-specific bits, wherein the per-analyte, central features have M feature channels, wherein the per-analyte, channel-specific bits have N bit channels, and wherein M>N;
    state generation logic configured to generate per-channel states for the per-analyte, channel-specific bits;
    temporal processing logic configured to process the per-analyte, channel-specific bits and the per-channel states, and produce a temporally compact output; and
    base calling logic configured to produce base calls based on the temporally compact output.

Clauses Set 4—Per-Well State to Per-Pixel State Transformation

1. A system, comprising:
    per-analyte state generation logic configured to generate per-analyte states in response to processing sequencing images for analytes, and to encode the per-analyte states in a sparse representation;
    per-pixel state generation logic configured to transform the per-analyte states into per-pixel states of pixels in the sequencing images in response to processing the sparse representation, and to encode the per-pixel states in a dense representation; and a base caller configured to generate base calls in response to processing the pixels in the sequencing images supplemented with the per-pixel states encoded in the dense representation.
2. The system of clause 1, wherein the per-pixel state generation logic uses transposed convolutions.
3. The system of clause 2, wherein the transposed convolutions are trained to transform the per-analyte states encoded in the sparse representation into the per-pixel states encoded in the dense representation.
4. The system of clause 2, wherein the base caller includes spatial convolution layers and temporal convolution layers.
5. The system of clause 4, wherein the per-pixel states encoded in the dense representation are pixel-wise encoded with the pixels in the sequencing images for processing by a first spatial convolution layer of the base caller.
6. The system of clause 5, wherein the per-pixel states encoded in the dense representation are supplied as input to subsequent spatial convolution layers of the base caller.
7. The system of clause 1, wherein the per-analyte states are intensity variation correction coefficients generated on an analyte-by-analyte basis by a linear model in response to processing the sequencing images.
8. The system of clause 7, wherein the intensity variation correction coefficients include an amplification coefficient that compensates for scale variation between intensity profiles of the analytes.
9. The system of clause 8, wherein the intensity variation correction coefficients include channel-specific offset coefficients that compensate for shift variation between the intensity profiles of the analytes along a plurality of channels.
10. The system of clause 9, wherein the intensity variation correction coefficients include a common offset coefficient that compensates for the shift variation.
11. The system of clause 10, wherein the intensity variation correction coefficients are generated on the analyte-by-analyte basis based on combining analysis of current intensity statistics determined at a current sequencing cycle of a sequencing run with analysis of historic intensity statistics determined at one or more previous sequencing cycles of the sequencing run that precede the current sequencing cycle.
12. The system of clause 1, wherein the intensity profiles of the analytes are characterized by channel-specific intensity values for channels in the plurality of channels.
13. The system of clause 12, wherein the per-analyte states are characterized by channel-specific state values for the channels.
14. The system of clause 1, wherein the per-pixel state generation logic uses interpolation.

What we claim is:

1. A system, comprising:
    memory storing, for a current sequencing cycle of a sequencing run, respective current intensity values for respective pixels in a plurality of pixels;
    the memory storing, for one or more previous sequencing cycles of the sequencing run that precede the current sequencing cycle, sequences of respective previous intensity values for the respective pixels;
    a state generator, having access to the memory, configured to generate respective current state values for the respective pixels in dependence upon
        (i) the respective current intensity values, and
        (ii) respective previous intensity values in the sequences of respective previous intensity values, and to store the respective current state values in the memory; and
    a base caller, having access to the memory, configured to generate base calls for the current sequencing cycle in response to processing
        (i) the respective current intensity values, and
        (ii) the respective current state values.
2. The system of claim 1, wherein respective intensity values for the respective pixels are each characterized by channel-specific intensity values for a plurality of channels.
3. The system of claim 2, wherein respective state values for the respective pixels are each characterized by channel-specific state values for the plurality of channels.

4. The system of claim 3, wherein the respective current state values are pixel-wise encoded with the respective current intensity values.

5. The system of claim 3, wherein channel-specific state values for a subset of channels in the plurality of channels are pixel-wise encoded with the respective current intensity values.

6. The system of claim 3, wherein the channel-specific state values are averaged across channels in the plurality of channels to generate respective pan-channel current state values, wherein the respective pan-channel current state values are pixel-wise encoded with the respective current intensity values.

7. The system of claim 4, wherein the pixel-wise encoding includes pixel-wise concatenation.

8. The system of claim 4, wherein the pixel-wise encoding includes pixel-wise summing.

9. The system of claim 1, wherein the respective current state values are respective current average intensities determined for the respective pixels at the current sequencing cycle from
  (i) the respective previous intensity values, and
  (ii) the respective current intensity values.

10. The system of claim 9, wherein the respective current average intensities are each characterized by channel-specific current average intensities.

11. The system of claim 10, wherein the respective current state values are respective current maximum intensities determined for the respective pixels at the current sequencing cycle from
  (i) the respective previous intensity values, and
  (ii) the respective current intensity values.

12. The system of claim 11, wherein the respective current maximum intensities are each characterized by channel-specific current maximum intensities.

13. The system of claim 12, wherein the respective current state values are respective current minimum intensities determined for the respective pixels at the current sequencing cycle from
  (i) the respective previous intensity values, and
  (ii) the respective current intensity values.

14. The system of claim 13, wherein the respective current minimum intensities are each characterized by channel-specific current minimum intensities.

15. The system of claim 14, wherein the respective current state values are respective current exponentially weighted average intensities determined for the respective pixels at the current sequencing cycle from
  (i) the respective previous intensity values, and
  (ii) the respective current intensity values.

16. The system of claim 15, wherein the respective current exponentially weighted average intensities are determined based on weighting recent sequencing cycles more than earlier sequencing cycles.

17. The system of claim 16, wherein the respective current exponentially weighted average intensities are each characterized by channel-specific current exponentially weighted average intensities.

18. The system of claim 17, wherein the respective current state values are respective current moving average intensities determined for the respective pixels at the current sequencing cycle from
  (i) the respective current intensity values, and
  (ii) a rolling subset of the respective previous intensity values.

19. The system of claim 18, wherein the respective current moving average intensities are each characterized by channel-specific current moving average intensities.

20. The system of claim 19, wherein each of the respective current intensity values is attributed to an active state bucket or an inactive state bucket based on comparison of the respective current intensity values to respective current active state intensities and respective current inactive state intensities.

21. The system of claim 20, wherein the respective current active state intensities are respective current global maximum intensities determined for the respective pixels at the current sequencing cycle from
  (i) the respective previous intensity values.

22. The system of claim 21, wherein the respective current global maximum intensities are each characterized by channel-specific current global maximum intensities.

23. The system of claim 22, wherein the respective current inactive state intensities are respective current global minimum intensities determined for the respective pixels at the current sequencing cycle from
  (i) the respective previous intensity values.

24. The system of claim 23, wherein the respective current global minimum intensities are each characterized by channel-specific current global minimum intensities.

25. The system of claim 24, wherein the respective current state values further include respective current active state values and respective current inactive state values generated for the respective pixels at the current sequencing cycle.

26. The system of claim 25, wherein the respective current active state values are each characterized by channel-specific current active state values.

27. The system of claim 26, wherein the respective current inactive state values are each characterized by channel-specific current inactive state values.

28. The system of claim 27, wherein a current active state value for a pixel in a subject channel is determined at the current sequencing cycle from
  (i) a current intensity value for the pixel in the subject channel that is detected and attributed to the active state bucket at the current sequencing cycle, and
  (ii) previous intensity values for the pixel in the subject channel that were detected at the one or more previous sequencing cycles.

29. A computer-implemented method, including:
accessing current window sequenced signal data for a first plurality of sequencing cycles in a current sliding window of sequencing cycles;
accessing previous sequenced signal data for a second plurality of sequencing cycles that precede sequencing cycles in the first plurality of sequencing cycles;
generating state signal data based on the current window sequenced signal data and the previous sequenced signal data; and
base calling at least one sequencing cycle in the first plurality of sequencing cycles in response to processing the current window sequenced signal data and the state signal data.

30. A system, comprising:
memory storing current sequencing images for clusters for a current sequencing cycle of a sequencing run, and previous sequencing images for the clusters for one or more previous sequencing cycles of the sequencing run that precede the current sequencing cycle;
a host processor having access to the memory and configured to generate, for the current sequencing cycle, current per-pixel states for pixels in at least the current sequencing images based on the current sequencing images and the previous sequencing images;

a configurable processor having access to the memory and configured to execute a neural network to produce base call classification scores; and a data flow logic having access to the memory, the host processor, and the configurable processor and configured to provide the current per-pixel states and the current sequencing images to the neural network and cause the neural network to produce current base call classification scores for the clusters for the current sequencing cycle in response to processing the current per-pixel states and the current sequencing images, and to provide the current base call classification scores to the host processor.

* * * * *